US007622486B2

(12) United States Patent
Pal et al.

(10) Patent No.: US 7,622,486 B2
(45) Date of Patent: Nov. 24, 2009

(54) PYRIDINE COMPOUNDS, PROCESS FOR THEIR PREPARATION AND COMPOSITIONS CONTAINING THEM

(75) Inventors: Manojit Pal, Andhra Pradesh (IN); Christopher W. Alexander, Atlanta, GA (US); Ish Khanna, Alpharetta, GA (US); Javed Iqbal, Andhra Pradesh (IN); Ram Pillarisetti, Norcross, GA (US); Santanu Maitra, Andhra Pradesh (IN); Gayla W. Roberts, Atlanta, GA (US); Lavanya Sagi, Atlanta, GA (US); Chintakunta Vamsee Krishna, Andhra Pradesh (IN); Jennepalli Sreenu, Andhra Pradesh (IN)

(73) Assignee: Reddy US Therapeutics, Inc., Norcross, GA (US)

( * ) Notice: Subject to any disclaimer, the term of this patent is extended or adjusted under 35 U.S.C. 154(b) by 473 days.

(21) Appl. No.: 11/234,257

(22) Filed: Sep. 23, 2005

(65) Prior Publication Data

US 2006/0084644 A1    Apr. 20, 2006

Related U.S. Application Data

(60) Provisional application No. 60/612,374, filed on Sep. 23, 2004.

(51) Int. Cl.
*A61K 31/445* (2006.01)
*A61K 31/44* (2006.01)
*C07D 401/02* (2006.01)

(52) U.S. Cl. .................... 514/318; 514/231.5; 514/332; 514/343; 514/352; 544/124; 546/194; 546/255; 546/276.4; 546/304

(58) Field of Classification Search .................. None
See application file for complete search history.

(56) References Cited

U.S. PATENT DOCUMENTS

| | | | |
|---|---|---|---|
| 4,980,350 A | 12/1990 | MacCoss et al. |
| 5,023,258 A | 6/1991 | Gymer et al. |
| 5,149,699 A | 9/1992 | Ellingbue et al. |
| 5,155,166 A | 10/1992 | Danielson et al. |
| 5,179,123 A | 1/1993 | Djuric et al. |
| 5,202,224 A | 4/1993 | Yamakawa et al. |
| 5,231,094 A | 7/1993 | Bru-Magniez et al. |
| 5,256,408 A | 10/1993 | Babcock et al. |
| 5,316,890 A | 5/1994 | Okamura et al. |
| 5,332,582 A | 7/1994 | Babcock et al. |
| 5,336,677 A | 8/1994 | Sarantakis et al. |
| 5,374,514 A | 12/1994 | Kirk et al. |
| 5,387,747 A | 2/1995 | Bru-Magniez et al. |
| 5,451,486 A | 9/1995 | Pilot et al. |
| 5,510,345 A | 4/1996 | Tuba et al. |
| 5,514,505 A | 5/1996 | Limburg et al. |
| 5,527,914 A | 6/1996 | Hioki et al. |
| 5,550,240 A | 8/1996 | Mahó et al. |
| 5,559,108 A | 9/1996 | Kim et al. |
| 5,559,135 A | 9/1996 | Ashton et al. |
| 5,629,134 A | 5/1997 | Oikawa et al. |
| 5,654,298 A | 8/1997 | Mills et al. |
| 5,672,708 A | 9/1997 | Rauchschwalbe et al. |
| 5,681,954 A | 10/1997 | Yamamoto et al. |
| 5,696,282 A | 12/1997 | Shaw et al. |
| 5,763,438 A | 6/1998 | Inokuchi et al. |
| 5,801,179 A | 9/1998 | Van Lommen et al. |
| 5,929,248 A | 7/1999 | Barbachyn et al. |
| 5,942,384 A | 8/1999 | Arai et al. |
| 5,952,349 A | 9/1999 | Asberom et al. |
| 5,977,138 A | 11/1999 | Wang et al. |
| 5,990,123 A | 11/1999 | Van Lommen et al. |
| 6,008,234 A | 12/1999 | Kochanny et al. |
| 6,020,349 A | 2/2000 | Ankersen et al. |
| 6,040,302 A | 3/2000 | Hohlweg et al. |
| 6,043,242 A | 3/2000 | Grundler |
| 6,048,675 A | 4/2000 | Hirano et al. |
| 6,093,734 A | 7/2000 | Garst et al. |
| 6,100,268 A | 8/2000 | Van Lommen et al. |
| 6,156,903 A | 12/2000 | Yazaki et al. |
| 6,248,892 B1 | 6/2001 | Noerenberg et al. |
| 6,251,900 B1 | 6/2001 | Kawashima et al. |
| 6,306,884 B1 | 10/2001 | Buckman et al. |
| 6,335,444 B1 | 1/2002 | Jinbo et al. |
| 6,559,167 B1 | 5/2003 | Garst et al. |
| 6,559,186 B1 | 5/2003 | Campbell |
| 6,573,278 B2 | 6/2003 | Mittendorf et al. |
| 6,673,818 B2 | 1/2004 | Brown et al. |
| 6,693,295 B2 | 2/2004 | Nii |
| 6,767,671 B2 | 7/2004 | Itagaki et al. |
| 6,831,175 B2 | 12/2004 | Li et al. |
| 6,841,674 B2 | 1/2005 | Arnaiz et al. |
| 6,849,618 B2 | 2/2005 | Carlsen et al. |
| 6,864,261 B2 | 3/2005 | Gharagozloo et al. |

(Continued)

FOREIGN PATENT DOCUMENTS

CN         1173952 C        3/2003

(Continued)

OTHER PUBLICATIONS

Farhanullah et al, Journal of Organic Chemistry, 2003, vol. 68, No. 7, pp. 2983-2985.*

(Continued)

*Primary Examiner*—Zinna N Davis
(74) *Attorney, Agent, or Firm*—Nelson Mullins Riley & Scarborough, LLP

(57) ABSTRACT

The present invention provides new heterocyclic compounds, particularly substituted pyridines, methods and compositions for making and using these heterocyclic compounds, and methods for treating a variety of diseases and disease states, including atherosclerosis, arthritis, restenosis, diabetic nephropathy, or dyslipidemia, or disease states mediated by the low expression of Perlecan.

24 Claims, No Drawings

U.S. PATENT DOCUMENTS

| | | |
|---|---|---|
| 6,897,225 B1 | 5/2005 | Sircar et al. |
| 6,906,067 B2 | 6/2005 | Moriarty et al. |
| 2001/0027196 A1 | 10/2001 | Borroni et al. |
| 2002/0028329 A1 | 3/2002 | Ise et al. |
| 2003/0139435 A1 | 7/2003 | Ahmed et al. |
| 2003/0176416 A1 | 9/2003 | Peters et al. |
| 2003/0187026 A1 | 10/2003 | Li et al. |
| 2003/0205696 A1 | 11/2003 | Thoms et al. |
| 2004/0019190 A1 | 1/2004 | Erickson-Miller et al. |
| 2004/0082586 A1 | 4/2004 | Plant et al. |
| 2004/0082780 A1 | 4/2004 | Doherty et al. |
| 2004/0092552 A1 | 5/2004 | Brown et al. |
| 2004/0110031 A1 | 6/2004 | Fukuda et al. |
| 2004/0110757 A1 | 6/2004 | Arrhenius et al. |
| 2004/0122219 A1 | 6/2004 | Fujiwara et al. |
| 2004/0198728 A1 | 10/2004 | Hong et al. |
| 2004/0204584 A1 | 10/2004 | Flohr et al. |
| 2004/0220235 A1 | 11/2004 | Augelli-Szafran et al. |
| 2004/0248739 A1 | 12/2004 | Schaetzer et al. |

FOREIGN PATENT DOCUMENTS

| | | |
|---|---|---|
| CN | 1187341 C | 3/2003 |
| DE | 4425660 A1 | 1/1996 |
| EP | 0263213 B1 | 4/1988 |
| EP | 0352946 A1 | 1/1990 |
| EP | 0376870 A1 | 7/1990 |
| EP | 0451585 A2 | 10/1991 |
| EP | 0493670 B1 | 7/1992 |
| EP | 0517542 B1 | 12/1992 |
| EP | 0525768 A1 | 2/1993 |
| EP | 0624584 B1 | 11/1994 |
| EP | 1202608 B1 | 5/2002 |
| GB | 2297747 A | 8/1996 |
| GB | 2404855 A | 2/2005 |
| JP | 2235054 A | 9/1990 |
| JP | 5132461 A | 5/1993 |
| JP | 5132462 A | 5/1993 |
| JP | 6240163 A | 8/1994 |
| JP | 7099996 A | 4/1995 |
| JP | 7179771 A | 7/1995 |
| JP | 8175993 A | 7/1996 |
| JP | 8225535 A | 9/1996 |
| JP | 9194582 A | 7/1997 |
| JP | 10153838 A | 6/1998 |
| JP | 10207019 A | 8/1998 |
| JP | 10260512 A | 9/1998 |
| JP | 10310583 A | 11/1998 |
| JP | 10324671 A | 12/1998 |
| JP | 2000119256 A | 4/2000 |
| JP | 2002037777 A | 2/2002 |
| JP | 2002216969 A | 8/2002 |
| JP | 2003002834 A | 1/2003 |
| JP | 2003221518 A | 8/2003 |
| JP | 2003335753 A | 11/2003 |
| JP | 2003335754 A | 11/2003 |
| JP | 2003344970 A | 12/2003 |
| JP | 2004018448 A | 1/2004 |
| JP | 2004047229 A | 2/2004 |
| JP | 2004359642 A | 12/2004 |
| WO | WO-91/06542 A1 | 5/1991 |
| WO | WO-92/17448 A1 | 10/1992 |
| WO | WO-92/19615 A2 | 11/1992 |
| WO | WO-93/00342 A1 | 1/1993 |
| WO | WO-93/11134 A1 | 6/1993 |
| WO | WO-93/22311 A1 | 11/1993 |
| WO | WO-96/02532 A1 | 2/1996 |
| WO | WO-97/15555 A2 | 5/1997 |
| WO | WO-98/01425 A1 | 1/1998 |
| WO | WO-98/06697 A1 | 2/1998 |
| WO | WO-98/16224 A1 | 4/1998 |
| WO | WO-98/25912 A1 | 6/1998 |
| WO | WO-98/26127 A1 | 6/1998 |
| WO | WO-98/44925 A1 | 10/1998 |
| WO | WO-99/20606 A2 | 4/1999 |
| WO | WO-99/57103 A1 | 11/1999 |
| WO | WO-00/43385 A1 | 7/2000 |
| WO | WO-00/21954 A1 | 4/2001 |
| WO | WO-01/27119 A2 | 4/2001 |
| WO | WO02/22608 | 3/2002 |
| WO | WO02/88079 | 11/2002 |
| WO | WO02/88080 | 11/2002 |
| WO | WO-2003/022285 A1 | 3/2003 |
| WO | WO-2003/026664 A1 | 4/2003 |
| WO | WO-2003/029226 A1 | 4/2003 |
| WO | WO-2003/045941 A1 | 6/2003 |
| WO | WO-2003/048137 A1 | 6/2003 |
| WO | WO-2003/050087 A2 | 6/2003 |
| WO | WO-2003/051366 A2 | 6/2003 |
| WO | WO-2003/062392 A2 | 7/2003 |
| WO | WO-2003/080060 A1 | 10/2003 |
| WO | WO-2003/087067 A1 | 10/2003 |
| WO | WO-2003/091226 A1 | 11/2003 |
| WO | WO-2003/099771 A2 | 12/2003 |
| WO | WO-2003/101959 A1 | 12/2003 |
| WO | WO-2003/101989 A1 | 12/2003 |
| WO | WO-2004/000820 A2 | 12/2003 |
| WO | WO-2004/014366 A1 | 2/2004 |
| WO | WO-2004/039795 A2 | 5/2004 |
| WO | WO-2004/050643 A2 | 6/2004 |
| WO | WO-2004/062665 A1 | 7/2004 |
| WO | WO-2004/085423 A1 | 10/2004 |
| WO | WO-2004/089286 A2 | 10/2004 |
| WO | WO-2004/089910 A1 | 10/2004 |
| WO | WO-2004/094361 A1 | 11/2004 |
| WO | WO-2005-007646 A1 | 1/2005 |
| WO | WO-2005/007648 A1 | 1/2005 |
| WO | WO-2005/028467 A1 | 3/2005 |
| WO | WO-2005/030714 A1 | 4/2005 |
| WO | WO-2005/033105 A2 | 4/2005 |

OTHER PUBLICATIONS

Iwamoto, K. et al., "Ring Transformation of Fused Pyridazines. IV. Reaction of Halo-Substituted Fused Pyridazines with Ynamines", Heterocycles, Jan. 1996, pp. 199-204, vol. 43 (1), The Japan Institute of Heterocyclic Chemistry, Japan.

Dorwald, F.A. Side Reactions in Organic Synthesis, 2005, Wiley: VCH, Weinheim p. IX of Preface.

Banker, et al., Modern Pharmaceuticals, $3^{rd}$ Ed. p. 596 (1996).

Wolff, Manfred E. Burger's Medicinal Chemistry, $5^{th}$ Ed. Part 1, pp. 975-977 (1995).

Sedova, et al., Khimiya Geterotsiklicheskikh Soedinenii (1997), (5), pp. 678-683.

Katritzky, et al., Journal of the Chemical Society, Perkin Transactions 1: Organic and Bio-Organic Chemistry (1972-1999), (1982), (1) pp. 153-158.

* cited by examiner

PYRIDINE COMPOUNDS, PROCESS FOR THEIR PREPARATION AND COMPOSITIONS CONTAINING THEM

RELATED APPLICATION DATA

This application claims the benefit of U.S. Provisional Patent Application Ser. No. 60/612,374, filed Sep. 23, 2004, which is incorporated herein by reference in its entirety.

FIELD OF THE INVENTION

The present invention relates to substituted pyridine compounds, methods and compositions for making and using substituted pyridine compounds, and methods for preventing or treating diseases in humans or animals employing such compounds and compositions.

BACKGROUND OF THE INVENTION

Novel compounds for new therapeutic interventions are needed for many areas of medicine and disease treatment. For example, chronic and acute inflammatory conditions form the basis for diseases affecting all organ systems including, but not limited to, asthma, acute inflammatory diseases, vascular inflammatory disease, chronic inflammation, atherosclerosis, angiopathy, myocarditis, nephritis, Crohn's disease, arthritis, type I and II diabetes and associated vascular pathologies. The incidence of these inflammatory conditions is on the rise in the population as a whole, with diabetes alone affecting 16 million people. Therefore, synthesis of novel compounds leads to new possibilities for discovery of novel therapeutic interventions.

While inflammation in and of itself is a normal immune response, chronic inflammation leads to complications and ongoing system damage due to the interactions of unknown cellular factors. In particular, chronic inflammation can cause endothelial damage resulting in vascular complications. Coronary artery, cerbrovascular and peripheral vascular disease resulting from atherosclerotic and thromboembolic macroangiopathy are the primary causes of mortality in chronic inflammatory diseases.

Many humans and animals have limited lifespans and lifestyles because of conditions relating to lifestyle choices, such as diet and exercise, or because of genetic predispositions to develop a disease. For example, vascular smooth muscle cell proliferation is a common consequence of endothelial injury and is believed to be an early pathogenetic event in the formation of atherosclerotic plaques or complications related to vascular injury or as a result surgical interventions. Abnormal vascular smooth muscle cell (SMC) proliferation is thought to contribute to the pathogenesis of vascular occlusive lesions, including arteriosclerosis, atherosclerosis, restenosis, and graft atherosclerosis after organ transplantation.

Percutaneous coronary artery intervention (PTCA) procedures are the most common in-patient hospital procedure in the United States. According to the American Heart Association, about one-third of the patients that undergo balloon angioplasty have restenosis of the widened segment of the vessel within approximately 6 months. It may be necessary to perform another angioplasty or coronary artery bypass surgery on restenosed arteries. A key feature of restenosis is an injury response that results in activation of an inflammatory cascade and remodeling of the cells both inside and outside the carotid artery wall. This includes excessive growth of connective tissue and smooth muscle into the lumen of the artery known as neointimal hyperplasia. Currently there are no effective pharmacological treatments available that control the pathogenesis of vascular occlusive lesions, such as, but not limited to, arteriosclerosis, atherosclerosis, restenosis, and graft atherosclerosis after organ transplantation. Identification of effective therapeutics with minimal side effects will restore quality of life without requiring additional surgical procedures such as coronary artery bypass surgery.

Control or modulation of factors produced by the body in response to injury, surgery, metabolic factors or loss of control of in feedback mechanisms, leading to too much or too little of a factor has long been the goal of administering pharmacological agents. One disease that rapidly growing in the industrialized countries is the occurrence of diabetes and all of its attendant sequellae. One of the factors important in the damage associated with diabetes is the presence of glycated proteins.

Glycated proteins and advanced glycation end products (AGE) contribute to cellular damage, particularly, diabetic tissue injury, by at least by two major mechanisms: modulation of cellular functions through interactions with specific cell surface receptors; and alteration of the extracellular matrix leading to the formation of protein cross-links. Studies suggest that glycated protein and AGE interactions with cells may promote inflammatory processes and oxidative cellular injury. AGE increases lipoprotein oxidizability and atherogenicity. Its binding to matrix proteins induces synthesis of cytokines and activates cellular messengers. Diseases where glycated protein and AGE accumulation is a suspected etiological factor include vascular complications of diabetes, microangiopathies, renal insufficiency and Alzheimer's disease.

The exact mechanisms by which high plasma glucose, as seen in diabetes, causes microvascular damage are not completely understood. One potential mechanism by which hyperglycemia can be linked to microangiopathies is through the process of non-enzymatic glycation of critical proteins. Non-enzymatic glycation, i.e., the linking of proteins with glucose, leads to the formation of glycated proteins. The first step in this glycation pathway involves the non-enzymatic condensation of glucose with free amino groups in the protein, primarily the epsilon-amino groups of lysine residues, forming the Amadori adducts. These early glycation products can undergo further reactions such as rearrangements, dehydration and condensations to form irreversible advanced glycation end products (AGE). These are a highly reactive group of molecules whose interaction with specific receptors on the cell-surface which are thought to lead to pathogenic outcomes.

Other major area of disease of where treatments are needed and for which adequate and effective therapies do not exist are cellular proliferative disorders, or disorders caused by unwanted or unintended cellular growth. As mentioned, smooth muscle cell (SMC) hyperplasia is a major event in the development of atherosclerosis and is also responsible for the significant number of failure rates following vascular procedures such as angioplasty, stent implantation and coronary artery bypass surgery. In the normal vessel, SMC are quiescent, but they proliferate when damage to the endothelium occurs. Naturally occurring growth modulators, many of which are derived from the endothelium, tightly control SMC proliferation in vivo. When the control becomes unregulated, a pathological state is induced in the subject.

Another major area of unwanted cellular growth, that is unchecked by the body's regulatory systems, is cancer or oncological conditions. Many therapies have been used and are being used in an effort to restore health or at least stop the unwanted cell growth. Many times, therapeutic agents can have an effect individually, but often, therapeutic regimes require combinations of different pharmacological agents with treatments such as surgery or radiation.

There is a present need for treatments of chronic or acute diseases, such as atherosclerosis, unwanted cellular growth or cellular proliferation, diabetes, inflammatory conditions and vascular occlusive pathologic conditions. Because of occurrence is frequent, the currently available treatments are costly and the conditions are refractory to many pharmacological therapies. The mechanisms involved in the control or prevention of such diseases are not clear and there exists a need for preventive and therapeutic treatments of these and other diseases. Thus, what is presently needed are novel compounds that find utility in methods and compositions for treatment and prevention of chronic and acute diseases, to which the present invention is directed.

SUMMARY OF THE INVENTION

The present invention is directed to novel pyridines, novel compositions comprising pyridines, and novel methods employing such pyridines and compositions. Disclosed herein are methods for making pyridines, compositions comprising pyridines, and methods and compositions for using pyridines. The pyridine compounds and compositions comprising the pyridine compounds have utility in treating and preventing a variety of diseases.

In one aspect, compounds in accordance with the present invention, and compositions comprising these compounds, comprise nitrogen heterocyclic compounds of formulas (I):

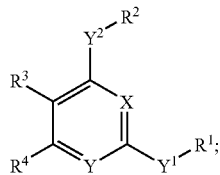

(I)

or a salt, including a pharmaceutically acceptable or a non-pharmaceutically acceptable salt, a prodrug, a diastereomeric mixture, an enantiomer, a tautomer, or a racemic mixture thereof;

wherein one of X and Y is nitrogen and the other of X and Y is CH;

$Y^1$ and $Y^2$, in each occurrence, are independently >$NR^5$, —$(CH_2)n$—, —$(CH_2)p$-(CH=CH)$(CH_2)q$-, >$CR^5R^6$, —$(CH_2)p(C\equiv C)(CH_2)q$-, —O—, >CO, —S—, >SO or >$SO_2$;

wherein n, p, and q are independently an integer from 0 to 3;

$R^5$ and $R^6$, in each occurrence, are independently: 1) a substituted or an unsubstituted alkyl, aryl, alkoxyalkyl, heteroaryl, cycloalkyl, or heterocyclyl, any of which having up to 10 carbon atoms; wherein any heteroaryl or heterocyclyl comprises at least one heteroatom or heterogroup selected from —O—, >N—, —S—, >$SO_2$, or >CO; or 2) hydrogen;

wherein when $Y^1$ or $Y^2$ is independently >$NR^5$;
1) the corresponding $R^z$, wherein z is 1 or 2, in each occurrence is independently selected from: a) a substituted or an unsubstituted alkyl, aryl, alkoxyalkyl, cycloalkyl, —$COR^9$, aralkyl, heterocyclyl or heteroaryl comprising at least one heteroatom or heterogroup selected from —O—, >N—, —S—, >$SO_2$, or >CO; any of which having up to 10 carbon atoms; b) hydrogen; or c) halogen; or
2) the corresponding $Y^zR^z$, wherein z is 1 or 2, is a cyclic structure selected from: a) a substituted or an unsubstituted cyclic ring, which optionally comprises at least one additional heteroatom or heterogroup selected from —O—, >N—, —S—, >$SO_2$, or >CO; or b) a substituted or an unsubstituted morpholinyl, piperazinyl, thiomorpholinyl, pyrrolidinyl, or piperidinyl; any of which having up to 10 carbon atoms; wherein the optional substituents on the cyclic $Y^zR^z$ structure are independently selected from at least one of: i) hydroxyl or halogen; or ii) alkyl, alkoxy, haloalkyl, cycloalkyl, aryl, or heteroaryl any of which having up to 10 carbon atoms;

wherein when $Y^zR^z$ is piperazinyl, the piperazine nitrogen is optionally substituted by an alkyl, a cycloalkyl, an acyl, a haloalkyl, an alkoxyalkyl, $SO_2R^7$, $SO_2NR^7{}_2$, or $CO_2R^7$, wherein $R^7$ is independently selected from: a) an alkyl or an aryl having up to 8 carbon atoms; or b) hydrogen;

wherein when $Y^1$ or $Y^2$ is independently —O— or —S—; the corresponding $R^z$, wherein z is 1 or 2, in each occurrence is independently selected from: 1) a substituted or an unsubstituted alkyl, aryl, alkoxyalkyl, cycloalkyl, —$COR^9$, aralkyl, heterocyclyl or heteroaryl comprising at least one heteroatom or heterogroup selected from —O—, >N—, —S—, >$SO_2$, or >CO; any of which having up to 10 carbon atoms; or 2) hydrogen;

wherein when $Y^1$ or $Y^2$ is independently —$(CH_2)n$-, —$(CH_2)p(CH=CH)(CH_2)q$-, >$CR^5R^6$, —$(CH_2)p(C\equiv C)(CH_2)q$-, >CO, >SO or >$SO_2$; the corresponding $R^z$, wherein z is 1 or 2, in each occurrence is independently selected from: 1) a substituted or an unsubstituted alkyl, haloalkyl, cycloalkyl, —$COR^9$, aralkyl, alkoxy, alkenyl, alkynyl, alkoxyalkyl, aryl, —$CO_2R^5$, —$COR^5$, heterocyclyl or heteroaryl comprising at least one heteroatom or heterogroup selected from —O—, >N—, —S—, >$SO_2$, or >CO; any of which having up to 10 carbon atoms; or 2) hydrogen, halogen, cyano, or hydroxyl;

wherein $R^3$ and $R^4$, in each occurrence, are independently: 1) a substituted or an unsubstituted alkyl, alkenyl, alkynyl, alkoxy, cycloalkyl, haloalkyl, haloalkoxy, alkylthio, alkylsufonyl, aryl, —$CO_2R^5$, —$COR^5$, —$NR^5R^6$, —$SO_2NR^5R^6$, —$SO_3R^5$, heterocycly or heteroaryl comprising at least one heteroatom or heterogroup selected from —O—, >N—, —S—, >$SO_2$, or >CO; any of which having up to 10 carbon atoms; 2) hydrogen; halogen; hydroxyl; or cyano; or 3) $Y^1R^1$;

wherein any of $R^1$, $R^2$, $R^5$, or $R^6$ is optionally substituted with at least one group independently selected from: 1) alkyl; alkoxy; alkylthio; haloalkyl; cycloalkyls; aryl; heterocyclyl or heteroaryl comprising at least one heteroatom or heterogroup selected from —O—, >N—, —S—, >$SO_2$, or >CO; haloalkoxy; —$OCH_2O$—; —$OCOR^9$; $N(R^8)_2$; —$COR^9$; —$CON(R^8)_2$; —$(CH_2)_b CO_2R^8$ wherein b is an integer from 0 to 3; —OCO$(CH_2)_b CO_2R^{10}$ wherein b is an integer from 0 to 3; —$SO_2R^9$; —$NHSO_2R^9$; or —$SO_2N(R^8)_2$; any of which having up to 10 carbon atoms; or 2) hydrogen, halogen, hydroxyl, or cyano;

wherein $R^8$, in each occurrence, is independently: 1) an alkyl; a haloalkyl; a heterocyclyl or heteroaryl comprising at least one heteroatom or heterogroup selected from —O—, >N—, —S—, >$SO_2$, or >CO; or an aryl having up to 10 carbon atoms; or 2) hydrogen;

wherein $R^9$, in each occurrence, is independently an alkyl; a haloalkyl; an aryl; or a heterocyclyl or heteroaryl comprising at least one heteroatom or heterogroup selected from —O—, >N—, —S—, >SO$_2$, or >CO; having up to 8 carbon atoms; wherein $R^9$ is optionally substituted with: 1) an alkyl, an alkoxy, a carboxylic acid, or a carboxylic acid ester, any of which having up to 8 carbon atoms; 2) halogen; or 3) hydroxyl; and wherein any of $R^3$ or $R^4$ is optionally substituted with at least one group independently selected from: 1) alkyl, alkoxy, haloalkyl, haloalkoxy, cycloalkyl, aryl, heteroaryl, heterocyclyl, alkenyl, alkynyl, —COR$^{10}$, —CO$_2$R$^{10}$, —CON(R$^{10}$)$_2$, —SO$_2$R$^{10}$, —SO$_2$N(R$^{10}$)$_2$, or —N(R$^{10}$)$_2$, any of which having up to 10 carbon atoms; 2) halogen; or 3) hydroxyl; and wherein $R^{10}$, in each occurrence, is independently: 1) an alkyl or an aryl having up to 10 carbon atoms; or hydrogen.

In another aspect, compounds in accordance with the present invention, and compositions comprising these compounds, comprise nitrogen heterocyclic compounds of formula (III):

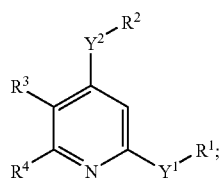

(III)

or a salt, including a pharmaceutically acceptable or non-pharmaceutically acceptable salt, a prodrug, a diastereomeric mixture, an enantiomer, a tautomer, or a racemic mixture thereof;

wherein $R^1$, $R^2$, $R^3$, $R^4$, $Y^1$, $Y^2$, as well as other substituents of formula (III), are as disclosed above for the compounds of formula (I).

The present invention is directed to methods and compositions comprising compounds that have utility in treatment of pathological conditions. One aspect of the present invention comprises pyridines and compositions comprising pyridines in methods for treating diseases related to unwanted cellular proliferation. Vascular diseases, such as cardiovascular diseases, organ transplant sequellae, vascular occlusive conditions including, but not limited to, neointimal hyperplasia, restenosis, transplant vasculopathy, cardiac allograft vasculopathy, atherosclerosis, and arteriosclerosis, are caused by or have collateral damage due to unwanted cellular proliferation, such as smooth muscle cell (SMC) hyperplasia. At least one activity of one or more of these compounds is that the compound has the activity of affecting the synthesis of proteoglycans including induction and synthesis of proteoglycans and active fragments of proteoglycans. Methods comprise administration of compositions comprising compounds that have at least the activity of affecting cellular proliferation and affecting proteoglycan synthesis and activity. Further, the pyridines and compositions comprising pyridines disclosed herein can be employed to prevent or to treat the aforementioned diseases.

The present invention also comprises methods and compositions comprising pyridines described herein that have an activity associated with modulation of glycosidase enzymes and thus, affecting the substrates for such enzymes. Glycosidase enzymes and their activity with their substrates, such as proteoglycans or glycated proteins, are aspects of a variety of diseases such as vascular conditions, proteoglycan-associated diseases, kidney disease, autoimmune disease and inflammatory diseases. Pyridines described herein that have an activity that affects the concentrations of substrates of glycosidase enzymes are used in methods of treatment of such vascular, inflammatory, metastatic and systemic diseases.

Another aspect of the present invention comprises methods and compositions comprising pyridines of the present invention for the treatment and prevention of conditions or diseases that have as an aspect of the disease or condition, inflammation. An aspect of the present invention is directed to methods and compositions comprising pyridines that are effective in inhibiting inflammation, particularly inflammation associated with the accumulation or presence of glycated proteins or AGE. Methods of treatment comprise administration of compositions comprising pyridines having at least the activity of modulating inflammatory reactions that are components of biological conditions including, but not limited to, vascular complications of type I and type II diabetic-induced vasculopathies, other vasculopathies, microangiopathies, renal insufficiency, Alzheimer's syndrome, and inflammation-induced diseases such as atherosclerosis. An aspect of the present invention also comprises methods and compositions for the treatment of diseases, preconditions or pathologies associated with inflammatory cytokines and other inflammation related molecules.

Another aspect of the present invention comprises methods and compositions comprising compounds that have at least the activity of causing cellular death or a cessation of cellular activity, referred to herein as cytotoxic activity. This activity can be used in methods for in vitro or in vivo cytotoxicity. For example, compounds having this activity can be selectively delivered to an area within a living organism to selectively kill cells in that area. Such methods are using in treating hyperproliferative cells, such as cancers, or other unwanted cellular growth or cellular activities. One aspect of the invention provides compositions comprising compounds that nonselectively kill cells. Another aspect of the invention provides compounds that selectively kill cells, for example, cells that have a particular cellular marker or other identifying characteristic such as metabolic rate or uptake of a particular compound.

Accordingly, in one aspect, this invention also provides compositions comprising a pharmaceutically acceptable carrier and at least one compound as disclosed herein, and further comprising: optionally, a pharmaceutically acceptable auxiliary; optionally, a pharmaceutically acceptable preservative; optionally, a pharmaceutically acceptable excipient; optionally, a pharmaceutically acceptable diluent; and optionally, a pharmaceutically acceptable solvate. In this aspect, this composition can be in the form of, for example, a tablet, a capsule, a syrup, a cachet, a powder, a granule, a solution, a suspension, an emulsion, a bolus, a lozenge, a suppository, a pessary, a tampon, a cream, a gel, a paste, a foam, a spray, an aerosol, a microcapsule, a liposome, a transdermal patch, a pastille, a paste, or a mouthwash, and the like. Also in this aspect, this composition can further comprise an agent selected from a chemotherapeutic agent, an immunosuppressive agent, a cytokine, a cytotoxic agent, an anti-inflammatory agent, an antirheumatic agent, a cardiovascular agent, or any combination thereof.

The present invention also comprises pharmaceutical compositions comprising the compounds disclosed herein. Routes of administration and dosages of effective amounts of the compounds and pharmaceutical compositions are also disclosed. For example, the compounds of the present invention can be administered in combination with other pharmaceutical agents in a variety of protocols for effective treatment of disease.

In another aspect, the present invention relates to drug delivering or eluting medical devices that contain or are coated with at least one compound disclosed herein. The medical device suitable for use with the compounds of the present invention include, but are not limited to, stents and other medical devices that can provide a substrate for delivery of at least one compound.

Other aspects of the present invention comprise compositions and methods for microarray devices. Such microarray devices and methods comprise a variety of microarrays that may be used, for example, to study and monitor gene expression in response to treatment with the compounds of the present invention. The microarrays may comprise nucleic acid sequences, carbohydrates or proteins that are determinative for specific cells, tissues, species, disease states, prognoses, disease progression, or any other combination of molecules that can be used to determine an effect of one or more of the compounds of the present invention. Other aspects of the present invention comprise methods using databases and computer applications.

DETAILED DESCRIPTION OF THE INVENTION

In accordance with the present invention, novel pyridine compounds, and novel compositions comprising pyridine compounds are described herein. In one aspect, compounds in accordance with the present invention, and compositions comprising these compounds, comprise nitrogen heterocyclic compounds of formula (IIIi):

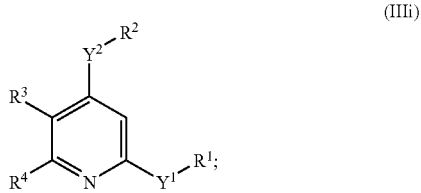

(IIIi)

or a salt, including a pharmaceutically acceptable or a non-pharmaceutically acceptable salt, a prodrug, a diastereomeric mixture, an enantiomer, a tautomer, or a racemic mixture thereof;

wherein:

$Y^1$ and $Y^2$, in each occurrence, are independently $>NR^5$, —$(CH_2)n$- wherein n is 0 or 1, —S—, —O—, $>CO$, or $>SO_2$;

$R^5$, in each occurrence, is independently: 1) a substituted or an unsubstituted alkyl, aryl, alkoxyalkyl, heteroaryl, cycloalkyl, or heterocyclyl, any of which having up to 10 carbon atoms; wherein any heteroaryl or heterocyclyl comprises at least one heteroatom or heterogroup selected from —O—, $>N$—, —S—, $>SO_2$, or $>CO$; or 2) hydrogen;

wherein when $Y^1$ or Y2 is independently $>NR^{5;}$ 1) the corresponding $R^z$, wherein z is 1 or 2, in each occurrence is independently selected from: a) a substituted or an unsubstituted alkyl, aryl, alkoxyalkyl, cycloalkyl, —$COR^9$, aralkyl, heterocyclyl or heteroaryl comprising at least one heteroatom or heterogroup selected from —O—, $>N$—, —S—, $>SO_2$, or $>CO$; any of which having up to 10 carbon atoms; b) hydrogen; or c) halogen; or 2) the corresponding $Y^zR^z$, wherein z is 1 or 2, is selected from a morpholinyl, a piperazinyl, or a piperidinyl; any of which having up to 10 carbon atoms, wherein when $Y^zR^z$ is piperazinyl, the piperazine nitrogen is optionally substituted by an alkyl, a cycloalkyl, an acyl, a haloalkyl, an alkoxyalkyl, $SO_2R^7$, $SO_2NR^7{}_2$, or $CO_2R^7$, wherein $R^7$ is independently selected from:
a) an alkyl or an aryl having up to 8 carbon atoms; or
b) hydrogen;

wherein when $Y^1$ or $Y^2$ is independently —O— or —S—; the corresponding $R^z$, wherein z is 1 or 2, in each occurrence is independently selected from: 1) a substituted or an unsubstituted alkyl, aryl, alkoxyalkyl, cycloalkyl, —$COR^9$, aralkyl, heterocyclyl or heteroaryl comprising at least one heteroatom or heterogroup selected from —O—, $>N$—, —S—, $>SO_2$, or $>CO$; any of which having up to 10 carbon atoms; or 2) hydrogen;

wherein when $Y^1$ or $Y^2$ is independently —$(CH_2)n$-, $>CO$, or $>SO_2$; the corresponding $R^z$, wherein z is 1 or 2, in each occurrence is independently selected from: 1) a substituted or an unsubstituted alkyl, haloalkyl, cycloalkyl, —$COR^9$, aralkyl, alkoxy, alkenyl, alkynyl, alkoxyalkyl, aryl, —$CO_2R^5$, —$COR^5$, heterocyclyl or heteroaryl comprising at least one heteroatom or heterogroup selected from —O—, $>N$—, —S—, $>SO_2$, or $>CO$; any of which having up to 10 carbon atoms; or 2) hydrogen, halogen, cyano, or hydroxyl;

wherein $R^3$ and $R^4$, in each occurrence, are independently: 1) haloalkyl having less than 3 carbon atoms; 2) alkyl, haloalkoxy, aryl, cycloalkyl, heteroaryl, or heterocyclyl having up to 10 carbon atoms, wherein any heteroaryl or heterocyclyl comprises at least one heteroatom or heterogroup selected from —O—, $>N$—, —S—, $>SO_2$, or $>CO$; 3) hydrogen; or 4) $Y^1R^1$;

wherein any of $R^1$, $R^2$, or $R^5$ is optionally substituted with at least one group independently selected from: 1) alkyl, alkoxy, haloalkyl, haloalkoxy, —$OCH_2O$—, $N(R^8)_2$, —$SO_2R^9$, —$OCOR^9$ or —$SO_2N(R^8)_2$, any of which having up to 10 carbon atoms; or 2) hydrogen, halogen, or cyano;

wherein $R^8$, in each occurrence, is independently: 1) an alkyl; a haloalkyl; a heterocyclyl or heteroaryl comprising at least one heteroatom or heterogroup selected from —O—, $>N$—, —S—, $>SO_2$, or $>CO$; or an aryl having up to 10 carbon atoms; or 2) hydrogen;

wherein $R^9$, in each occurrence, is independently an alkyl; a haloalkyl; an aryl; or a heterocyclyl or heteroaryl comprising at least one heteroatom or heterogroup selected from —O—, $>N$—, —S—, $>SO_2$, or $>CO$; having up to 8 carbon atoms; wherein $R^9$ is optionally substituted with: 1) an alkyl, an alkoxy, a carboxylic acid, or a carboxylic acid ester, any of which having up to 8 carbon atoms; 2) halogen; or 3) hydroxyl; and wherein any of $R^3$ or $R^4$ is optionally substituted with at least one group independently selected from: 1) alkyl, alkoxy, haloalkyl, haloalkoxy, cycloalkyl, aryl, heteroaryl, heterocyclyl, alkenyl, alkynyl, —$COR^{10}$, —$CO_2R^{10}$, —$CON(R^{10})_2$, —$SO_2R^{10}$, —$SO_2N(R^{10})_2$, or —$N(R^{10})_2$, any of which having up to 10 carbon atoms; 2) halogen; or 3) hydroxyl; and wherein $R^{10}$, in each occurrence, is independently: 1) an alkyl, a heterocyclyl, or an aryl having up to 10 carbon atoms; or hydrogen.

2. (Revised 17)

In another aspect, the present invention provides for compounds and compositions comprising these compounds, wherein the compounds have the following formula:

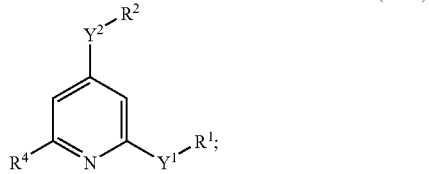

(III-A)

or a salt, including a pharmaceutically acceptable or a non-pharmaceutically acceptable salt, a prodrug, a diastereomeric mixture, an enantiomer, a tautomer, or a racemic mixture thereof;

wherein:

$Y^1$ and $Y^2$ are independently selected from $>NR^5$, —(CH$_2$)n- wherein n is 0 or 1, or —O—;

$R^5$ is selected from: 1) a substituted or an unsubstituted alkyl, aryl, cycloalkyl, or heteroaryl or heterocyclyl comprising at least one heteroatom or heterogroup selected from —O—, >N—, —S—, >SO$_2$, or >CO, any of which having up to 10 carbon atoms; or 2) hydrogen;

wherein when $Y^1$ or $Y^2$ is independently $>NR^5$;

1) the corresponding $R^z$, wherein z is 1 or 2, in each occurrence is independently selected from: a) a substituted or an unsubstituted alkyl, aryl, cycloalkyl, or heterocyclyl or heteroaryl comprising at least one heteroatom or heterogroup selected from —O—, >N—, —S—, >SO$_2$, or >CO, any of which having up to 10 carbon atoms; or b) hydrogen; or 2) the corresponding $Y^zR^z$, wherein z is 1 or 2, is a cyclic structure selected from: a) a substituted or an unsubstituted heterocyclic ring, which optionally comprises at least one additional heteroatom or heterogroup selected from —O—, >N—, —S—, >SO$_2$, or >CO; or b) a substituted or an unsubstituted morpholinyl, piperazinyl, thiomorpholinyl, pyrrolidinyl, or piperidinyl; any of which having up to 10 carbon atoms; wherein the optional substituents on the heterocyclic $Y^zR^z$ structure are independently selected from a) hydroxyl; or b) alkyl, alkoxy, haloalkyl, aryl, or heteroaryl; any of which having up to 10 carbon atoms;

wherein when $Y^zR^z$ is piperazinyl, the piperazine nitrogen is optionally substituted by an alkyl, a cycloalkyl, an acyl, a haloalkyl, an alkoxyalkyl, SO$_2$R$^7$, SO$_2$NR$^7_2$, or CO$_2$R$^7$, wherein R$^7$ is independently selected from: a) an alkyl or an aryl having up to 8 carbon atoms; or b) hydrogen;

wherein when $Y^1$ or $Y^2$ is independently —(CH$_2$)n-, the corresponding $R^z$, wherein z is 1 or 2, in each occurrence is independently selected from: 1) an alkyl, a haloalkyl, —COR$^9$, an alkoxy, an alkenyl, an alkynyl, an alkoxyalkyl, an aryl, —CO$_2$R$^5$, —COR$^5$, or a heterocyclyl or heteroaryl comprising at least one heteroatom or heterogroup selected from —O—, >N—, —S—, >SO$_2$, or >CO; any of which having up to 10 carbon atoms; or 2) hydrogen, halogen, cyano, or hydroxyl;

wherein R$^4$, in each occurrence, is independently selected from: 1) an alkyl, an alkenyl, an alkynyl, an alkoxy, a haloalkyl, an alkylsufonyl, an aryl, —CO$_2$R$^5$, —COR$^5$, —NR$^5$R$^6$, —SO$_2$NR$^5$R$^6$, or a heterocyclyl or heteroaryl comprising at least one heteroatom or heterogroup selected from —O—, >N—, —S—, >SO$_2$, or >CO; any of which having up to 10 carbon atoms; or 2) hydrogen, halogen, hydroxyl, or cyano;

wherein R$^1$ and R$^2$ are optionally substituted with at least one group independently selected from: 1) an alkyl, an alkoxy, an alkylthio, a haloalkyl, a cycloalkyl, an aryl, a haloalkoxy, NR$^8_2$, —COR$^9$, —CONR$^8_2$, —SO$_2$R$^9$, —NHSO$_2$R$^9$, or —SO$_2$NR$^8_2$, or a heterocyclyl or heteroaryl comprising at least one heteroatom or heterogroup selected from —O—, >N—, —S—, >SO$_2$, or >CO; any of which having up to 10 carbon atoms; or 2) hydrogen, halogen, —OCH$_2$O—, hydroxyl, or cyano;

R$^8$, in each occurrence, is selected independently from: 1) an alkyl or a haloalkyl, any of which having up to 10 carbon atoms; or 2) hydrogen;

R$^9$, in each occurrence, is selected independently from: 1) an alkyl or a haloalkyl, any of which having up to 10 carbon atoms; or 2) hydrogen or hydroxyl; and R$^4$ is optionally substituted with at least one group independently selected from: 1) an alkyl, an alkoxy, a haloalkyl, a haloalkoxy, a cycloalkyl, an aryl, an alkenyl, an alkynyl, —COR$^{10}$, —CO$_2$R$^{10}$, —CONR$^{10}_2$, —SO$_2$R$^{10}$, —SO$_2$NR$^{10}_2$, —NR$^{10}_2$, or a heterocyclyl or heteroaryl comprising at least one heteroatom or heterogroup selected from —O—, >N—, —S—, >SO$_2$, or >CO, any of which having up to 10 carbon atoms; or 2) halogen or hydroxyl; and wherein R$^{10}$, in each occurrence, is selected independently from: 1) an alkyl or an aryl having up to 10 carbon atoms; or 2) hydrogen.

In still another aspect, the present invention provides for compounds and compositions comprising these compounds, wherein the compounds have the following formula:

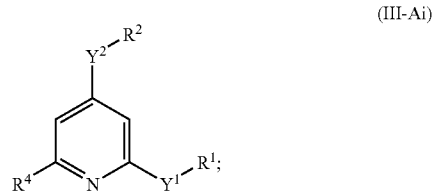

(III-Ai)

or a salt, including a pharmaceutically acceptable or a non-pharmaceutically acceptable salt, a prodrug, a diastereomeric mixture, an enantiomer, a tautomer, or a racemic mixture thereof;

wherein:

$Y^1$ and $Y^2$ are selected independently from $>NR^5$ or —(CH$_2$)n- wherein n is 0 or 1;

$R^5$ is hydrogen or methyl;

wherein when $Y^1$ or $Y^2$ is independently $>NR^5$;

1) the corresponding $R^z$, wherein z is 1 or 2, in each occurrence is selected independently from: a) an alkyl, an aryl, a cycloalkyl, or a heterocyclyl or heteroaryl comprising at least one heteroatom or heterogroup selected from —O—, >N—, —S—, >SO$_2$, or >CO, any of which having up to 10 carbon atoms; or b) hydrogen; or 2) the corresponding $Y^zR^z$, wherein z is 1 or 2, is selected independently from a morpholinyl, a piperazinyl, a piperidinyl, or a pyrrolidinyl;

wherein when $Y^zR^z$ is a piperazinyl, the piperazine nitrogen is optionally substituted by an alkyl, a cycloalkyl, an acyl, a haloalkyl, an alkoxyalkyl, $SO_2R^7$, or $SO_2NR^7{}_2$, any of which having up to 10 carbon atoms, wherein $R^7$ is selected independently from: a) an alkyl or an aryl having up to 8 carbon atoms; or b) hydrogen;

wherein when $Y^zR^z$ is a piperidinyl or a pyrrolidinyl, the ring is optionally substituted by: a) an alkyl or a haloalkyl having up to 10 carbon atoms; or 2) hydroxyl;

wherein when $Y^1$ or $Y^2$ is independently —$(CH_2)$n-, the corresponding $R^z$, wherein z is 1 or 2, in each occurrence is selected independently from: 1) an alkyl, a cycloalkyl, a haloalkyl, an alkoxy, an aryl, or a heterocyclyl or heteroaryl comprising at least one heteroatom or heterogroup selected from —O—, >N—, —S—, >$SO_2$, or >CO, any of which having up to 10 carbon atoms; or 2) hydrogen, halogen, cyano, or hydroxyl;

$R^4$ is selected independently from: 1) a haloalkyl having less than 3 carbon atoms; 2) an alkyl, a haloalkoxy, an aryl, or a heteroaryl or heterocyclyl comprising at least one heteroatom or heterogroup selected from —O—, >N—, —S—, >$SO_2$, or >CO, any of which having up to 10 carbon atoms; 3) hydrogen or halogen; or 4) $Y^1R^1$;

wherein any of $R^1$, $R^2$, or $R^5$ is optionally substituted with at least one group independently selected from: 1) an alkyl, an alkoxy, a haloalkyl, a haloalkoxy, $NR^8{}_2$, —$COR^9$, —$CO_2R^8$, —$CONR^8$, —$SO_2R^9$, or —$SO_2NR^8{}_2$, any of which having up to 10 carbon atoms; or 2) hydrogen, hydroxyl, halogen, —$OCH_2O$—, or cyano;

$R^8$, in each occurrence, is selected independently from: 1) an alkyl, a haloalkyl, or an aryl, any of which having up to 10 carbon atoms; or 2) hydrogen;

$R^9$, in each occurrence, is selected independently from an alkyl, a haloalkyl, an aryl, or a heteroaryl comprising at least one heteroatom or heterogroup selected from —O—, >N—, or —S—, any of which having up to 10 carbon atoms;

$R^4$ is optionally substituted with at least one group selected independently from: 1) an alkyl, an alkoxy, a haloalkyl, a haloalkoxy, a cycloalkyl, an aryl, —$COR^9$, —$COR^{10}$, —$CO_2R^{10}$, —$CONR^{10}{}_2$, —$SO_2R^9$, —$SO_2R^{10}$, —$SO_2NR^{10}{}_2$, —$NR^{10}{}_2$, or a heteroaryl or heterocyclyl comprising at least one heteroatom or heterogroup selected from —O—, >N—, —S—, >$SO_2$, or >CO, any of which having up to 10 carbon atoms; or 2) halogen, cyano, or hydroxyl; and wherein $R^{10}$, in each occurrence, is selected independently from: 1) an alkyl or an aryl having up to 10 carbon atoms; or hydrogen.

In this aspect in the formula (III-Ai), $Y^1$ and $Y^2$ can be —$(CH_2)$n- wherein n is 0, that is, $R^1$ and $R^2$ can be bonded directly to the pyridine core.

In another aspect, the present invention provides for compounds and compositions comprising these compounds, wherein the compounds have the following formula:

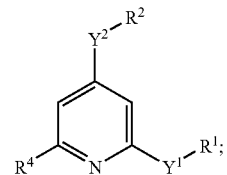

(III-Aii)

or a salt, including a pharmaceutically acceptable or a non-pharmaceutically acceptable salt, a prodrug, a diastereomeric mixture, an enantiomer, a tautomer, or a racemic mixture thereof;

wherein:

$Y^1$ and $Y^2$ are selected independently from >$NR^5$ or —$(CH_2)$n- wherein n is 0;

$R^5$ is hydrogen or methyl;

wherein when $Y^1$ or $Y^2$ is independently >$NR^5$;
1) the corresponding $R^z$, wherein z is 1 or 2, in each occurrence is selected independently from: a) a substituted or an unsubstituted alkyl, aryl, cycloalkyl, or heterocyclyl or heteroaryl comprising at least one heteroatom or heterogroup selected from —O—, >N—, —S—, >$SO_2$, or >CO, any of which having up to 10 carbon atoms; or b) hydrogen; or
2) the corresponding $Y^zR^z$, wherein z is 1 or 2, is selected independently from a substituted or an unsubstituted morpholinyl, piperazinyl, piperidinyl, or pyrrolidinyl;

wherein when $Y^zR^z$ is a piperazinyl, the piperazine nitrogen is optionally substituted by an alkyl, a cycloalkyl, an acyl, a haloalkyl, an alkoxyalkyl, $SO_2R^7$, or $SO_2NR^7{}_2$, any of which having up to 10 carbon atoms, wherein $R^7$ is selected independently from: a) an alkyl or an aryl having up to 8 carbon atoms; or b) hydrogen;

wherein when $Y^zR^z$ is a piperidinyl or a pyrrolidinyl, the ring is optionally substituted by: a) an alkyl or a haloalkyl having up to 10 carbon atoms; or 2) hydroxyl;

wherein when $Y^1$ or $Y^2$ is independently —$(CH_2)$n-, the corresponding $R^z$, wherein z is 1 or 2, in each occurrence is selected independently from a substituted or an unsubstituted alkyl, cycloalkyl, aryl, or heterocyclyl or heteroaryl comprising at least one heteroatom or heterogroup selected from —O—, >N—, —S—, >$SO_2$, or >CO, any of which having up to 10 carbon atoms;

$R^4$ is selected independently from: 1) a substituted or an unsubstituted aryl, or a substituted or an unsubstituted heteroaryl or heterocyclyl comprising at least one heteroatom or heterogroup selected from —O—, >N—, —S—, >$SO_2$, or >CO, any of which having up to 10 carbon atoms; or 2) $Y^1R^1$;

wherein any of $R^1$ or $R^2$, is also optionally substituted with at least one group independently selected from: 1) an alkyl, an alkoxy, a haloalkyl, a haloalkoxy, $NR^8{}_2$, —$COR^9$, —$CO_2R^8$, —$OCOCH_2CH_2CO_2R^8$, —$CONR^8{}_2$, —$SO_2R^9$, —$NHSO_2R^9$, or —$SO_2NR^8{}_2$, any of which having up to 10 carbon atoms; or 2) hydroxyl, halogen, —$OCH_2O$—, or cyano;

$R^8$, in each occurrence, is selected independently from: 1) an alkyl, a haloalkyl, or an aryl, any of which having up to 10 carbon atoms; or 2) hydrogen;

$R^9$, in each occurrence, is selected independently from an alkyl, a haloalkyl, an aryl, or a heterocyclyl or heteroaryl comprising at least one heteroatom selected from —O—, —S—, or >N—, any of which having up to 10 carbon atoms;

R⁴ is optionally substituted with at least one group selected independently from: 1) an alkyl, an alkoxy, a haloalkyl, a haloalkoxy, a cycloalkyl, an aryl, —COR⁹, —CO₂R⁸, —CO₂R¹⁰, —OCOCH₂CH₂CO₂R¹⁰, —CONR⁸₂, —CONR¹⁰₂, —SO₂R⁹, —SO₂NR⁸₂, —SO₂NR¹⁰₂, —NHSO₂R⁹, —NR¹⁰₂, or a heteroaryl or heterocyclyl comprising at least one heteroatom or heterogroup selected from —O—, >N—, —S—, >SO₂, or >CO, any of which having up to 10 carbon atoms; or 2) halogen, —OCH₂O—, cyano, or hydroxyl; and R¹⁰, in each occurrence, is selected independently from: 1) an alkyl, an aryl, or a heterocyclyl comprising at least one heteroatom selected from —O— or >N—, any of which having up to 10 carbon atoms; or 2) hydrogen.

Another aspect of the present invention provides for compounds and compositions comprising these compounds, wherein the compounds have the following formula:

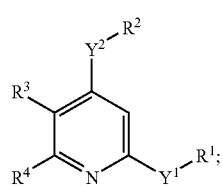

(IIIii)

or a salt, including a pharmaceutically acceptable or a non-pharmaceutically acceptable salt, a prodrug, a diastereomeric mixture, an enantiomer, a tautomer, or a racemic mixture thereof;

wherein:

Y¹ and Y² are independently selected from >NR⁵, —(CH₂)n- wherein n is 0 or 1, —O—, >CO, or >SO₂;

R⁵, in each occurrence, is selected independently from: 1) a substituted or an unsubstituted alkyl, aryl, alkoxyalkyl, cycloalkyl, or heterocyclyl or heteroaryl comprising at least one heteroatom or heterogroup selected from —O—, >N—, —S—, >SO₂, or >CO, any of which having up to 10 carbon atoms; or 2) hydrogen;

wherein when Y¹ or Y² is independently >NR⁵;

1) the corresponding Rᶻ, wherein z is 1 or 2, in each occurrence is independently selected from: a) a substituted or an unsubstituted alkyl, aryl, alkoxyalkyl, cycloalkyl, —COR⁹, aralkyl, heterocyclyl or heteroaryl comprising at least one heteroatom or heterogroup selected from —O—, >N—, —S—, >SO₂, or >CO; any of which having up to 10 carbon atoms; or b) hydrogen; or 2) the corresponding YᶻRᶻ, wherein z is 1 or 2, is selected from a morpholinyl, a piperazinyl, or a piperidinyl; wherein when YᶻRᶻ is piperazinyl, the piperazine nitrogen is optionally substituted by an alkyl, a cycloalkyl, an acyl, a haloalkyl, an alkoxyalkyl, SO₂R⁷, SO₂NR⁷₂, or CO₂R⁷, wherein R⁷ is independently selected from: a) an alkyl or an aryl having up to 8 carbon atoms; or b) hydrogen;

wherein when Y¹ or Y² is independently —O—; the corresponding Rᶻ, wherein z is 1 or 2, in each occurrence is independently selected from: 1) a substituted or an unsubstituted alkyl, aryl, cycloalkyl, —COR⁹, aralkyl, heterocyclyl or heteroaryl comprising at least one heteroatom or heterogroup selected from —O—, >N—, —S—, >SO₂, or >CO; any of which having up to 10 carbon atoms; or 2) hydrogen; and wherein when Y¹ or Y² is independently —(CH₂)n-, >CO, or >SO₂; the corresponding Rᶻ, wherein z is 1 or 2, in each occurrence is independently selected from: 1) a substituted or an unsubstituted alkyl, haloalkyl, cycloalkyl, —COR⁹, aralkyl, alkoxy, aryl, or heterocyclyl or heteroaryl comprising at least one heteroatom or heterogroup selected from —O—, >N—, —S—, >SO₂, or >CO; any of which having up to 10 carbon atoms; or 2) hydrogen, halogen, cyano, or hydroxyl;

wherein R³ and R⁴ in each occurrence, are independently: 1) haloalkyl having less than 3 carbon atoms; 2) alkyl, haloalkoxy, aryl, cycloalkyl, heteroaryl, or heterocyclyl having up to 10 carbon atoms, wherein any heteroaryl or heterocyclyl comprises at least one heteroatom or heterogroup selected from —O—, >N—, —S—, >SO₂, or >CO; 3) hydrogen; or 4) Y¹R¹;

wherein any of R¹, R², or R⁵ is optionally substituted with at least one group independently selected from: 1) alkyl, alkoxy, haloalkyl, haloalkoxy, —O—CH₂—O—, —OCOR⁹, NR⁸₂, —SO₂R⁹, or —SO₂NR⁸₂, any of which having up to 10 carbon atoms; or 2) hydrogen, halogen, or cyano;

wherein any of R³ or R⁴ is optionally substituted with at least one group independently selected from alkyl, haloalkyl, —SO₂R¹⁰, —SO₂NR¹⁰₂, or —NR¹⁰₂, any of which having up to 10 carbon atoms; and wherein R⁸, R⁹, and R¹⁰, in each occurrence, is independently: 1) an alkyl; an aryl; or a heterocyclyl or heteroaryl comprising at least one heteroatom or heterogroup selected from —O—, >N—, —S—, >SO₂, or >CO; having up to 8 carbon atoms; or 2) hydrogen; wherein each of R⁸, R⁹, and R¹⁰ are optionally substituted with: 1) an alkyl, an alkoxy, a carboxylic acid, or a carboxylic acid ester, any of which having up to 8 carbon atoms; 2) halogen; or 3) hydroxyl.

Another aspect of the present invention provides for compounds and compositions comprising these compounds, wherein the compounds have the following formula:

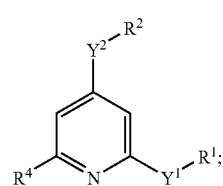

(III-Aiii)

or a salt, including a pharmaceutically acceptable or a non-pharmaceutically acceptable salt, a prodrug, a diastereomeric mixture, an enantiomer, a tautomer, or a racemic mixture thereof;

wherein:

Y¹ and Y² are selected independently from >NR⁵ or —(CH₂)n- wherein n is 0 or 1;

R⁵ is methyl or hydrogen;

wherein when Y¹ or Y² is independently >NR⁵;

1) the corresponding Rᶻ, wherein z is 1 or 2, in each occurrence is selected independently from: a) an alkyl, an aryl, or a heterocyclyl or heteroaryl comprising at least one heteroatom or heterogroup selected from —O—, >N—, —S—, >SO$_2$, or >CO, any of which having up to 10 carbon atoms; or b) hydrogen; or 2) the corresponding Y$^z$R$^z$, wherein z is 1 or 2, is selected independently from a morpholinyl, a piperazinyl, a pyrrolidinyl, or a piperidinyl, wherein Y$^z$R$^z$ is optionally substituted with: a) an alkyl or an acyl having up to 10 carbon atoms; or b) hydroxyl;

wherein when Y$^1$ or Y$^2$ is independently —(CH$_2$)n-, the corresponding R$^z$, wherein z is 1 or 2, in each occurrence is selected independently from: 1) a substituted or an unsubstituted aryl, or a substituted or an unsubstituted heterocyclyl or heteroaryl comprising at least one heteroatom or heterogroup selected from —O—, >N—, —S—, >SO$_2$, or >CO, any of which having up to 10 carbon atoms; or 2) hydrogen, halogen, cyano, or hydroxyl;

wherein R$^1$ and R$^2$ are optionally substituted with at least one group independently selected from: 1) an alkyl, an alkoxy, a haloalkyl, a haloalkoxy, —OCOR$^9$, NR$^8{}_2$, —SO$_2$R$^9$, or —SO$_2$NR$^8{}_2$, any of which having up to 10 carbon atoms; or 2) hydrogen, —OCH$_2$O—, halogen, or cyano;

R$^8$ and R$^9$, in each occurrence, are selected independently from: 1) an alkyl or an aryl having up to 10 carbon atoms; or 2) hydrogen; and R$^4$ is selected independently from: 1) an alkyl, an aryl, —COR$^5$, a cycloalkyl, a haloalkoxy, or a heteroaryl or heterocyclyl comprising at least one heteroatom or heterogroup selected from —O—, >N—, —S—, >SO$_2$, or >CO, any of which having up to 10 carbon atoms; or 2) hydrogen.

In another aspect, the present invention encompasses compounds and compositions comprising these compounds, wherein the compounds have the following formula:

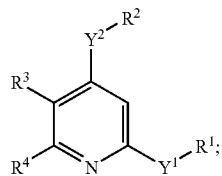

(IIIiii)

or a salt, including a pharmaceutically acceptable or a non-pharmaceutically acceptable salt, a prodrug, a diastereomeric mixture, an enantiomer, a tautomer, or a racemic mixture thereof;

wherein:

Y$^1$ and Y$^2$ are selected independently from >NR$^5$, —(CH$_2$)n- wherein n is 0 or 1, or —O—;

R$^5$ is selected independently from: 1) an alkyl, an aryl, a cycloalkyl, or a heteroaryl or a heterocyclyl comprising at least one heteroatom or heterogroup selected from —O—, >N—, —S—, >SO$_2$, or >CO; any of which having up to 10 carbon atoms; or 2) hydrogen;

wherein when Y$^1$ or Y$^2$ is independently >NR$^5$;

1) the corresponding R$^z$, wherein z is 1 or 2, in each occurrence is independently selected from: a) a substituted or an unsubstituted alkyl, aryl, cycloalkyl, —COR$^9$, aralkyl, or heterocyclyl or heteroaryl comprising at least one heteroatom or heterogroup selected from —O—, >N—, —S—, >SO$_2$, or >CO; any of which having up to 10 carbon atoms; b) hydrogen; or c) halogen; or 2) the corresponding Y$^z$R$^z$, wherein z is 1 or 2, is selected from a morpholinyl, a piperazinyl, or a piperidinyl; wherein when Y$^z$R$^z$ is piperazinyl, the piperazine nitrogen is optionally substituted by an alkyl, a cycloalkyl, a haloalkyl, an alkoxyalkyl, any of which having up to 10 carbon atoms; 2) SO$_2$R$^7$, SO$_2$NR$^7{}_2$, or CO$_2$R$^7$, wherein R$^7$ is independently selected from: a) an alkyl or an aryl having up to 8 carbon atoms; or b) hydrogen;

wherein when Y$^1$ or Y$^2$ is independently —(CH$_2$)n- or —O—; the corresponding R$^z$, wherein z is 1 or 2, in each occurrence is independently selected from: 1) a substituted or an unsubstituted alkyl, aryl, cycloalkyl, —COR$^9$, aralkyl, or heterocyclyl or heteroaryl comprising at least one heteroatom or heterogroup selected from —O—, >N—, —S—, >SO$_2$, or >CO; any of which having up to 10 carbon atoms; or 2) hydrogen;

wherein any of R$^1$, R$^2$, or R$^5$ is optionally substituted with at least one group independently selected from: 1) an alkyl, an alkoxy, a haloalkyl, a haloalkoxy, —OCOR$^9$, NR$^8{}_2$, —SO$_2$R$^9$, or —SO$_2$NR$^8{}_2$, any of which having up to 10 carbon atoms; or 2) hydrogen, —OCH$_2$O—, halogen, or cyano;

R$^8$ and R$^9$, in each occurrence, are selected independently from: 1) an alkyl, an aryl, or a heterocyclyl or heteroaryl comprising at least one heteroatom or heterogroup selected from —O—, >N—, —S—, >SO$_2$, or >CO, any of which having up to 10 carbon atoms; or 2) hydrogen;

wherein R$^8$ and R$^9$ are optionally substituted with: 1) an alkyl, an alkoxy, a carboxylic acid, or a carboxylic acid ester, any of which having up to 8 carbon atoms; or 2) halogen or hydroxyl; and wherein R$^3$ and R$^4$ are, in each occurrence, independently: 1) R$^1$ or 2) Y$^1$R$^1$.

In still another aspect, the present invention encompasses compounds and compositions comprising these compounds, wherein the compounds have the following formula:

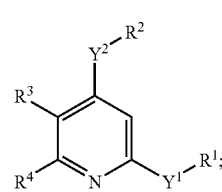

(IIIiv)

or a salt, including a pharmaceutically acceptable or a non-pharmaceutically acceptable salt, a prodrug, a diastereomeric mixture, an enantiomer, a tautomer, or a racemic mixture thereof;

wherein:

Y$^1$ and Y$^2$ are selected independently from >NR$^5$, >CH$_2$, or —O—;

R$^5$ is selected independently from: 1) an alkyl, an aryl, a cycloalkyl, or a heteroaryl or a heterocyclyl comprising at least one heteroatom or heterogroup selected from —O—, >N—, —S—, >SO$_2$, or >CO, any of which having up to 10 carbon atoms; or 2) hydrogen;

wherein when Y$^1$ or Y$^2$ is independently >NR$^5$;

1) the corresponding R$^z$, wherein z is 1 or 2, in each occurrence is independently selected from: a) an alkyl, an aryl, a cycloalkyl, —COR$^9$, aralkyl, or a heterocyclyl or a heteroaryl comprising at least one heteroatom or heterogroup selected from —O—, >N—, —S—, >SO$_2$, or >CO, any of which having up to 10 carbon atoms; or b) halogen; or 2) the corresponding Y$^z$R$^z$, wherein z is 1 or 2, is selected from a morpholinyl, a piperazinyl, or a piperidinyl;

wherein when Y$^1$ or Y$^2$ is independently >CH$_2$ or —O—; the corresponding R$^z$, wherein z is 1 or 2, in each occurrence is selected independently from: 1) a substituted or an unsubstituted alkyl, aryl, cycloalkyl, —COR$^9$, aralkyl, or heterocyclyl or heteroaryl comprising at least one heteroatom or heterogroup selected from —O—, >N—, —S—, >SO$_2$, or >CO, any of which having up to 10 carbon atoms; or 2) hydrogen; and R$^3$ and R$^4$ are selected independently from: 1) R$^1$ or 2) Y$^1$R$^1$.

In another aspect, the present invention encompasses compounds and compositions comprising these compounds, wherein the compounds have the following formula:

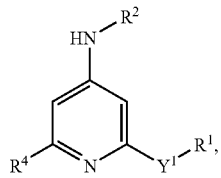

(III-C)

or a salt, including a pharmaceutically acceptable or a non-pharmaceutically acceptable salt, a prodrug, a diastereomeric mixture, an enantiomer, a tautomer, or a racemic mixture thereof;

wherein:

Y$^1$ is selected from >NR$^5$ or —(CH$_2$)n-wherein n is 0 or 1;

R$^1$ and R$^2$ are selected independently from: a) a substituted or an unsubstituted alkyl, cycloalkyl, aryl, or heterocyclyl or heteroaryl comprising at least one heteroatom or heterogroup selected from —O—, >N—, —S—, >CO or >SO$_2$, any of which having up to 10 carbon atoms; or b) hydrogen, halogen, or hydroxy;

R$^5$ is an alkyl having up to 3 carbon atoms or hydrogen;

R$^4$ is selected from: 1) a substituted or an unsubstituted alkyl, aryl, or heterocyclyl or heteroaryl comprising at least one heteroatom or heterogroup selected from —O—, >N—, —S—, or >CO, any of which having up to 10 carbon atoms; or 2) hydrogen or halogen;

R$^1$ and R$^2$ are optionally substituted with at least one group independently selected from: 1) an alkyl, an alkoxy, a haloalkyl, a haloalkoxy, —COR$^9$, —CO$_2$R$^8$, —CONR$^8_2$, —SO$_2$R$^9$, —NHSO$_2$R$^9$, or —SO$_2$NR$^8_2$, any of which having up to 10 carbon atoms; or 2) halogen, —OCH$_2$O—, hydroxyl, or cyano;

R$^8$, in each occurrence, is selected independently from: 1) an alkyl, a haloalkyl, or an aryl, any of which having up to 10 carbon atoms; or 2) hydrogen;

R$^9$, in each occurrence, is selected independently from an alkyl, a haloalkyl, an aryl, or a heterocyclyl or heteroaryl comprising at least one heteroatom selected from —O— or >N—, any of which having up to 10 carbon atoms;

R$^4$ is optionally substituted with at least one group selected independently from: 1) an alkyl, a haloalkoxy, an alkoxy, —COR$^9$, —COR$^{10}$, —CONR$^8_2$, —CO$_2$R$^8$, —SO$_2$R$^9$, —SO$_2$R$^{10}$, —SO$_2$NR$^{10}_2$, or —NR$^{10}_2$, any of which having up to 10 carbon atoms; or 2) halogen or hydroxyl; and R$^{10}$, in each occurrence, is selected independently from: 1) an alkyl, an aryl, or a heterocyclyl comprising at least one heteroatom selected from —O— or >N—, any of which having up to 10 carbon atoms; or 2) hydrogen.

In this aspect in the formula (III-C), Y$^1$ can be —(CH$_2$)n- wherein n is 0, that is, R$^1$ can be bonded directly to the pyridine core. Also in this aspect in the formula (III-C), R$^5$ can be methyl or hydrogen.

In still another aspect, the present invention encompasses compounds and compositions comprising these compounds, wherein the compounds have the following formula:

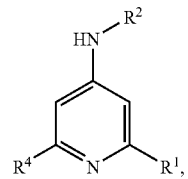

(III-G)

or a salt, including a pharmaceutically acceptable or a non-pharmaceutically acceptable salt, a prodrug, a diastereomeric mixture, an enantiomer, a tautomer, or a racemic mixture thereof;

wherein:

R$^1$ and R$^2$ are selected independently from: a) a substituted or an unsubstituted aryl or heteroaryl comprising at least one heteroatom selected from —O—, >N—, or —S—, any of which having up to 10 carbon atoms; or b) hydrogen, halogen, or hydroxy;

R$^4$ is selected from: 1) a substituted or an unsubstituted alkyl, aryl, or heterocyclyl or heteroaryl comprising at least one heteroatom or heterogroup selected from —O—, >N—, —S—, or >CO, any of which having up to 10 carbon atoms; or 2) hydrogen or halogen;

R$^1$ and R$^2$ are optionally substituted with at least one group independently selected from: 1) an alkyl, an alkoxy, a haloalkyl, a haloalkoxy, —COR$^9$, —CONR$^8_2$, SO$_2$R$^9$, —NHSO$_2$R$^9$, or —SO$_2$NR$^8_2$, any of which having up to 10 carbon atoms; or 2) halogen, —OCH$_2$O—, cyano, or hydroxyl;

R$^8$, in each occurrence, is selected independently from: 1) an alkyl, a haloalkyl, or an aryl having up to 10 carbon atoms; or 2) hydrogen;

R$^9$, in each occurrence, is selected independently from an alkyl, a haloalkyl, an aryl, or a heterocyclyl or heteroaryl comprising at least one heteroatom selected from —O— or >N—, any of which having up to 10 carbon atoms;

R$^4$ is optionally substituted with at least one group independently selected from: 1) an alkyl, a haloalkoxy, an alkoxy, —COR$^{10}$, —CONR$^8_2$, —SO$_2$R$^{10}$, —SO$_2$NR$^{10}_2$, or —NR$^{10}_2$, any of which having up to 10 carbon atoms; or 2) halogen or hydroxyl; and R$^{10}$, in each occurrence, is selected independently from: 1) an alkyl, an aryl, or a heterocyclyl comprising at least one heteroatom selected from —O— or >N—, or 2) hydrogen.

Another aspect of the present invention provides compounds and compositions comprising these compounds, wherein the compounds have the following formula:

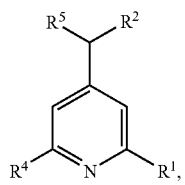

(III-H)

or a salt, including a pharmaceutically acceptable or a non-pharmaceutically acceptable salt, a prodrug, a diastereomeric mixture, an enantiomer, a tautomer, or a racemic mixture thereof;
wherein:
$R^1$ and $R^2$ are selected independently from: 1) a substituted or an unsubstituted aryl or a substituted or an unsubstituted heteroaryl or heterocyclyl comprising at least one heteroatom selected from —O—, >N—, or —S—, any of which having up to 10 carbon atoms; or 2) hydrogen, halogen, or hydroxy;
$R^4$ is selected from a substituted or an unsubstituted aryl or heteroaryl comprising at least one heteroatom selected from —O—, >N—, or —S—, any of which having up to 10 carbon atoms;
$R^5$ is an alkyl having up to 3 carbon atoms or hydrogen;
$R^1$ and $R^2$ are optionally substituted with at least one group independently selected from: 1) an alkyl, an alkoxy, a haloalkyl, a haloalkoxy, —$COR^9$, —$CO_2R^8$, —$CONR^8_2$, —$SO_2R^9$, —$NHSO_2R^9$, or —$SO_2NR^8_2$, any of which having up to 10 carbon atoms; or 2) halogen, —$OCH_2O$—, or hydroxyl;
$R^8$, in each occurrence, is selected independently from: 1) an alkyl, a haloalkyl, or an aryl having up to 10 carbon atoms; or 2) hydrogen;
$R^9$, in each occurrence, is selected independently from an alkyl, a haloalkyl, an aryl, or a heterocyclyl or heteroaryl comprising at least one heteroatom selected from —O— or >N—, any of which having up to 10 carbon atoms;
$R^4$ is optionally substituted with at least one group independently selected from: 1) an alkyl, a haloalkoxy, an alkoxy, —$COR^9$, —$COR^{10}$, —$CO_2R^8$, —$CONR^8_2$, —$SO_2R^9$, —$SO_2R^{10}$, —$SO_2NR^{10}_2$, or —$NR^{10}_2$, any of which having up to 10 carbon atoms; or 2) halogen or hydroxyl; and
$R^{10}$, in each occurrence, is selected independently from: 1) an alkyl, an aryl, or a heterocyclyl comprising at least one heteroatom selected from —O— or >N—, any of which having up to 10 carbon atoms; or 2) hydrogen.

In this aspect of formula (III-H), $R^5$ can be methyl or hydrogen.

Another aspect of the present invention provides compounds and compositions comprising these compounds, wherein the compounds have the following formula:

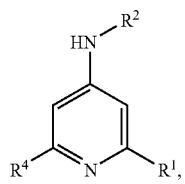

(III-Gi)

or a salt, including a pharmaceutically acceptable or a non-pharmaceutically acceptable salt, a prodrug, a diastereomeric mixture, an enantiomer, a tautomer, or a racemic mixture thereof;
wherein:
$R^1$ and $R^2$ are selected independently from: a) a substituted or an unsubstituted aryl or heteroaryl comprising at least one heteroatom selected from —O—, >N—, or —S—, any of which having up to 10 carbon atoms; or b) hydrogen, halogen, or hydroxy;
$R^4$ is selected from a substituted or an unsubstituted alkyl or heterocyclyl comprising at least one heteroatom or heterogroup selected from —O—, >N—, —S—, or >CO, any of which having up to 10 carbon atoms;
$R^1$ and $R^2$ are optionally substituted with at least one group independently selected from: 1) an alkyl, an alkoxy, a haloalkyl, a haloalkoxy, —$COR^9$, —$CONR^8_2$, $SO_2R^9$, —$NHSO_2R^9$, or —$SO_2NR^8_2$, any of which having up to 10 carbon atoms; or 2) halogen, —$OCH_2O$—, cyano, or hydroxyl;
$R^8$, in each occurrence, is selected independently from: 1) an alkyl, a haloalkyl, or an aryl, any of which having up to 10 carbon atoms; or 2) hydrogen;
$R^9$, in each occurrence, is selected independently from an alkyl, a haloalkyl, an aryl, or a heterocyclyl or heteroaryl comprising at least one heteroatom selected from —O— or >N—, any of which having up to 10 carbon atoms;
$R^4$ is optionally substituted with at least one group independently selected from: 1) an alkyl, a haloalkoxy, an alkoxy, —$COR^{10}$, —$CONR^8_2$, —$SO_2R^{10}$, —$SO_{10}NR^2$, or —$NR^{10}_2$, any of which having up to 10 carbon atoms; or 2) halogen or hydroxyl; and
$R^{10}$, in each occurrence, is selected independently from: 1) an alkyl, an aryl, or a heterocyclyl comprising at least one heteroatom selected from —O— or >N—, any of which having up to 10 carbon atoms; or 2) hydrogen.

Still another aspect of the present invention provides compounds and compositions comprising these compounds, wherein the compounds have the following formula:

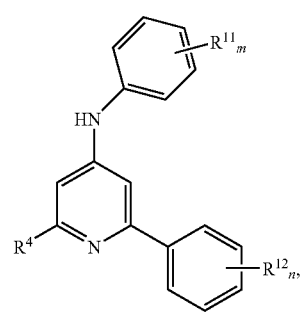

(III-I)

or a salt, including a pharmaceutically acceptable or a non-pharmaceutically acceptable salt, a prodrug, a diastereomeric mixture, an enantiomer, a tautomer, or a racemic mixture thereof;
wherein:
$R^4$ is selected from: 1) a substituted or an unsubstituted heterocyclyl comprising at least one heteroatom or heterogroup selected from —O—, >N—, —S—, >$SO_2$, or >CO,
n and m are independently an integer from 0 to 3, inclusive;
$R^{11}$ and $R^{12}$, in each occurrence, are selected independently from: 1) an alkyl, an alkoxy, a haloalkyl, a haloalkoxy, —COR⁹, —CONR⁸₂, —CO₂R⁸, —CO₂R⁹, —SO₂R⁹, —NHSO₂R⁹, or —SO₂NR⁸₂, any of which having up to 10 carbon atoms; or 2) halogen, —OCH₂O—, cyano, or hydroxyl;

R⁸, in each occurrence, is selected independently from: 1) an alkyl, a haloalkyl, or an aryl, any of which having up to 10 carbon atoms; or 2) hydrogen;

R⁹, in each occurrence, is selected independently from an alkyl, a haloalkyl, an aryl, or a heterocyclyl or heteroaryl comprising at least one heteroatom selected from —O— or >N—, any of which having up to 10 carbon atoms;

R⁴ is optionally substituted with at least one group selected independently from: 1) an alkyl, a linear alkyl, a branched alkyl, a cycloalkyl, —COR¹⁰, —CONR⁸₂, —OCOCH₂CH₂CO₂R¹⁰, —SO₂R¹⁰, or —SO₂NR¹⁰₂, any of which having up to 10 carbon atoms; or 2) hydroxyl; and R¹⁰, in each occurrence, is selected independently from: 1) an alkyl, an aryl, or a heterocyclyl comprising at least one heteroatom selected from —O— or >N—, any of which having up to 10 carbon atoms; or 2) hydrogen.

In this aspect of the formula (III-I), R⁴ can be selected from

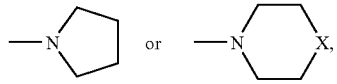

wherein X is selected from CH₂, O, NH, NMe, NEt, S, SO₂, CH(OCOCH₂CH₂CO₂H), or CH(OH);

n and m are independently an integer from 0 to 2, inclusive; and

R¹¹ and R¹², in each occurrence, are selected independently from OCF₃, OMe, Cl, F, SO₂Me, CF₃, Me, COMe, CONHMe, NHSO₂Me, SO₂NH₂, SO₂NHMe, SO₂NMe₂, CONH₂, CONMe₂, CO₂Me, —OCH₂O—, or OH.

Yet another, aspect of the present invention provides compounds and compositions comprising these compounds, wherein the compounds have the following formula:

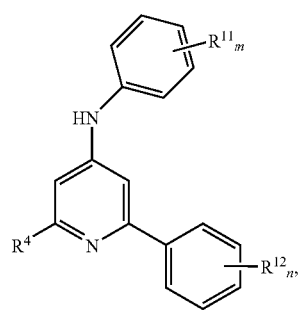

(III-Ii)

or a salt, including a pharmaceutically acceptable or a non-pharmaceutically acceptable salt, a prodrug, a diastereomeric mixture, an enantiomer, a tautomer, or a racemic mixture thereof;

wherein:

R⁴ is selected from: 1) a substituted or an unsubstituted aryl, alkoxy, or heteroaryl comprising at least one heteroatom selected from —O—, —S—, or >N—, any of which having up to 10 carbon atoms; or 2) hydrogen, chloro, or hydroxyl;

n and m are independently an integer from 0 to 3, inclusive;

R¹¹ and R¹², in each occurrence, are selected independently from: 1) an alkyl, an alkoxy, a haloalkyl, a haloalkoxy, —COR⁹, —CONR⁸₂, —CO₂R⁸, —CO₂R⁹, —SO₂R⁹, —NHSO₂R⁹, or —SO₂NR⁸₂, any of which having up to 10 carbon atoms; or 2) halogen, —OCH₂O—, cyano, or hydroxyl;

R⁸, in each occurrence, is selected independently from: 1) an alkyl, a haloalkyl, or an aryl, any of which having up to 10 carbon atoms; or 2) hydrogen;

R⁹, in each occurrence, is selected independently from an alkyl, a haloalkyl, an aryl, or a heterocyclyl or heteroaryl comprising at least one heteroatom selected from —O— or >N—, any of which having up to 10 carbon atoms;

wherein when R⁴ is optionally substituted with at least one group selected independently selected from: 1) an alkyl, a haloalkoxy, an alkoxy, —COR⁹, —COR¹⁰, —CONR⁸₂, —SO₂R⁹, —SO₂R¹⁰, —SO₂NR¹⁰₂, or —NR¹⁰₂, any of which having up to 10 carbon atoms; or 2) halogen, cyano, or hydroxyl; and R¹⁰, in each occurrence, is selected independently from: 1) an alkyl, an aryl, or a heterocyclyl comprising at least one heteroatom selected from —O— or >N—, any of which having up to 10 carbon atoms; or 2) hydrogen.

Still another aspect of the present invention provides compounds and compositions comprising these compounds, wherein the compounds have the following formula:

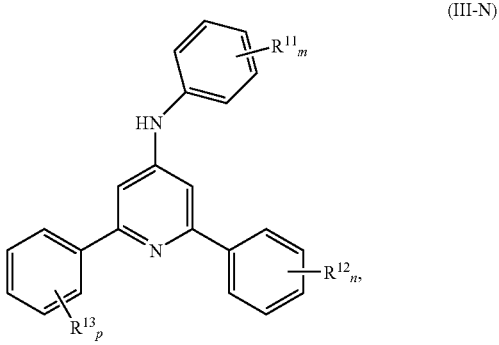

(III-N)

or a salt, including a pharmaceutically acceptable or a non-pharmaceutically acceptable salt, a prodrug, a diastereomeric mixture, an enantiomer, a tautomer, or a racemic mixture thereof;

wherein:

m, n, and p are independently an integer from 0 to 3, inclusive;

R¹¹, R¹² and R¹³, in each occurrence, are selected independently from: 1) an alkyl, an alkoxy, a haloalkyl, a haloalkoxy, —COR⁹, —CONR⁸₂, —CO₂R⁸, —SO₂R⁹, —NHSO₂R⁹, or —SO₂NR⁸₂, any of which having up to 10 carbon atoms; or 2) halogen, —OCH₂O—, or hydroxyl;

R⁸, in each occurrence, is selected independently from: 1) an alkyl, a haloalkyl, or an aryl, any of which having up to 10 carbon atoms; or 2) hydrogen; and R⁹, in each occurrence, is selected independently from an alkyl, a haloalkyl, an aryl, or a heterocyclyl or heteroaryl comprising at least one heteroatom selected from —O— or >N—, any of which having up to 10 carbon atoms.

In this aspect of the formula (III-N), n, m and p can be independently an integer from 0 to 2, inclusive; and $R^{11}$, $R^{12}$ and $R^{13}$, in each occurrence, can be selected independently from $OCF_3$, OMe, Cl, F, $SO_2Me$, $CF_3$, Me, COMe, CONHMe, $NHSO_2Me$, $SO_2NH_2$, $SO_2NHMe$, $SO_2NMe_2$, $CONH_2$, $CONMe_2$, $CO_2Me$, —$OCH_2O$—, or OH.

Another aspect of the present invention provides compounds and compositions comprising these compounds, wherein the compounds have the following formula:

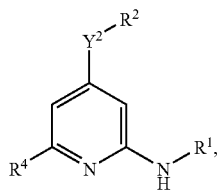

(III-D)

or a salt, including a pharmaceutically acceptable or a non-pharmaceutically acceptable salt, a prodrug, a diastereomeric mixture, an enantiomer, a tautomer, or a racemic mixture thereof;
wherein:
$Y^2$ is selected from $>NR^5$ or $>(CH_2)n$ wherein n is 0 or 1;
$R^1$ and $R^2$ are selected independently from: a) a substituted or an unsubstituted alkyl, cycloalkyl, aryl, or heterocyclyl or heteroaryl comprising at least one heteroatom or heterogroup selected from —O—, >N—, —S—, >CO or $>SO_2$, any of which having up to 10 carbon atoms; or b) hydrogen, halogen, or hydroxy;
$R^5$ is selected from an alkyl having up to 3 carbon atoms or hydrogen;
$R^4$ is selected from: 1) a substituted or an unsubstituted alkyl, aryl, or heterocyclyl or heteroaryl comprising at least one heteroatom or heterogroup selected from —O—, >N—, —S—, or >CO, any of which having up 10 carbon atoms; or 2) hydrogen or halogen;
$R^1$ and $R^2$ are optionally substituted with at least one group independently selected from: 1) an alkyl, an alkoxy, a haloalkyl, a haloalkoxy, —$COR^9$, —$CO_2R^8$, —$CONR^8_2$, —$SO_2R^9$, —$NHSO_2R^9$, or —$SO_2NR^8_2$, any of which having up to 10 carbon atoms; or 2) halogen, —$OCH_2O$—, cyano, or hydroxyl;
$R^8$, in each occurrence, is selected independently from: 1) an alkyl, a haloalkyl, or an aryl, any of which having up to 10 carbon atoms; or 2) hydrogen;
$R^9$, in each occurrence, is selected independently from an alkyl, a haloalkyl, an aryl, or a heterocyclyl or heteroaryl comprising at least one heteroatom selected from —O— or >N—, any of which having up to 10 carbon atoms;
$R^4$ is optionally substituted with at least one group independently selected from: 1) an alkyl, a haloalkoxy, an alkoxy, —$COR^9$, —$COR^{10}$, —$CONR^8_2$, —$SO_2R^9$, —$SO_2R^{10}$, —$SO_2NR^{10}_2$, or —$NR^{10}_2$, any of which having up to 10 carbon atoms; or 2) halogen, cyano, or hydroxyl; and
$R^{10}$, in each occurrence, is selected independently from: 1) an alkyl, an aryl, or a heterocyclyl comprising at least one heteroatom selected from —O— or >N—, any of which having up to 10 carbon atoms; or 2) hydrogen. In this aspect in the formula (III-D), $Y^2$ can be —$(CH_2)n$- wherein n is 0, that is, $R^2$ can be bonded directly to the pyridine core.

Yet another aspect of the present invention provides compounds and compositions comprising these compounds, wherein the compounds have the following formula:

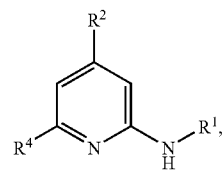

(III-Ji)

or a salt, including a pharmaceutically acceptable or a non-pharmaceutically acceptable salt, a prodrug, a diastereomeric mixture, an enantiomer, a tautomer, or a racemic mixture thereof;
wherein:
$R^1$ and $R^2$ are selected independently from: a) a substituted or an unsubstituted aryl or a substituted or an unsubstituted heteroaryl comprising at least one heteroatom selected from —O—, >N—, or —S—, any of which having up to 10 carbon atoms; or b) hydrogen, halogen, or hydroxyl;
$R^4$ is selected from: 1) a substituted or an unsubstituted alkyl, aryl, or heterocyclyl or heteroaryl comprising at least one heteroatom or heterogroup selected from —O—, >N—, —S—, or >CO, any of which having up to 10 carbon atoms; or 2) hydrogen or halogen;
$R^1$ and $R^2$ are optionally substituted with at least one group independently selected from: 1) an alkyl, an alkoxy, a haloalkyl, a haloalkoxy, —$COR^9$, —$CONR^8_2$, —$SO_2R^9$, —$NHSO_2R^9$, or —$SO_2NR^8_2$, any of which having up to 10 carbon atoms; or 2) halogen, —$OCH_2O$—, cyano, or hydroxyl;
$R^8$, in each occurrence, is selected independently from: 1) an alkyl, a haloalkyl, or an aryl, any of which having up to 10 carbon atoms; or 2) hydrogen;
$R^9$, in each occurrence, is selected independently from an alkyl, a haloalkyl, an aryl, or a heterocyclyl or heteroaryl comprising at least one heteroatom selected from —O— or >N—, any of which having up to 10 carbon atoms;
$R^4$ is optionally substituted with at least one group independently selected from: 1) an alkyl, a haloalkoxy, an alkoxy, —$COR^9$, —$COR^{10}$, —$CONR^8_2$, —$SO_2R^9$, —$SO_2R^{10}$, —$SO_2NR^{10}_2$, or —$NR^{10}_2$, any of which having up to 10 carbon atoms; or 2) halogen or hydroxyl; and
$R^{10}$, in each occurrence, is selected independently from: 1) an alkyl, an aryl, or a heterocyclyl comprising at least one heteroatom selected from —O— or >N—, any of which having up to 10 carbon atoms; or 2) hydrogen.

Yet another aspect of the present invention provides compounds and compositions comprising these compounds, wherein the compounds have the following formula:

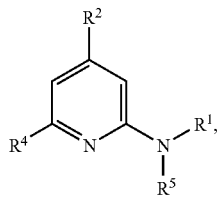

(III-K)

or a salt, including a pharmaceutically acceptable or a non-pharmaceutically acceptable salt, a prodrug, a diastereomeric mixture, an enantiomer, a tautomer, or a racemic mixture thereof;
wherein:
$R^1$ and $R^2$ are, in each occurrence, selected independently from: 1) a substituted or an unsubstituted aryl or a substituted or an unsubstituted heteroaryl comprising at least one heteroatom selected from —O—, >N—, or —S—, any of which having up to 10 carbon atoms; or b) hydrogen, halogen, or hydroxyl;

$R^4$ is selected from a substituted or an unsubstituted aryl or a substituted or an unsubstituted heteroaryl comprising at least one heteroatom selected from —O—, >N—, or —S—, any of which having up to 10 carbon atoms;

$R^5$ is selected from an alkyl having up to 3 carbon atoms or hydrogen;

$R^1$ and $R^2$ are optionally substituted with at least one group independently selected from: 1) an alkyl, an alkoxy, a haloalkyl, a haloalkoxy, —COR$^9$, —CONR$^8_2$, —SO$_2$R$^9$, —NHSO$_2$R$^9$, or —SO$_2$NR$^8_2$, any of which having up to 10 carbon atoms; or 2) halogen, —OCH$_2$O—, or hydroxyl;

$R^8$, in each occurrence, is selected independently from: 1) an alkyl, a haloalkyl, or an aryl, any of which having up to 10 carbon atoms; or 2) hydrogen;

$R^9$, in each occurrence, is selected independently from an alkyl, a haloalkyl, an aryl, or a heterocyclyl or heteroaryl comprising at least one heteroatom selected from —O— or >N—, any of which having up to 10 carbon atoms;

$R^4$ is optionally substituted with at least one group independently selected from: 1) an alkyl, a haloalkoxy, an alkoxy, —COR$^{10}$, —CONR$^8_2$, —SO$_2$R$^{10}$, —SO$_2$NR$^{10}_2$, or —NR$^{10}_2$, any of which having up to 10 carbon atoms; or 2) halogen or hydroxyl; and $R^{10}$, in each occurrence, is selected independently: 1) an alkyl, an aryl, or a heterocyclyl comprising at least one heteroatom selected from —O— or >N—, any of which having up to 10 carbon atoms; or 2) hydrogen.

In one aspect, the present invention encompasses compounds and compositions comprising these compounds, wherein the compounds have the following formula:

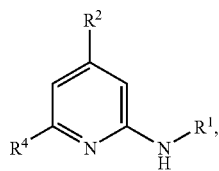

(III-Ji)

or a salt, including a pharmaceutically acceptable or a non-pharmaceutically acceptable salt, a prodrug, a diastereomeric mixture, an enantiomer, a tautomer, or a racemic mixture thereof;
wherein:
$R^1$ and $R^2$ are selected independently from: 1) a substituted or an unsubstituted aryl, or a substituted or an unsubstituted heteroaryl comprising at least one heteroatom selected from —O—, >N—, or —S—, any of which having up to 10 carbon atoms; or 2) hydrogen, halogen, or hydroxy;

$R^4$ is selected from a substituted or an unsubstituted alkyl, or a substituted or an unsubstituted heterocyclyl comprising at least one heteroatom or heterogroup selected from —O—, >N—, —S—, or >CO, any of which having up to 10 carbon atoms;

$R^1$ and $R^2$ are optionally substituted with at least one group independently selected from: 1) an alkyl, an alkoxy, a haloalkyl, a haloalkoxy, —COR$^9$, —CONR$^8_2$, —SO$_2$R$^9$, —NHSO$_2$R$^9$, or —SO$_2$NR$^8_2$, any of which having up to 10 carbon atoms; or 2) halogen, —OCH$_2$O—, or hydroxyl;

$R^8$, in each occurrence, is selected independently from: 1) an alkyl, a haloalkyl, or an aryl, any of which having up to 10 carbon atoms; or 2) hydrogen;

$R^9$, in each occurrence, is selected independently from an alkyl, a haloalkyl, an aryl, or a heterocyclyl or heteroaryl comprising at least one heteroatom selected from —O— or >N—, any of which having up to 10 carbon atoms;

$R^4$ is optionally substituted with at least one group independently selected from: 1) an alkyl, a haloalkoxy, an alkoxy, —COR$^{10}$, —CONR$^8_2$, —SO$_2$R$^{10}$, —SO$_2$NR$^{10}_2$, or —NR$^{10}_2$, any of which having up to 10 carbon atoms; or 2) halogen or hydroxyl; and $R^{10}$, in each occurrence, is selected independently from: 1) an alkyl, an aryl, or a heterocyclyl comprising at least one heteroatom selected from —O— or >N—, any of which having up to 10 carbon atoms; or 2) hydrogen.

In another aspect, the present invention encompasses compounds and compositions comprising these compounds, wherein the compounds have the following formula:

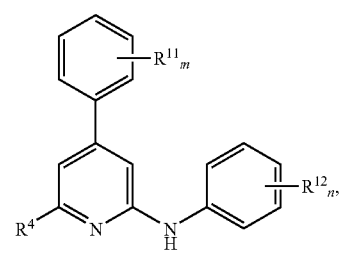

(III-L)

or a salt, including a pharmaceutically acceptable or a non-pharmaceutically acceptable salt, a prodrug, a diastereomeric mixture, an enantiomer, a tautomer, or a racemic mixture thereof;
wherein:
$R^4$ is selected from a substituted or an unsubstituted heterocyclyl comprising at least one heteroatom or heterogroup selected from —O—, >N—, —S—, or >CO, any of which having up to 10 carbon atoms;

n and m are independently an integer from 0 to 3, inclusive;

$R^{11}$ and $R^{12}$, in each occurrence, are selected independently from: 1) an alkyl, an alkoxy, a haloalkyl, a haloalkoxy, —COR⁹, —CONR⁸₂, —CO₂R⁸, —CO₂R⁹, —SO₂R⁹, —NHSO₂R⁹, or —SO₂NR⁸₂, any of which having up to 10 carbon atoms; or 2) halogen, —OCH₂O—, cyano, or hydroxyl;

$R^8$, in each occurrence, is selected independently from: 1) an alkyl, a haloalkyl, or an aryl, any of which having up to 10 carbon atoms; or 2) hydrogen;

$R^9$, in each occurrence, is selected independently from an alkyl, a haloalkyl, an aryl, or a heterocyclyl or heteroaryl comprising at least one heteroatom selected from —O— or >N—, any of which having up to 10 carbon atoms;

$R^4$ is optionally substituted with at least one group independently selected from: 1) an alkyl, a branched alkyl, a linear alkyl, a cycloalkyl, —COR¹⁰, —CONR⁸₂, —SO₂R¹⁰, or —SO₂NR¹⁰₂, any of which having up to 10 carbon atoms; or 2) hydroxyl; and $R^{10}$, in each occurrence, is selected independently from: 1) an alkyl, an aryl, or a heterocyclyl comprising at least one heteroatom selected from —O— or >N—, any of which having up to 10 carbon atoms; or 2) hydrogen.

In another aspect, the present invention encompasses compounds and compositions comprising these compounds, wherein the compounds have the following formula:

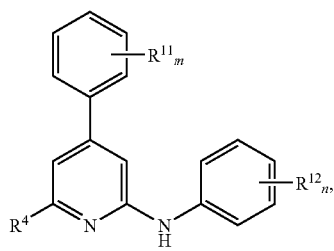

(III-Li)

or a salt, including a pharmaceutically acceptable or a non-pharmaceutically acceptable salt, a prodrug, a diastereomeric mixture, an enantiomer, a tautomer, or a racemic mixture thereof;

wherein:
$R^4$ is selected from: 1) a substituted or an unsubstituted aryl, alkoxy, or heteroaryl comprising at least one heteroatom selected from —O—, —S—, or >N—, any of which having up to 10 carbon atoms; or 2) hydrogen, chloro, or hydroxyl;

n and m are independently an integer from 0 to 3, inclusive;

$R^{11}$ and $R^{12}$, in each occurrence, are selected independently from: 1) an alkyl, an alkoxy, a haloalkyl, a haloalkoxy, —COR⁹, —CONR⁸₂, —SO₂R⁹, —NHSO₂R⁹, or —SO₂NR⁸₂, any of which having up to 10 carbon atoms; or 2) halogen, —OCH₂O—, or hydroxyl;

$R^8$, in each occurrence, is selected independently from: 1) an alkyl, a haloalkyl, or an aryl, any of which having up to 10 carbon atoms; or 2) hydrogen;

$R^9$, in each occurrence, is selected independently from an alkyl, a haloalkyl, an aryl, or a heterocyclyl or heteroaryl comprising at least one heteroatom selected from —O— or >N—, any of which having up to 10 carbon atoms;

$R^4$ is optionally substituted with at least one group independently selected from: 1) an alkyl, a haloalkyl, an alkoxy, —COR⁹, —COR¹⁰, —CONR⁸₂, —SO₂R⁹, —SO₂R¹⁰, —SO₂NR¹⁰₂, or —NR¹⁰₂, any of which having up to 10 carbon atoms; or 2) halogen or hydroxyl; and $R^{10}$, in each occurrence, is selected independently from: 1) an alkyl, an aryl, or a heterocyclyl comprising at least one heteroatom selected from —O— or >N—, any of which having up to 10 carbon atoms; or 2) hydrogen.

In another aspect, the present invention encompasses compounds and compositions comprising these compounds, wherein the compounds have the following formula:

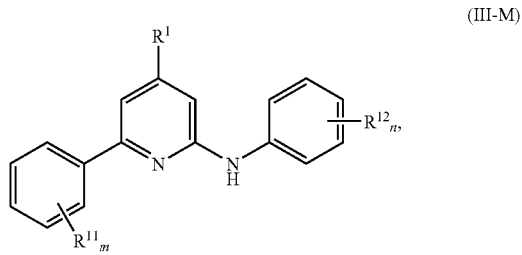

(III-M)

or a salt, including a pharmaceutically acceptable or a non-pharmaceutically acceptable salt, a prodrug, a diastereomeric mixture, an enantiomer, a tautomer, or a racemic mixture thereof;

wherein:
$R^1$ is selected from a substituted or an unsubstituted heterocyclyl comprising at least one heteroatom or heterogroup selected from —O—, >N—, —S—, >SO₂, or >CO, any of which having up to 10 carbon atoms;

n and m are independently an integer from 0 to 3, inclusive;

$R^{11}$ and $R^{12}$, in each occurrence, are selected independently from: 1) an alkyl an alkoxy, a haloalkyl, a haloalkoxy, —COR⁹, —CO₂R⁸, —CONR⁸₂, —SO₂R⁹, —NHSO₂R⁹, or —SO₂NR⁸₂, any of which having up to 10 carbon atoms; or 2) halogen, —OCH₂O—, cyano, or hydroxyl;

$R^8$, in each occurrence, is selected independently from: 1) an alkyl, a haloalkyl, or an aryl, any of which having up to 10 carbon atoms; or 2) hydrogen;

$R^9$, in each occurrence, is selected independently from an alkyl, a haloalkyl, an aryl, or a heterocyclyl or heteroaryl comprising at least one heteroatom selected from —O— or >N—, any of which having up to 10 carbon atoms;

$R^1$ is optionally substituted with at least one group independently selected from: 1) an alkyl, a branched alkyl, a linear alkyl, a cycloalkyl, a haloalkyl, —COR¹⁰, —CONR⁸₂, —OCOCH₂CH₂CO₂R¹⁰, —SO₂R¹⁰, or —SO₂NR¹⁰₂, any of which having up to 10 carbon atoms; or 2) hydroxyl; and $R^{10}$, in each occurrence, is selected independently from: 1) an alkyl, an aryl, or a heterocyclyl comprising at least one heteroatom selected from —O— or >N—, any of which having up to 10 carbon atoms; or 2) hydrogen.

In this aspect of the formula (III-M), $R^1$ can be selected from or

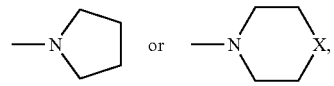

wherein X is selected from CH₂, O, NH, NMe, NEt, S, SO₂, CH(OCOCH₂CH₂CO₂H), or CH(OH);

n and m are independently an integer from 0 to 2, inclusive; and $R^{11}$ and $R^{12}$, in each occurrence, are selected independently from $OCF_3$, OMe, Cl, F, $SO_2Me$, $CF_3$, Me, COMe, CONHMe, $NHSO_2Me$, $SO_2NH_2$, $SO_2NHMe$, $SO_2NMe_2$, $CONH_2$, $CONMe_2$, $CO_2Me$, —$OCH_2O$—, or OH.

In another aspect, the present invention encompasses compounds and compositions comprising these compounds, wherein the compounds have the following formula:

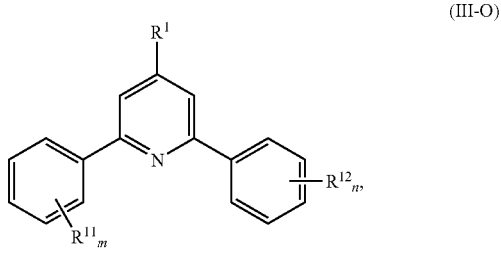

(III-O)

or a salt, including a pharmaceutically acceptable or a non-pharmaceutically acceptable salt, a prodrug, a diastereomeric mixture, an enantiomer, a tautomer, or a racemic mixture thereof;
wherein:
$R^1$ is selected from a substituted or an unsubstituted heterocyclyl comprising at least one heteroatom or heterogroup selected from —O—, >N—, —S—, >$SO_2$, or >CO, any of which having up to 10 carbon atoms;
n and m are independently an integer from 0 to 3, inclusive;
$R^{11}$ and $R^{12}$, in each occurrence, are selected independently from: 1) an alkyl, an alkoxy, a haloalkyl, a haloalkoxy, —$COR^9$, —$CO_2R^8$, —$CONR^8_2$, —$SO_2R^9$, —$NHSO_2R^9$, or —$SO_2NR^8_2$, any of which having up to 10 carbon atoms; or 2) halogen, cyano, —$OCH_2O$—, or hydroxyl;
$R^8$, in each occurrence, is selected independently from: 1) an alkyl, a haloalkyl, or an aryl, any of which having up to 10 carbon atoms; or 2) hydrogen;
$R^9$, in each occurrence, is selected independently from an alkyl, a haloalkyl, an aryl, or a heterocyclyl or heteroaryl comprising at least one heteroatom selected from —O— or >N—, any of which having up to 10 carbon atoms; and
$R^1$ is optionally substituted with at least one group independently selected from: 1) an alkyl, a cycloalkyl, a haloalkyl, or —$OCOCH_2CH_2CO_2R^8$, any of which having up to 10 carbon atoms; or 2) hydroxyl.

In this aspect of the formula (III-O), $R^1$ can be selected from

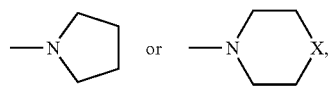

wherein X is selected from $CH_2$, O, NH, NMe, NEt, S, $SO_2$, $CH(OCOCH_2CH_2CO_2H)$, or CH(OH);
n and m can be independently an integer from 0 to 2, inclusive; and
$R^{11}$ and $R^{12}$, in each occurrence, can be selected independently from $OCF_3$, OMe, Cl, F, $SO_2Me$, $CF_3$, Me, COMe, CONHMe, $NHSO_2Me$, $SO_2NH_2$, $SO_2NHMe$, $SO_2NMe2$, $CONH2$, $CONMe2$, $CO2Me$, —$OCH2O$—, or OH.

In yet another aspect, the present invention encompasses compounds and compositions comprising these compounds, wherein the compounds have the following formula:

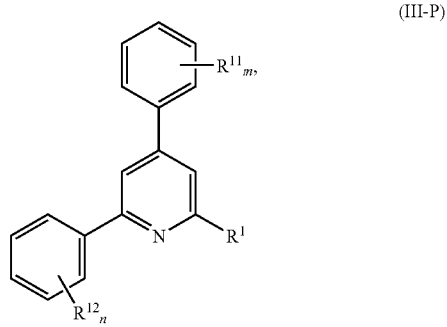

(III-P)

or a salt, including a pharmaceutically acceptable or a non-pharmaceutically acceptable salt, a prodrug, a diastereomeric mixture, an enantiomer, a tautomer, or a racemic mixture thereof;
wherein:
$R^1$ is selected from a substituted or an unsubstituted heterocyclyl comprising at least one heteroatom or heterogroup selected from —O—, >N—, —S—, >$SO_2$, or >CO, any of which having up to 10 carbon atoms;
n and m are independently an integer from 0 to 3, inclusive;
$R^{11}$ and $R^{12}$, in each occurrence, are selected independently from: 1) an alkyl, an alkoxy, a haloalkyl, a haloalkoxy, —$COR^9$, —$CO_2R^8$, —$CONR^8_2$, —$SO_2R^9$, —$NHSO_2R^9$, or —$SO_2NR^8_2$, any of which having up to 10 carbon atoms; or 2) halogen, cyano, —$OCH_2O$—, or hydroxyl;
$R^8$, in each occurrence, is selected independently from: 1) an alkyl, a haloalkyl, or an aryl, any of which having up to 10 carbon atoms; or 2) hydrogen;
$R^9$, in each occurrence, is selected independently from an alkyl, a haloalkyl, an aryl, or a heterocyclyl or heteroaryl comprising at least one heteroatom selected from —O— or >N—, any of which having up to 10 carbon atoms; and
$R^1$ is optionally substituted with at least one group independently selected from: 1) an alkyl, a cycloalkyl, a haloalkyl, or —$OCOCH_2CH_2CO_2R^8$, any of which having up to 10 carbon atoms; or 2) hydroxyl.

In this aspect of the formula (III-P), $R^1$ can be selected from

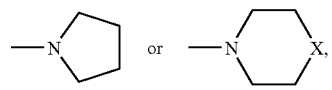

wherein X is selected from $CH_2$, O, NH, NMe, NEt, S, $SO_2$, $CH(OCOCH_2CH_2CO_2H)$, or CH(OH);
n and m can be independently an integer from 0 to 2, inclusive; and
$R^{11}$ and $R^{12}$, in each occurrence, can be selected independently from $OCF_3$, OMe, Cl, F, $SO_2Me$, $CF_3$, Me, COMe, CONHMe, $NHSO_2Me$, $SO_2NH_2$, $SO_2NHMe$, $SO_2NMe_2$, $CONH_2$, $CONMe_2$, $CO_2Me$, —$OCH_2O$—, or OH.

In still another aspect, the present invention encompasses compounds and compositions comprising these compounds, wherein the compounds have the following formula:

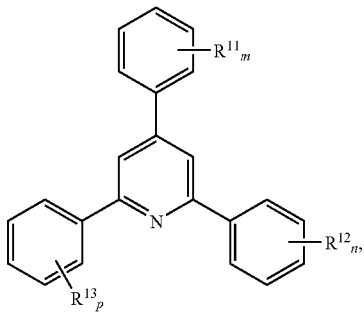

(III-Q)

or a salt, including a pharmaceutically acceptable or a non-pharmaceutically acceptable salt, a prodrug, a diastereomeric mixture, an enantiomer, a tautomer, or a racemic mixture thereof;

wherein:
m, n and p are independently an integer from 0 to 3, inclusive;
$R^{11}$, $R^{12}$ and $R^{13}$, in each occurrence, are selected independently from: 1) an alkyl, an alkoxy, a haloalkyl, a haloalkoxy, —$COR^9$, —$CONR^8_2$, —$CO_2R^8$, —$SO_2R^9$, —$NHSO_2R^9$, or —$SO_2NR^8_2$, any of which having up to 10 carbon atoms; or 2) halogen, —$OCH_2O$—, or hydroxyl;
$R^8$, in each occurrence, is selected independently from: 1) an alkyl, a haloalkyl, or an aryl, any of which having up to 10 carbon atoms; or 2) hydrogen; and
$R^9$, in each occurrence, is selected independently from an alkyl, a haloalkyl, an aryl, or a heterocyclyl or heteroaryl comprising at least one heteroatom selected from —O— or >N—, any of which having up to 10 carbon atoms.

In this aspect of the formula (III-Q), n and m can be independently an integer from 0 to 2, inclusive; and $R^{11}$ and $R^{12}$, in each occurrence, can be selected independently from $OCF_3$, OMe, Cl, F, $SO_2Me$, $CF_3$, Me, COMe, CONHMe, $NHSO_2Me$, $SO_2NH_2$, $SO_2NHMe$, $SO_2NMe_2$, $CONH_2$, $CONMe_2$, $CO_2Me$, —$OCH_2O$—, or OH.

Yet another aspect of this invention encompasses compounds and compositions comprising these compounds, wherein the compounds have the following formula:

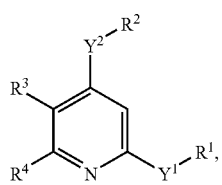

(IIIv)

or a salt, including a pharmaceutically acceptable or a non-pharmaceutically acceptable salt, a prodrug, a diastereomeric mixture, an enantiomer, a tautomer, or a racemic mixture thereof;

wherein:
Y1 and Y2, in each occurrence, are independently selected from —O—, —S—, >NR5, or >CH2;

R1 and R2 are, in each occurrence, selected independently from: a) a substituted or an unsubstituted alkyl, cycloalkyl, aryl, heterocyclyl or heteroaryl comprising at least one heteroatom or heterogroup selected from —O—, >N—, —S—, >CO or >$SO_2$, any of which having up to 10 carbon atoms; b) hydrogen, or c) halogen;
R5 is an alkyl having up to 10 carbon atoms or hydrogen;
R3 is hydrogen;
$R^4$ is selected from: 1) a substituted or an unsubstituted alkyl, aryl, heterocyclyl or heteroaryl comprising at least one heteroatom or heterogroup selected from —O—, >N—, —S—, or >CO, 2) hydrogen; or 3) halogen;
R1 and R2 are optionally substituted with at least one group independently selected from: 1) alkyl, alkoxy, haloalkyl, haloalkoxy, —OCH2O—, —COR9, —OCOR9, —CON(R8)2, —(CH2)bCO2R8 wherein b is an integer from 0 to 3, —SO2R9, —NHSO2R9, or —SO2N(R8)2, any of which having up to 10 carbon atoms; 2) halogen; or 3) or hydroxyl;
R8, in each occurrence, is selected independently from: 1) an alkyl, a haloalkyl, or an aryl having up to 10 carbon atoms; or 2) hydrogen;
R9, in each occurrence, is independently an alkyl, a haloalkyl, an aryl, a heterocyclyl or heteroaryl comprising at least one heteroatom selected from —O— or >N—; wherein R9 is optionally substituted with: 1) an alkyl, an alkoxy, a carboxylic acid, or a carboxylic acid ester, any of which having up to 8 carbon atoms; 2) halogen; or 3) hydroxyl;
R4 is optionally substituted with at least one group independently selected from: 1) alkyl, haloalkoxy, alkoxy, —COR10, —CON(R8)2, —SR10, —SO2R10, —SO2N(R10)2, or —N($R^{10}$)$_2$, any of which having up to 10 carbon atoms; 2) halogen; or 3) hydroxyl; and
R10, in each occurrence, is independently: 1) an alkyl, an aryl, or a heterocyclyl comprising at least one heteroatom selected from —O— or >N—, any of which having up to 10 carbon atoms; or 2) hydrogen.

Still another aspect of this invention encompasses compounds and compositions comprising these compounds, wherein the compounds have the following formula:

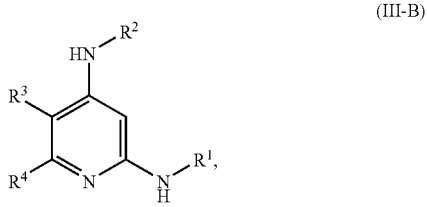

(III-B)

or a salt, including a pharmaceutically acceptable or a non-pharmaceutically acceptable salt, a prodrug, a diastereomeric mixture, an enantiomer, a tautomer, or a racemic mixture thereof;

wherein:
R1 and R2 are, in each occurrence, selected independently from a substituted or an unsubstituted cycloalkyl; aryl; aralkyl; heterocyclyl or heteroaryl comprising at least one heteroatom selected from —O—, >N—, or —S—; any of which having up to 10 carbon atoms;
R3 is hydrogen;
R4 is a substituted or unsubstituted heterocyclyl or heteroaryl comprising a nitrogen atom directly bonded to the pyridine ring and having up to 10 carbon atoms, wherein the heterocyclyl or heteroaryl optionally comprises at least one additional heteroatom selected from —O—, >N— or —S—;

R1 and R2 are optionally substituted with at least one group independently selected from: 1) alkyl, alkoxy, haloalkyl, haloalkoxy, —COR9, —OCOR9, —CON(R8)2, —SO2R9, —NHSO2R9, or —SO2N(R8)2, any of which having up to 10 carbon atoms; 2) halogen; or 3) or hydroxyl; and R4 is optionally substituted with at least one group independently selected from: 1) haloalkoxy, —COR10, —CON(R8)2, —SO2R10, or —SO2N(R10)2, any of which having up to 10 carbon atoms; 2) halogen; or 3) hydroxyl.

R8, in each occurrence, is selected independently from: 1) an alkyl, a haloalkyl, or an aryl having up to 10 carbon atoms; or 2) hydrogen;

R9, in each occurrence, is independently an alkyl, a haloalkyl, an aryl, a heterocyclyl or heteroaryl comprising at least one heteroatom selected from —O— or >N—; wherein R9 is optionally substituted with: 1) an alkyl, an alkoxy, a carboxylic acid, or a carboxylic acid ester, any of which having up to 8 carbon atoms; 2) halogen; or 3) hydroxyl;

R10, in each occurrence, is independently: 1) an alkyl, an aryl, or a heterocyclyl comprising at least one heteroatom selected from —O— or >N—, any of which having up to 10 carbon atoms; or 2) hydrogen.

Still another aspect of this invention encompasses compounds and compositions comprising these compounds, wherein the compounds have the following formula:

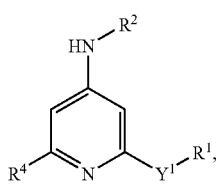

(III-Ci)

or a salt, including a pharmaceutically acceptable or a non-pharmaceutically acceptable salt, a prodrug, a diastereomeric mixture, an enantiomer, a tautomer, or a racemic mixture thereof;

wherein:

$Y^1$ is >CH$_2$;

$R^1$ and $R^2$ are, in each occurrence, selected independently from a substituted or an unsubstituted aryl, heterocyclyl, or heteroaryl, any of which having up to 10 carbon atoms, wherein the heterocyclyl and heteroaryl comprise at least one heteroatom selected from —O—, >N—, or —S—;

$R^4$ is a substituted or an unsubstituted aryl having up to 10 carbon atoms;

$R^1$ and $R^2$ are optionally substituted with at least one group independently selected from: 1) alkoxy, haloalkoxy, —COR$^9$, —CON(R$^8$)$_2$, —SO$_2$R$^9$, —NHSO$_2$R$^9$, or —SO$_2$N(R$^8$)$_2$, any of which having up to 10 carbon atoms; or 2) halogen;

$R^4$ is optionally substituted with at least one group independently selected from: 1) haloalkoxy, —COR$^{10}$, —CON(R$^8$)$_2$, —SO$_2$R$^{10}$, or —SO$_2$N(R$^{10}$)$_2$, any of which having up to 10 carbon atoms; 2) halogen; or 3) hydroxyl; and $R^8$, in each occurrence, is selected independently from: 1) an alkyl, a haloalkyl, or an aryl having up to 10 carbon atoms; or 2) hydrogen;

$R^9$, in each occurrence, is selected independently from an alkyl, a haloalkyl, an aryl, or a heteroaryl comprising at least one heteroatom selected from —O— or >N—; any of which having up to 10 carbon atoms; and $R^{10}$, in each occurrence, is selected independently from: 1) an alkyl, an aryl, or a heterocyclyl comprising at least one heteroatom selected from —O— or >N—, any of which having up to 10 carbon atoms; or 2) hydrogen.

Yet a further aspect of this invention encompasses compounds and compositions comprising these compounds, wherein the compounds have the following formula:

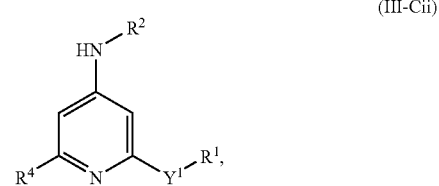

(III-Cii)

or a salt, including a pharmaceutically acceptable or a non-pharmaceutically acceptable salt, a prodrug, a diastereomeric mixture, an enantiomer, a tautomer, or a racemic mixture thereof;

wherein:

$Y^1$ is >CH$_2$;

$R^1$ is a substituted or unsubstituted aryl or heterocyclyl having up to 10 carbon atoms, wherein the heterocyclyl comprises a nitrogen atom directly bonded to the pyridine ring and optionally comprising at least one additional heteroatom selected from —O—, >N— or —S—;

$R^2$ is a substituted or an unsubstituted aryl having up to 10 carbon atoms;

$R^4$ is a substituted or an unsubstituted aryl, heterocyclyl, or heteroaryl, any of which having up to 10 carbon atoms, wherein the heterocyclyl and heteroaryl comprise at least one heteroatom selected from —O—, >N—, or —S—;

$R^1$ and $R^2$ are optionally substituted with at least one group independently selected from: 1) alkoxy, haloalkoxy, haloalkyl, —COR$^9$, —CON(R$^8$)$_2$, —SO$_2$R$^9$, — or —SO$_2$N(R$^8$)$_2$, any of which having up to 10 carbon atoms; or 2) halogen;

$R^4$ is optionally substituted with at least one group independently selected from: 1) haloalkoxy, —COR$^{10}$, —CON(R$^8$)$_2$, —SO$_2$R$^{10}$, or —SO$_2$N(R$^{10}$)$_2$, any of which having up to 10 carbon atoms; 2) halogen; or 3) hydroxyl; and $R^8$, in each occurrence, is selected independently from: 1) an alkyl, a haloalkyl, or an aryl having up to 10 carbon atoms; or 2) hydrogen;

$R^9$, in each occurrence, is selected independently from an alkyl, a haloalkyl, an aryl, or a heteroaryl comprising at least one heteroatom selected from —O— or>N—; any of which having up to 10 carbon atoms; and $R^{10}$, in each occurrence, is selected independently from: 1) an alkyl, an aryl, or a heterocyclyl comprising at least one heteroatom selected from —O— or>N—, any of which having up to 10 carbon atoms; or 2) hydrogen.

Yet another aspect of this invention encompasses compounds and compositions comprising these compounds, wherein the compounds have the following formula:

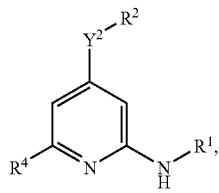

(III-Di)

or a salt, including a pharmaceutically acceptable or a non-pharmaceutically acceptable salt, a prodrug, a diastereomeric mixture, an enantiomer, a tautomer, or a racemic mixture thereof;
wherein:
$Y^2$ is $>CH_2$;
$R^1$ and $R^2$ are, in each occurrence, selected independently from a substituted or an unsubstituted aryl, heterocyclyl, or heteroaryl, any of which having up to 10 carbon atoms, wherein the heterocyclyl and heteroaryl comprise at least one heteroatom selected from —O—, $>N$—, or —S—;
$R^4$ is a substituted or an unsubstituted aryl having up to 10 carbon atoms;
$R^1$ and $R^2$ are optionally substituted with at least one group independently selected from: 1) alkoxy, haloalkoxy, —COR$^9$, —CON(R$^8$)$_2$, —SO$_2$R$^9$, —NHSO$_2$R$^9$, or —SO$_2$N(R$^8$)$_2$, any of which having up to 10 carbon atoms; or 2) halogen;
$R^4$ is optionally substituted with at least one group independently selected from: 1) haloalkoxy, —COR$^{10}$, —CON(R$^8$)$_2$, —SO$_2$R$^{10}$, or —SO$_2$N(R$^{10}$)$_2$, any of which having up to 10 carbon atoms; 2) halogen; or 3) hydroxyl; and
$R^8$, in each occurrence, is selected independently from: 1) an alkyl, a haloalkyl, or an aryl having up to 10 carbon atoms; or 2) hydrogen;
$R^9$, in each occurrence, is selected independently from an alkyl, a haloalkyl, an aryl, or a heteroaryl comprising at least one heteroatom selected from —O— or $>N$—; any of which having up to 10 carbon atoms; and
$R^{10}$, in each occurrence, is selected independently from: 1) an alkyl, an aryl, or a heterocyclyl comprising at least one heteroatom selected from —O— or $>N$—, any of which having up to 10 carbon atoms; or 2) hydrogen.

Yet a further aspect of this invention encompasses compounds and compositions comprising these compounds, wherein the compounds have the following formula:

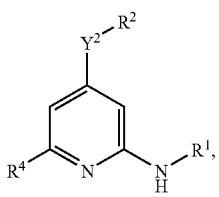

(III-Dii)

or a salt, including a pharmaceutically acceptable or a non-pharmaceutically acceptable salt, a prodrug, a diastereomeric mixture, an enantiomer, a tautomer, or a racemic mixture thereof;
wherein:
$Y^2$ is $>CH_2$;
$R^1$ is a substituted or unsubstituted aryl or heterocyclyl having up to 10 carbon atoms, wherein the heterocyclyl comprises a nitrogen atom directly bonded to the pyridine ring and optionally comprising at least one additional heteroatom selected from —O—, $>N$— or —S—;
$R^2$ is a substituted or an unsubstituted aryl having up to 10 carbon atoms;
$R^4$ is a substituted or an unsubstituted aryl, heterocyclyl, or heteroaryl, any of which having up to 10 carbon atoms, wherein the heterocyclyl and heteroaryl comprise at least one heteroatom selected from —O—, $>N$—, or —S—;
$R^1$ and $R^2$ are optionally substituted with at least one group independently selected from: 1) alkoxy, haloalkoxy, haloalkyl, —COR$^9$, —CON(R$^8$)$_2$, —SO$_2$R$^9$, — or —SO$_2$N(R$^8$)$_2$, any of which having up to 10 carbon atoms; or 2) halogen;
$R^4$ is optionally substituted with at least one group independently selected from: 1) haloalkoxy, —COR$^{10}$, —CON(R$^8$)$_2$, —SO$_2$R$^{10}$, or —SO$_2$N(R$^{10}$)$_2$, any of which having up to 10 carbon atoms; 2) halogen; or 3) hydroxyl; and
$R^8$, in each occurrence, is selected independently from: 1) an alkyl, a haloalkyl, or an aryl having up to 10 carbon atoms; or 2) hydrogen;
$R^9$, in each occurrence, is selected independently from an alkyl, a haloalkyl, an aryl, or a heteroaryl comprising at least one heteroatom selected from —O— or $>N$—; any of which having up to 10 carbon atoms; and
$R^{10}$, in each occurrence, is selected independently from: 1) an alkyl, an aryl, or a heterocyclyl comprising at least one heteroatom selected from —O— or $>N$—, any of which having up to 10 carbon atoms; or 2) hydrogen.

DEFINITIONS

The groups defined for various symbols used in the formulas of this disclosure, as well as the optional substituents defined on those groups, may be defined in the detailed manner as follows. Further definitions related to the more biological aspects of this disclosure are provided further below in their respective sections. Unless otherwise specified, any recitation of the number of carbon atoms in a particular group is intended to refer to the unsubstituted "base" group, therefore, any substituent recited on a base group is described by its own definition, including its own limitation of the number of carbon atoms. Unless otherwise specified, all structural isomers of a given structure, for example, all enantiomers, diasteriomers, and regioisomers, are included within this definition.

The terms 'halogen' or 'halo' includes fluorine, chlorine, bromine, or iodine.

The term 'alkyl' group is used to refer to both linear and branched alkyl groups. Exemplary alkyl groups include, but are not limited to, methyl, ethyl, propyl, butyl, pentyl, pentyl, hexyl, heptyl, octyl, nonyl, or decyl, and the like. Unless otherwise specified, an alkyl group has from 1 to 10 carbon atoms. Also unless otherwise specified, all structural isomers of a given structure, for example, all enantiomers and all diasteriomers, are included within this definition. For example, unless otherwise specified, the term propyl is meant to include n-propyl and iso-propyl, while the term butyl is meant to include n-butyl, iso-butyl, t-butyl, sec-butyl, and so forth.

'Haloalkyl' is a group containing at least one halogen and an alkyl portion as define above. Unless otherwise specified, all structural isomers of a given structure, for example, all enantiomers and all diasteriomers, are included within this definition. Exemplary haloalkyl groups include fluoromethyl, chloromethyl, fluoroethyl, chloroethyl, trilfluoromethyl, and the like. Unless otherwise specified, a haloalkyl group has from 1 to 10 carbon atoms.

'Acyl' is used to refer to an H—CO— or an alkyl-CO— group, where alkyl is defined herein. Exemplary acyl groups include, but are not limited to, acetyl, propionyl, iso-propionyl, tert-butionyl, and the like.

'Cycloalkyl' group refers to a cyclic alkyl group which may be mono or polycyclic. Exemplary cycloalkyl groups include cyclopropyl, cyclobutyl, cyclopentyl, cyclohexyl, cycloheptyl, cyclooctyl, cyclononyl, and cyclodecyl. Unless otherwise specified, a cycloalkyl group has from 3 to 10 carbon atoms.

'Alkoxy' refers to an —O(alkyl) group, where alkyl is as defined above. Therefore, unless otherwise specified, all isomers of a given structure are included within a definition. Exemplary alkyl groups include methoxy, ethoxy, n-propoxy, iso-propoxy, n-butoxy, iso-butoxy, t-butoxy, and the like. Unless otherwise specified, an alkoxy group has from 1 to 10 carbon atoms.

'Alkoxyalkyl' is an alkyl group with an alkoxy substituent, where alkoxy and alkyl groups are as defined above. Exemplary alkoxyalkyl groups include methoxymethyl, methoxyethyl, methoxypropyl, ethoxymethyl, ethoxyethyl, propoxymethyl, isopropoxymethyl isopropoxyethyl, isopropoxypropyl, t-butoxymethyl, t-butoxyethyl, t-butoxypropyl, and the like. Unless otherwise specified, an alkoxyalkyl group typically has from 1 to 10 carbon atoms.

'Haloalkoxy' is an alkoxy group with a halo substituent, where alkoxy and halo groups are as defined above. Exemplary haloalkoxy groups include chloromethoxy, trichloroethoxy, trifloroethoxy, perfluoroethoxy (—OCF$_2$CF$_3$), trifluoro-t-butoxy, hexafluoro-t-butoxy, perfluoro-t-butoxy (—OC(CF$_3$)$_3$), and the like. Unless otherwise specified, an haloalkoxy group typically has from 1 to 10 carbon atoms.

'Alkylthio' refers to an —S(alkyl) goup, where alkyl group is as defined above. Exemplary alkyl groups include methylthio, ethylthio, propylthio, butylthio, iso-propylthio, iso-butylthio, and the like. Unless otherwise specified, an alkylthio group typically has from 1 to 10 carbon atoms.

'Alkylsulfonyl' refers to a —SO$_2$(alkyl) group, where alkyl group is as defined above. Exemplary alkylsulfonyl groups include methylsulfonyl, ethylsulfonyl and the like. Unless otherwise specified, an alkylsulfonyl group typically has from 1 to 10 carbon atoms.

'Alkenyl' is an unsaturated aliphatic group containing a C=C double bond. Exemplary alkenyl groups include ethenyl, propenyl, prop-1-enyl, isopropenyl, butenyl, but-1-enyl, isobutenyl, pentenyl, pent-1-enyl, hexenyl, pent-2-enyl, 2-methyl-but-2-ene, 2-methyl-pent-2-enyl and the like. Unless otherwise specified, an alkenyl group typically has from 2 to 10 carbon atoms.

'Alkynyl' is an unsaturated aliphatic group containing a C≡C triple bond. Exemplary alkynyl groups include ethenyl, propynyl, prop-1-ynyl, butynyl, butaynyl and the like. Unless otherwise specified, an alkynyl group typically has from 2 to 10 carbon atoms.

'Aryl' is optionally substituted monocylic or polycyclic aromatic ring system of 6 to 14 carbon atoms. Exemplary groups include phenyl, naphthyl and the like. Unless otherwise specified, an aryl group typically has from 6 to 14 carbon atoms.

'Aralkyl' is an alkyl group with an aryl substituent, where alkyl and aryl groups are as defined above. Exemplary aralkyl groups include, but are not limited to, benzyl, phenethyl (for example, 2-phenethyl), phenylpropyl (for example, 3-phenylpropyl), naphthylmethyl (for example, 1-naphthylmethyl and 2-naphthylmethyl) and the like.

'Heteroaryl' is an aromatic monocyclic or polycyclic ring system of 4 to 10 carbon atoms, having at least one heteroatom or heterogroup selected from —O—, >N—, —S—, >NH or NR, and the like, wherein R is a substituted or unstubstituted alkyl, aryl, or acyl, as defined herein. In this aspect, >NH or NR are considered to be included when the heteroatom or heterogroup can be >N—. Exemplary heteroaryl groups include as pyrazinyl, isothiazolyl, oxazolyl, pyrazolyl, pyrrolyl, pyridazinyl, thienopyrimidyl, furanyl, indolyl, isoindolyl, benzo[1,3]dioxolyl, 1,3-benzoxathiole, quinazolinyl, pyridyl, thiophenyl and the like. Unless otherwise specified, a heteroaryl group typically has from 4 to 10 carbon atoms. Moreover, the heteroaryl group can be bonded to the pyrimidine core structure at a ring carbon atom, or, if applicable for a N-substituted heteroaryl such as pyrrole, can be bonded to the pyrimidine core structure through the heteroatom that is formally deprotonated to form a direct heteroatom-pyrimdine ring bond.

'Heterocyclyl' is a non-aromatic saturated monocyclic or polycyclic ring system of 3 to 10 member having at least one heteroatom or heterogroup selected from —O—, >N—, —S—, >SO$_2$, or >CO. Exemplary heterocyclyl groups include aziridinyl, pyrrolidinyl, piperdinyl, piperazinyl, morpholinyl, thiomorpholinyl, thiazolidinyl, 1,3-dioxolanyl, 1,4-dioxanyl and the like. Unless otherwise specified, a heterocyclyl group typically has from 2 to 10 carbon atoms. A heterocyclyl group can be bonded through a heteroatom that is formally deprotonated or a heterocyclyl group can be bonded through a carbon atom of the heterocyclyl group.

'Carboxylic acid or its derivatives' may be amides or esters. Exemplary carboxylic acid groups include CONH$_2$, CONHMe, CONMe$_2$, CONHEt, CONEt$_2$, CONHPh, COOH, COOCH$_3$, COOC$_2$H$_5$ or COOC$_3$H$_7$.

'Cyclic amines' means nitrogen containing heteroaryl or heterocyclyl groups.

Accordingly, in one aspect, compounds according to the present invention can have the formula:

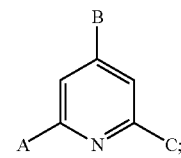

or a salt, including a pharmaceutically acceptable or a non-pharmaceutically acceptable salt, a prodrug, a diastereomeric mixture, an enantiomer, a tautomer, or a racemic mixture thereof, wherein:

A is selected from A1, A2, or A3, wherein:

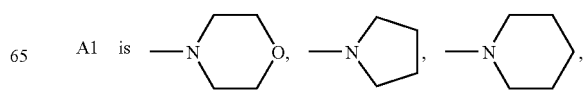

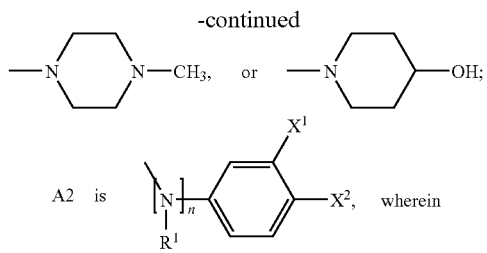

n is 0 or 1;
R¹ is H or CH₃;
X¹ is H, F, Cl, OCH₃, SO₂H, SO₂CH₃, SO₂NHCH₃, C(O)NHCH₃,, C(O)NHCH₂CH₃,, C(O)CH₃, C(O)N(CH₃)₂, C(O)(NC₄H₈), or C(O)(NC₅H₁₀); and
X² is H, F, CH₃, OCH₃, OCF₃, SO₂CH₃, SO₂NHCH₃, C(O)CH₃, C(O)(morpholino), or X¹ and X² form a fused 1,3-dioxolane ring; and

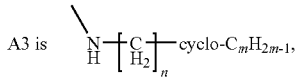

wherein n is 0 or 1; and m is 5, 6, 7, or 8;
B is selected from A1, A2, A3, or I; and
C is selected from A1, A2, A3, —H, —Cl, or —Br.

In another aspect, compounds according to the present invention can have the formula:

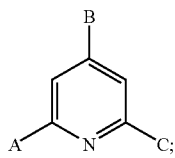

or a salt, including a pharmaceutically acceptable or a non-pharmaceutically acceptable salt, a prodrug, a diastereomeric mixture, an enantiomer, a tautomer, or a racemic mixture thereof, wherein:
B is selected from A1, A2', or A3, wherein:

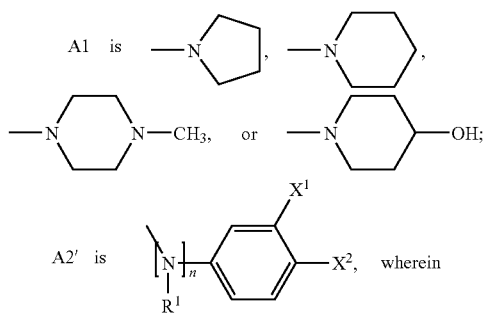

n is 0 or 1;
R¹ is H or CH₃;
X¹ is H, F, Cl, OCH₃, SO₂H, SO₂CH₃, SO₂NHCH₃, C(O)NHCH₃,, C(O)NHCH₂CH₃,, C(O)CH₃, C(O)N(CH₃)₂, C(O)(NC₄H8), or C(O)(NC₅H₁₀); and
X2 is H, F, CH₃, OCH₃, OCF₃, SO₂CH₃, SO₂NHCH₃, C(O)CH₃, C(O)(morpholino), or X¹ and X² form a fused 1,3-dioxolane ring;
wherein X¹ and X² are not concurrently H; and

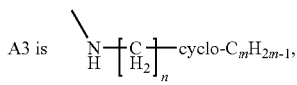

wherein n is 0 or 1; and m is 5, 6, 7, or 8;
A and C are selected independently from A1, A2', A3, —H, —Cl, or —Br.

In a further aspect, compounds according to the present invention can have the formula:

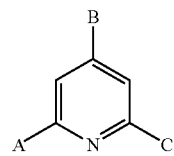

according to claim 2;
or a salt, including a pharmaceutically acceptable or a non-pharmaceutically acceptable salt, a prodrug, a diastereomeric mixture, an enantiomer, a tautomer, or a racemic mixture thereof, wherein:
B is selected from

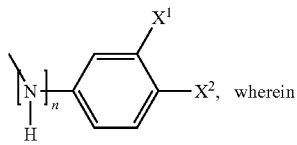

n is 0 or 1;
X¹ is H, F, OCH₃, or SO₂CH₃; and
X² is H, F, OCH₃, or SO₂CH₃, or X¹ and X² form a fused 1,3-dioxolane ring;
wherein X¹ and X² are not concurrently H; and
A and C are selected independently from —H or —Cl.

In yet another aspect, compounds according to the present invention can have the formula:

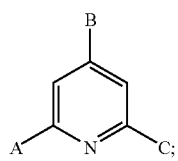

or a salt, including a pharmaceutically acceptable or a non-pharmaceutically acceptable salt, a prodrug, a diastereomeric mixture, an enantiomer, a tautomer, or a racemic mixture thereof, wherein:

A and C are selected independently from A1, A2', or A3, wherein:

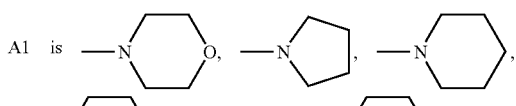

n is 0 or 1;
R¹ is H or CH₃;
X¹ is H, F, Cl, OCH₃, SO₂H, SO₂CH₃, SO₂NHCH₃, C(O)NHCH₃, C(O)NHCH₂CH₃, C(O)CH₃, C(O)N(CH₃)₂, C(O)(NC₄H₈), or C(O)(NC₅H₁₀); and
X² is H, F, CH3, OCH₃, OCF₃, SO₂CH₃, SO₂NHCH₃, C(O)CH₃, C(O)(morpholino), or X¹ and X² form a fused 1,3-dioxolane ring;
wherein X¹ and X² are not concurrently H; and

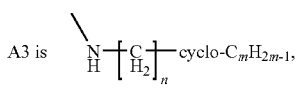

wherein n is 0 or 1; and m is 5, 6, 7, or 8; and
B is selected from A1, A2', A3, —H or —I.

In still a further aspect, compounds according to the present invention can have the formula:

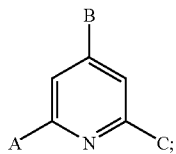

or a salt, including a pharmaceutically acceptable or a non-pharmaceutically acceptable salt, a prodrug, a diastereomeric mixture, an enantiomer, a tautomer, or a racemic mixture thereof, wherein:

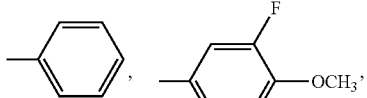

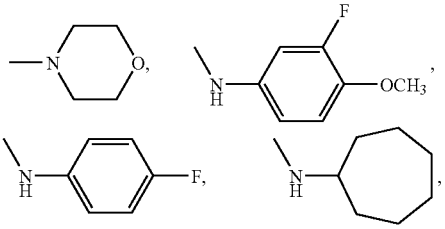

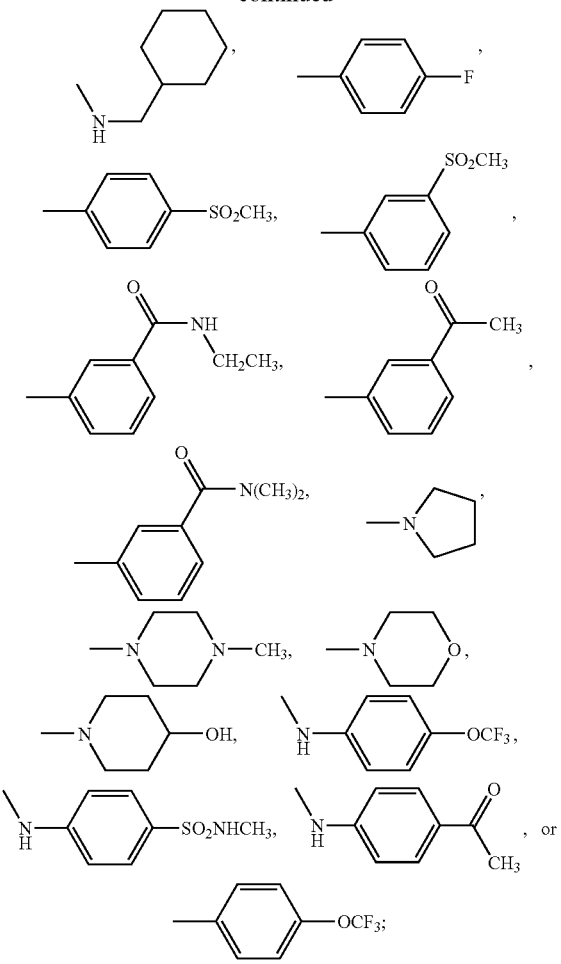

B is selected from

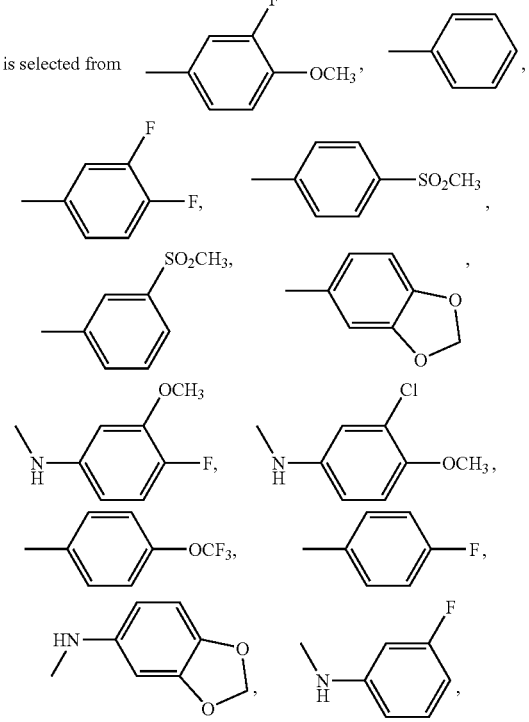

-continued
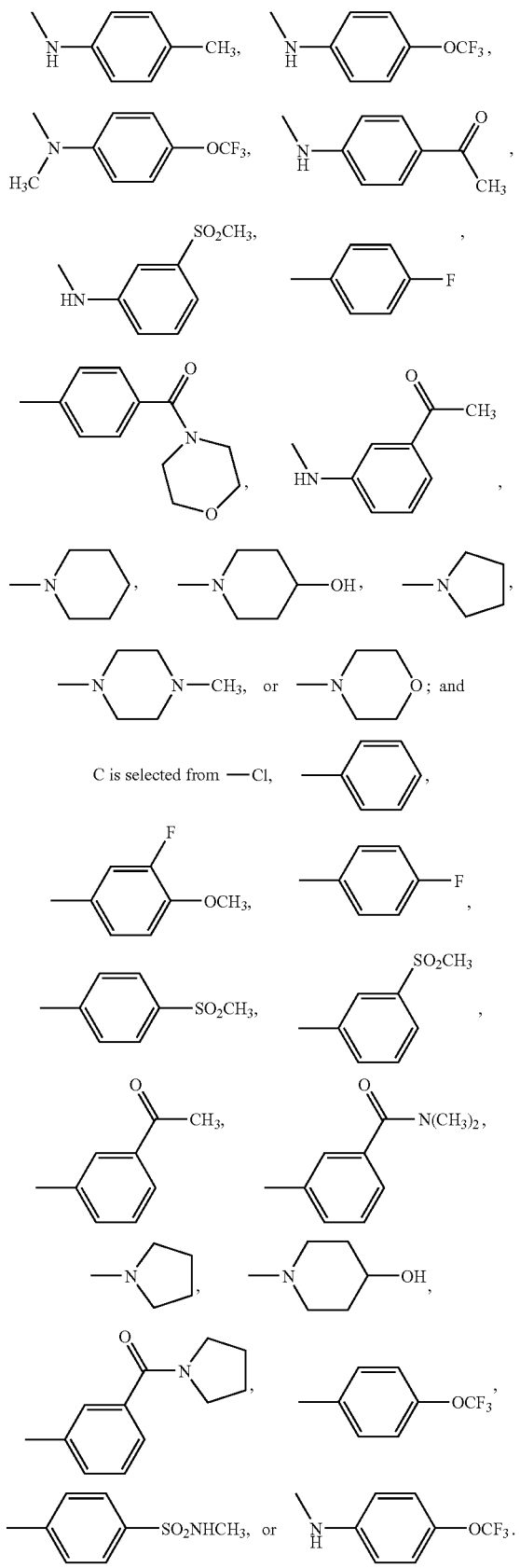
In another aspect, compounds according to the present invention can have the formula:
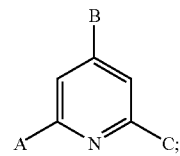
or a salt, including a pharmaceutically acceptable or a non-pharmaceutically acceptable salt, a prodrug, a diastereomeric mixture, an enantiomer, a tautomer, or a racemic mixture thereof, wherein:
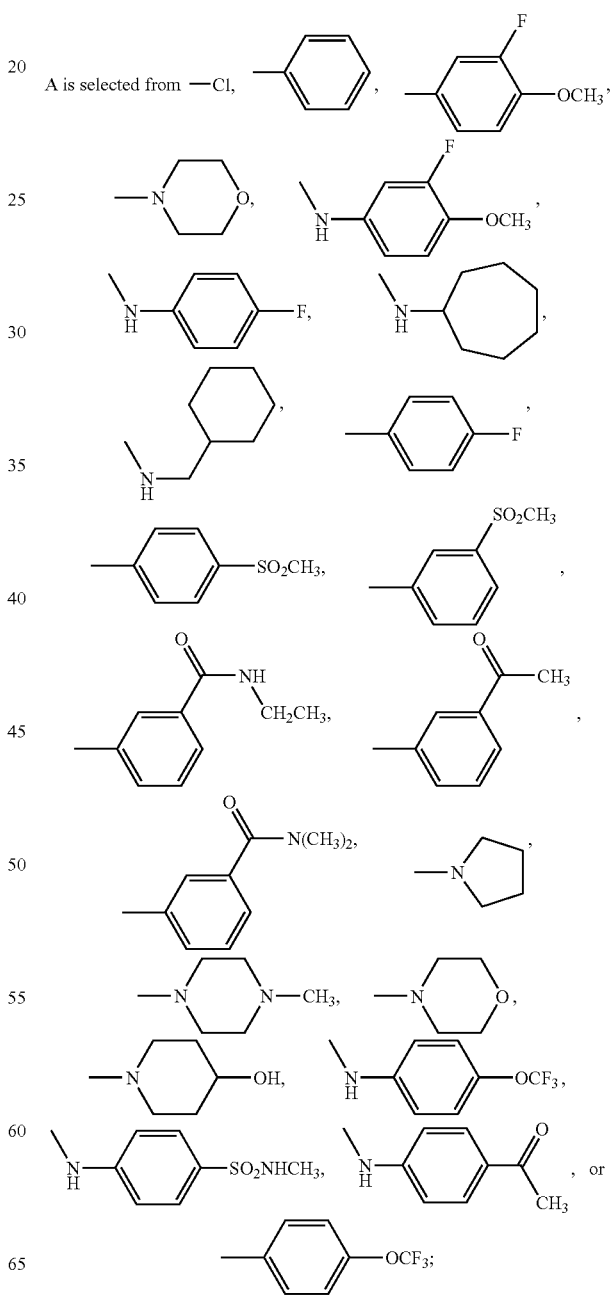

B is selected from

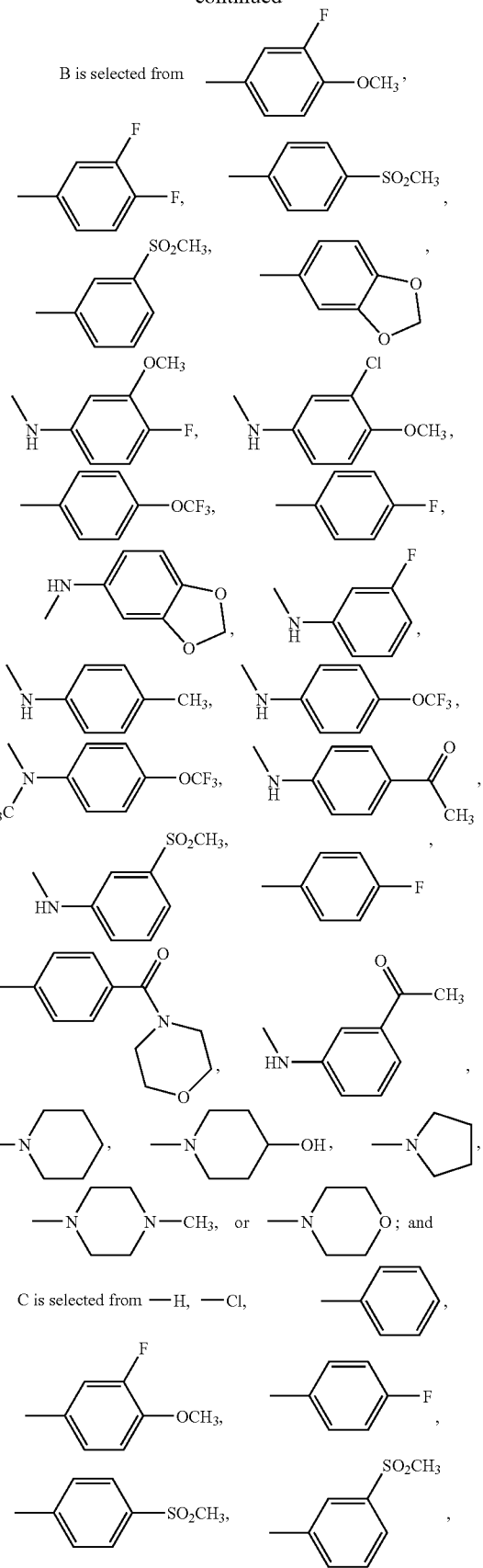

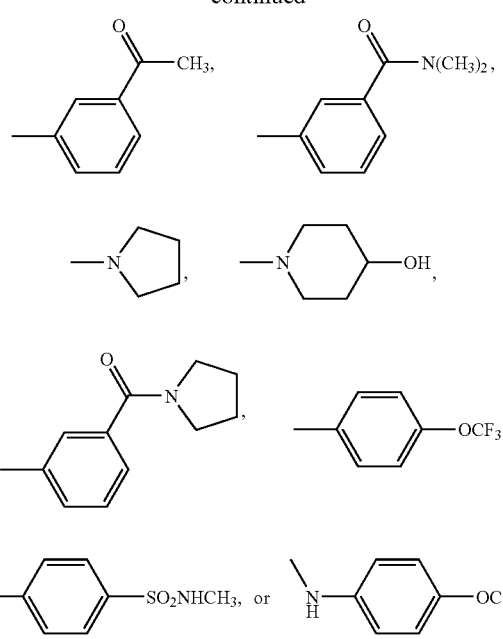

In a different further aspect, compounds according to the present invention can have the formula:

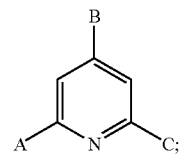

or a salt, including a pharmaceutically acceptable or a non-pharmaceutically acceptable salt, a prodrug, a diastereomeric mixture, an enantiomer, a tautomer, or a racemic mixture thereof, wherein:

A is selected from A1 or A2, and

B and C are selected from A2, wherein:

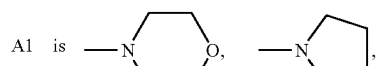

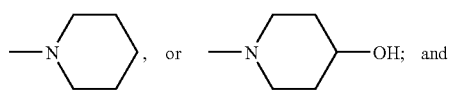

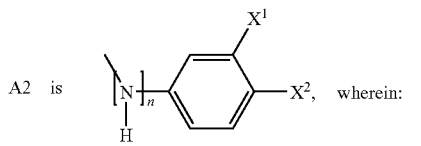

n is 0 or 1;

$X^1$ is H, $SO_2CH_3$, $C(O)CH_3$, or $C(O)(NC_4H8)$; and $X^2$ is H, F, $OCF_3$, $SO_2CH_3$, $SO_2NHCH_3$, or $C(O)CH_3$.

Compounds of the present invention can, in yet another aspect, have the formula

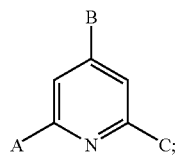

or a salt, including a pharmaceutically acceptable or a non-pharmaceutically acceptable salt, a prodrug, a diastereomeric mixture, an enantiomer, a tautomer, or a racemic mixture thereof, wherein:

A is selected from, phenyl, 4-fluorophenyl, morpholinyl, 4-hydroxypiperidinyl, 4-(trifluoromethoxy)anilino, 4-(N-methylsulfamoyl)anilino, 4-acetylanilino;

B is selected from 4-(methylsulfonyl)phenyl, 4-(trifluoromethoxy)phenyl, 4-fluorophenyl, 4-(trifluoromethoxy)anilino, 4-acetylanilino, 3-acetylanilino, piperidinyl, 4-hydroxypiperidinyl, pyrrolidinyl, or morpholinyl; and C is selected from phenyl, 4-fluorophenyl, 3-(methylsulfonyl)phenyl, 3-acetylphenyl, 3-(pyrrolidin-1-ylcarbonyl)phenyl, 4-(trifluoromethoxy)phenyl, or 4-(N-methylsulfamoyl)phenyl.

Accordingly, in one aspect, compounds according to the present invention can have the formula:

or a salt, including a pharmaceutically acceptable or a non-pharmaceutically acceptable salt, a prodrug, a diastereomeric mixture, an enantiomer, a tautomer, or a racemic mixture thereof, wherein:

A is selected from H, —Cl, phenyl, 3-fluoro-4-methoxyphenyl, morpholinyl, 3-fluoro-4-methoxyanilino, 4-fluoroanilino, cycloheptylamino, 4-hydroxypiperidinyl, pyrrolidinyl, cyclohexylmethylamino, 4-fluorophenyl, 4-(methylsulfonyl)phenyl, 3-(methylsulfonyl)phenyl, 3-acetylphenyl, 3-(N,N-dimethylcarbamoyl)phenyl, -continued
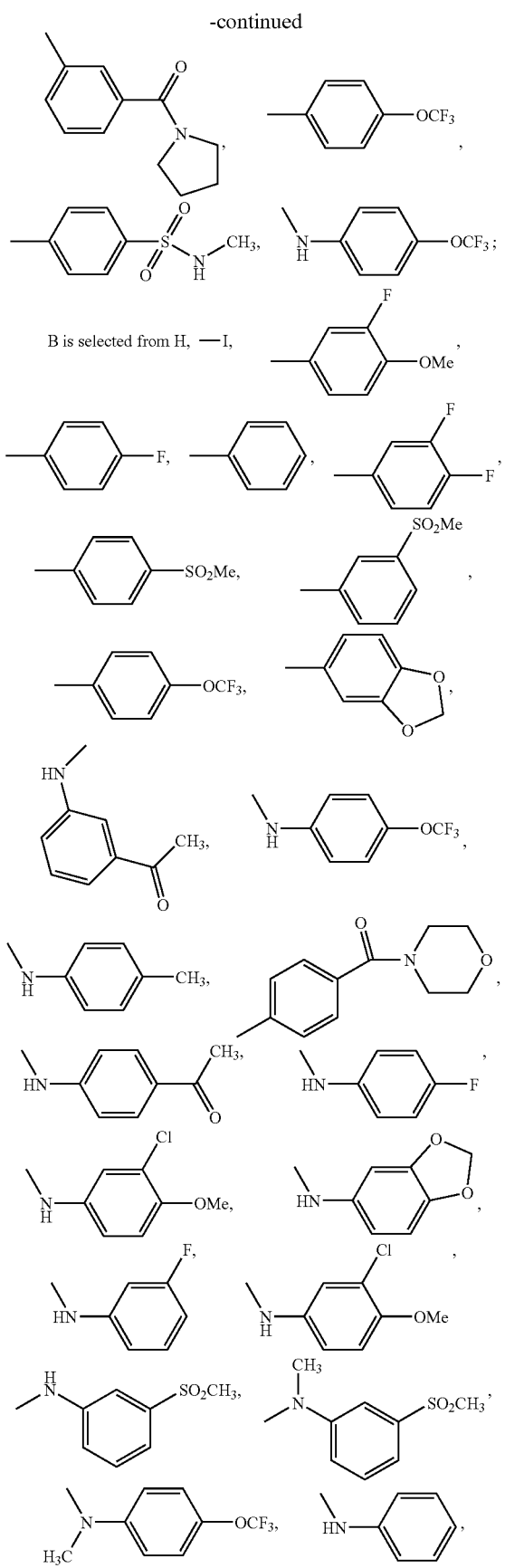
B is selected from H, —I,
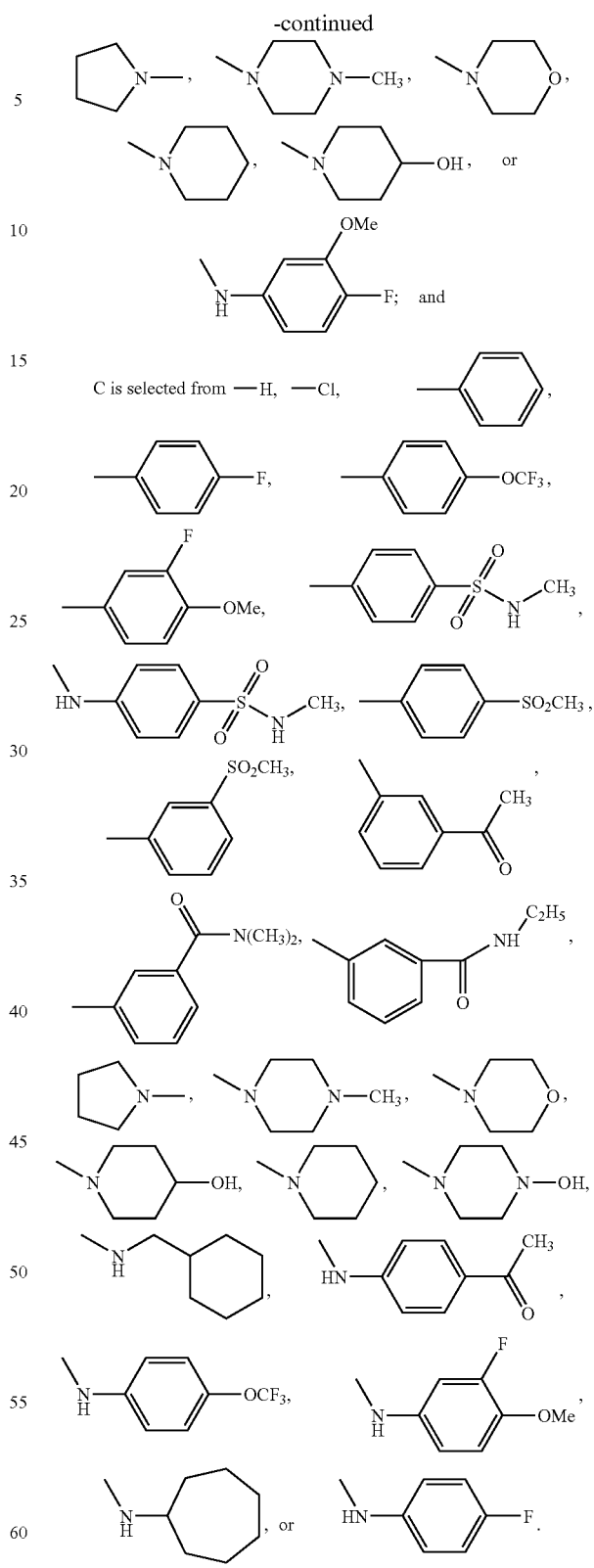
C is selected from —H, —Cl,
According to another aspect of this invention, and consistent with the definitions provided herein, the present invention also provides for compounds of the following general structure III:

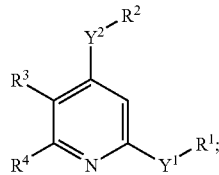

(III)

wherein within structure III, the substituents $Y^1$, $R^1$, $Y^2$, $R^2$, $R^3$ and $R^4$ can be selected according to the following listings, wherein each substituent is defined in Table 1.

The substituent $Y^1$ and $Y^2$ can be selected independently from $Y^A$, $Y^B$, $Y^C$, $Y^D$, $Y^E$, $Y^F$, $Y^G$, $Y^H$, $Y^I$, or $Y^J$.

The substituent $R^1$ can be selected independently from $R^{1A}$, $R^{1B}$, $R^{1C}$, $R^{1D}$, $R^{1E}$, $R^{1F}$, $R^{1G1}$, $R^{1G2}$, $R^{1G3}$, $R^{1G4}$, $R^{1G5}$, $R^{1H1}$, $R^{1H2}$, $R^{1H3}$, $R^{1H4}$, $R^{1H5}$, $R^{1I}$, $R^{1J}$, $R^{1K}$, $R^{1L}$, $R^{1M}$, $R^{1N}$, $R^{1O}$, $R^{1P}$, $R^{1Q}$.

The substituent $R^2$ can be selected independently from $R^{2A}$, $R^{2B}$, $R^{2C}$, $R^{2D}$, $R^{2E}$, $R^{2F}$, $R^{2G1}$, $R^{2G2}$, $R^{2G3}$, $R^{2G4}$, $R^{2G5}$, $R^{2H1}$, $R^{2H2}$, $R^{2H3}$, $R^{2H4}$, $R^{2H5}$, $R^{2I}$, $R^{2J}$, $R^{2K}$, $R^{2L}$, $R^{2M}$, $R^{2N}$, $R^{2O}$, $R^{2P}$, or $R^{2Q}$.

Alternatively, the moieties $Y^1R^1$ and $Y^2R^2$ can be selected independently from $YR^A$, $YR^B$, $YR^C$, $YR^D$, $YR^E$, $YR^F$, $YR^G$, $YR^H$, $YR^I$, $YR^J$, or $YR^K$, as defined herein.

The substituent $R^3$ can be selected independently from $R^{3A}$, $R^{3B}$, $R^{3C}$, $R^{3D}$, $R^{3E}$, $R^{3F}$, $R^{3G}$, $R^{3H}$, $R^{3I}$, $R^{3J}$, $R^{3K}$, $R^{3L}$, $R^{3M}$, $R^{3N}$, $R^{3O}$, $R^{3P1}$, $R^{3P2}$, $R^{3P3}$, $R^{3P4}$, $R^{3P5}$, $R^{3Q1}$, $R^{3Q2}$, $R^{3Q3}$, $R^{3Q4}$, $R^{3Q5}$, $R^{3R}$, $R^{3S}$, $R^{3T}$, $R^{3U}$, or $R^{3V}$.

The substituent $R^4$ can be selected independently from $R^{4A}$, $R^{4B}$, $R^{4C}$, $R^{4D}$, $R^{4E}$, $R^{4F}$, $R^{4G}$, $R^{4H}$, $R^{4I}$, $R^{4J}$, $R^{4K}$, $R^{4L}$, $R^{4M}$, $R^{4N}$, $R^{4O}$, $R^{4P1}$, $R^{4P2}$, $R^{4P3}$, $R^{4P4}$, $R^{4P5}$, $R^{4Q1}$, $R^{4Q2}$, $R^{4Q3}$, $R^{4Q4}$, $R^{4Q5}$, $R^{4R}$, $R^{4S}$, $R^{4T}$, $R^{4U}$, or $R^{4V}$.

The substituents recited above are defined as follows, consistent with the definitions provided herein.

TABLE 1

| | Substituent abbreviations |
|---|---|
| $Y^A$ | $>NR^5$, wherein $R^5$ is selected from $R^{5A}$ through $R^{5G}$ |
| $Y^B$ | —(CH$_2$)n—, n is 0 to 3 |
| $Y^C$ | —(CH$_2$)p(CH=CH)(CH$_2$)q—, p and q are independently 0 to 3 |
| $Y^D$ | $>CR^5R^6$, wherein $R^5$ is selected from $R^{5A}$ through $R^{5G}$, and $R^6$ is selected from $R^{6A}$ through $R^{6G}$ |
| $Y^E$ | —(CH$_2$)p(C≡C)(CH$_2$)q—, p and q are independently 0 to 3 |
| $Y^F$ | —O— |
| $Y^G$ | >CO |
| $Y^H$ | —S— |
| $Y^I$ | >SO |
| $Y^J$ | >SO$_2$ |
| $YR^A$ | saturated or unsaturated carbocyclic or N-heterocyclic ring having up to 10 carbon atoms |
| $YR^B$ | saturated or unsaturated carbocyclic or N-heterocyclic ring having up to 10 carbon atoms, further comprising —O— in the ring |
| $YR^C$ | saturated or unsaturated carbocyclic or N-heterocyclic ring having up to 10 carbon atoms, further comprising —S— in the ring |
| $YR^D$ | saturated or unsaturated carbocyclic or N-heterocyclic ring having up to 10 carbon atoms, further comprising >N— in the ring |
| $YR^E$ | saturated or unsaturated carbocyclic or N-heterocyclic ring having up to 10 carbon atoms, further comprising >SO$_2$ in the ring |
| $YR^F$ | saturated or unsaturated carbocyclic or N-heterocyclic ring having up to 10 carbon atoms, further comprising >CO in the ring |
| $YR^G$ | substituted or an unsubstituted morpholinyl |
| $YR^H$ | substituted or an unsubstituted piperazinyl |
| $YR^I$ | substituted or an unsubstituted thiomorpholinyl |
| $YR^J$ | substituted or an unsubstituted pyrrolidinyl |
| $YR^K$ | substituted or an unsubstituted piperidinyl |
| $R^{1A}$, $R^{2A}$ | Alkyl having up to 10 carbon atoms |
| $R^{1B}$, $R^{2B}$ | Aryl having up to 10 carbon atoms |
| $R^{1C}$, $R^{2C}$ | Alkoxyalkyl having up to 10 carbon atoms |
| $R^{1D}$, $R^{2D}$ | Cycloalky having up to 10 carbon atoms |
| $R^{1E}$, $R^{2E}$ | —COR$^9$ having up to 10 carbon atoms |
| $R^{1F}$, $R^{2F}$ | Aralkyl having up to 10 carbon atoms |
| $R^{1G1}$, $R^{2G1}$ | Heterocyclyl having up to 10 carbon atoms, comprising —O— |
| $R^{1G2}$, $R^{2G2}$ | Heterocyclyl having up to 10 carbon atoms, comprising >N— |
| $R^{1G3}$, $R^{2G3}$ | Heterocyclyl having up to 10 carbon atoms, comprising —S— |
| $R^{1G4}$, $R^{2G4}$ | Heterocyclyl having up to 10 carbon atoms, comprising >SO$_2$ |
| $R^{1G5}$, $R^{2G5}$ | Heterocyclyl having up to 10 carbon atoms, comprising >CO |
| $R^{1H1}$, $R^{2H1}$ | Heteroaryl having up to 10 carbon atoms, comprising —O— |
| $R^{1H2}$, $R^{2H2}$ | Heteroaryl having up to 10 carbon atoms, comprising >N— |
| $R^{1H3}$, $R^{2H3}$ | Heteroaryl having up to 10 carbon atoms, comprising —S— |
| $R^{1H4}$, $R^{2H4}$ | Heteroaryl having up to 10 carbon atoms, comprising >SO$_2$ |
| $R^{1H5}$, $R^{2H5}$ | Heteroaryl having up to 10 carbon atoms, comprising >CO |
| $R^{1I}$, $R^{2I}$ | hydrogen |
| $R^{1J}$, $R^{2J}$ | Halogen |
| $R^{1K}$, $R^{2K}$ | Cyano |
| $R^{1L}$, $R^{2L}$ | Hydroxyl |
| $R^{1M}$, $R^{2M}$ | Alkoxy having up to 10 carbon atoms |
| $R^{1N}$, $R^{2N}$ | Alkenyl having up to 10 carbon atoms |
| $R^{1O}$, $R^{2O}$ | Alkynyl having up to 10 carbon atoms |

TABLE 1-continued

Substituent abbreviations

| | |
|---|---|
| $R^{1P}, R^{2P}$ | —$CO_2R^5$ having up to 10 carbon atoms |
| $R^{1Q}, R^{2Q}$ | —$COR^5$ having up to 10 carbon atoms |
| $R^{3A}, R^{4A}$ | Alkyl having up to 10 carbon atoms |
| $R^{3B}, R^{4B}$ | Alkenyl having up to 10 carbon atoms |
| $R^{3C}, R^{4C}$ | Alkynyl having up to 10 carbon atoms |
| $R^{3D}, R^{4D}$ | Alkoxy having up to 10 carbon atoms |
| $R^{3E}, R^{4E}$ | Cycloalkyl having up to 10 carbon atoms |
| $R^{3F}, R^{4F}$ | Haloalkyl having up to 10 carbon atoms |
| $R^{3G}, R^{4G}$ | Haloalkoxy having up to 10 carbon atoms |
| $R^{3H}, R^{4H}$ | Alkylthio having up to 10 carbon atoms |
| $R^{3I}, R^{4I}$ | Alkylsufonyl having up to 10 carbon atoms |
| $R^{3J}, R^{4J}$ | Aryl having up to 10 carbon atoms |
| $R^{3K}, R^{4K}$ | —$CO_2R^5$ having up to 10 carbon atoms |
| $R^{3L}, R^{4L}$ | —$COR^5$ having up to 10 carbon atoms |
| $R^{3M}, R^{4M}$ | —$NR^5R^6$ having up to 10 carbon atoms |
| $R^{3N}, R^{4N}$ | —$SO_2NR^5R^6$ having up to 10 carbon atoms |
| $R^{3O}, R^{4O}$ | —$SO_3R^5$ having up to 10 carbon atoms |
| $R^{3P1}, R^{4P1}$ | Heterocyclyl having up to 10 carbon atoms, comprising —O— |
| $R^{3P2}, R^{4P2}$ | Heterocyclyl having up to 10 carbon atoms, comprising >N— |
| $R^{3P3}, R^{4P3}$ | Heterocyclyl having up to 10 carbon atoms, comprising —S— |
| $R^{3P4}, R^{4P4}$ | Heterocyclyl having up to 10 carbon atoms, comprising >$SO_2$ |
| $R^{3P5}, R^{4P5}$ | Heterocyclyl having up to 10 carbon atoms, comprising >CO |
| $R^{3Q1}, R^{4Q1}$ | Heteroaryl having up to 10 carbon atoms, comprising —O— |
| $R^{3Q2}, R^{4Q2}$ | Heteroaryl having up to 10 carbon atoms, comprising >N— |
| $R^{3Q3}, R^{4Q3}$ | Heteroaryl having up to 10 carbon atoms, comprising —S— |
| $R^{3Q4}, R^{4Q4}$ | Heteroaryl having up to 10 carbon atoms, comprising >$SO_2$ |
| $R^{3Q5}, R^{4Q5}$ | Heteroaryl having up to 10 carbon atoms, comprising >CO |
| $R^{3R}, R^{4R}$ | Hydrogen |
| $R^{3S}, R^{4S}$ | Halogen |
| $R^{3T}, R^{4T}$ | Hydroxyl |
| $R^{3U}, R^{4U}$ | Cyano |
| $R^{3V}, R^{4V}$ | $Y^1R^1$, independent of the selection of $Y^1R^1$ |
| $R^{5A}, R^{6A}$ | Alkyl having up to 10 carbon atoms |
| $R^{5B}, R^{6B}$ | Aryl having up to 10 carbon atoms |
| $R^{5C}, R^{6C}$ | Alkoxyalkyl having up to 10 carbon atoms |
| $R^{5D1}, R^{6D1}$ | Heteroaryl having up to 10 carbon atoms, comprising —O— |
| $R^{5D2}, R^{6D2}$ | Heteroaryl having up to 10 carbon atoms, comprising >N— |
| $R^{5D3}, R^{6D3}$ | Heteroaryl having up to 10 carbon atoms, comprising —S— |
| $R^{5D4}, R^{6D4}$ | Heteroaryl having up to 10 carbon atoms, comprising >$SO_2$ |
| $R^{5D5}, R^{6D5}$ | Heteroaryl having up to 10 carbon atoms, comprising >CO |
| $R^{5E}, R^{6E}$ | Cycloalkyl having up to 10 carbon atoms |
| $R^{5F1}, R^{6F1}$ | Heterocyclyl having up to 10 carbon atoms, comprising —O— |
| $R^{5F2}, R^{6F2}$ | Heterocyclyl having up to 10 carbon atoms, comprising >N— |
| $R^{5F3}, R^{6F3}$ | Heterocyclyl having up to 10 carbon atoms, comprising —S— |
| $R^{5F4}, R^{6F4}$ | Heterocyclyl having up to 10 carbon atoms, comprising >$SO_2$ |
| $R^{5F5}, R^{6F5}$ | Heterocyclyl having up to 10 carbon atoms, comprising >CO |
| $R^{5G}, R^{6G}$ | Hydrogen |

In these selections, unless otherwise indicated, the number of carbon atoms on the substituents refers to the carbon atoms on the base chemical moiety, and does not include the carbon atoms in any optional substituent. Again, unless otherwise indicated, any substituents are limited in size by the carbon atoms listed in the definitions of the subsitutents.

In these selections, the following features are applicable. Any carbocyclic ring, N-heterocyclic ring, morpholinyl, piperazinyl, thiomorpholinyl, pyrrolidinyl, or piperidinyl can be optionally substituted with at least one hydroxyl, halogen, alkyl, alkoxy, haloalkyl, cycloalkyl, aryl, or heteroaryl any of which having up to 10 carbon atoms. Further any when a piperazinyl moiety is present in the substituted pyridine compound, the piperazine nitrogen is optionally substituted by an alkyl, a cycloalkyl, an acyl, a haloalkyl, an alkoxyalkyl, $SO_2R^7$, $SO_2NR^7{}_2$, or $CO_2R^7$, wherein $R^7$ is independently selected from: a) an alkyl or an aryl having up to 8 carbon atoms; or b) hydrogen.

Any of the $R^1$, $R^2$, $R^5$, or $R^6$ moieties that do not constitute hydrogen, halogen, cyano, or hydroxyl (for example, $R^{1A}$ through $R^{1H}$, $R^{1M}$ through $R^{1Q}$, $R^{2A}$ through $R^{2H}$, $R^{2M}$ through $R^{2Q}$, $R^{3A}$ through $R^{3Q}$ and $R^{3V}$, $R^{4A}$ through $R^{4Q}$ and $R^{4V}$, $R^{5A}$ through $R^{5F}$, and $R^{6A}$ through $R^{6F}$) can be optionally substituted with at least one group independently selected from: 1) alkyl; alkoxy; alkylthio; haloalkyl; cycloalkyls; aryl; heterocyclyl or heteroaryl comprising at least one heteroatom or heterogroup selected from —O—, >N—, —S—, >$SO_2$, or >CO; haloalkoxy; —$OCH_2O$—; —$OCOR^9$; $N(R^8)_2$; —$COR^9$; —$CON(R^8)_2$; —$(CH_2)_bCO_2R^8$ wherein b is an integer from 0 to 3; —$OCO(CH_2)_bCO_2R^{10}$ wherein b is an integer from 0 to 3; —$SO_2R^9$; —$NHSO_2R^9$; or —$SO_2N(R^8)_2$; any of which having up to 10 carbon atoms; or 2) hydrogen, halogen, hydroxyl, or cyano. In these groups, $R^8$, in each occurrence, is independently: 1) an alkyl; a haloalkyl; a heterocyclyl or heteroaryl comprising at least one heteroatom or heterogroup selected from —O—, >N—, —S—, >$SO_2$, or >CO; or an aryl having up to 10 carbon atoms; or 2) hydrogen. Further, in these moieties, $R^9$, in each occurrence, is independently an alkyl; a haloalkyl; an aryl; or a heterocyclyl or heteroaryl comprising at least one heteroatom or heterogroup selected from —O—, >N—, —S—, >$SO_2$, or >CO; having up to 8 carbon atoms; wherein $R^9$ is optionally substituted with: 1) an alkyl, an alkoxy, a carboxylic acid, or a carboxylic acid ester, any of which having up to 8 carbon atoms; 2) halogen; or 3) hydroxyl; and Any of the $R^3$ or $R^4$ moieties that do not constitute hydrogen, halogen, cyano, or hydroxyl can be optionally substituted with at least one group independently selected from: 1) alkyl, alkoxy, haloalkyl, haloalkoxy, cycloalkyl, aryl, heteroaryl, heterocyclyl, alkenyl, alkynyl, —$COR^{10}$, —$CO_2R^{10}$, —$CON(R^{10})_2$, —$SO_2R^{10}$, —$SO_2N(R^{10})_2$, or —$N(R^{10})_2$, any of which having up to 10 carbon atoms; 2) halogen; or 3) hydroxyl; wherein $R^{10}$, in each occurrence, is independently: 1) an alkyl or an aryl having up to 10 carbon atoms; or hydrogen.

Accordingly, this invention encompasses compounds of the formula III-E, corresponding to formula III in which $Y^2$ is >$NR^5$, and formula III-F, corresponding to formula III in which $Y^1$ is >$NR^5$.

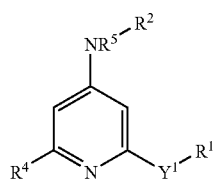

(III-E)

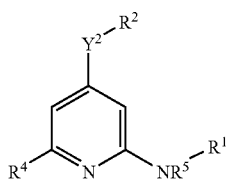

(III-F)

According to the various aspects of this invention, $Y^1$, $R^1$, $R^2$, $R^4$, and $R^5$ of formulas III-E and $Y^2$, $R^1$, $R^2$, $R^4$, and $R^5$ III-F can be selected according to the listings of substituent definitions provided herein.

In one aspect, the novel compound of the present invention encompasses any one of the following compounds, and any combination of the following compounds, including salts of the following compounds: [2-(3-methanesulfonyl-phenyl)-6-morpholin-4-yl-pyridin-4-yl]-(4-trifluoromethoxy-phenyl)-amine; 1-{3-[6-morpholin-4-yl-4-(4-trifluoromethoxy-phenylamino)-pyridin-2-yl]-phenyl}-ethanone; (2,6-di-phenyl-pyridin-4-yl)-(4-trifluoromethoxy-phenyl)-amine; [2,6-bis-(3-fluoro-phenyl)-pyridin-4-yl]-(4-trifluoromethoxy-phenyl)-amine; 1-[3-(4-hydroxy-6'-phenyl-3,4,5,6-tetrahydro-2H-[1,2']bipyridinyl-4'-ylamino)-phenyl]-ethanone; [2-(4-fluoro-phenyl)-6-morpholin-4-yl-pyridin-4-yl]-(4-trifluoromethoxy-phenyl)-amine; {3-[6-morpholin-4-yl-4-(4-trifluoromethoxy-phenylamino)-pyridin-2-yl]-phenyl}-pyrrolidin-1-yl-methanone; [6'-(4-Fluoro-phenyl)-3,4,5,6-tetrahydro-2H-[1,4']bipyridinyl-2'-yl]-(4-trifluoromethoxy-phenyl)-amine; (6'-Phenyl-3,4,5,6-tetrahydro-2H-[1,4']bipyridinyl-2'-yl)-(4-trifluoromethoxy-phenyl)-amine; [6'-(3-Methanesulfonyl-phenyl)-3,4,5,6-tetrahydro-2H-[1,4']bipyridinyl-2'-yl]-(4-trifluoromethoxy-phenyl)-amine; 4-[6'-(4-Fluoro-phenyl)-3,4,5,6-tetrahydro-2H-[1,4']bipyridinyl-2'-ylamino]-N-methyl-benzenesulfonamide; 1-[4-(4-Hydroxy-6'-phenyl-3,4,5,6-tetrahydro-2H-[1,4']bi-pyridinyl-2'-ylamino)-phenyl]-ethanone; [6-(3-Methanesulfonyl-phenyl)-4-morpholin-4-yl-pyridin-2-yl]-(4-trifluoromethoxy-phenyl)-amine; N-Methyl-4-[4-morpholin-4-yl-6-(4-trifluoromethoxy-phenylamino)-pyridin-2-yl]-benzene-sulfonamide; 1-[4-(2-morpholin-4-yl-6-phenyl-pyridin-4-ylamino)-phenyl]-ethanone; 6'-(4-fluoro-phenyl)-4'-(4-trifluoromethoxy-phenylamino)-3,4,5,6-tetrahydro-2H-[1,2']bipyridinyl-4-ol; 1-[4-(4-Hydroxy-6'-phenyl-3,4,5,6-tetrahydro-2H-[1,2']bipyridinyl-4'-ylamino)-phenyl]-ethanone; 6'-(4-fluoro-phenyl)-4'-(4-methanesulfonyl-phenyl)-3,4,5,6-tetrahydro-2H-[1,2'] bipyridinyl-4-ol; N-Methyl-4-[4-pyrrolidin-1-yl-6-(4-trifluoromethoxy-phenyl)-pyridin-2-ylamino]-benzene-sulfonamide; and the like, including any pharmaceutically acceptable salt, a prodrug, a diastereomeric mixture, an enantiomer, a tautomer, or a racemic mixture thereof.

Representative compounds in accordance with the present invention are presented in Table 2. This table is not intended to be exclusive of the compounds of the present invention, but rather exemplary of the heterocyclic compounds that are encompassed by this invention.

TABLE 2

Representative compounds in accordance with the present invention

| Cmpd. No. | Structure | Name |
| --- | --- | --- |
| B1 | 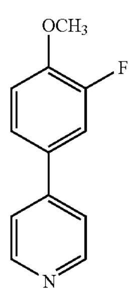 | 4-(3-fluoro-4-methoxy-phenyl)-pyridine; |

TABLE 2-continued

Representative compounds in accordance with the present invention

| Cmpd. No. | Structure | Name |
| --- | --- | --- |
| B2 | 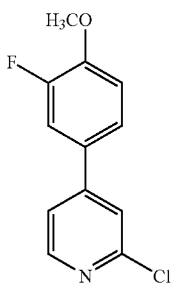 | 2-chloro-4-(3-fluoro-4-methoxy-phenyl)-pyridine; |
| B3 | 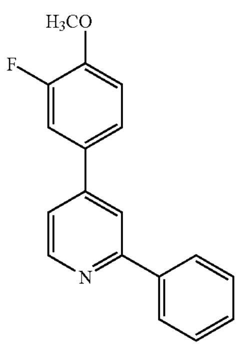 | 4-(3-fluoro-4-methoxy-phenyl)-2-phenyl-pyridine; |
| B5 | 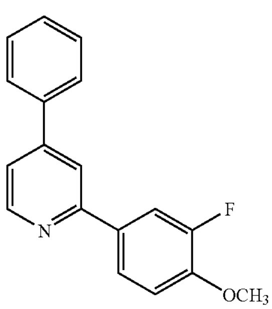 | 2-(3-fluoro-4-methoxy-phenyl)-4-phenyl-pyridine; |
| B6 | 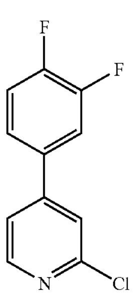 | 2-chloro-4-(3,4-difluoro-phenyl)-pyridine; |

TABLE 2-continued

Representative compounds in accordance with the present invention

| Cmpd. No. | Structure | Name |
|---|---|---|
| B7 | 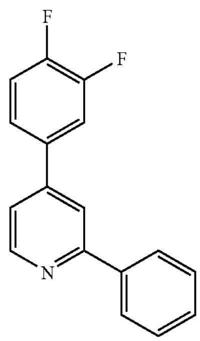 | 4-(3,4-difluoro-phenyl)-2-phenyl-pyridine; |
| B8 | 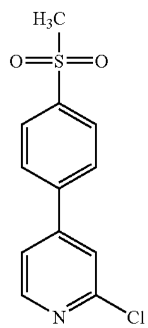 | 2-chloro-4-(4-methanesulfonyl-phenyl)-pyridine; |
| B9 | 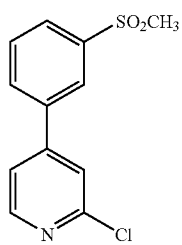 | 2-chloro-4-(3-methanesulfonyl-phenyl)-pyridine; |
| B10 | 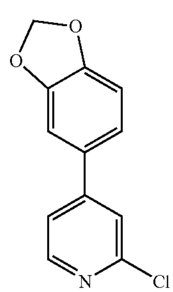 | 4-benzo[1,3]dioxol-5-yl-2-chloro-pyridine; |
| B11 | 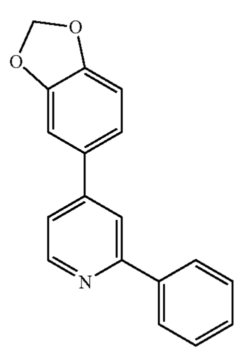 | 4-benzo[1,3]dioxol-5-yl-2-phenyl-pyridine; |

TABLE 2-continued

Representative compounds in accordance with the present invention

| Cmpd. No. | Structure | Name |
|---|---|---|
| B12 | 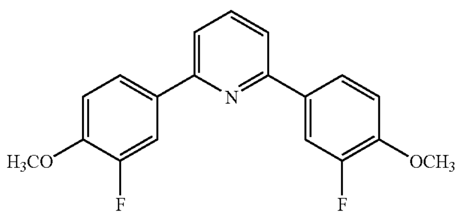 | 2,6-bis-(3-fluoro-4-methoxy-phenyl)-pyridine; |
| B13 | 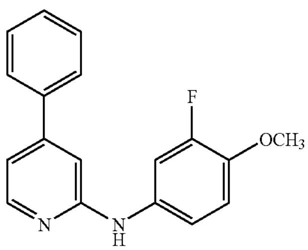 | (3-fluoro-4-methoxy-phenyl)-(4-phenyl-pyridin-2-yl)-amine; |
| B14 | 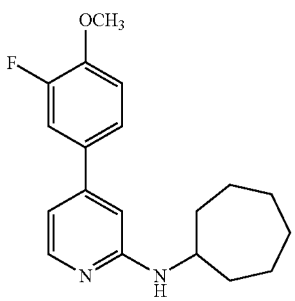 | cycloheptyl-[4-(3-fluoro-4-methoxy-phenyl)-pyridin-2-yl]-amine; |
| B15 | 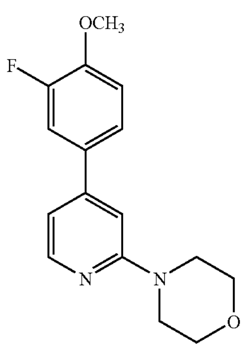 | [4-(3-fluoro-4-methoxy-phenyl)-pyridin-2-yl]-morpholine; |
| B16 | 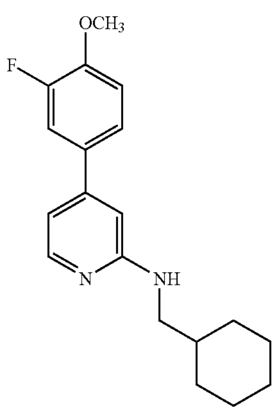 | cyclohexylmethyl-[4-(3-fluoro-4-methoxy-phenyl)-pyridine-2-yl]-amine; |

TABLE 2-continued

Representative compounds in accordance with the present invention

| Cmpd. No. | Structure | Name |
|---|---|---|
| B17 | 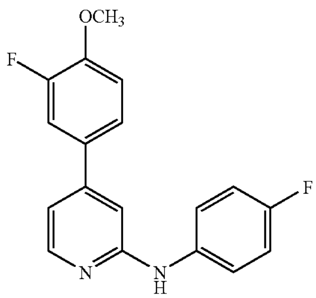 | [4-(3-fluoro-4-methoxy-phenyl)-pyridin-2-yl]-(4-fluoro-phenyl)-amine; |
| B18 | 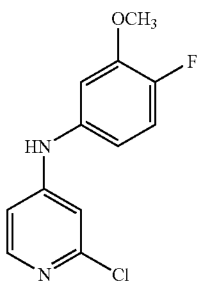 | (2-Chloro-pyridin-4-yl)-(4-fluoro-3-methoxy-phenyl)-amine; |
| B19 | 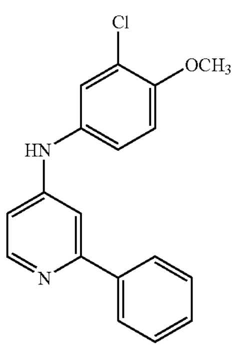 | (3-chloro-4-methoxy-phenyl)-(2-phenyl-pyridin-4-yl)-amine; |
| B20 | 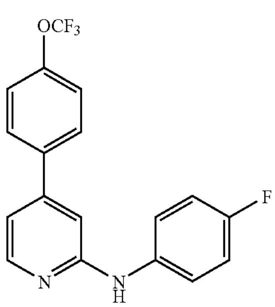 | (4-fluoro-phenyl)-[4-(4-trifluoromethoxy-phenyl)-pyridin-2-yl]-amine; |

TABLE 2-continued

Representative compounds in accordance with the present invention

| Cmpd. No. | Structure | Name |
|---|---|---|
| B22 | 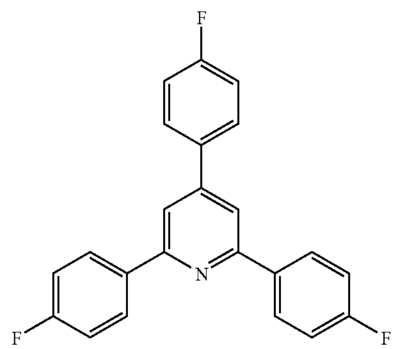 | 2,4,6-tris-(4-fluoro-phenyl)-pyridine; |
| B23 | 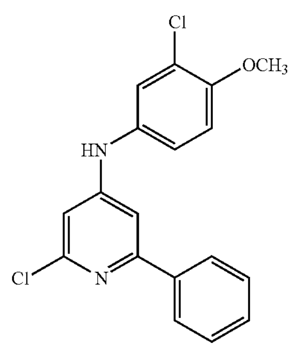 | (3-chloro-4-methoxy-phenyl)-(2-chloro-6-phenyl-pyridin-4-yl)-amine; |
| B24 | 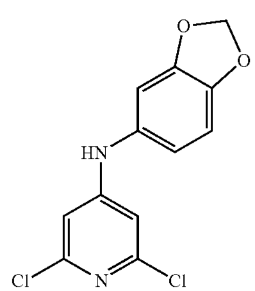 | benzo[1,3]dioxol-5-yl-(2,6-dichloro-pyridin-4-yl)-amine; |
| B25 | 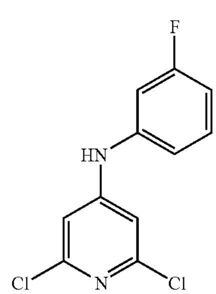 | (2,6-dichloro-pyridin-4-yl)-(3-fluoro-phenyl)-amine; |

TABLE 2-continued

Representative compounds in accordance with the present invention

| Cmpd. No. | Structure | Name |
| --- | --- | --- |
| B26 | 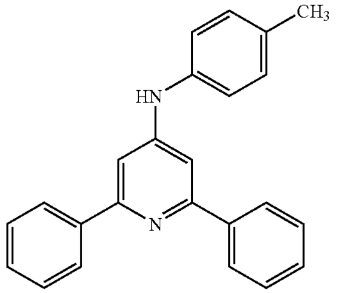 | (2,6-diphenyl-pyridin-4-yl)-p-tolyl-amine; |
| B27 | 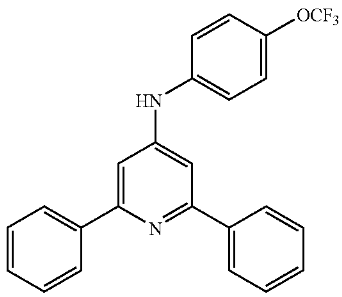 | (2,6-diphenyl-pyridin-4-yl)-(4-trifluoromethoxy-phenyl)-amine; |
| B28 | 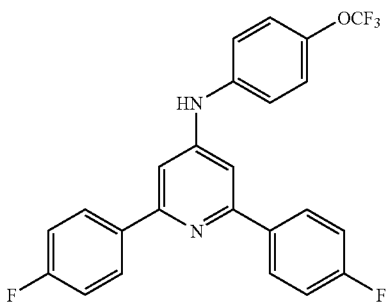 | [2,6-bis-(3-fluoro-phenyl)-pyridin-4-yl]-(4-trifluoromethoxy-phenyl)-amine; |
| B29 | 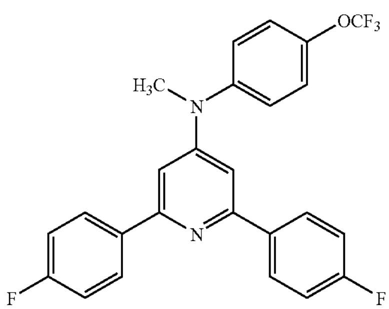 | [2,6-bis-(4-fluoro-phenyl)-pyridin-4-yl]-methyl-(4-trifluoromethoxy-phenyl)-amine; |
| B30 | 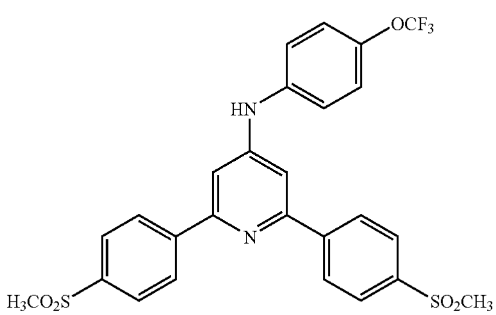 | [2,6-bis-(4-methanesulfonyl-phenyl)-pyridin-4-yl]-(4-trifluoromethoxy-phenyl)-amine; |

TABLE 2-continued

Representative compounds in accordance with the present invention

| Cmpd. No. | Structure | Name |
| --- | --- | --- |
| B31 | 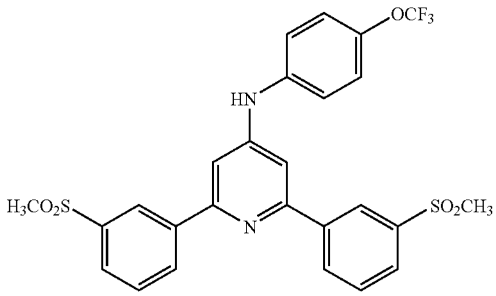 | [2,6-bis-(3-(methylsulfonyl)-phenyl)-pyridin-4-yl]-(4-trifluoromethoxy-phenyl)-amine; |
| B32 | 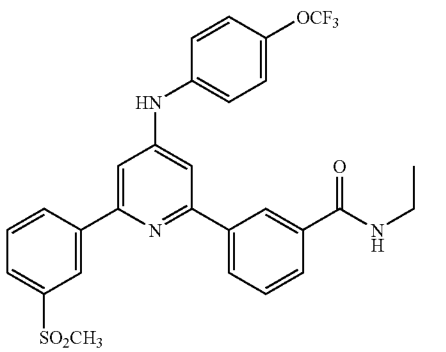 | N-ethyl-3-[6-(3-methanesulfonyl-phenyl)-4-(4-trifluoromethoxy-phenylamino)-pyridin-2-yl]-benzamide; |
| B33 | 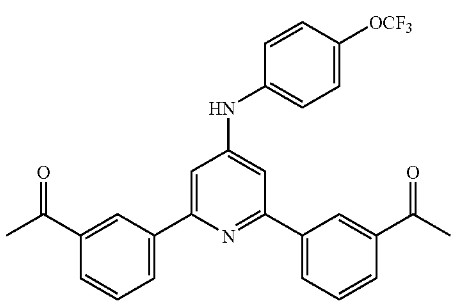 | 1-{3-[6-(3-acetyl-phenyl)-4-(4-trifluoromethoxy-phenylamino)-pyridin-2-yl]-phenyl}-ethanone; |
| B34 | 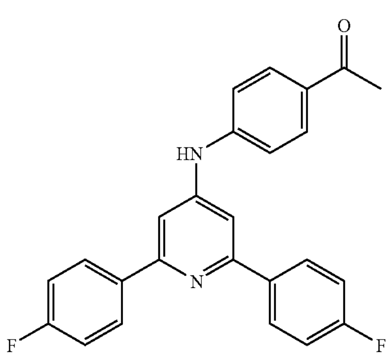 | 1-{4-[2,6-bis-(4-fluoro-phenyl)-pyridin-4-ylamino]-phenyl}-ethanone; |

TABLE 2-continued

Representative compounds in accordance with the present invention

| Cmpd. No. | Structure | Name |
| --- | --- | --- |
| B35 | 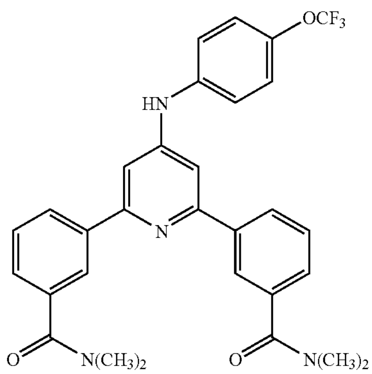 | [2,6-bis-(3-N,N-dimethyl-benzamide)-pyridin-2-yl]-(4-trifluoromethoxy-phenyl)-amine; |
| B36 | 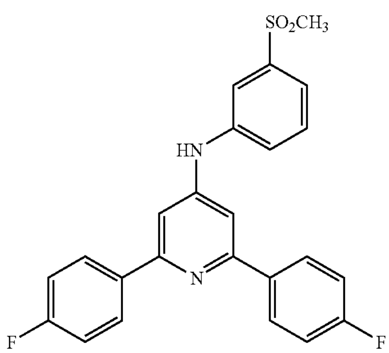 | 3-{2,6-bis-(4-fluoro-phenyl)-pyridin-4-ylamino]-benzenethiol; compound with acetic acid methyl ester; |
| B37 | 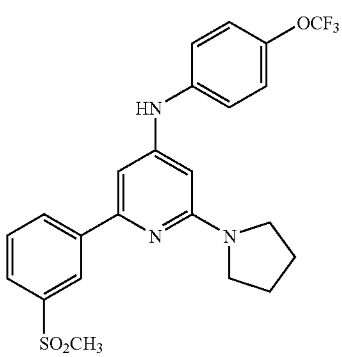 | thiocarbonic acid O-methyl ester S-{3-[6-pyrrolidin-1-yl-4-(4-trifluoromethoxy-phenylamino)-pyridin-2-yl]-phenyl}ester; |
| B38 | 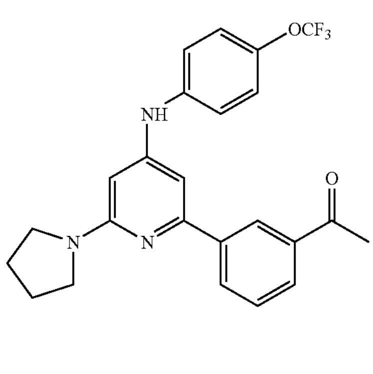 | 1-{3-[6-pyrrolidin-1-yl-4-(4-trifluoromethoxy-phenylamino)-pyridin-2-yl]-phenyl}-ethanone; |

TABLE 2-continued

Representative compounds in accordance with the present invention

| Cmpd. No. | Structure | Name |
|---|---|---|
| B39 | 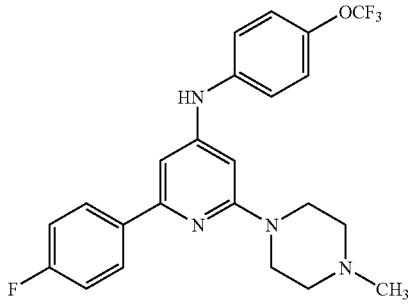 | [2-(4-fluoro-phenyl)-6-(4-methyl-piperazin-1-yl)-pyridin-4-yl]-(4-trifluoromethoxy-phenyl)-amine; |
| B40 | 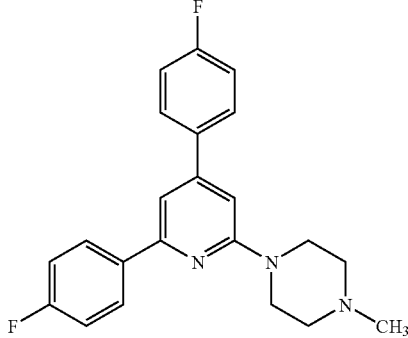 | 1-[4,6-bis-(4-fluoro-phenyl)-pyridin-2-yl]-4-methyl-piperazine; |
| B41 | 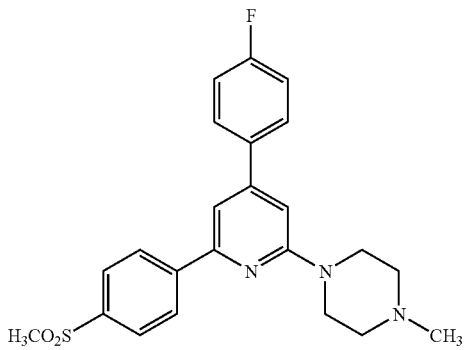 | 1-[4-(4-fluoro-phenyl)-6-(4-methanesulfonyl-phenyl)-pyridin-2-yl]-4-methyl-piperazine; |
| B42 | 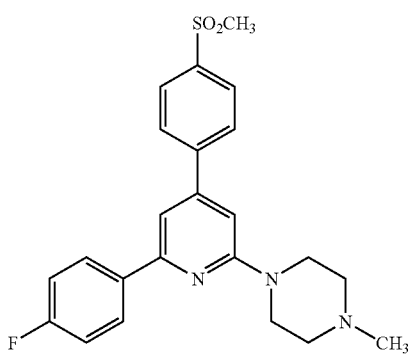 | 1-[6-(4-fluoro-phenyl)-4-(4-methanesulfonyl-phenyl)-pyridin-2-yl]-4-methyl-piperazine; |

TABLE 2-continued

Representative compounds in accordance with the present invention

| Cmpd. No. | Structure | Name |
| --- | --- | --- |
| B43 | 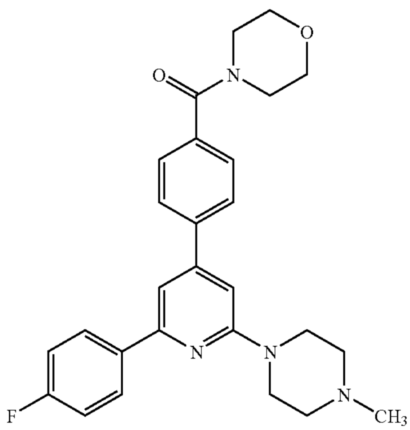 | {4-[2-(4-fluoro-phenyl)-6-(4-methyl-piperazin-1-yl)-pyridin-4-yl]-phenyl}-morpholin-4-yl-methanone; |
| B44 | 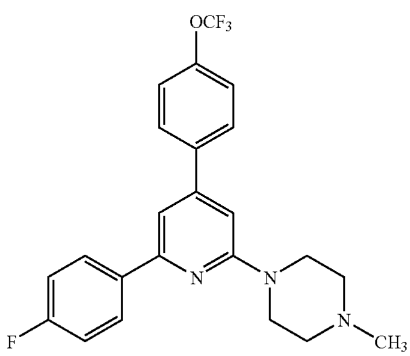 | 1-[6-(4-fluoro-phenyl)-4-(4-trifluoromethoxy-phenyl)-pyridin-2-yl]-4-methyl-piperazine; |
| B45 | 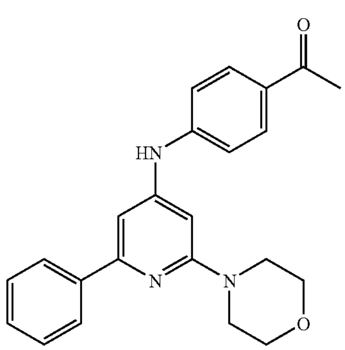 | [4-(2-morpholin-4-yl-6-phenyl-pyridin-4-ylamino)-phenyl]-ethanone; |
| B46 | 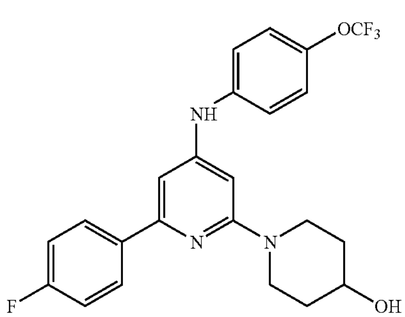 | 6'-(4-fluoro-phenyl)-4'-(4-trifluoromethoxy-phenylamino)-3,4,5,6-tetrahydro-2H-[1,2']bipyridinyl-4-ol; |

TABLE 2-continued

Representative compounds in accordance with the present invention

| Cmpd. No. | Structure | Name |
|---|---|---|
| B47 | 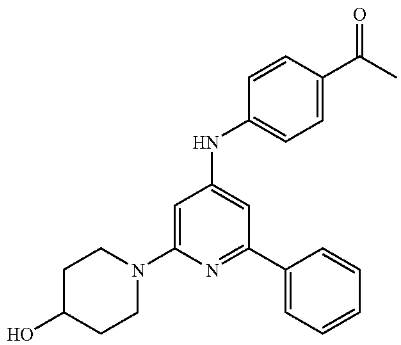 | 1-[4-(4-hydroxy-6'-phenyl-3,4,5,6-tetrahydro-2H-[1,2']bipyridinyl-4'-ylamino)-phenyl]-ethanone; |
| B48 | 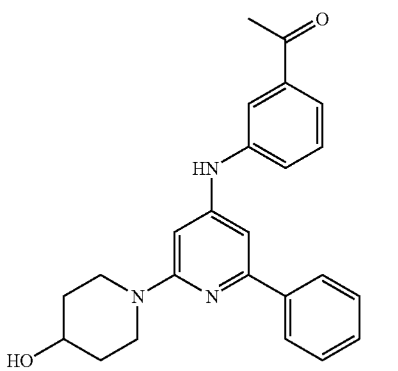 | 1-[3-(4-hydroxy-6'-phenyl-3,4,5,6-tetrahydro-2H-[1,2']bipyridinyl-4'-ylamino)-phenyl]-ethanone; |
| B49 | 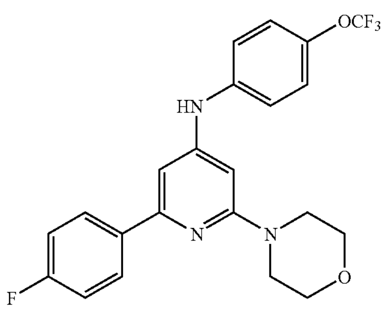 | [2-(4-fluoro-phenyl)-6-morpholin-4-yl-pyridin-4-yl]-(4-trifluoromethoxy-phenyl)-amine; |
| B50 | 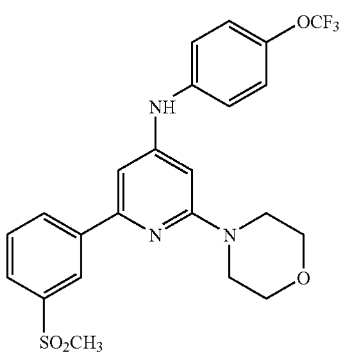 | [2-(3-methanesulfonyl-phenyl)-6-morpholin-4-yl-pyridin-4-yl]-(4-trifluoromethoxy-phenyl)-amine; |

TABLE 2-continued

Representative compounds in accordance with the present invention

| Cmpd. No. | Structure | Name |
|---|---|---|
| B51 | 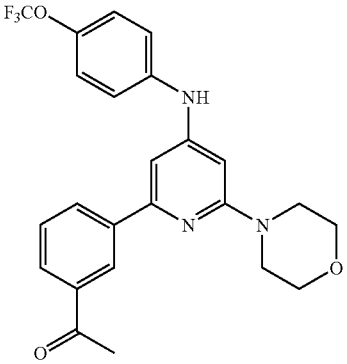 | 1-{3-[6-morpholin-4-yl-4-(4-trifluoromethoxy-phenylamino)-pyridin-2-yl]-phenyl}-ethanone; |
| B52 | 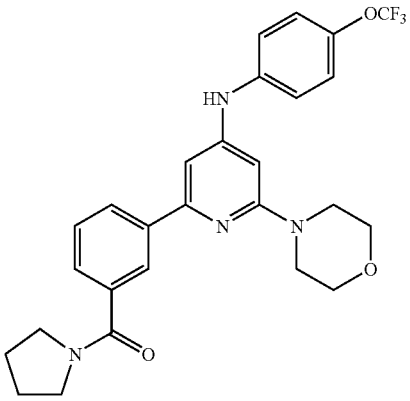 | {3-[6-morpholin-4-yl-4-(4-trifluoromethoxy-phenylamino)-pyridin-2-yl]-phenyl}-pyrrolidin-1-yl-methanone; |
| B53 | 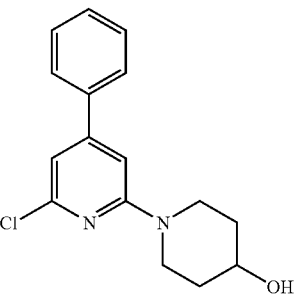 | 6'-chloro-4'-phenyl-3,4,5,6-tetrahydo-2H-[1,2']bipyridinyl-4-ol; |
| B54 | 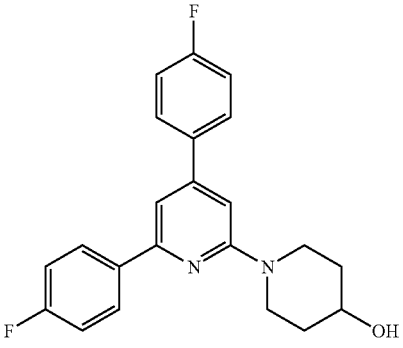 | 4',6'-bis-(4-fluoro-phenyl)-3,4,5,6-tetrahydro-2H-[1,2']bipyridinyl-4-ol; |

TABLE 2-continued

Representative compounds in accordance with the present invention

| Cmpd. No. | Structure | Name |
|---|---|---|
| B55 | 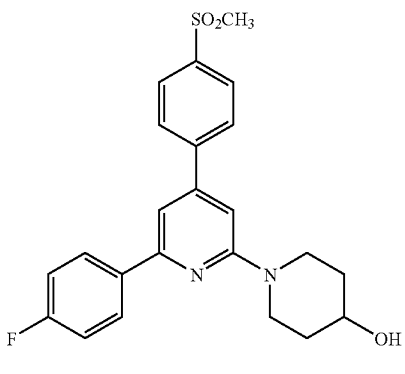 | 6'-(4-fluoro-phenyl)-4'-(4-methanesulfonyl-phenyl)-3,4,5,6-tetrahydro-2H-[1,2']bipyridinyl-4-ol; |
| B56 | 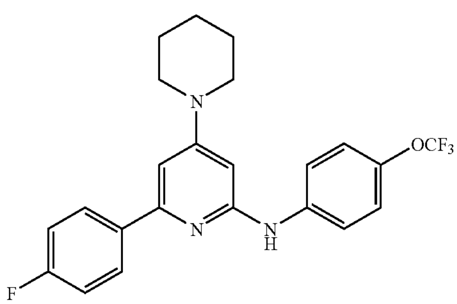 | [6'-(4-fluoro-phenyl)-3,4,5,6-tetrahydro-2H-[1,4']bipyridinyl-2'-yl]-(4-trifluoromethoxy-phenyl)-amine; |
| B57 | 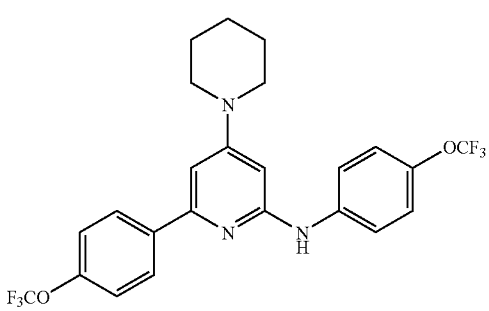 | (4-trifluoromethoxy-phenyl)-[6'-(4-trifluoromethoxy-phenyl)-3,4,5,6-tetrahydro-2H-[1,4']bipyridinyl-2'-yl]-amine; |
| B58 | 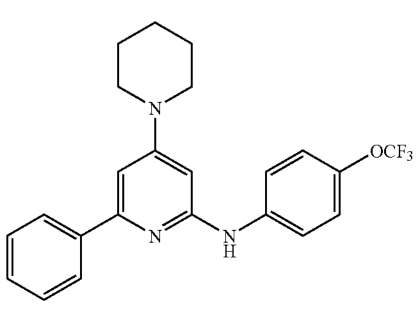 | (6'-phenyl-3,4,5,6-tetrahydro-2H-[1,4']bipyridinyl-2'-yl)-(4-trifluoromethoxy-phenyl)-amine; |

TABLE 2-continued

Representative compounds in accordance with the present invention

| Cmpd. No. | Structure | Name |
| --- | --- | --- |
| B59 | 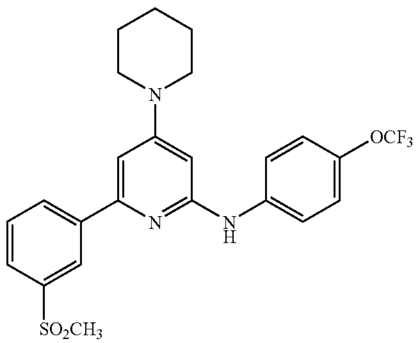 | [6'-(3-methanesulfonyl-phenyl)-3,4,5,6-tetrahydro-2H-[1,4']bipyridinyl-2'-yl]-(4-trifluoromethoxy-phenyl)-amine; |
| B60 | 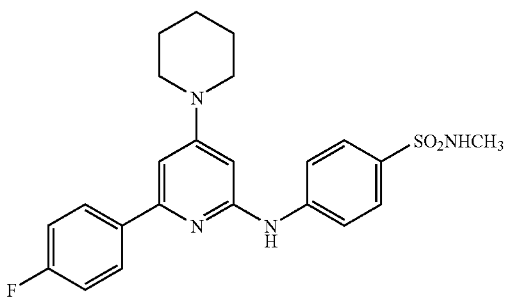 | 4-[6'-(4-fluoro-phenyl)-3,4,5,6-tetrahydro-2H-[1,4']bipyridinyl-2'-ylamino]-N-methyl-benzene-sulfonamide; |
| B61 | 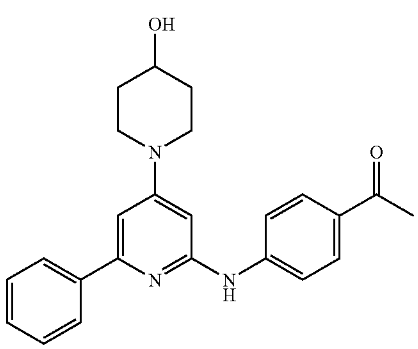 | 1-[4-(4-hydroxy-6'-phenyl-3,4,5,6-tetrahydro-2H-[1,4']bipyridinyl-2'-ylamino)-phenyl]-ethanone; |
| B62 | 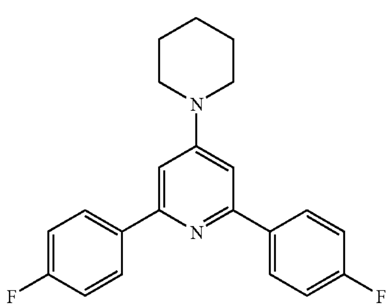 | 2',6'-bis-(4-fluoro-phenyl)-3,4,5,6-tetrahydro-2H-[1,4']bipyridinyl; |

TABLE 2-continued

Representative compounds in accordance with the present invention

| Cmpd. No. | Structure | Name |
|---|---|---|
| B63 | 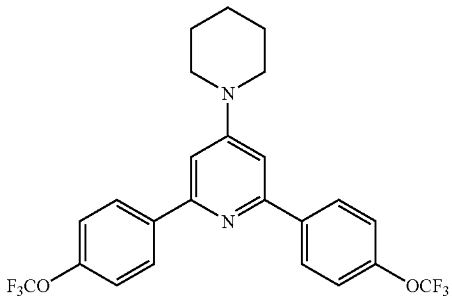 | 2',6'-bis-(4-trifluoromethoxy-phenyl)-3,4,5,6-tetrahydro-2H-[1,4']bipyridinyl; |
| B64 | 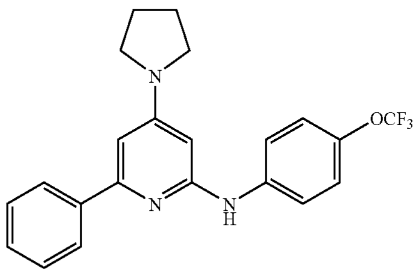 | (6-phenyl-4-pyrrolidin-1-yl-pyridin-2-yl)-(4-trifluoromethoxy-phenyl)-amine; |
| B65 | 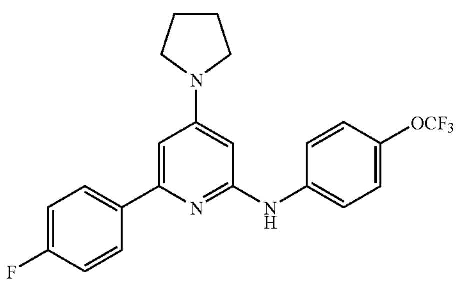 | [6-(4-fluoro-phenyl)-4-pyrrolidin-1-yl-pyridin-2-yl]-(4-trifluoromethoxy-phenyl)-amine; |
| B66 | 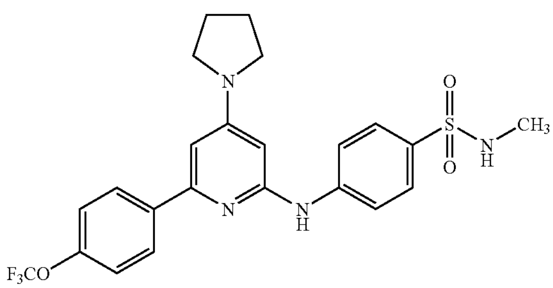 | N-methyl-4-[4-pyrrolidin-1-yl-6-(4-trifluoromethoxy-phenyl)-pyridin-2-ylamino]-benzenesulfonamide; |
| B67 | 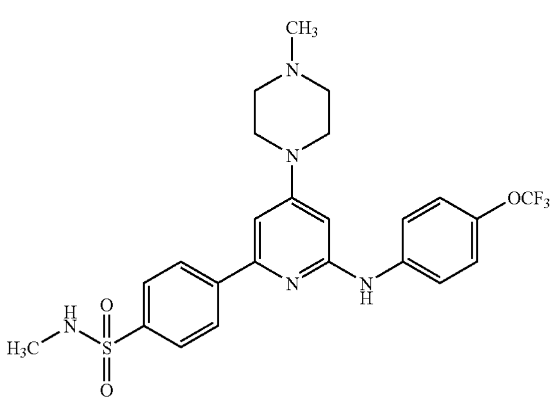 | N-methyl-4-[4-(4-methyl-piperazin-1-yl)-6-(4-trifluoromethoxy-phenylamino)-pyridin-2-yl]-benzenesulfonamide; |

TABLE 2-continued

Representative compounds in accordance with the present invention

| Cmpd. No. | Structure | Name |
|---|---|---|
| B68 | 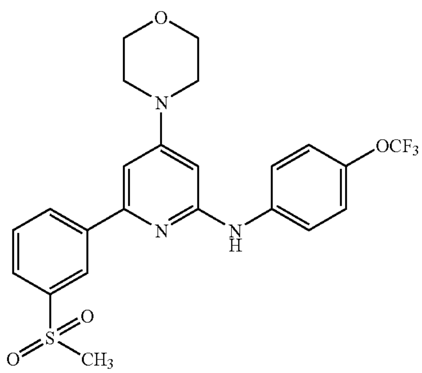 | [6-(3-methanesulfonyl-phenyl)-4-morpholin-4-yl-pyridin-2-yl]-(4-trifluoromethoxy-phenyl)-amine; |
| B69 | 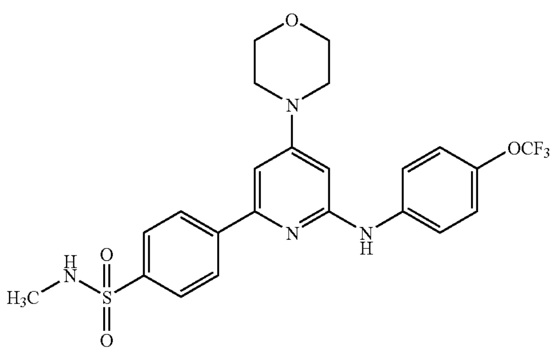 | N-methyl-4-[4-morpholin-4-yl-6-(4-trifluoromethoxy-phenylamino)-pyridin-2-yl]-benzenesulfonamide; |
| B70 | 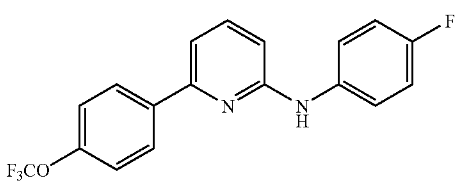 | (4-fluoro-phenyl)-[6-(4-trifluoromethoxy-phenyl)-pyridin-2-yl]-amine; |
| B71 | 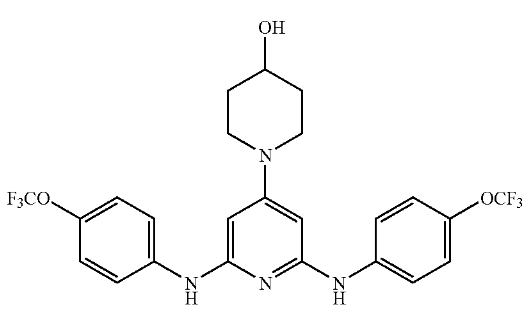 | 2',6'-bis-(4-trifluoromethoxy-phenylamino)-3,4,5,6-tetrahydro-2H-[1,4']bipyridinyl-4-ol; |

TABLE 2-continued

Representative compounds in accordance with the present invention

| Cmpd. No. | Structure | Name |
|---|---|---|
| B72 | 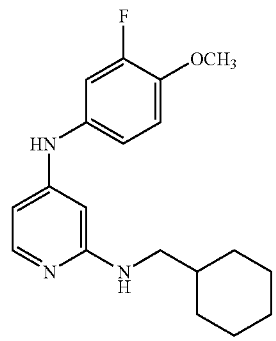 | $N^2$-cyclohexylmethyl-$N^4$-(3-fluoro-4-methoxy-phenyl)-pyridine-2,4-diamine; |
| B73 | 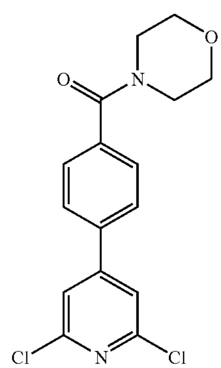 | [4-(2,6-dichloro-pyridin-4-yl)-phenyl]-morpholin-4-yl-methanone; |
| B74 | 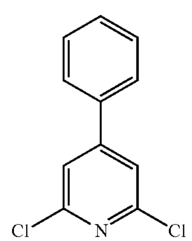 | 2,6-dichloro-4-phenyl-pyridine; |
| B75 | 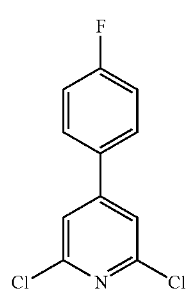 | 2,6-dichloro-4-(4-fluoro-phenyl)-pyridine; |
| B76 | 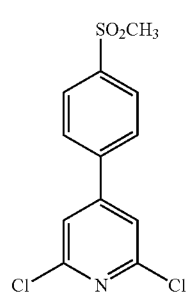 | 2,6-dichloro-4-(4-methanesulfonyl-phenyl)-pyridine; |

TABLE 2-continued
Representative compounds in accordance with the present invention
| Cmpd. No. | Structure | Name |
|---|---|---|
| B77 | 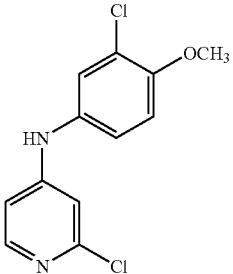 | (3-chloro-4-methoxy-phenyl)-(2-chloro-pyridin-4-yl)-amine |
| B78 | 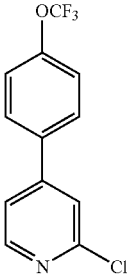 | 2-chloro-4-(4-trifluoromethoxy-phenyl)-pyridine |
| B79 | 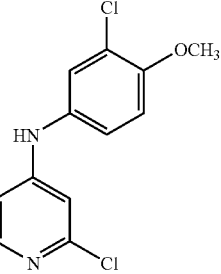 | (3-chloro-4-methoxy-phenyl)-(2,6-dichloro-pyridin-4-yl)-amine |
| B80 | 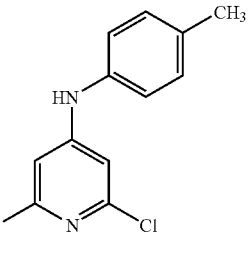 | (2,6-dichloro-pyridin-4-yl)-p-tolyl-amine |
| B81 | 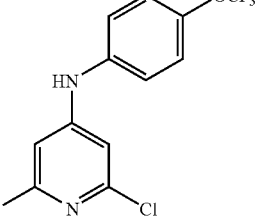 | (2,6-dichloro-pyridin-4-yl)-(4-trifluoromethoxy-phenyl)-amine |

TABLE 2-continued

Representative compounds in accordance with the present invention

| Cmpd. No. | Structure | Name |
|---|---|---|
| B82 | 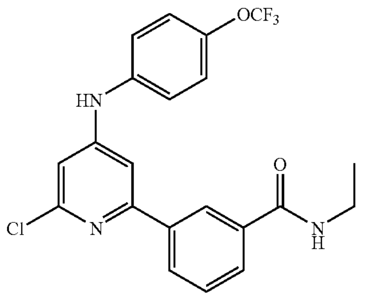 | 3-[6-chloro-4-(4-trifluoromethoxy-phenylamino)-pyridin-2-yl]-N-ethyl-benzamide |
| B83 | 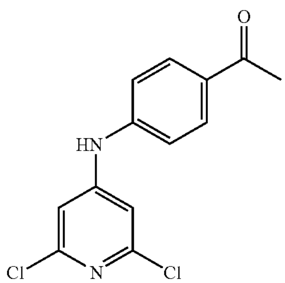 | 1-[4-(2,6-dichloro-pyridin-4-ylamino)-phenyl]-ethanone |
| B84 | 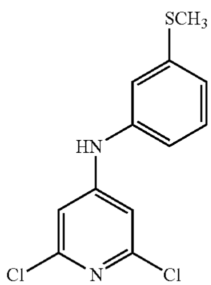 | (2,6-dichloro-pyridin-4-yl)-(3-methylsulfanyl-phenyl)-amine |
| B85 | 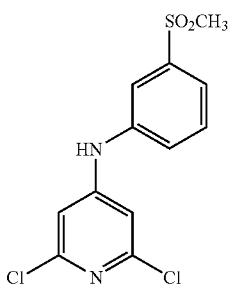 | S-[3-(2,6-dichloro-pyridin-4-ylamino)-phenyl]ester-O-methyl ester |
| B86 | 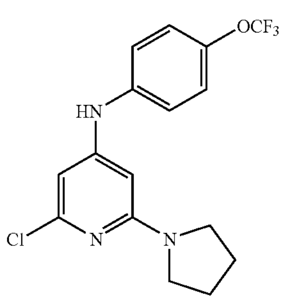 | (2-chloro-6-pyrrolidin-1-yl-pyridin-4-yl)-(4-trifluoromethoxy-phenyl)-amine |

TABLE 2-continued
Representative compounds in accordance with the present invention
| Cmpd. No. | Structure | Name |
|---|---|---|
| B87 | 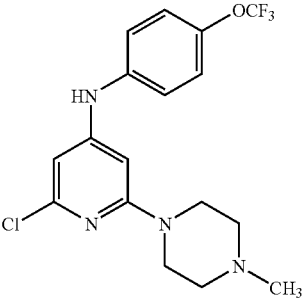 | [2-chloro-6-(4-methyl-piperazin-1-yl)-pyridin-4-yl]-(4-trifluoromethoxy-phenyl)-amine |
| B88 | 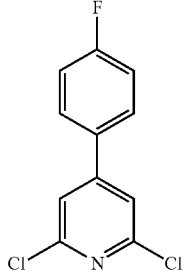 | 2,6-dichloro-4-(4-fluoro-phenyl)-pyridine |
| B89 | 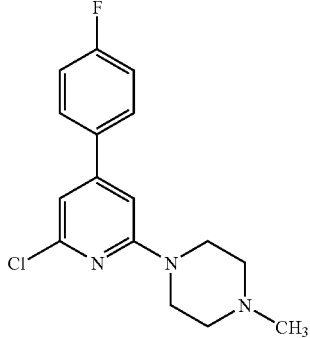 | 1-[6-chloro-4-(4-fluoro-phenyl)-pyridin-2-yl]-4-methyl-piperazine |
| B90 | 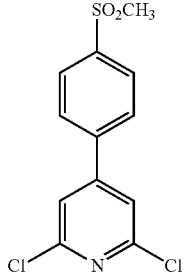 | 2,6-dichloro-4-(4-methanesulfonyl-phenyl)-pyridine |

TABLE 2-continued

Representative compounds in accordance with the present invention

| Cmpd. No. | Structure | Name |
|---|---|---|
| B91 | 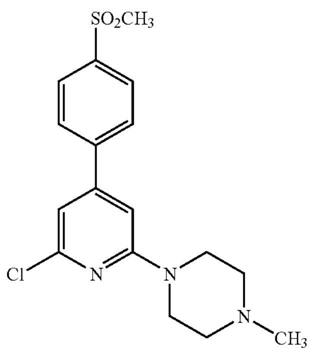 | 1-[6-chloro-4-(4-methanesulfonyl-phenyl)-pyridin-2-yl]-4-methyl-piperazine |
| B92 | 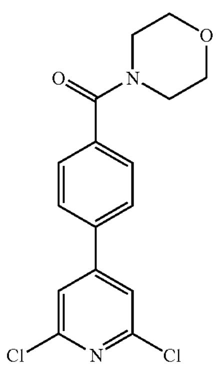 | [4-(2,6-dichloro-pyridin-4-yl)-phenyl]-morpholin-4-yl-methanone |
| B93 | 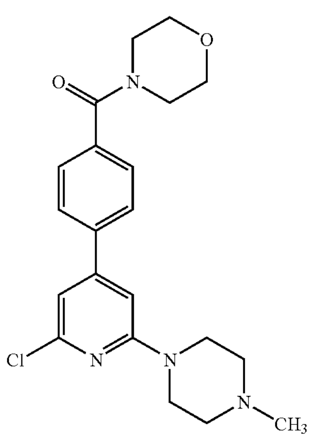 | {4-[2-chloro-6-(4-methyl-piperazin-1-yl)-pyridin-4-yl]-phenyl}-morpholin-4-yl-methanone |
| B94 | 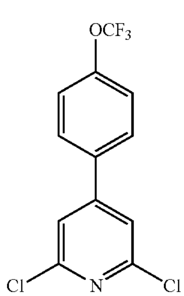 | 2,6-dichloro-4-(4-trifluoromethoxy-phenyl)-pyridine |

TABLE 2-continued

Representative compounds in accordance with the present invention

| Cmpd. No. | Structure | Name |
|---|---|---|
| B95 | 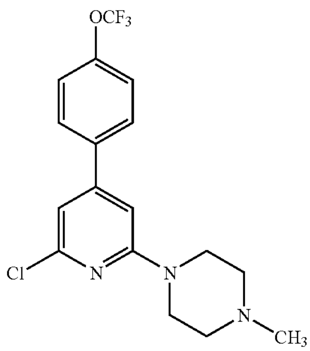 | 1-[6-chloro-4-(4-trifluoromethoxy-phenyl)-pyridin-2-yl]-4-methyl-piperazine |
| B96 | 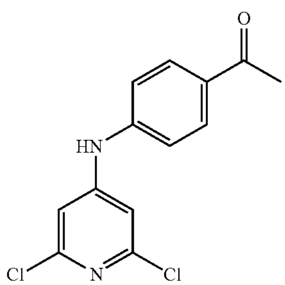 | 1-[4-(2,6-dichloro-pyridin-4-ylamino)-phenyl]-ethanone |
| B97 | 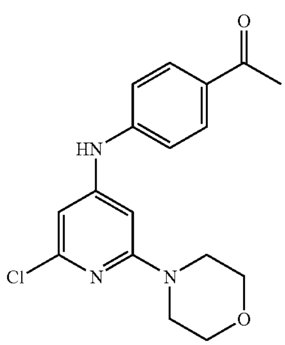 | 1-[4-(2-chloro-6-morpholin-4-yl-pyridin-4-ylamino)-phenyl]-ethanone |
| B98 | 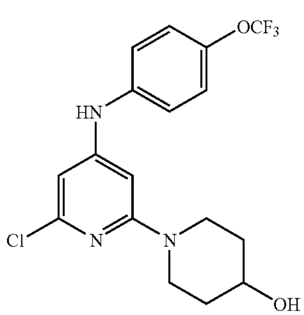 | 6'-chloro-4'-(4-trifluoromethoxy-phenylamino)-3,4,5,6-tetrahydro-2H-[1,2']bipyridinyl-4-ol |

TABLE 2-continued

Representative compounds in accordance with the present invention

| Cmpd. No. | Structure | Name |
| --- | --- | --- |
| B99 | 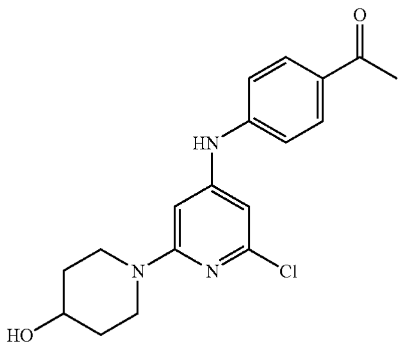 | 1-[4-(6'-chloro-4-hydroxy-3,4,5,6-tetrahydro-2H-[1,2']bipyridinyl-4'-ylamino)-phenyl]-ethanone |
| B100 | 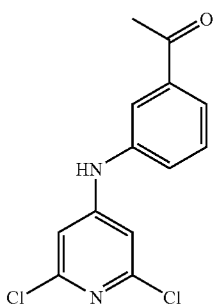 | 1-[4-(4-hydroxy-6'-phenyl-3,4,5,6-tetrahydro-2H-[1,2']bipyridinyl-4'-ylamino)-phenyl]-ethanone |
| B101 | 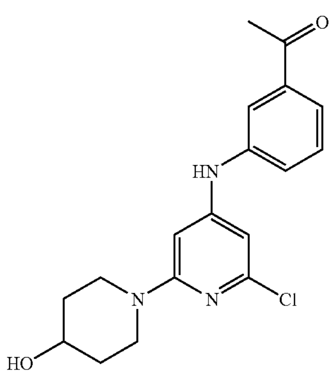 | 1-[3-(6'-chloro-4-hydroxy-3,4,5,6-tetrahydro-2H-[1,2']bipyridinyl-4'-ylamino)-phenyl]-ethanone |
| B102 | 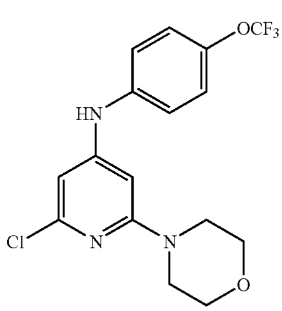 | (2-chloro-6-morpholin-4-yl-pyridin-4-yl)-(4-trifluoromethoxy-phenyl)-amine |

TABLE 2-continued

Representative compounds in accordance with the present invention

| Cmpd. No. | Structure | Name |
|---|---|---|
| B103 | 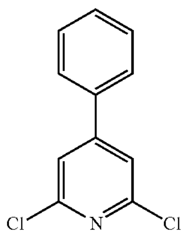 | 2,6-dichloro-4-phenyl-pyridune |
| B104 | 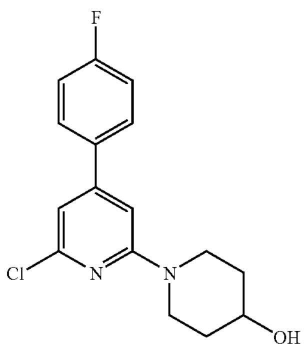 | 6'-chloro-4'-(4-fluoro-phenyl)-3,4,5,6-tetrahydro-2H-[1,2']bipyridinyl-4-ol |
| B105 | 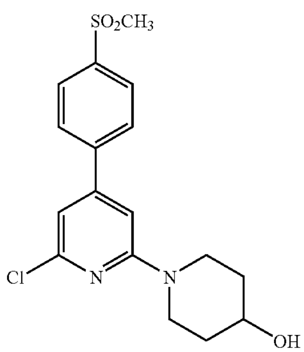 | 6'-chloro-4'-(4-methanesulfonyl-phenyl)-3,4,5,6-tetrahydro-2H-[1,2']bipyridinyl-4-ol |
| B106 | 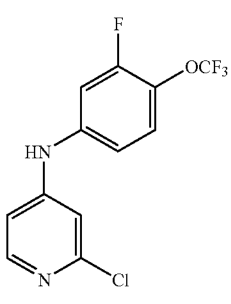 | (2-chloro-pyridin-4-yl)-(3-fluoro-4-methoxy-phenyl)-amine |
| B107 | 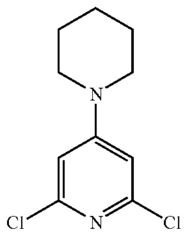 | 2',6'-dichloro-3,4,5,6-tetrahydro-2H-[1,4']bipyridinyl (alternatively, 2,6-dichloro-4-piperdino pyridine) |

TABLE 2-continued

Representative compounds in accordance with the present invention

| Cmpd. No. | Structure | Name |
|---|---|---|
| B108 | 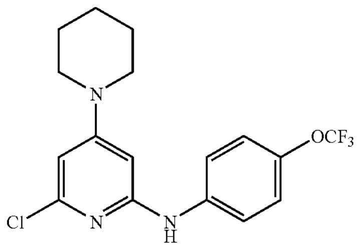 | (6'-chloro-3,4,5,6-tetrahydro-2H-[1,4']bipyridinyl-2'-yl]-(4-trifluoromethoxyphenyl)-amine |
| B109 | 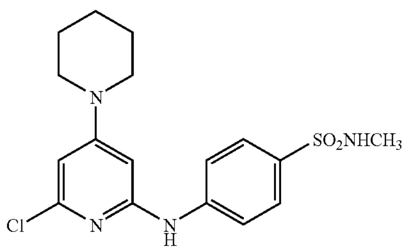 | 4-(6'-chloro-3,4,5,6-tetrahydro-2H-[1,4']bipyridinyl-2'-ylamino)-N-methyl-benzenesulfonamide |
| B110 | 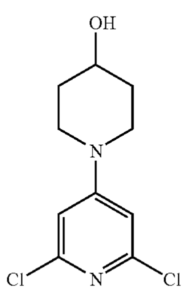 | 2',6'-dichloro-3,4,5,6-tetrahydro-3H-[1,4']bipyridinyl-4-ol |
| B111 | 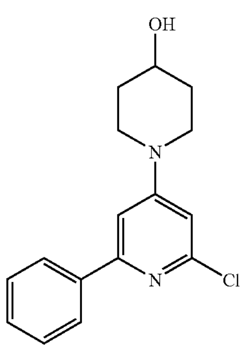 | 2'-chloro-6'-phenyl-3,4,5,6-tetrahydro-2H-[1,4']bipyridinyl-4-ol |
| B112 | 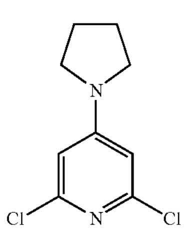 | 2,6-dichloro-4-pyrrolidino pyridine |

TABLE 2-continued

Representative compounds in accordance with the present invention

| Cmpd. No. | Structure | Name |
|---|---|---|
| B113 | 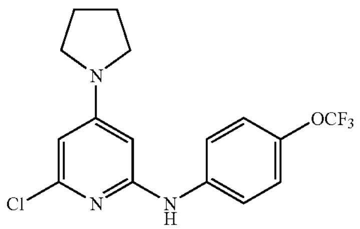 | (6-chloro-4-pyrrolidin-1-yl-pyridin-2-yl)-(4-trifluoromethoxy-phenyl)-amine |
| B114 | 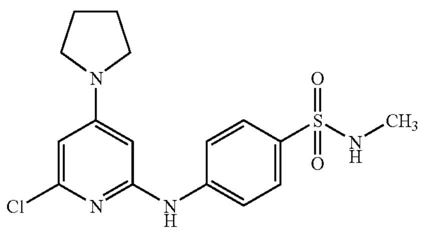 | 4-(6-chloro-4-pyrrolidin-1-yl-pyridin-2-ylamino)-N-methyl-benzenesulfonamide |
| B115 | 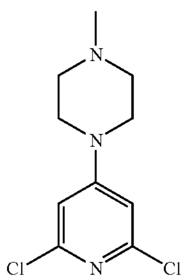 | 1-(2,6-dichloro-pyridin-4-yl)-4-methyl-piperazine |
| B116 | 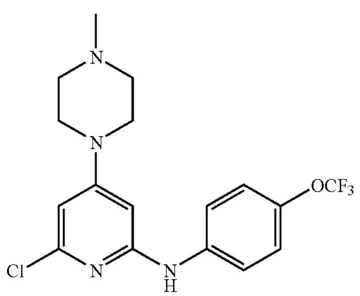 | [6-chloro-4-(4-methyl-piperazin-1-yl)-pyridin-2-yl]-(4-trifluoromethoxy-phenyl)-amine |
| B117 | 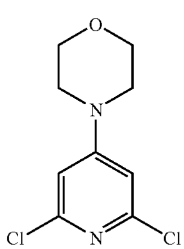 | 4-(2,6-dichloro-pyridin-4-yl)-morpholine |
| B118 | 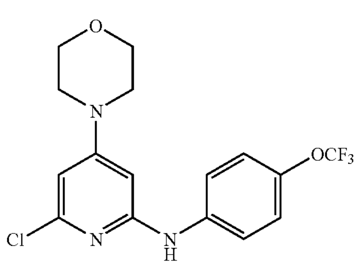 | (6-chloro-4-morpholin-4-yl-pyridin-2-yl)-(4-trifluoromethoxy-phenyl)-amine |

TABLE 2-continued

Representative compounds in accordance with the present invention

| Cmpd. No. | Structure | Name |
|---|---|---|
| B119 | 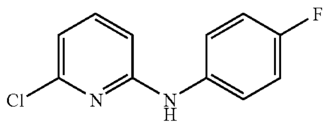 | (6-chloro-pyridine-2-yl)-(4-fluoro-phenyl)-amine |

In this aspect of the present invention, compounds provided herein may be chiral or achiral, or they may exist as racemic mixtures, diastereomers, pure enantiomers, a prodrug, a tautomer, or any mixture thereof. For chiral compounds, separate enantiomers, separate diastereomers, and any mixture of enantiomers, diastereomers, or both are encompassed herein. Further, the present invention also encompasses any combination of compounds provided herein, including any salts, including pharmaceutically acceptable or non-pharmaceutically acceptable salts, or any mixture thereof.

As used herein, the terms "pharmaceutically acceptable" salt or "pharmacologically acceptable" salt refers generally to a salt or complex of the compound or compounds in which the compound can be either anionic or cationic, and have associated with it a counter cation or anion, respectively, that is generally considered suitable for human or animal consumption. For example, a pharmaceutically acceptable salt can refer to a salt of a compound disclosed herein that forms upon reaction or complexation with an acid whose anion is generally considered suitable for human or animal consumption. In this aspect, pharmacologically acceptable salts include salts with organic acids or inorganic acids. Examples of pharmacologically acceptable salts include, but are not limited to, hydrochloride, hydrobromide, hydroiodide, sulfate, phosphate, propionate, lactate, maleate, malate, succinate, tartarate, and the like.

Salts may also be formed by deprotonating acid moiety of compound, such as a carboxylic acid moiety, OH, or NH, and the like, using a base such as an organic base, an inorganic base, an organometallic base, a Lewis base, a BrØnsted base, or any mixture thereof. In cases where compounds carry an acidic moiety, suitable pharmaceutically acceptable salts can include alkali metal salts, alkaline earth metal salts, or salts with organic basis, and the like. In this aspect, examples of alkali metal salts include, but are not limited to, sodium and potassium salts, and examples of salts with organic basis include, but are not limited to, meglumine salts, and the like. The pharmacologically acceptable salts may be prepared by conventional means. Additional examples of pharmaceutically acceptable salts, and methods of preparing such salts, are found, for example, in Berg et.al., J. Pharma. Sci, 66, 1-19 (1977).

In a further aspect, this invention also provides a composition comprising at least one compound as disclosed herein, including a composition comprising a pharmaceutically acceptable carrier and at least one compound as disclosed herein. In this aspect, the at least one compound can be present as a neutral compound, as a salt, or as any combination thereof. This invention also encompasses a composition comprising at least one compound as disclosed herein, and optionally comprising a pharmaceutically acceptable additive selected from a carrier, an auxiliary, a diluent, an excipient, a preservative, a solvate, or any combination thereof.

Further, this invention encompasses a pharmaceutical composition, comprising at least one compound as disclosed herein, and optionally comprising a pharmaceutically acceptable additive selected from a carrier, an auxiliary, a diluent, an excipient, a preservative, a solvate, or any combination thereof, wherein the pharmaceutical composition is in the form of a tablet, a capsule, a syrup, a cachet, a powder, a granule, a solution, a suspension, an emulsion, a bolus, a lozenge, a suppository, a cream, a gel, a paste, a foam, a spray, an aerosol, a microcapsule, a liposome, or a transdermal patch.

In another aspect, this invention encompasses a pharmaceutical composition, comprising at least one compound as disclosed herein, and optionally comprising a pharmaceutically acceptable additive selected from a carrier, an auxiliary, a diluent, an excipient, a preservative, a solvate, or any combination thereof; and further comprising an agent selected from a chemotherapeutic agent, an immunosuppressive agent, a cytokine, a cytotoxic agent, an anti-inflammatory agent, an antirheumatic agent, a cardiovascular agent, or any combination thereof.

Another aspect of this invention is directed to using the compounds and compositions disclosed herein in a method of treating a condition or disease state mediated by the low expression of Perlecan, comprising administering an amount of at least one compound as disclosed herein, effective to induce Perlecan expression.

A further aspect of this invention is directed to using the compounds and compositions disclosed herein in a method of treating atherosclerosis, arthritis, restenosis, diabetic nephropathy, or dyslipidemia, comprising administering an effective amount of at least one compound as disclosed herein.

Preparation of Substituted Pyridine Compounds

One more aspect of the present invention provides a process for the preparation of the compounds of general formulas (I) and (III). Thus, substituted pyridine analogs can be prepared generally using standard synthetic methods and employing starting materials that are readily available commercially. As demonstrated by the general reaction schemes and examples disclosed herein, the general synthetic methods provided will be readily understood by one of ordinary skill in the art, and any variations needed for a particular species are simple and readily understood and appreciated by the skilled artisan. In the following general reaction schemes, variable chemical moieties refer to any chemical group consistent with the description of the compound and substituents on that compound as provided herein. Further, in the schemes that follow, the term "palladium catalyst" refers to a suitable palladium catalyst, typically a complex of Pd(0) or Pd(II), including but not limited to, such compounds as palladium(0)

tetrakis-(triphenylphosphine), tris(dibenzylideneacetone)dipalladium(0), palladium(II) acetate, that is known to catalyze the reaction shown. In one aspect, the catalytic system can also include monodentate or chelating ligands, examples of which include, but are not limited to, 2,2'-bis(diphenyl phosphino)-1,1-binapthyl, tri-tert-butyl phosphine, and the like, and can also include a base such as sodium carbonate, sodium or potassium tert-butoxide, or potassium phosphate. Transition metal catalyzed reactions can be typically carried out at ambient temperature or at elevated temperatures using various inert solvents, examples of which include, but are not limited to, toluene, dioxane, DMF, N-methyl pyrrolidine, ethylene glycol, dimethyl ether, diglyme, acetonitrile, or any combination thereof. In one aspect, for example, commonly employed reagent and catalyst pairs include, but are not limited to, aryl boronic acids and palladium(0), (Suzuki reaction, Miyaura and Suzuki, *Chem. Rev.* 1995, 95, 2457).

The following general reaction schemes provide some of the synthetic methods that can be used to prepare the pyridine compounds disclosed herein.

In one aspect of this invention, as provided in Scheme 1, a compound of formula 1a was aminated with any of a variety of substituted or unsubstituted anilines to provide a compound of the formula 1b, wherein $R^1$ is typically an aryl group such as a substituted or unsubstituted phenyl group and Y is a leaving group, in presence of tris(dibenzylideneacetone)dipalladium(0), 1,3-bis(diphenylphosphino)propane, and sodium tert-butoxide. Compound 1b was converted to compound of the type 1c, where one or both of the $R^2$ substituents can be a substituted or unsubstituted phenyl and one of the $R^2$ is optionally hydrogen, by palladium-catalyzed cross-coupling of substituted or unsubstituted phenyl boronic acids. For example, palladium tetrakis-(triphenyl-phosphine) was used as palladium catalyst in this reaction scheme. These fundamental reactions appear in additional reaction sequences provided throughout.

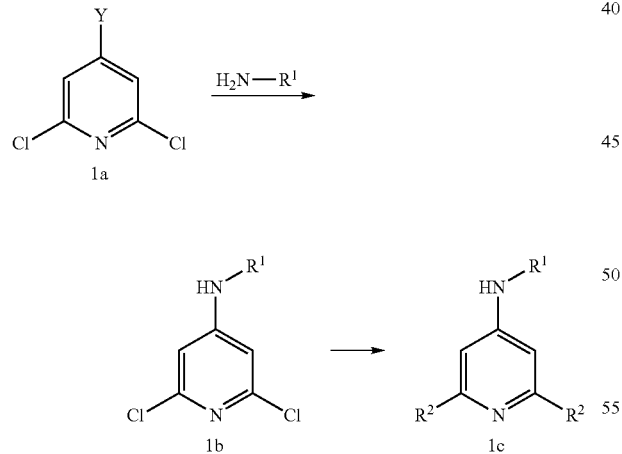

In another aspect of this invention, as provided in Scheme 2, a compound of formula 2a, prepared for example according to Scheme 1, was useful in further amination reactions. For example, compound 2a was treated with various primary ($H_2NR^1$, as illustrated in Scheme 2) or secondary amines ($HNR^1_2$, not illustrated in Scheme 2) in an appropriate solvent such as dimethylformamide, N-methyl pyrollidine, and a base such as potassium carbonate. Examples of secondary amines that were used include, but are not limited to, the heterocyclic compounds such as piperidine, pyrrolidine, and the like. Compounds of the formula 2b were then converted to compounds of the type 2c, where $R^3$, in one aspect, is an aryl group such as a substituted or unsubstituted phenyl, by a palladium-catalyzed cross-coupling of substituted or unsubstituted phenyl boronic acids. For example, palladium tetrakis (triphenylphosphine) was used as palladium catalyst in this reaction scheme.

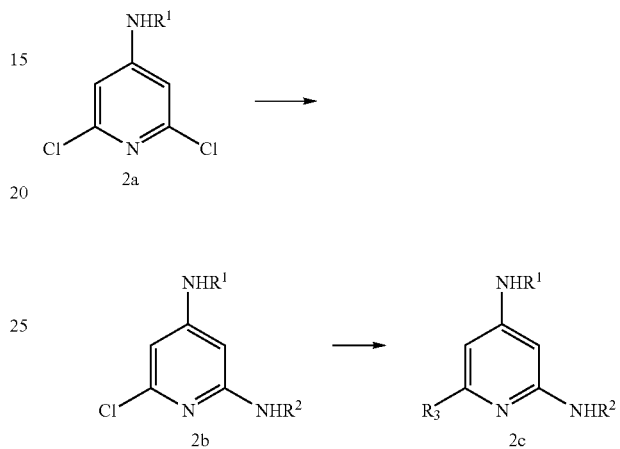

In still another aspect of this invention, a compound of formula 1a, which was prepared, for example, as illustrated in Scheme 1, was converted to a compound of formula 3a, Scheme 3, where $R^1$ represents at least one optional substituent on the aryl group, by reacting 1a with appropriately substituted or unsubstituted phenyl boronic acids. Compound 3a was then converted to compound 3b, wherein $R^2$ is an amino group, by its reaction with, for example, a primary or secondary amine or aniline, in an appropriate solvent such as dimethylformamide, N-methyl pyrollidine, and a base such as potassium carbonate. Compound 3b was converted to a compound of formula 3c, where $R^3$, in one aspect, is an aryl group such as a substituted or unsubstituted phenyl, by a palladium-catalyzed cross-coupling of substituted or unsubstituted phenyl boronic acids, in the presence of a base such as potassium carbonate or sodium carbonate. For example, tris(dibenzylideneacetone)dipalladium(0) was used as palladium catalyst in this step of the reaction scheme.

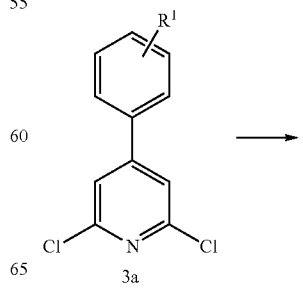

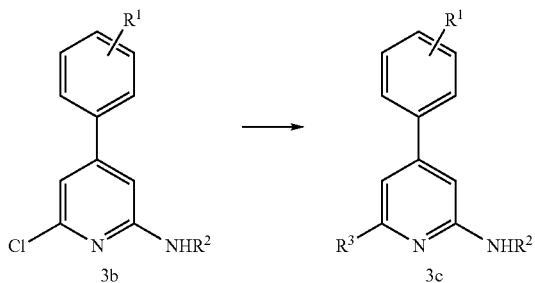

In yet another aspect of this invention, a compound of formula 4a is converted to compound of formula 4b, where $R^1$ was a range of hydrocarbyl groups, such as substituted or unsubstituted alkyl or aryl groups, by the reaction of 4a with the appropriate substituted or unsubstituted primary amine ($H_2NR^1$, as illustrated in Scheme 4) or secondary amine ($HNR^1{}_2$, not illustrated in Scheme 4), or aniline (also not illustrated in Scheme 4). This reaction was typically effected in a polar solvent, including but not limited to, dimethylsulfoxide, and in the presence of base, for example sodium hydride. In a further amidation reaction, compound 4b was converted to compound 4c by its reaction with a range of substituted or unsubstituted anilines $H_2NR^2$ in the presence of a base and a palladium catalyst, where $R^2$ is typically a substituted or unsubstituted aryl group. Compound 4c was converted to compounds of the type 4d, where $R^3$, in one aspect, is an aryl group such as a substituted or unsubstituted phenyl, by a palladium-catalyzed cross-coupling of substituted or unsubstituted phenyl boronic acids. For example, palladium tetrakis(triphenylphosphine) was used as palladium catalyst in this reaction scheme.

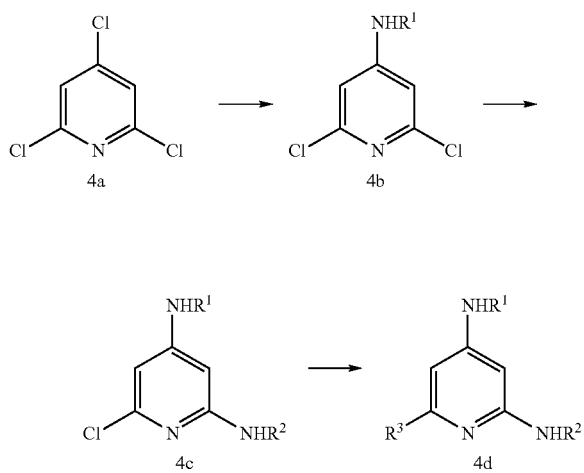

In a further aspect of this invention and as provided in Scheme 5, pyridines with leaving groups at the 2-, 4-, and 6-positions such as trihalogenated pyridines, were useful in preparing a number of substituted pyridines. For example, 2,4,6-trichloropyridine, formula 5a, was aminated using primary ($H_2NR^1$, as illustrated in Scheme 5) or secondary amines ($HNR^1{}_2$, not illustrated in Scheme 5) to prepared the 2,6-dihalogenated pyridines of formula 5b. The palladium-catalyzed cross-coupling reaction of substituted or unsubstituted phenyl boronic acids with compound 5b afforded the 2,6-diarylated pyridine compounds of formula 5c. Treatment of 2,6-dihalogenated pyridines 5b with any of a variety of substituted or unsubstituted anilines $H_2NR^2$ wherein $R^2$ is typically an aryl group such as a substituted or unsubstituted phenyl group, in the presence of a palladium catalyst such as a palladium (II) catalyst, provided the 2,6-bis(aryl)amino pyridine derivatives 5d. The conversion of 5b to 5d can be accomplished stepwise, such that two different —$NHR^2$ moieties can be substituted at the pyridine core.

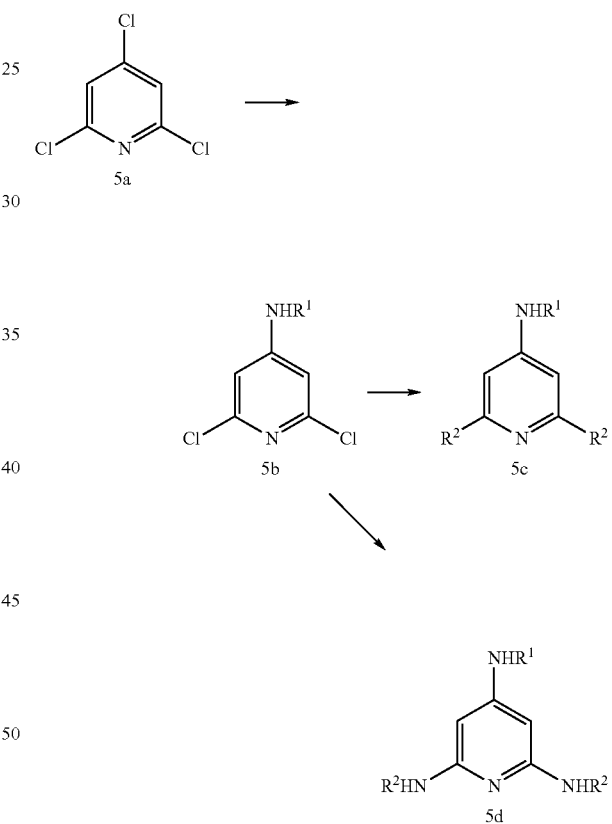

In another aspect, the following reaction Scheme 6 is a general reaction scheme that illustrates one aspect of how the compounds of the present invention can be prepared. The compound of formula (I-A) wherein L represents leaving group selected from halogen, aryloxy, alkylsulfinyl, alkylsulfonyl such as trifluoromethanesulfonyloxy, arylsulfinyl, arylsulfonyl, siloxy, cyano, pyrazolo, triazolo and the like, is converted to a compound of formula (I) by reacting with the compound $GR^2$ wherein G represents hydrogen, $NH_2$, $NHR^5$, OH, SH, $B(OH)_2$, Li or MgZ where Z represents halogen;

when G represents $NR^5$, $R^2$ and $R^5$ together may also form an optionally substituted cyclic ring along with adjacent N atom, which may be optionally containing one or more hetero atoms selected from oxygen, nitrogen or sulfur; and all other symbols are as defined earlier, in presence of a base such as sodium hydroxide, potassium hydroxide, potassium carbonate and the like or Lewis acid such as aluminum chloride ($AlCl_3$) or palladium catalyst such as tetrakis-(triphenylphosphine)-palladium(0) [($PPh_3$)$_4$Pd], bis-(triphenylphosphine)-palladium(II)chloride [($PPh_3$)$_2$PdCl$_2$] and the like. The reaction is carried out in presence of solvent such as acetone, dimethylformamide (DMF), dimethylacetamide (DMA), benzene, toluene and the like. The temperature of the reaction may be in the range of about 25° C. to about 150° C. The duration of the reaction is variable, but can be, for example, in the range of about 2 to about 48 hours.

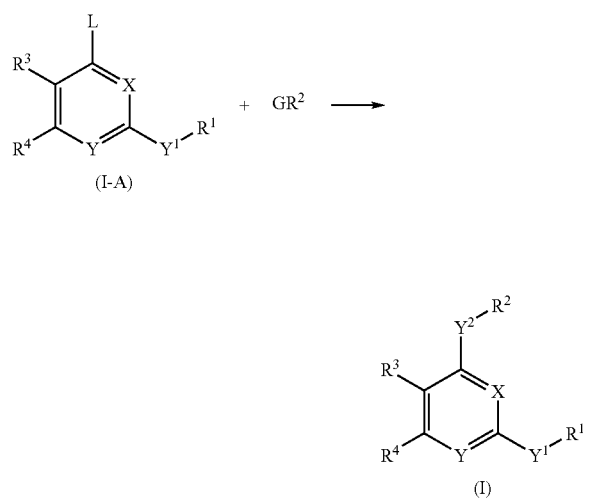

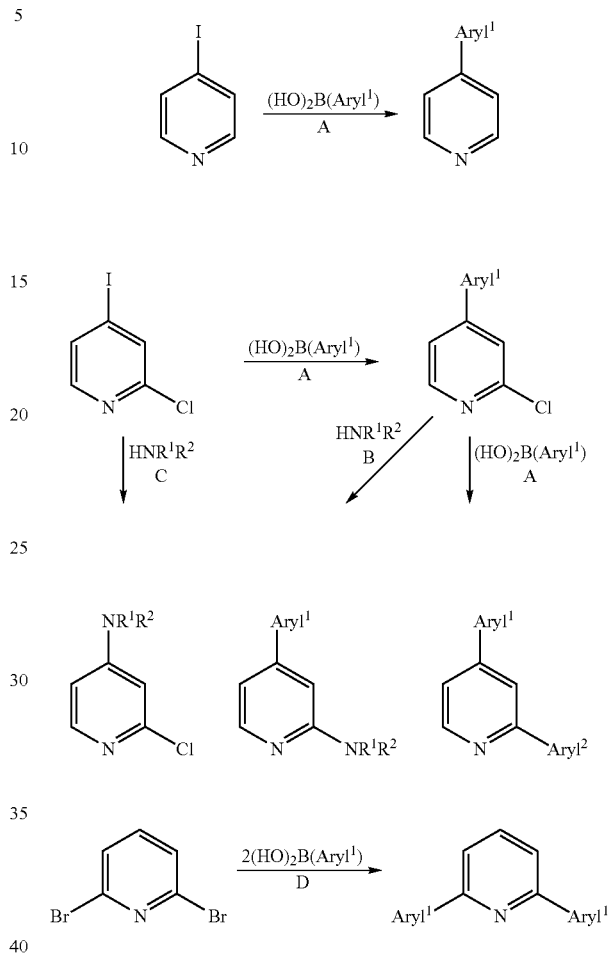

Thus, in accordance with the reaction schemes provided herein, typical reactions and reaction conditions that can be used to prepare the novel compounds of this invention include, but are not limited to, for example, the reactions provided in Scheme 7. Thus, in Scheme 7, typical reaction conditions include, but by no means are limited to the following. These conditions are provided solely as a guide for one of ordinary skill, such that the skilled artisan will readily appreciate how modifications of these conditions can selected according to the particular chemical moiety being substituted at the pyridine core. Thus, Examples of conditions include, but are not limited to: A, acetonitrile, sodium carbonate (0.4 M), tetrakis(triphenylphosphine)palladium(0), reflux; B, (PhCH=CHCOCH=CHPh)$_3$Pd$_2$ (tris(dibenzylidineacetone)dipalladium(0)), sodium-tert-butoxide, 2,8,9-triisobutyl-2,5,8,9-tetraaza-1-phosphabicyclo[3.3.3]undecane (CAS number 331465-71-5), toluene, reflux; C, (PhCH=CHCOCH=CBPh)$_3$Pd$_2$ (tris(dibenzylidineacetone)dipalladium(0)), 1,3-bis(diphenylphosphino)propane, sodium-tert-butoxide, toluene, reflux; D, dimethoxy ethane, sodium carbonate (2 M), tetrakis(triphenylphosphine)palladium(O), reflux under nitrogen.

The following reaction schemes provide additional synthetic methods that can be used to prepare the pyridine compounds disclosed herein.

Synthesis of 2,4,6-trisubstituted pyridines comprising a 4-cycloalkylamino substituent. As illustrated in Scheme 8, the intermediate compound shown as compound 8a can be used to prepare several tri-substituted pyridines such as those exemplified in this scheme. Conditions "a" for the reaction shown are as follows. The heterocyclic amine was reacted with trichloropyridine under basic conditions [NaOH (aq) or NaH (anhydrous)] in a polar organic solvent at temperatures ranging from 0° C. to 60° C. to yield compound 8a. For conditions "b", the intermediate was coupled with a boronic acid under Suzuki conditions using a Pd catalyst [for example, Pd(PPh$_3$)$_4$] in the presence of a base (for example, Na$_2$CO$_3$ or K$_2$CO$_3$) in a polar solvent under thermal conditions, either traditional thermal conditions or under microwave heating conditions. For conditions "c", the monochloropyridine was aminated using Buchwald-Hartwig conditions using a Pd catalyst [for example, Pd(OAc)$_2$] and a ligand such as BINAP, under basic conditions (for example, using potassium tert-butoxide) in a toluene solvent, in a laboratory microwave (at about 150° C.).

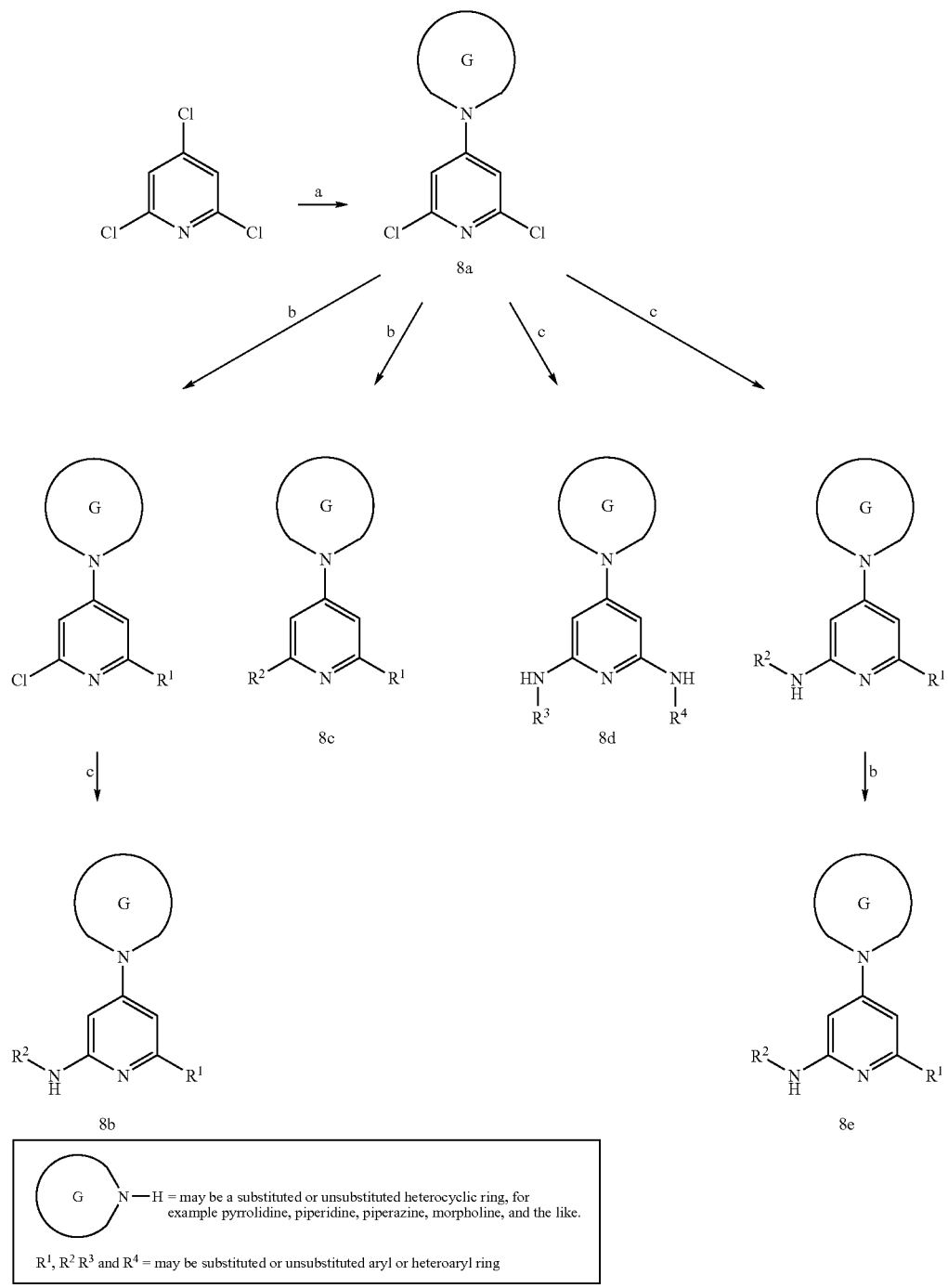

Scheme 8

Synthesis of 2,4,6-trisubstituted pyridines comprising a 4-arylamino substituent. As illustrated in Scheme 9, the intermediate compound shown as compound 9a can be used to prepare various tri-substituted pyridines such as those exemplified in this scheme. Conditions "a" for the reaction shown are as follows. The compound 2,6-dichloro-4-iodopyridine was aminated using Buchwald-Hartwig conditions using a Pd catalyst [for example, $Pd_2(dba)_3$] and a ligand (for example, dpp), under basic conditions (sodium tert-butoxide) in an toluene solution at reflux. For conditions "b", the intermediate was coupled with a boronic acid under Suzuki conditions using a Pd catalyst [for example, $Pd(PPh_3)_4$] in the presence of a based (for example, $Na_2CO_3$) in a polar solvent at reflux. For conditions "c", the intermediate was aminated with the heterocyclic amine using excess amine or in $DMF/K_2CO_3$ at reflux. For conditions "d", the intermediate was alkylated using a base followed by an alkyl halide.

Scheme 9

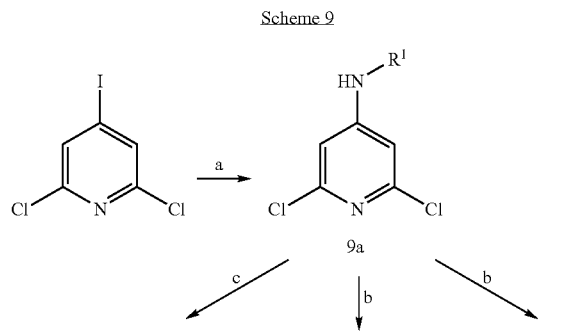

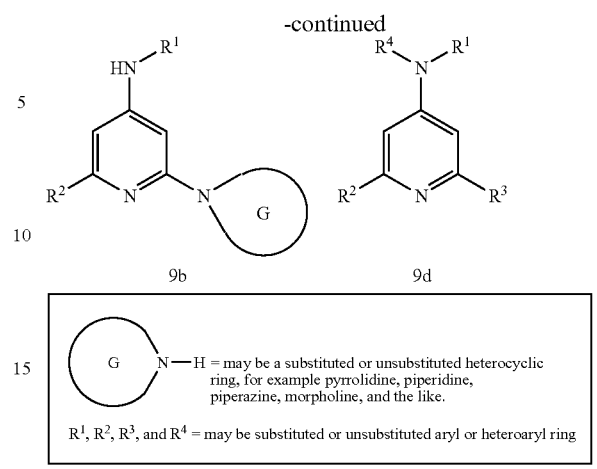

G⟩N—H = may be a substituted or unsubstituted heterocyclic ring, for example pyrrolidine, piperidine, piperazine, morpholine, and the like.

$R^1$, $R^2$, $R^3$, and $R^4$ = may be substituted or unsubstituted aryl or heteroaryl ring

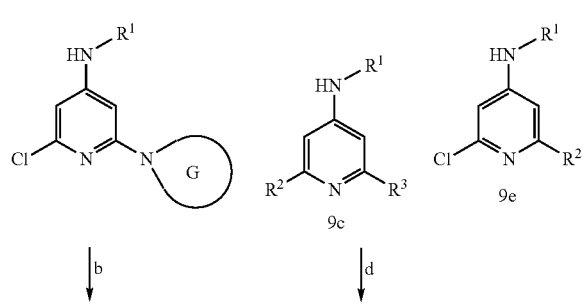

Synthesis of 2,4,6-trisubstituted pyridines comprising a 4-aryl substituent. As illustrated in Scheme 10, the substituted pyridines such as those exemplified in this scheme were prepared as follows. For conditions "a", 2,6-dichloro-4-iodopyridine was coupled with an boronic acid under Suzuki conditions using a Pd catalyst [for example, $Pd(PPh_3)_4$] in the presence of a base (such as $Na_2CO_3$) in a polar solvent at reflux to give intermediate 10a. For conditions "b", the intermediate 10a was aminated with the heterocyclic amine under basic conditions (such as $K_2CO_3$) in a DMF at about 90° C. After isolation and another Suzuki coupling, compound 10b was prepared. Compound 10c was prepared under Suzuki conditions.

Scheme 10

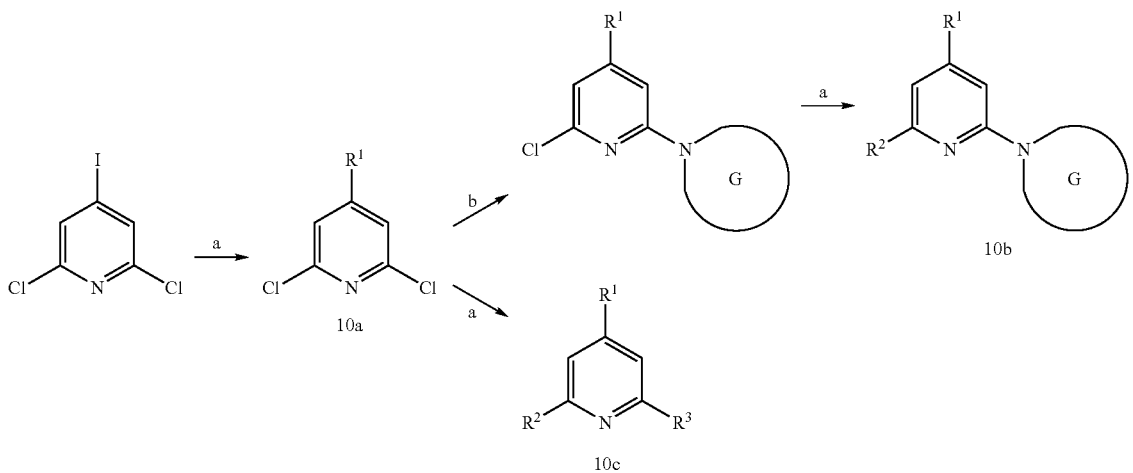

G⟩N—H = may be a substituted or unsubstituted heterocyclic ring, for example, N-methylpiperazine, pyrrolidine, piperidine, morpholine, and the like.

$R_1$, $R_2$, and $R_3$ = may be substituted or unsubstituted aryl or heteroaryl ring, General synthesis of 4-mono-substituted pyridines that can be used for the synthesis of 2,4,6-trisubstituted pyridines. Scheme 11 illustrates the preparation of 4-aryl substituted pyridines that were synthesized under standard Suzuki conditions as described in various other reaction schemes disclosed herein. Compound 11a is drawn to indicate that the chemistry could potentially be expanded if further functionality was in the 2-position (A), the 6-position (B), or both the 2- and 6-positions. Thus, if Compound 11a was appropriately halo-substituted, then other Pd-mediated coupling/amination chemistry could be employed to yield substituted 2,4,6-substituted pyridines.

compound shown could then be subjected to conditions "a" as illustrated. For example, for synthesizing compound 12b, 2,6-dibromopyridine was used as the starting compound, and for synthesizing compound 12c, 2,6-dichloropyridine was used as the starting compound. However, X can be at least Cl, Br, or I, as indicated in the compound 12a. Additionally, 12a is shown indicating a further functionality located at the 4 (C) position, which also occurs in compounds 12b and 12c. For example, if the pyridine 12a is halo-substituted at the 4-position (C is halide), then other Pd-mediated coupling/amination chemistry could be employed to yield substituted 2,4,6-substituted pyridines.

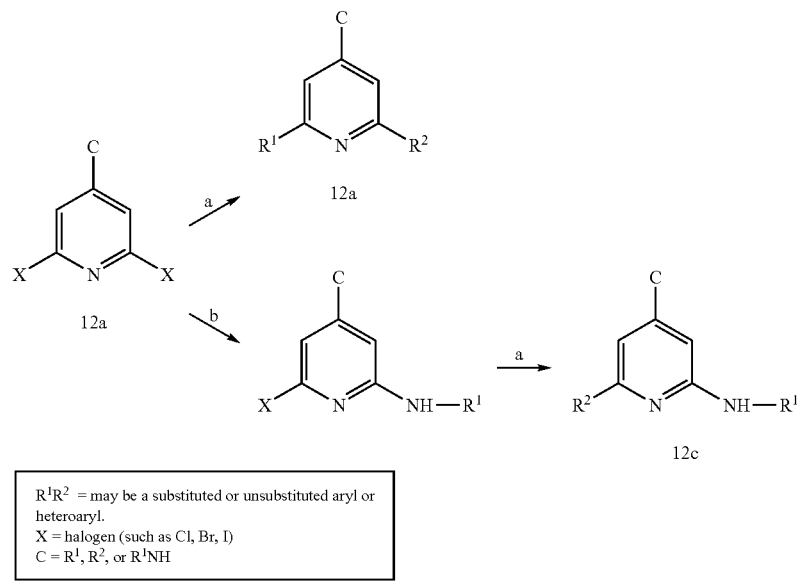

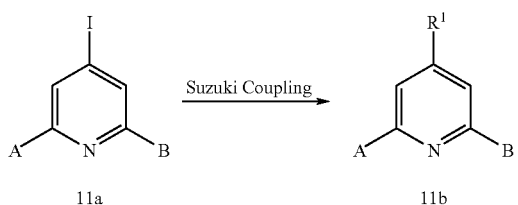

Synthesis of 2,6-disubstituted pyridines that can be used for the synthesis of 2,4,6-trisubstituted amines). Scheme 12 illustrates the typical preparation of 2,6-di-aryl substituted pyridines (12b) that were prepared under standard Suzuki conditions ("a") as described the various reaction schemes disclosed herein. For the 2-amino-6-aryl substituted pyridines (12c), compound 12a was aminated under microwave conditions (thermal) in the presence of a base such as potassium tert-butoxide (conditions "b"). The intermediate Synthesis of 2,4-disubstituted pyridines that can be used for the synthesis of 2,4,6-trisubstituted amines. Scheme 13 illustrates the typical preparation of 2,4-di-aryl substituted pyridines that were prepared under sequential Pd-mediated couplings. For conditions "a", 2,6-dichloro-4-iodopyridine was coupled with an boronic acid under Suzuki conditions using a Pd catalyst [for example, Pd(PPh$_3$)$_4$] in the presence of a base (such as Na$_2$CO$_3$) in a polar solvent at reflux to give intermediates or final products. For conditions "b", Buchwald or Buchwald-Hartwig Pd-mediated amination conditions [Pd$_2$(dba)$_3$, dpp, sodium tert-butoxide in refluxing toluene] were used. For conditions "c", the Verkade Pd-mediated amination conditions were used which comprising employing the Verkade ligand, 2,8,9-triisobutyl-2,5,8,9-tetraza-1-phosphabi-cyclo [3.3.3]undecane, dpp, Pd$_2$(dba)$_3$, sodium tert-butoxide in refluxing toluene. Compound 13a is drawn to indicate that the chemistry could potentially be expanded if further functionality was at the 6-position (D). For example, if the pyridine 6-position is halo-substituted, then other Pd-mediated coupling/amination chemistry could be employed to yield substituted 2,4,6-substituted pyridines. Otherwise the functionality could already be in place prior to initiating the reaction sequence.

Scheme 13

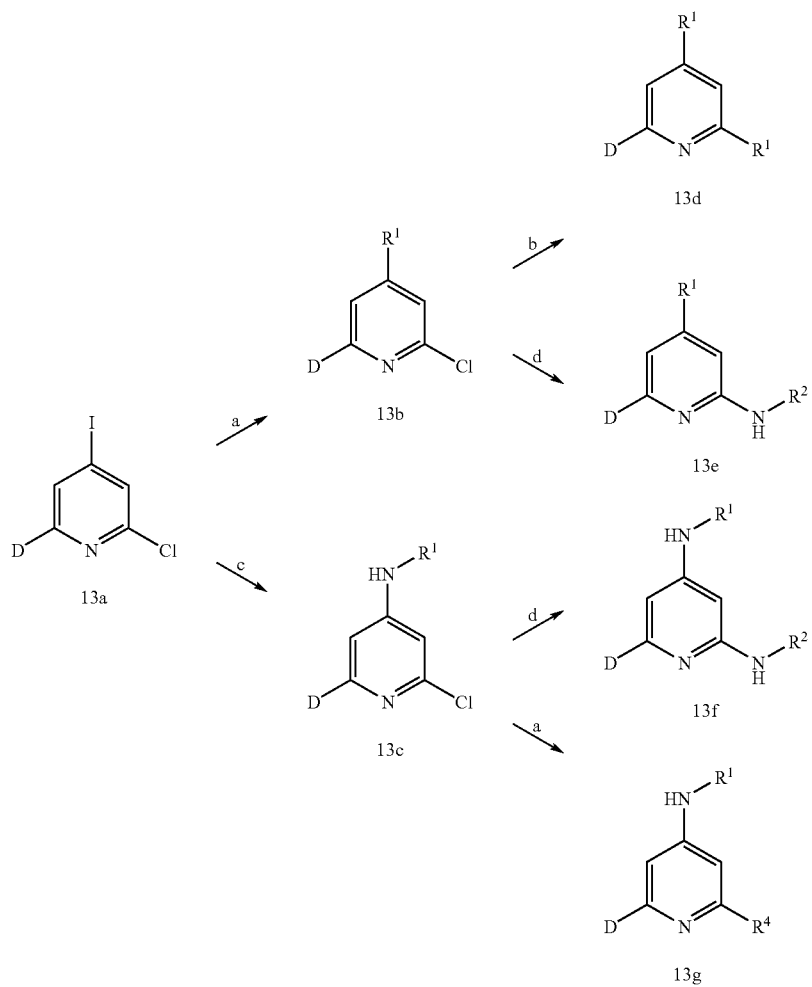

D = Cl, Br, I, R¹, R², R³ or R¹⁻³NH, wherein
R¹, R³, and R⁴ = may be a substituted or
unsubstituted aryl or heteroaryl ring.
R² = may be a substituted or unsubstituted
aryl, heteroaryl, or methylcycloalkyl ring.

Prodrugs

The compounds alternatively can be formulated and administered in a prodrug form. In general, prodrugs comprise functional derivatives of the claimed compounds which are capable of being enzymatically activated or converted into the more active parent form. Thus, in the treatment methods of the present invention, the term "administering" encompasses the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in Wihnan, 14 *Biochem. Soc. Trans.* 375-82 (1986); Stella et al., *Prodrugs: A Chemical Approach to Targeted Drug Delivery in Directed Drug Delivery*, 247-67 (1985).

The prodrugs of present invention include, but are not limited to, derivatives of carboxylic acid, sulfonamide, amine, hydroxyl, and the like, including other functional groups and including any combination thereof.

In another aspect, this invention provides a pharmaceutical composition, comprising a compound any of the formulas shown above, including any combination thereof, and optionally comprising a pharmaceutically acceptable additive selected from a carrier, an auxiliary, a diluent, an excipient, a preservative, a solvate, and the like, or any combination thereof. In a related aspect, this invention affords a method of treating a condition or disease state mediated by the low expression of Perlecan, comprising administering at least one compound as disclosed herein, in an amount effective to induce Perlecan expression. In a related aspect, this invention also provides a method of treating atherosclerosis, arthritis, restenosis, diabetic nephropathy, or dyslipidemia, comprising administering an effective amount of at least one compound as disclosed herein.

Antiproliferative Activities

One aspect of the present invention comprises methods and compositions comprising the compounds of the present invention for the treatment and prevention of conditions or diseases that have as an aspect of the disease or condition, unwanted cellular proliferation occurring or are the result of cellular proliferation. For example, many vascular diseases, such as cardiovascular diseases, organ transplant sequellae, vascular occlusive conditions including, but not limited to, neointimal hyperplasia, restenosis, transplant vasculopathy, cardiac allograft vasculopathy, atherosclerosis, and arteriosclerosis, are caused by or have collateral damage due to unwanted cellular proliferation.

One aspect of the present invention relates to methods and compositions for the treatment and prevention of SMC proliferation, such compositions comprising compounds having cellular antiproliferative activity. These compounds and compositions comprising such compounds are referred to as antiproliferative compounds or compositions. At least one activity of one or more of these compounds is that the compound has the activity of affecting the synthesis of proteoglycans including induction and synthesis of proteoglycans and active fragments of proteoglycans. Thus, one aspect of the activity of one or more of the compounds and compositions of the present invention comprise molecules that induce HSPG production and that regulate SMC proliferation.

Compounds of the present invention that have at least the activity of affecting cellular proliferation are shown in Table 3.

TABLE 3

Compounds of the present invention that have at least the activity of affecting cellular proliferation

| Entry | Structure | Compound Name |
|---|---|---|
| 1 | 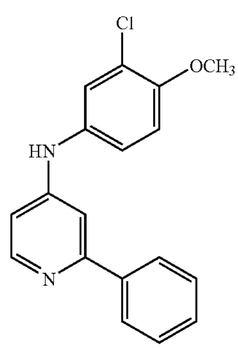 | 3-chloro-4-methoxy-phenyl)-(2-phenyl-pyridin-4-yl)-amine |
| 2 | 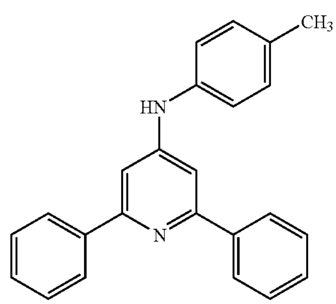 | (2,6-diphenyl-pyridin-4-yl)-p-tolyl-amine |
| 3 | 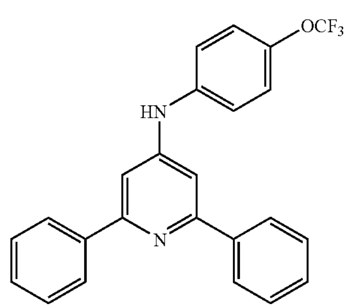 | (2,6-diphenyl-pyridin-4-yl)-(4-trifluoromethoxy-phenyl)-amine |

TABLE 3-continued

Compounds of the present invention that have at least the activity of affecting cellular proliferation

| Entry | Structure | Compound Name |
|---|---|---|
| 4 | 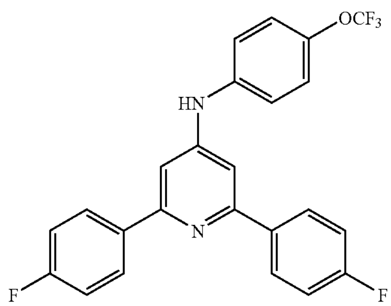 | [2,6-bis-(3-fluoro-phenyl)-pyridin-4-yl]-(4-trifluoromethoxy-phenyl)-amine |
| 5 | 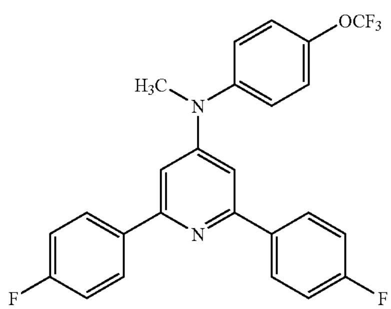 | [2,6-bis-(4-fluoro-phenyl)-pyridin-4-yl]-methyl-(4-trifluoromethoxy-phenyl)-amine |
| 6 | 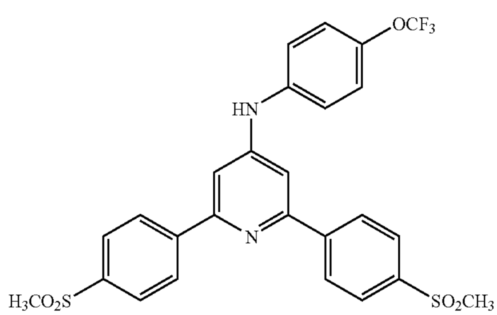 | [2,6-bis-(4-methanesulfonyl-phenyl)-pyridin-4-yl]-(4-trifluoromethoxy-phenyl)-amine |
| 7 | 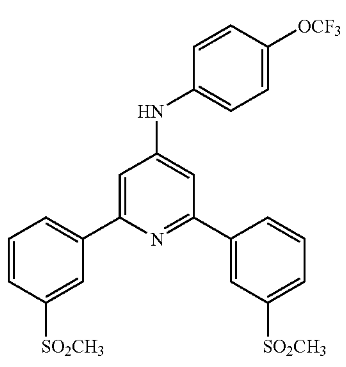 | 2,6-Bis-(3-methanesulfonyl-phenyl)-pyridin-4-yl]-(4-trifluoromethoxy-phenyl)-amine |

TABLE 3-continued

Compounds of the present invention that have at least the activity of affecting cellular proliferation

| Entry | Structure | Compound Name |
|---|---|---|
| 8 | 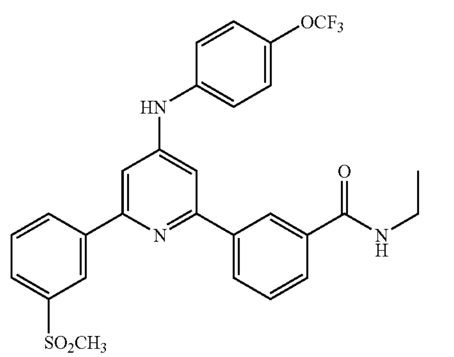 | N-ethyl-3-[6-(3-methanesulfonyl-phenyl)-4-(4-trifluoromethoxy-phenylamino)-pyridin-2-yl]-benzamide |
| 9 | 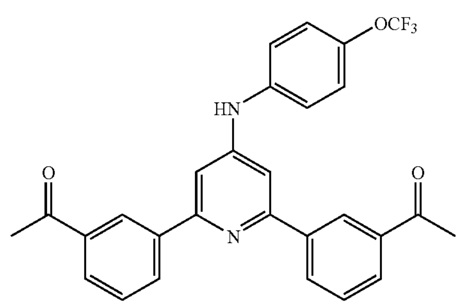 | 1-{3-[6-(3-acetyl-phenyl)-4-(4-trifluoromethoxy-phenylamino)-pyridin-2-yl]-phenyl}-ethanone |
| 10 | 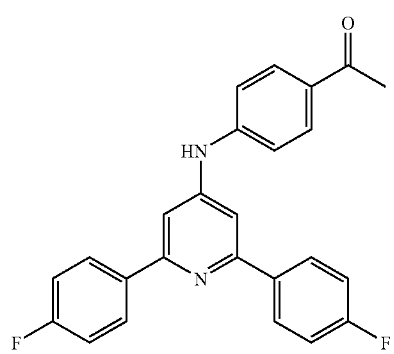 | 1-{4-[2,6-bis-(4-fluoro-phenyl)-pyridin-4-ylamino]-phenyl}-ethanone |
| 11 | 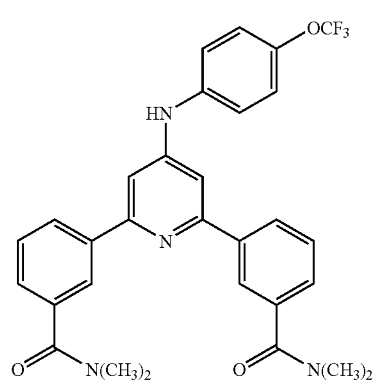 | [2,6-bis-(3-N,N-dimethyl-benzamide)-pyridin-2-yl]-(4-trifluoromethoxy-phenyl)-amine |

TABLE 3-continued

Compounds of the present invention that have at least the activity of affecting cellular proliferation

| Entry | Structure | Compound Name |
|---|---|---|
| 12 | 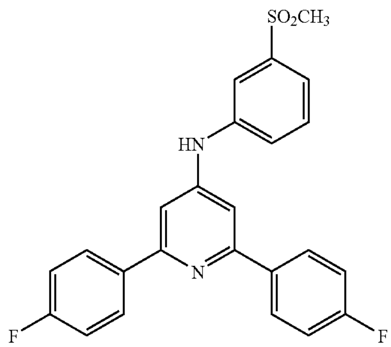 | [2,6-Bis-(4-fluoro-phenyl)-pyridin-4-yl]-(3-methanesulfonyl-phenyl)-amine |
| 13 | 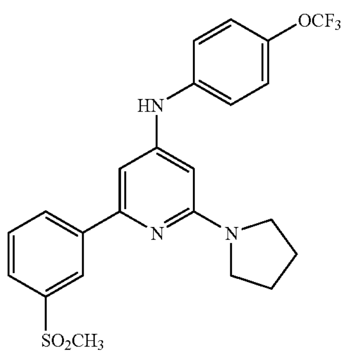 | [2-(3-Methanesulfonyl-phenyl)-6-pyrrolidin-1-yl-pyridin-4-yl]-(4-trifluoromethoxy-phenyl)-amine |
| 14 | 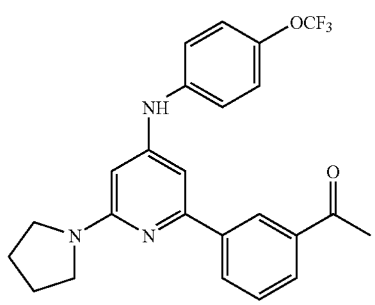 | 1-{3-[6-pyrrolidin-1-yl-4-(4-trifluoromethoxy-phenylamino)-pyridin-2-yl]-phenyl}-ethanone |
| 15 | 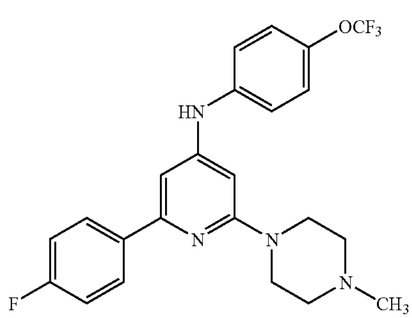 | [2-(4-fluoro-phenyl)-6-(4-methyl-piperazin-1-yl)-pyridin-4-yl]-(4-trifluoromethoxy-phenyl)-amine |

TABLE 3-continued

Compounds of the present invention that have at least the activity of affecting cellular proliferation

| Entry | Structure | Compound Name |
|---|---|---|
| 16 | 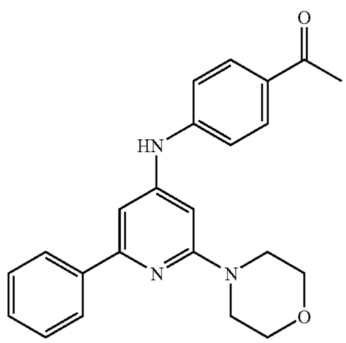 | 1-[4-(2-morpholin-4-yl-6-phenyl-pyridin-4-ylamino)-phenyl]-ethanone |
| 17 | 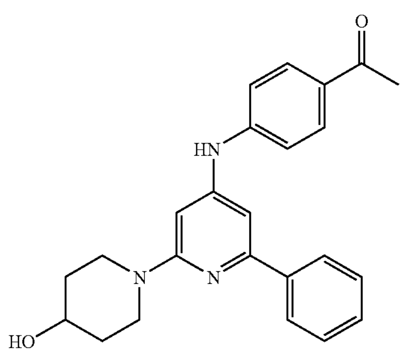 | 1-[4-(4-hydroxy-6'-phenyl-3,4,5,6-tetrahydro-2H-[1,2']bipyridinyl-4'-ylamino)-phenyl]-ethanone |
| 18 | 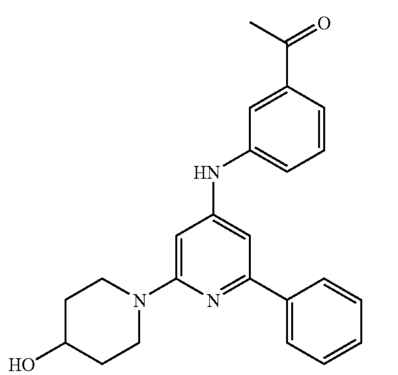 | 1-[3-(4-hydroxy-6'-phenyl-3,4,5,6-tetrahydro-2H-[1,2']bipyridinyl-4'-ylamino)-phenyl]-ethanone |
| 19 | 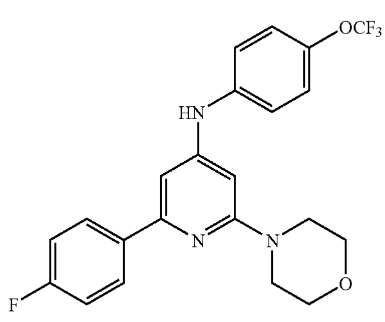 | [2-(4-fluoro-phenyl)-6-morpholin-4-yl-pyridin-4-yl]-(4-trifluoromethoxy-phenyl)-amine |

TABLE 3-continued

Compounds of the present invention that have at least the activity of affecting cellular proliferation

| Entry | Structure | Compound Name |
|---|---|---|
| 20 | 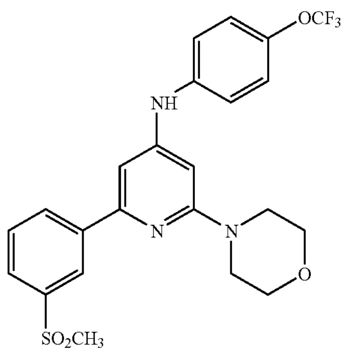 | [2-(3-methanesulfonyl-phenyl)-6-morpholin-4-yl-pyridin-4-yl]-(4-trifluoromethoxy-phenyl)-amine |
| 21 | 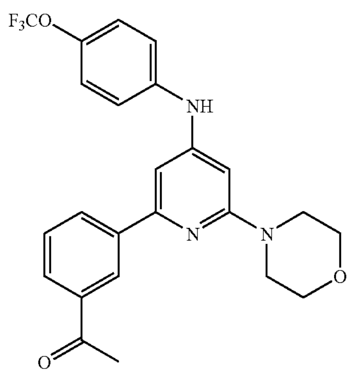 | 1-{3-[6-morpholin-4-yl-4-(4-trifluoromethoxy-phenylamino)-pyridin-2-yl]-phenyl}-ethanone |
| 22 | 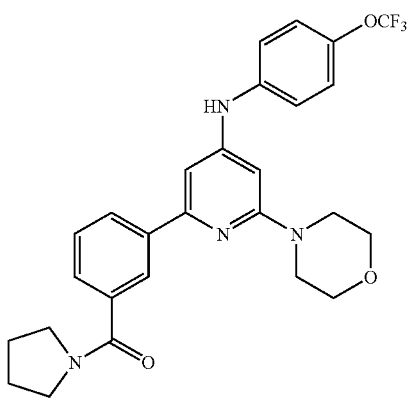 | {3-[6-morpholin-4-yl-4-(4-trifluoromethoxy-phenylamino)-pyridin-2-yl]-phenyl}-pyrrolidin-1-yl-methanone |
| 23 | 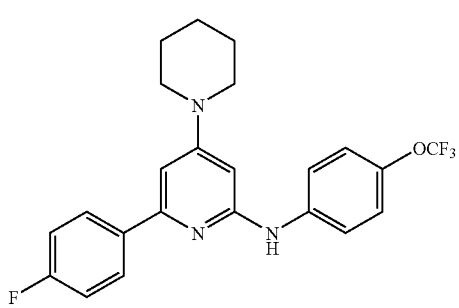 | [6'-(4-Fluoro-phenyl)-3,4,5,6-tetrahydro-2H-[1,4']bipyridinyl-2'-yl]-(4-trifluoromethoxy-phenyl)-amine |

TABLE 3-continued

Compounds of the present invention that have at least the activity of affecting cellular proliferation

| Entry | Structure | Compound Name |
|---|---|---|
| 24 | 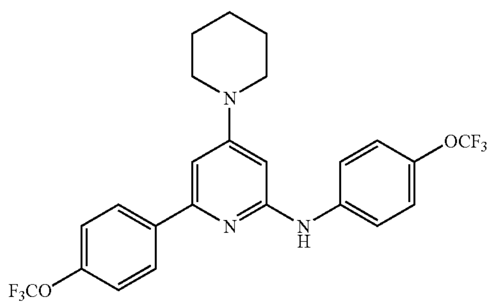 | (4-Trifluoromethoxy-phenyl)-[6'-(4-trifluoromethoxy-phenyl)-3,4,5,6-tetrahydro-2H-[1,4']bipyridinyl-2'-yl]-amine |
| 25 | 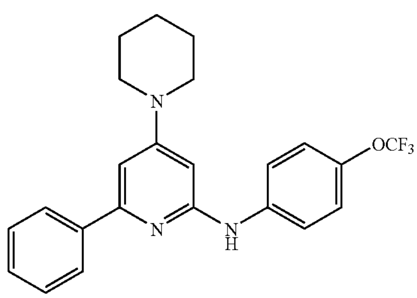 | (6'-Phenyl-3,4,5,6-tetrahydro-2H-[1,4']bipyridinyl-2'-yl)-(4-trifluoromethoxy-phenyl)-amine |
| 26 | 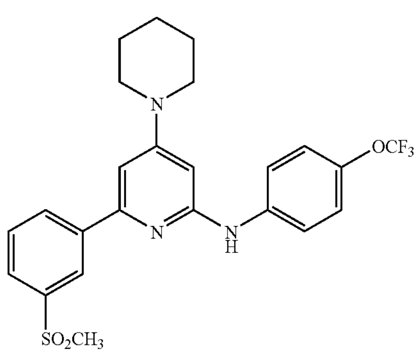 | 3[6'-(3-Methanesulfonyl-phenyl)-3,4,5,6-tetrahydro-2H-[1,4']bipyridinyl-2'-yl]-(4-trifluoromethoxy-phenyl)-amine |
| 27 | 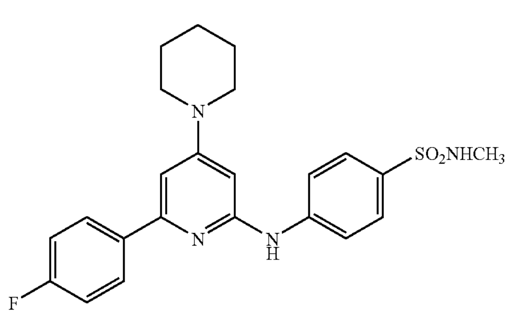 | 4-[6'-(4-Fluoro-phenyl)-3,4,5,6-tetrahydro-2H-[1,4']bipyridinyl-2'-yl-amino]-N-methyl-benzenesulfonamide |

TABLE 3-continued

Compounds of the present invention that have at least the activity of affecting cellular proliferation

| Entry | Structure | Compound Name |
|---|---|---|
| 28 | 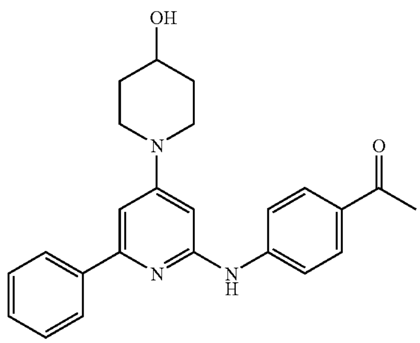 | 1-[4-(4-Hydroxy-6'-phenyl-3,4,5,6-tetrahydro-2H-[1,4']bipyridinyl-2'-yl-amino)-phenyl]-ethanone |
| 29 | 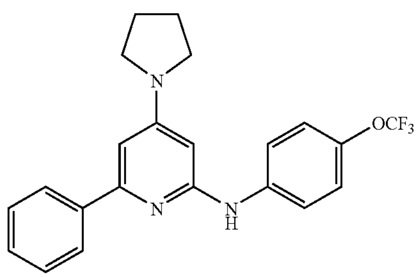 | (6-Phenyl-4-pyrrolidin-1-yl-pyridin-2-yl)-(4-trifluoromethoxy-phenyl)-amine |
| 30 | 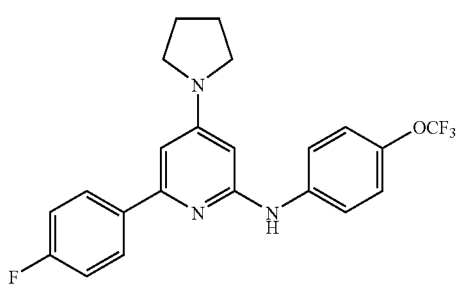 | [6-(4-Fluoro-phenyl)-4-pyrrolidin-1-yl-pyridin-2-yl]-(4-trifluoromethoxy-phenyl)-amine |
| 31 | 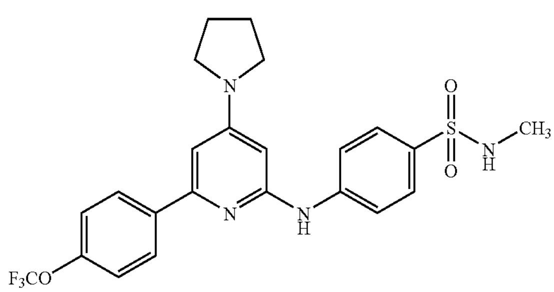 | N-Methyl-4-[4-pyrrolidin-1-yl-6-(4-trifluoromethoxy-phenyl)-pyridin-2-ylamino]-benzenesulfonamide |

TABLE 3-continued

Compounds of the present invention that have at least the activity of affecting cellular proliferation

| Entry | Structure | Compound Name |
|---|---|---|
| 32 | 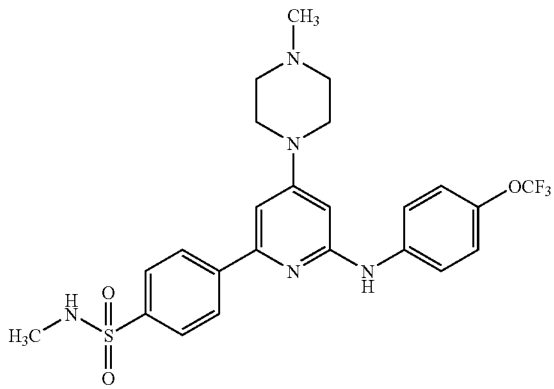 | N-Methyl-4-[4-(4-methyl-piperazin-1-yl)-6-(4-trifluoromethoxy-phenylamino)-pyridin-2-yl]-benzenesulfonamide |
| 33 | 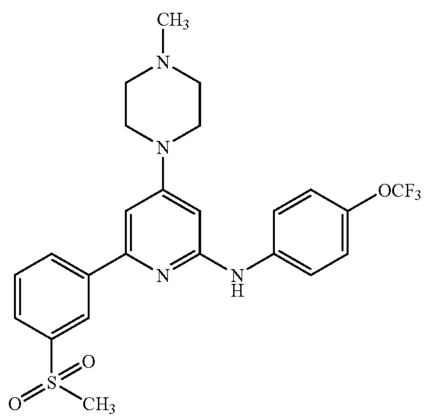 | [6-(3-Methanesulfonyl-phenyl)-4-morpholin-4-yl-pyridin-2-yl]-(4-trifluoromethoxy-phenyl)-amine |
| 34 | 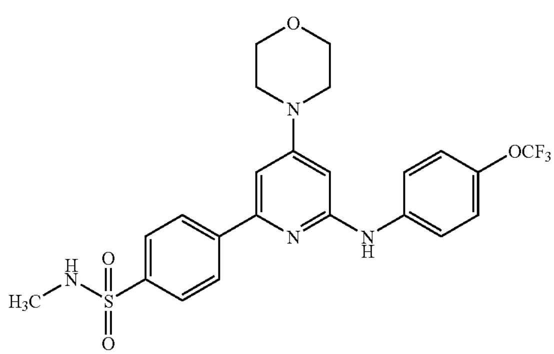 | N-Methyl-4-[4-morpholin-4-yl-6-(4-trifluoromethoxy-phenylamino)-pyridin-2-yl]-benzenesulfonamide |
| 35 | 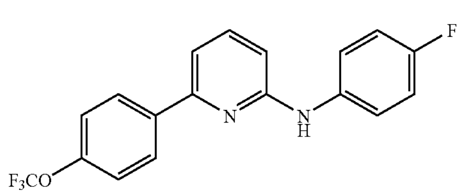 | (4-Fluoro-phenyl)-[6-(4-trifluoromethoxy-phenyl)-pyridin-2-yl]-amine |

TABLE 3-continued

Compounds of the present invention that have at least the activity of affecting cellular proliferation

| Entry | Structure | Compound Name |
|---|---|---|
| 36 | 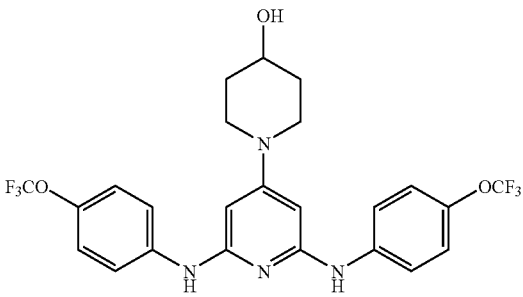 | 2',6'-Bis-(4-trifluoromethoxy-phenylamino)-3,4,5,6-tetrahydro-2H-[1,4']bipyridinyl-4-ol |

Methods for identifying the activity and screening for one or more of these compounds or molecules that induce synthesis of proteoglycans such as HSPG are taught in U.S. patent application Ser. No. 10/091,357, which is incorporated herein in its entirety. Assays of effects of compounds in vivo are also taught in the incorporated references and are known to those skilled in the art. In general, methods comprise the addition of such compounds to assays and measurement of HSPG synthesis including, but not limited to, the production of syndecans, glypicans, and perlecans, for example, syndecans 1, 2 and 4; and glypican-1. Other assays that can be used to determine the activity of the compounds of the present invention include other methods for measuring the induction of perlecan synthesis. For example, in one assay, perlecan is induced in cells by certain inducers, and the response is measured. Compounds of the present invention are then added to a replicate assay and the effect on perlecan induction is determined. Using such methods, compounds are determined that can either inhibit perlecan, elevate induction of perlecan, or have no effect at all. Those compounds that are effective as therapeutic agents can then be used in animals, humans or patients with cellular proliferation disease aspects, such as vascular-associated diseases or SMC (smooth muscle cell) proliferation pathologies.

Another assay for determining compounds having SMC effects comprises adding a composition suspected of effecting SMC proliferation to smooth muscle cells in growth medium or serum-free medium. The change in cell proliferation can be measured by methods known to those skilled in the art, such as incorporation of labeled nucleotides into dividing cells' DNA, and compared to the proliferation of cells which are not treated with the compound. Other measurements include directly determining levels of HSPG synthesis by measuring the amount or change in amount of HSPG such as with ELISA for HSPGs, and compared to the amount of HSPG synthesis in untreated cells. Other indirect or direct measurements are contemplated by the present invention and are known to those skilled in the art. For example, such methods include, but are not limited to, measurement of RNA levels, RT-PCR, Northern blotting, Western blotting promoter-based assays to identify compounds that affect one or more proteoglycans and assays for proteoglycan biological activity shown by recombinant proteins, partially purified proteins, or lysates from cells expressing proteoglycans in the presence or absence of compounds of interest.

An assay for identifying and determining an activity of one or more of the compounds of the present invention comprises identifying compounds that interact with the promoter regions of a gene, or interact and effect proteins that interact with the promoter region, and are important in the transcriptional regulation of the protein's expression. For example, if perlecan were the protein, in general, the method comprises a vector comprising regulatory sequences of the perlecan gene and an indicator region controlled by the regulatory sequences, such as an enzyme, in a promoter-reporter construct. The protein product of the indicator region is referred to herein as a reporter enzyme or reporter protein. The regulatory region of the sequence of perlecan comprises a range of nucleotides from approximately −4000 to +2000 wherein the transcription initiation site is +1, alternatively, from −2500 to +1200, and still alternatively, from −1500 to +800 relative to the transcription initiation site.

Cells are transfected with a vector comprising the promoter-reporter construct and then treated with one or more compositions comprising at least one compound of the present invention. For example, the transfected cells are treated with a composition comprising a compound suspected of effecting the transcription of perlecan and the level of activity of the perlecan regulatory sequences are compared to the level of activity in cells that were not treated with the compound. The levels of activity of the perlecan regulatory sequences are determined by measuring the amount of the reporter protein or determining the activity of the reporter enzyme controlled by the regulatory sequences. An increase in the amount of the reporter protein or the reporter enzyme activity shows a stimulatory effect on perlecan, by positively effecting the promoter, whereas a decrease in the amount or the reporter protein or the reporter enzyme activity shows a negative effect on the promoter and thus, on perlecan.

Additionally, the present invention comprises methods and compositions that can be used with gene therapy methods and composition, such as those gene therapy methods comprising administering compositions comprising nucleic acids that effect the synthesis or expression of HSPGs, particularly perlecan. Such methods and compositions are taught in U.S. patent application Ser. No. 10/091,357, incorporated herein by reference.

The present invention comprises methods and compositions for mediating proteoglycan synthesis, expression and for the maintenance of SMC in a quiescent state. Methods and compositions of the present invention comprise treatment and prevention of vascular diseases and pathologies related to cellular proliferation, such as SMC proliferation. Such methods and compositions comprise methods for inhibition of SMC growth and proliferation, and for induction of quiescence in smooth muscle cells. Aspects of the present invention comprise methods and compositions for inducing proteoglycan synthesis, particularly HSPG synthesis and expression including, but not limited to, the induction of HSPGs such as syndecans, glypicans, and perlecans, and preferably perlecan synthesis and gene expression. Perlecan is a major extracellular HSPG in the blood vessel matrix. It interacts with extracellular matrix proteins, growth factors and receptors. Perlecan is also present in basement membranes other than blood vessels and in other extracellular matrix structures.

The activities of the compounds included in the present invention affect cells or tissues to increase the synthesis of proteoglycans by those cells or tissues or can act directly upon one or more proteoglycans to modulate the biological activity or to increase the biological stability of the proteoglycan itself, for example, of the protein perlecan. Activities also included herein are ones that increase the biosynthesis of one or more proteoglycans by increasing the transcription of the poteoglycan gene, increasing the biological stability of the proteoglycan mRNA or increasing the translation of proteoglycan mRNA into protein. Further activites include activities of compounds that can block or decrease the effects of agents or proteins that inhibit the activity of proteoglycans.

The present invention comprises methods and compositions for the treatment and prevention of smooth muscle cell proliferation, including vascular occlusive pathologies. Such methods comprise administration of compositions comprising compounds capable of inhibiting SMC proliferation, such as compositions comprising compounds disclosed herein that inhibit SMC proliferation. Administration of such compounds that are effective in inhibiting SMC proliferation are administered to humans and animals suspected of having or who have, for example, vasculopathy or who have undergone angioplasty or other procedures damaging to the endothelium. Effective amounts are administered to such humans and animals in dosages that are safe and effective, including, but not limited to, the ranges taught herein. Routes of administration include, but are not limited to, those disclosed herein. As disclosed herein, compositions comprising such compounds may be used in conjunction with other therapeutic agents or in methods comprising steps such as altered patient activities, including, but not limited to, changes in exercise or diet.

Glycosidase Modulation Activity

The present invention also comprises methods and compositions comprising compounds described herein that have an activity associated with modulation of glycosidase enzymes and thus, effecting the substrates for such enzymes. Glycosidase enzymes and their activity with their substrates, such as proteoglycans or glycated proteins, are aspects of a variety of diseases such as vascular conditions, including those conditions discussed supra, proteoglycan-associated diseases, supra, associated diseases with vascular components, including but not limited to, kidney disease, ischemic heart disease, cardiovascular disease, generalized vascular disease, proliferative retinopathy, macroangeopathy, inflammatory diseases, and metastatic diseases such as cancer, cellular proliferative conditions, and solid and blood borne tumors, or other oncological conditions. Compounds described herein that have an activity that affects the concentrations of substrates of glycosidase enzymes are used in methods of treatment of such vascular, inflammatory, metastatic, and systemic diseases.

Compounds or compositions comprising such compounds that are effective in modulating glycosidase enzyme activity are useful in treating and/or preventing cancer including, but not limited to, malignant and non-malignant cell growth, and the like. In another aspect of the present invention, the compounds disclosed herein are useful in modulating heparanase activity or the activity of other glycosidases as a means for treating and preventing autoimmune diseases.

Thus, the inhibition of heparanase or the activity of other glycosidases using the compounds of the present invention finds utitlity in treating arthritis and other autoimmune diseases. More specifically, the compounds of the present invention are useful in the treatment or prophylaxis of at least one autoimmune-related disease in a cell, tissue, organ, animal, or patient including, but not limited to, rheumatoid arthritis, juvenile rheumatoid arthritis, systemic onset juvenile rheumatoid arthritis, psoriatic arthritis, ankylosing spondilitis, gastric ulcer, seronegative arthropathies, osteoarthritis, inflammatory bowel disease, ulcerative colitis, systemic lupus erythematosis, antiphospholipid syndrome, iridocyclitis/uveitis/optic neuritis, idiopathic pulmonary fibrosis, systemic vasculitis/wegener's granulomatosis, sarcoidosis, orchitis/vasectomy reversal procedures, allergic/atopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma/hemorrhage, burns, ionizing radiation exposure, acute pancreatitis, adult respiratory distress syndrome, rheumatoid arthritis, alcohol-induced hepatitis, chronic inflammatory pathologies, Crohn's pathology, sickle cell anemia, diabetes, nephrosis, atopic diseases, hypersensitity reactions, allergic rhinitis, hay fever, perennial rhinitis, conjunctivitis, endometriosis, asthma, urticaria, systemic anaphalaxis, dermatitis, pernicious anemia, hemolytic disesease, thrombocytopenia, graft rejection of any organ or tissue, kidney translplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynoud's disease, type B insulin-resistant diabetes, asthma, myasthenia gravis, type III hypersensitivity reactions, POEMS syndrome (polyneuropathy, organomegaly, endocrinopathy, monoclonal gammopathy, and skin changes syndrome), polyneuropathy, organomegaly, endocrinopathy, monoclonal gammopathy, skin changes syndrome, antiphospholipid syndrome, pemphigus, scleroderma, mixed connective tissue disease, idiopathic Addison's disease, autoimmune hemolytic anemia, autoimmune hepatitis, idiopathic pulmonary fibrosis, scleroderma, diabetes mellitus, chronic active hepatitis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, Hashimoto's thyroiditis, osteoporosis, hypothalamic-pituitary-adrenal axis evaluation, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, ankylosing spondylitis, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatricial pemphigoid, CREST syndrome, cold agglutinin disease, discoid lupus, essential mixed cryoglobulinemia, fibromyalgia-fibromyositis, Graves' disease, Guillain-Barré, Hashimoto's thyroiditis, idiopathic thrombocytopenia purpura (ITP), IgA nephropathy, insulin dependent diabetes, juvenile arthritis, lichen planus, ménière's disease, multiple sclerosis, pemphigus vulgaris, polyarteritis nodosa, Cogan's syndrome, polychondritis, polyglandular syndromes, polymyalgia rheumatica, polymyositis and dermatomyositis, primary agammaglobulinemia, Raynaud's phenomenon, Reiter's syndrome, rheumatic fever, Sjögren's syndrome, stiffman syndrome, Takayasu arteritis, temporal arteritis/giant cell arteritis, Wegener's granulomatosis; okt3 therapy, anti-cd3 therapy, cytokine therapy, chemotherapy, radiation therapy (e.g., including but not limited toasthenia, anemia, cachexia, and the like), chronic salicylate intoxication, and the like.

Compounds having heparanase activity inhibition, that are effective for example, in treatment of cancer and autoimmune disease, can be determined using assays such as those disclosed in U.S. patent application Ser. No. 09/952,648, which is incorporated herein in its entirety. Such assays, which are used for measurement of cellular and enzymatic activities, both qualitatively and quantitatively, and in methods for diagnosing metastases, metastatic potential, and inflammatory states, are performed with and without the addition of at least one of the compounds of the present invention to determine the activity of the compound. Existing heparanase assays are taught in Goshen et al., 2 MOL. HUM. REPROD. 679-84 (1996); Nakajima et al., 31 CANCER LETT. 277-83 (1986); and Vlodasky et al., 12 INVASION METASTASIS 112-27 (1992); Freeman and Parish, 325 BIOCHEM. J. 229-37 (1997); Kahn and Newman, 196 ANAL. BIOCHEM. 373-76 (1991). Solid-phase heparanase assays have also been developed where chemically and biosynthetically radiolabeled heparin and HS chains were attached to a solid support, with release of radiolabel from the solid support being a measure of enzyme activity. Assays using such procedures are taught in U.S. Pat. No. 4,859,581, which is incorporated herein by reference in its entirety.

The present invention comprises methods and compositions for the treatment and prevention of diseases or conditions that present or result from glycosidase activity. Such methods comprise administration of compositions comprising compounds capable of modulating heparanase activity, such as compositions comprising compounds disclosed herein that inhibit heparanase activity. Administration of such compounds that are effective in modulating heparanase activity are administered to humans and animals suspected of having or who have, for example, inflammatory conditions, autoimmune disease, or diabetic vasculopathy. Effective amounts are administered to such humans and animals in dosages that are safe and effective, including, but not limited to, the ranges taught herein. Routes of administration include, but are not limited to, those disclosed herein. As disclosed herein, compositions comprising such compounds can be used in conjunction with other therapeutic agents or in methods comprising steps such as altered patient activities.

Inflammation Modulation

One aspect of the present invention comprises methods and compositions comprising compounds of the present invention for the treatment and prevention of conditions or diseases that have as an aspect of the disease or condition, inflammation. An aspect of the present invention is directed to methods and compositions comprising compounds that are effective in inhibiting inflammation, particularly inflammation associated with the accumulation or presence of glycated proteins or AGE. The activity of modulating inflammation includes, but is not limited to, inhibiting inflammation and/or its associated cell activation by glycated proteins or AGE, blocking the glycation of proteins, blocking AGE interactions with receptors, blocking AGE-induced signaling or signaling-associated inflammatory responses, cytokine induction, synthesis, or release, AGE formation, or AGE cross-linking.

The present invention also provides compositions for and methods of treatment of biological conditions including, but not limited to, vascular complications of type I and type II diabetes and atherosclerosis. Other inflammatory related diseases include, but are not limited to, rheumatoid arthritis, osteoarthritis, intraoccular inflammation, psoriasis, and asthma.

The compounds of the present invention have utility in inhibiting inflammation and/or its associated cell activation by glycated proteins or AGE. Pharmacological inhibition of AGE-induced cell activation provides the basis for therapeutic intervention in many diseases, notably in diabetic complications and Alzheimer's disease. Therapeutic approaches for inhibition of AGE-induced inflammation include, but are not limited to, blocking the glycation of proteins, blocking AGE interactions with receptors, and blocking AGE-induced signaling or signaling-associated inflammatory responses.

Compounds of the present invention that have at least the activity of modulating inflammation activity are shown in Table 4. The compounds shown in this Table have the activity of modulating inflammation activity as measured by the assays taught herein.

TABLE 4

Compounds of the present invention that have at least the activity of modulating inflammation activity

| Entry | Structure | Compound Name |
|---|---|---|
| 1 | 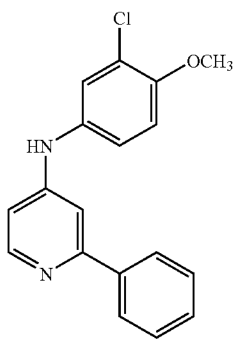 | 3-chloro-4-methoxy-phenyl)-(2-phenyl-pyridin-4-yl)-amine |
| 2 | 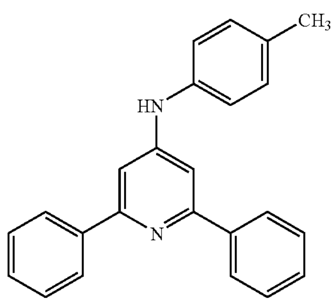 | (2,6-diphenyl-pyridin-4-yl)-p-tolyl-amine |
| 3 | 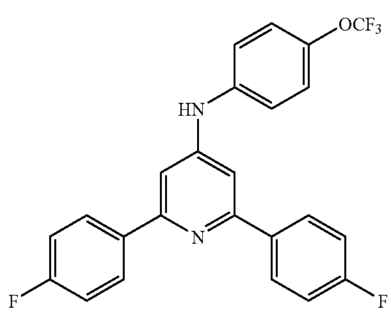 | [2,6-bis-(4-fluoro-phenyl)-pyridin-4-yl]-(4-trifluoromethoxy-phenyl)-amine |
| 4 | 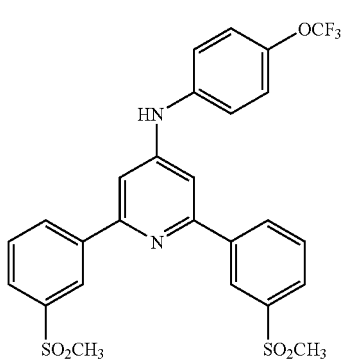 | 2,6-Bis-(3-methanesulfonyl-phenyl)-pyridin-4-yl]-(4-trifluoromethoxy-phenyl)-amine |

TABLE 4-continued

Compounds of the present invention that have at least the activity of modulating inflammation activity

| Entry | Structure | Compound Name |
|---|---|---|
| 5 | 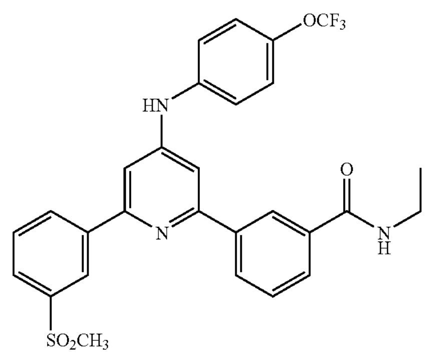 | N-ethyl-3-[6-(3-methanesulfonyl-phenyl)-4-(4-trifluoromethoxy-phenylamino)-pyridin-2-yl]-benzamide |
| 6 | 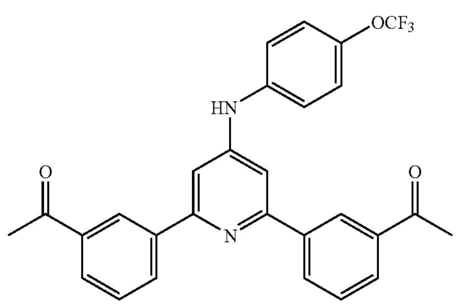 | 1-{3-[6-(3-acetyl-phenyl)-4-(4-trifluoromethoxy-phenylamino)-pyridin-2-yl]-phenyl}-ethanone |
| 7 | 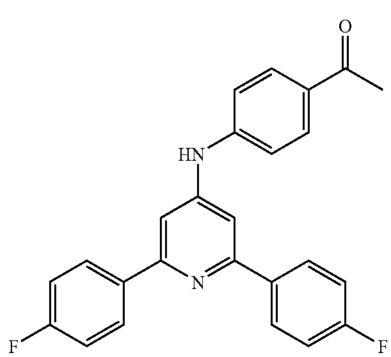 | 1-{4-[2,6-bis-(4-fluoro-phenyl)-pyridin-4-ylamino]-phenyl}-ethanone |
| 8 | 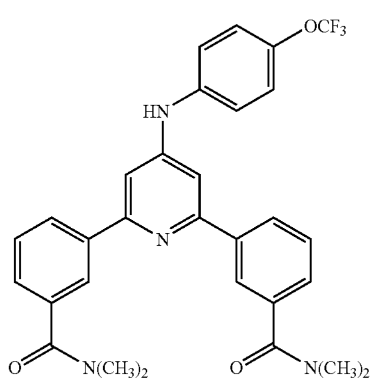 | [2,6-bis-(3-N,N-dimethyl-benzamide)-pyridin-2-yl]-(4-trifluoromethoxy-phenyl)-amine |

TABLE 4-continued

Compounds of the present invention that have at least the activity of modulating inflammation activity

| Entry | Structure | Compound Name |
|---|---|---|
| 9 | 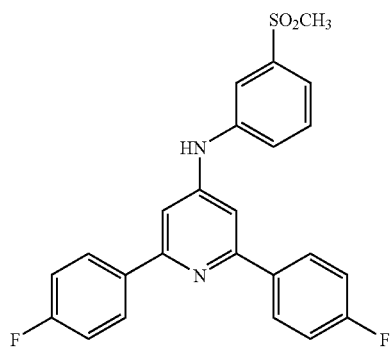 | [2,6-Bis-(4-fluoro-phenyl)-pyridin-4-yl]-(3-methanesulfonyl-phenyl)-amine |
| 10 | 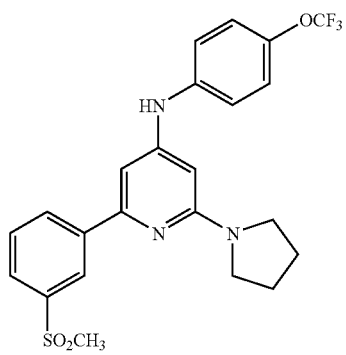 | [2-(3-Methanesulfonyl-phenyl)-6-pyrrolidin-1-yl-pyridin-4-yl]-(4-trifluoromethoxy-phenyl)-amine |
| 11 | 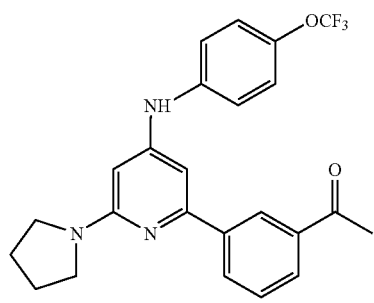 | 1-{3-[6-pyrrolidin-1-yl-4-(4-trifluoromethoxy-phenylamino)-pyridin-2-yl]-phenyl}-ethanone |
| 12 | 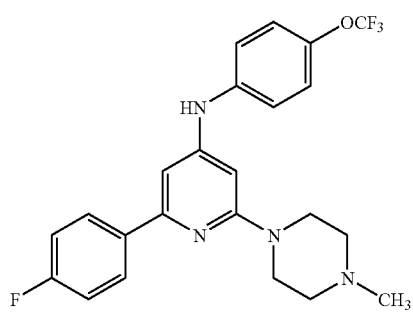 | [2-(4-fluoro-phenyl)-6-(4-methyl-piperazin-1-yl)-pyridin-4-yl]-(4-trifluoromethoxy-phenyl)-amine |

TABLE 4-continued

Compounds of the present invention that have at least the activity of modulating inflammation activity

| Entry | Structure | Compound Name |
|---|---|---|
| 13 | 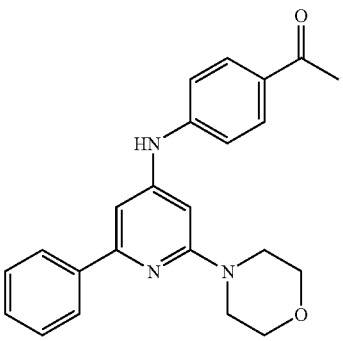 | 1-[4-(2-morpholin-4-yl-6-phenyl-pyridin-4-ylamino)-phenyl]-ethanone |
| 14 | 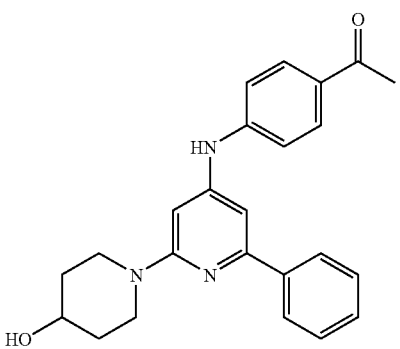 | 1-[4-(4-hydroxy-6'-phenyl-3,4,5,6-tetrahydro-2H-[1,2']bipyridinyl-4'-ylamino)-phenyl]-ethanone |
| 15 | 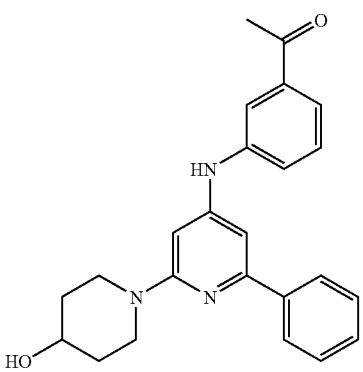 | 1-[3-(4-hydroxy-6'-phenyl-3,4,5,6-tetrahydro-2H-[1,2']bipyridinyl-4'-ylamino)-phenyl]-ethanone |
| 16 | 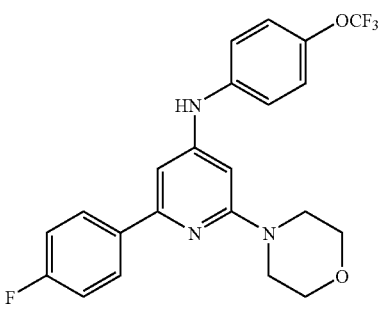 | [2-(4-fluoro-phenyl)-6-morpholin-4-yl-pyridin-4-yl]-(4-trifluoromethoxy-phenyl)-amine |

TABLE 4-continued

Compounds of the present invention that have at least the activity of modulating inflammation activity

| Entry | Structure | Compound Name |
|---|---|---|
| 17 | 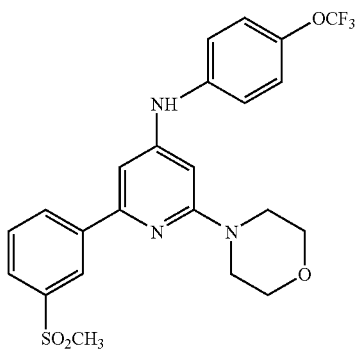 | [2-(3-methanesulfonyl-phenyl)-6-morpholin-4-yl-pyridin-4-yl]-(4-trifluoromethoxy-phenyl)-amine |
| 18 | 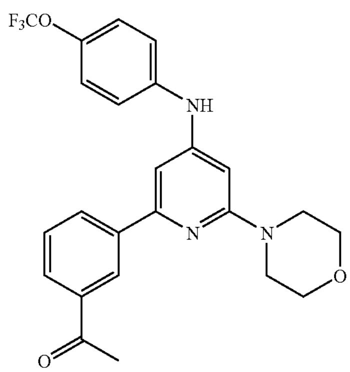 | 1-{3-[6-morpholin-4-yl-4-(4-trifluoromethoxy-phenylamino)-pyridin-2-yl]-phenyl}-ethanone |
| 19 | 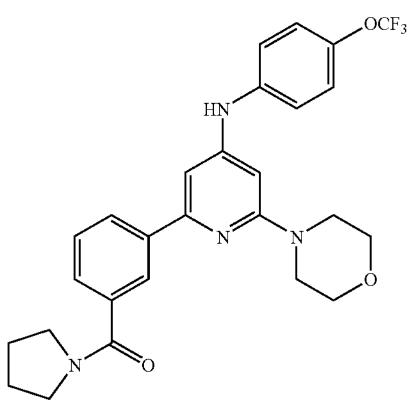 | {3-[6-morpholin-4-yl-4-(4-trifluoromethoxy-phenylamino)-pyridin-2-yl]-phenyl}-pyrrolidin-1-yl-methanone |
| 20 | 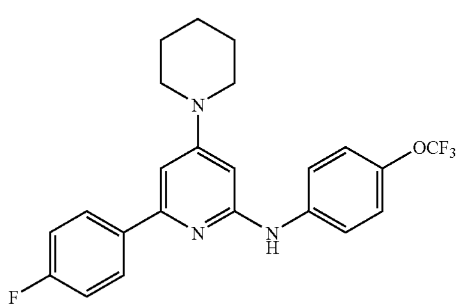 | [6'-(4-Fluoro-phenyl)-3,4,5,6-tetrahydro-2H-[1,4']bipyridinyl-2'-yl]-(4-trifluoromethoxy-phenyl)-amine |

TABLE 4-continued

Compounds of the present invention that have at least the activity of modulating inflammation activity

| Entry | Structure | Compound Name |
|---|---|---|
| 21 | 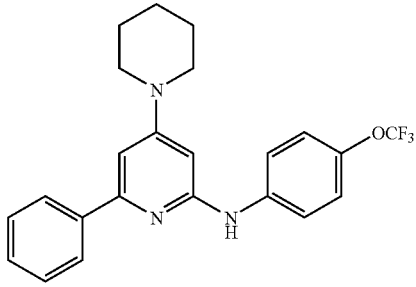 | (6'-Phenyl-3,4,5,6-tetrahydro-2H-[1,4']bipyridinyl-2'-yl)-(4-trifluoromethoxy-phenyl)-amine |
| 22 | 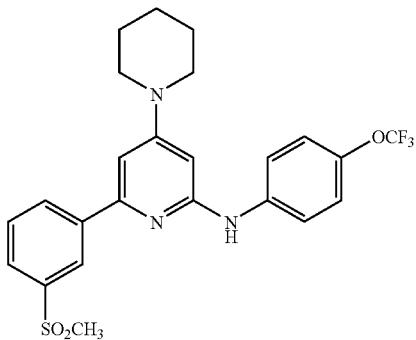 | [6'-(3-Methanesulfonyl-phenyl)-3,4,5,6-tetrahydro-2H-[1,4']bipyridinyl-2'-yl]-(4-trifluoromethoxy-phenyl)-amine |
| 23 | 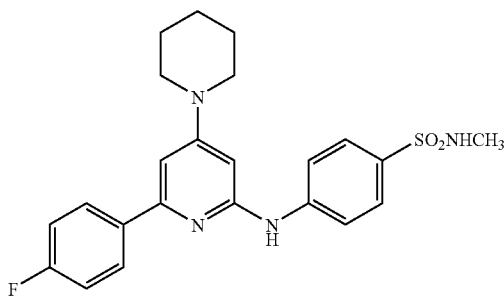 | 4-[6'-(4-Fluoro-phenyl)-3,4,5,6-tetrahydro-2H-[1,4']bipyridmyl-2'-yl-amino]-N-methyl-benzenesulfonamide |
| 24 | 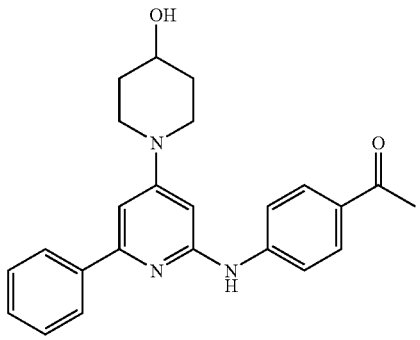 | 1-[4-(4-Hydroxy-6'-phenyl-3,4,5,6-tetrahydro-2H-[1,4']bipyridinyl-2'-ylamino)-phenyl]-ethanone |

TABLE 4-continued

Compounds of the present invention that have at least the activity of modulating inflammation activity

| Entry | Structure | Compound Name |
|---|---|---|
| 25 | 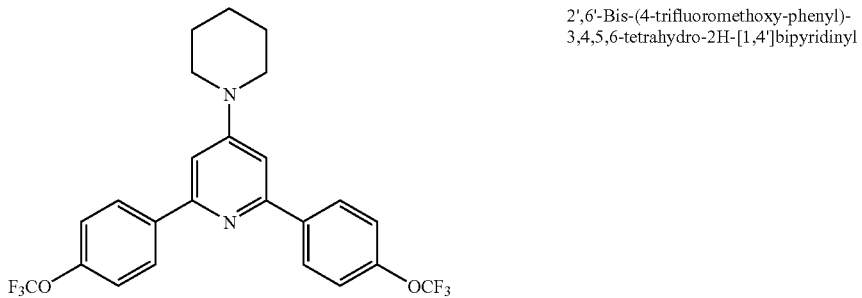 | 2',6'-Bis-(4-trifluoromethoxy-phenyl)-3,4,5,6-tetrahydro-2H-[1,4']bipyridinyl |
| 26 | 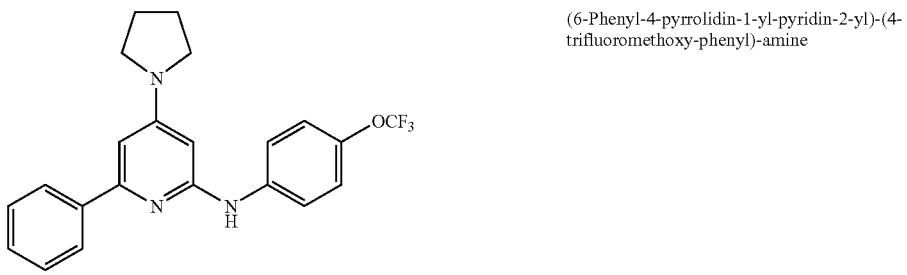 | (6-Phenyl-4-pyrrolidin-1-yl-pyridin-2-yl)-(4-trifluoromethoxy-phenyl)-amine |
| 27 | 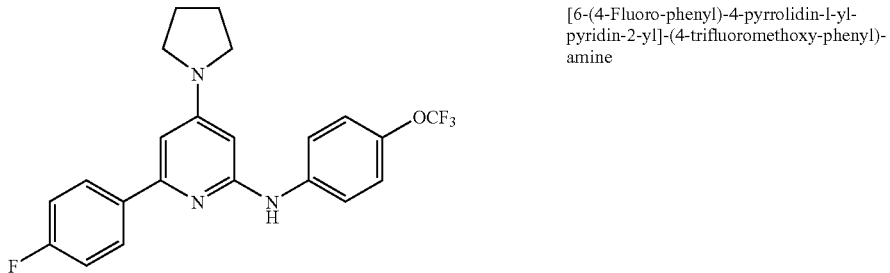 | [6-(4-Fluoro-phenyl)-4-pyrrolidin-1-yl-pyridin-2-yl]-(4-trifluoromethoxy-phenyl)-amine |
| 28 | 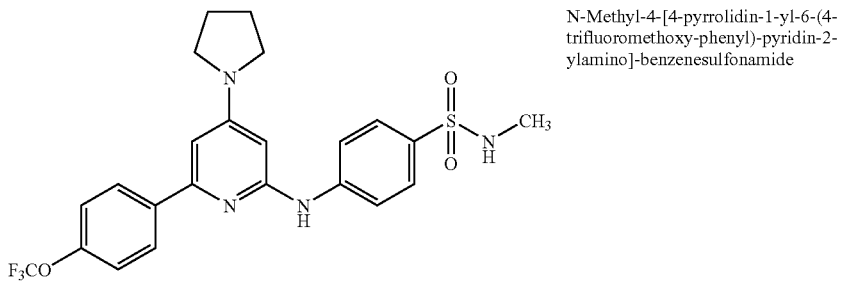 | N-Methyl-4-[4-pyrrolidin-1-yl-6-(4-trifluoromethoxy-phenyl)-pyridin-2-ylamino]-benzenesulfonamide |

TABLE 4-continued

Compounds of the present invention that have at least the activity of modulating inflammation activity

| Entry | Structure | Compound Name |
|---|---|---|
| 29 | 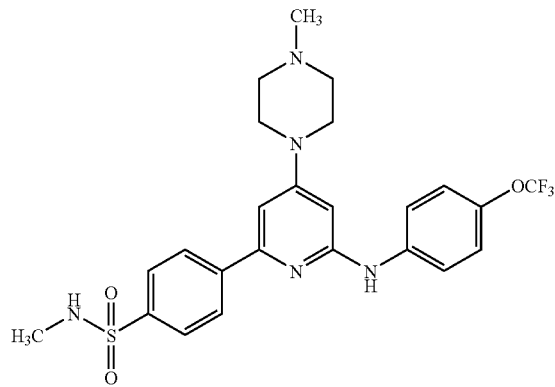 | N-Methyl-4-[4-(4-methyl-piperazin-1-yl)-6-(4-trifluoromethoxy-phenylamino)-pyridin-2-yl]-benzenesulfonamide |
| 30 | 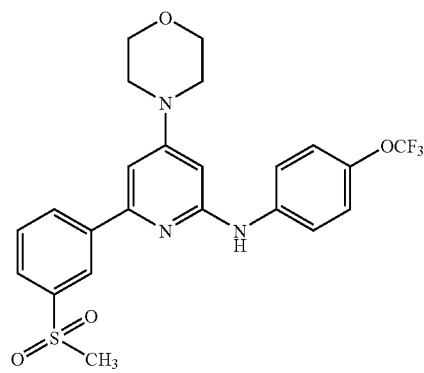 | [6-(3-Methanesulfonyl-phenyl)-4-morpholin-4-yl-pyridin-2-yl]-(4-trifluoromethoxy-phenyl)-amine |
| 31 | 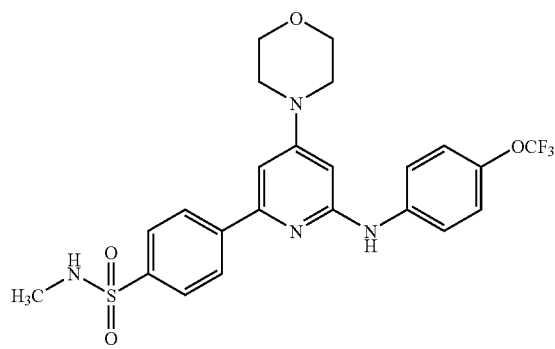 | N-Methyl-4-[4-morpholin-4-yl-6-(4-trifluoromethoxy-phenylamino)-pyridin-2-yl]-benzenesulfonamide |
| 32 | 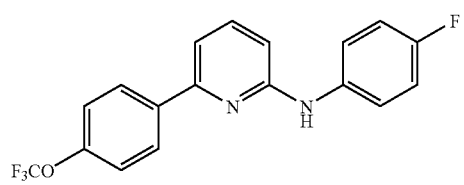 | (4-Fluoro-phenyl)-[6-(4-trifluoromethoxy-phenyl)-pyridin-2-yl]-amine |

TABLE 4-continued

Compounds of the present invention that have at least the activity of modulating inflammation activity

| Entry | Structure | Compound Name |
|---|---|---|
| 33 | [structure] | 2',6'-Bis-(4-trifluoromethoxy-phenylamino)-3,4,5,6-tetrahydro-2H-[1,4']bipyridinyl-4-ol |

The inclusion of compounds in the categories of the tables disclosed herein are not to be seen as limiting, in that compounds included in such tables have at least the activity shown for inclusion in the table and may have more or other activities. Nor are the tables to be seen as limiting in that these are the only compounds disclosed herein that have that activity, representative compounds are shown in the tables that have at least that particular activity for inclusion in the table. One or more compounds disclosed herein have at least an activity that has utility in treatment of disease states.

The activity of the compounds of the present invention in inhibiting glycated protein- and AGE-induced inflammation can be determined using the assays described herein and in U.S. patent application Ser. No. 10/026,335, which is incorporated by reference herein in its entirety. Such assays comprise measurement of the specific activity of biological components involved in a known cellular response. The assays provide a measurable response in which the activity of the compounds is determined. One assay comprises measurement of the effects of compounds on an inflammatory response by cells to the presence of a stimulating agent. Yet another assay comprises endothelial cells that are stimulated by the addition of a glycated protein, the stimulating agent. The endothelial cells respond by producing specific cytokines. The amount of cytokines produced are determined by measurement protocols known to those skilled in the art. The compounds of the present invention are then added to the assay and the production of cytokines is measured. From the comparison of the assay without the compound with the assay with the compound, the biological effect of the compound can be determined. The compound may have an inhibitory effect, a stimulatory effect, or no effect at all.

The amount and type of cytokine produced can be determined using immunological methods, such as ELISA assays. The methods of the present invention are not limited by the type of assay used to measure the amount of cytokine produced, and any methods known to those skilled in the art and later developed can be used to measure the amount of cytokines produced in response to the stimulating agent and to the compound having unknown activity.

An aspect of the present invention comprises methods and compositions for the treatment of diseases, preconditions, or pathologies associated with inflammatory cytokines and other inflammation related molecules including, but not limited to IL-6, VCAM-1, or AGE-induced MCP-1, (monocyte chemoattractant protein 1).

Assays for determining the activity of compounds capable of modulating inflammation include those taught in U.S. patent application Ser. Nos. 10/026,335 and 09/969,013, which are both expressly incorporated by reference in their entireties. In general, once the baseline response to the stimulating agent for the production of cytokines by the endothelial cells is established, thus comprising the control levels for the screening assay, the methods comprise addition of compounds of the present invention. The effect of the compound on the baseline response is determined by comparing the amount of cytokine produced in the presence of the stimulating agent and the amount of cytokine produced in the presence of the stimulating agent and the compound of the present invention. In one aspect, compounds that have inhibitory effects on the inflammation of the cells in the presence of glycated albumin are then used as therapeutic agents. One or more compounds can be added to the screening assay. Combinations or mixtures of compounds can be added. Different amounts and formulations of the compounds are added to determine the effects on the screening assay. The screening assay can also be used to determine stimulatory compounds or compounds that have no effects in the assay.

The present invention comprises methods and compositions for the treatment and prevention of disease, conditions and pathologies associated with inflammation. Such methods comprise administration of compositions comprising compounds capable of modulating the activity of molecules associated with inflammation such as AGE or cytokines or other cellular factors, including release rates or activity, and include compositions comprising compounds disclosed herein with inflammation modulating activity. Administration of such compounds that are effective in modulating inflammation are administered to humans and animals suspected of having or who have inflammatory diseases, for example, diabetic-induced vasculopathies, autoimmune diseases, renal insufficiency, Alzheimer's syndrome, and inflammation-induced diseases such as atherosclerosis. Effective amounts are administered to such humans and animals in dosages that are safe and effective, including, but not limited to, the ranges taught herein. Routes of administration include, but are not limited to, those disclosed herein. As disclosed herein, compositions comprising such compounds can be used in conjunction with other therapeutic agents or in methods comprising steps such as altered patient activities, including, but not limited to, changes in exercise or diet.

Correlation of Physiological Parameters and Assays to Diseases and Conditions

The following Tables 5-8 provide disclosure and references that relate the various physiological parameters and assays disclosed herein to general and specific diseases, disease states, and conditions. Among other things, the references and citations provided in these tables support the specification as fully enabled for treating or modulating all the diseases or conditions encompassed herein, based on the inhibiting activity of the compounds provided in the specification, and the predictive nature of the tests provided of the disclosed uses. In particular, Tables 5-8 provide specific references that link the parameters measured in the key assays disclosed in the application with a specific physiology, pathophysiology, or medical condition.

Table 5 provides scientific references that demonstrate, among other things, the connection between TNF-α and IL-6 in rheumatoid arthritis, vascular inflammation, and atherosclerosis. For example, these references demonstrate the importance of TNF inhibition in preventing rheumatoid arthritis, the therapeutic benefit of IL-6 inhibition in rheumatoid arthritis as well as its importance in preventing rheumatoid arthritis, the role of AGE in different diabetic vascular diseases, and AGE inhibition as a therapeutic strategy for vascular complications.

Further, Table 6 provides scientific references that demonstrate, among other things, the importance of HSPG in the prevention of atherosclerosis and diabetic vascular disease. For example, these references demonstrate that atherosclerotic vessels have reduced HSPG, and that cholesterol deposition is inversely correlated to HSPG content in the vessel.

Table 7 also provides scientific references that demonstrate, among other things, the connection between smooth muscle cell (SMC) proliferation in contributing to restenosis and atherosclerosis. For example, these references demonstrate that: smooth muscle proliferation contributes to unstable angina and restenosis; inhibition of SMC proliferation by LRP is important for atherosclerosis prevention; and the function of the SMC inhibitor, rapamycin, in preventing restenosis and vein graft disease.

Table 8 provides scientific references that demonstrate, among other things, the role of heparanase and TNF-α in promoting tumor angiogenesis and metastasis, as well as the use of inhibitors of heparanase and TNF-α in treating cancer. For example, these references demonstrate the role of heparanase inhibitors in treating tumor angiogenesis and metastasis, the role of TNF-α as a tumor-promoting agent, and the use of TNF-α inhibitors in the treatment of cancer.

The key assays described herein for screening the compounds in the present invention include, but are not limited to: a) the inhibition of smooth muscle cell (SMC) proliferation, that was used to identify, for example, compounds in Table 3; b) the induction of HSPG in smooth muscle cells; c) the induction of heparanase in endothelial cells; d) the inhibition of AGE-induced inflammatory response in endothelial cells as measured by IL-6 or other inflammatory cytokines, that was used to identify, for example, compounds in Table 4; and e) cytotoxicity effects of the disclosed compounds. By using these disclosed assays, the present disclosure is fully enabled for identification of compounds for the treatment of the diseases disclosed generically and specifically.

Accordingly, this evidence along with the references of Tables 5-8 demonstrate that the parameters measured in the key assays above are associated with and predictive of the specific physiology, pathophysiology, or medical conditions disclosed herein. The physiology, pathophysiology, or medical conditions disclosed include generically disclosed conditions and diseases such as, but are not limited to, unwanted cellular proliferation, inflammation mediated diseases, hyperproliferative diseases, and diseases involving a glycosidase. Specifically disclosed diseases include, but are not limited to, restenosis, vascular occlusive diseases, arthritis, cancer, and the like. Therefore, methods of treating diseases, disease states, or conditions disclosed in the specification, or methods of modulating, for example, the production or uptake of a biologically-active chemical, are disclosed in such as way as to allow the skilled artisan to make and use the invention, the tests provided are predictive of the claimed uses, and therefore are fully enabled for all the diseases or conditions encompassed therein.

TABLE 5

The Role of TNF-α, IL-6, and AGE in Rheumatoid Arthritis, Vascular Inflammation, and Atherosclerosis.

| Author | Title of Reference | Reference Citation | Physiological Parameter | Disease | Pages in reference arguing or showing connection | Other comments |
|---|---|---|---|---|---|---|
| Feldmann M Ref 1 | Discovery of TNF-α as a therapeutic target in rheumatoid arthritis: preclinical and clinical studies | Joint Bone Spine. January 2002; 69(1): 12-8 Review | TNF inhibition | Arthritis | All | Review detailing the importance of TNF-α inhibition in preventing rheumatoid arthritis |
| Choy et al Ref 2 | Therapeutic benefit of blocking interleukin-6 activity with an anti-interleukin-6 receptor monoclonal antibody in rheumatoid arthritis: a randomized, double-blind, placebo-controlled, dose-escalation trial. | Arthritis Rheum. December 2002; 46(12): 3143-50 | IL-6 inhibition | Arthritis | 3144 (abstract), 3146 | Human trial showing the therapeutic benefit of IL-6 inhibition in rheumatoid arthritis |
| Wong et al Ref 3 | The role of the interleukin-6 family of cytokines in inflammatory arthritis and bone turnover | Arthritis Rheum. May 2003; 48(5): 1177-89. Review | IL-6 inhibition | Arthrits | 1177 para 4 | Review detailing the importance of IL-6 in preventing rheumatoid arthritis |

TABLE 5-continued

The Role of TNF-α, IL-6, and AGE in Rheumatoid Arthritis, Vascular Inflammation, and Atherosclerosis.

| Author | Title of Reference | Reference Citation | Physiological Parameter | Disease | Pages in reference arguing or showing connection | Other comments |
| --- | --- | --- | --- | --- | --- | --- |
| Basta et al Ref 4 | Advanced glycation end products and vascular inflammation: implications for accelerated atherosclerosis in diabetes | Cardiovasc Res. Sep. 1, 2004; 63(4): 582-92 | AGE-IL6 inhibition | Diabetic vascular diseases | 582, 589 | Highlights the role of AGE in different diabetic vascular diseases and AGE inhibition as a therapeutic strategy for vascular complications |

TABLE 6

The Potential Role of HSPG Induction in the Prevention of Atherosclerosis and Diabetic Vascular Disease.

| Author | Title of Reference | Reference Citation | Physiological Parameter | Disease | Pages in reference arguing or showing connection | Other comments |
| --- | --- | --- | --- | --- | --- | --- |
| Engelberg H. Ref 5 | Endogenous heparin activity deficiency: the 'missing link' in atherogenesis? | Atherosclerosis. December 2001; 159(2): 253-60. Review | HSPG induction | Atherosclerosis | All | Review detailing the importance of HSPG in preventing events related to atherosclerosis development |
| Jensen T Ref 6 | Pathogenesis of diabetic vascular disease: evidence for the role of reduced heparan sulfate proteoglycan | Diabetes. September 1997; 46 Suppl 2: S98-100 | HSPG induction | Diabetic vascular disease | All | Review detailing the importance of HSPG in preventing diabetic vascular disease |
| Hollmann J et al, Ref 7 | Relationship of sulfated glycosaminoglycans and cholesterol content in normal and atherosclerotic human aorta | Artherosclerosis. 1989; 9: 154-8 | HSPG | Atherosclerosis | | Data show that atherosclerotic vessels have reduced HSPG and that cholesterol deposition is inversely correlated to HSPG content in the vessel |
| Kruse R et al Ref 8 | Cholesterol-dependent changes of glycosaminoglycan pattern in human aorta | Basic Res Cardiol. September-October 1996; 91(5): 344-52 | HSPG | Atherosclerosis | | Data show that atherosclerotic vessels have reduced HSPG and that cholesterol deposition is inversely correlated to HSPG content in the vessel |

TABLE 7

The Role of Smooth Muscle Cell (SMC) Proliferation in Restenosis and Atherosclerosis.

| Author | Title of Reference | Reference Citation | Physiological Parameter | Disease | Pages in reference arguing or showing connection | Other comments |
| --- | --- | --- | --- | --- | --- | --- |
| Chen et al Ref 9 | Electron microscopic studies of phenotypic modulation of smooth muscle cells in coronary arteries of patients with unstable angina pectoris and postangioplasty restenosis | Circulation. Mar. 4 1997; 95(5): 1169-75 | Smooth muscle cell (SMC) proliferation | Restenosis | 1175 (Conclusion) | Data suggest that smooth muscle proliferation contributes to unstable angina and restenosis |
| Braun-Dullaeus et al | Cell cycle progression: new therapeutic target for vascular | Circulation. Jul. 7, 1998; 98(1): 82-9 | Smooth muscle cell (SMC) | Restenosis | 82 | Review detailing the role of smooth muscle proliferation in restenosis |

TABLE 7-continued

The Role of Smooth Muscle Cell (SMC) Proliferation in Restenosis and Atherosclerosis.

| Author | Title of Reference | Reference Citation | Physiological Parameter | Disease | Pages in reference arguing or showing connection | Other comments |
|---|---|---|---|---|---|---|
| Ref 10 | proliferative disease | | proliferation | | | and pharmacological approaches to inhibit cell cycle progression |
| Boucher et al Ref 11 | LRP: role in vascular wall integrity and protection from atherosclerosis | Science. Apr. 11, 2003; 300(5617): 329-32 | Smooth muscle cell (SMC) proliferation | Atherosclerosis | Abstract | Study shows that inhibition of SMC proliferation by LRP (lipoprotein receptor-related protein) is critical for atherosclerosis prevention |
| Marx et al Ref 12 | Bench to bedside: the development of rapamycin and its application to stent restenosis | Circulation. Aug. 21, 2001 104(8): 852-5 | Smooth muscle cell (SMC) proliferation | Restenosis | 852 | Review highlighting the role of smooth muscle cell proliferation in restenosis and the application of smooth muscle cell inhibitor, rapamycin, in preventing restenosis and vein graft disease |

TABLE 8

The Role of Heparanase and TNF-α in Promoting Tumor Angiogenesis and Metastasis and the Use of Heparanase and TNF-α Inhibitors in Treating Cancer.

| Author | Title of Reference | Reference Citation | Physiological Parameter | Disease | Pages in reference arguing or showing connection | Other comments |
|---|---|---|---|---|---|---|
| Vlodavsky I et al Ref 13 | Molecular properties and involvement of heparanase in cancer metastasis and angiogenesis | J Clin Invest. August 2001; 108(3): 341-7. Review | Heparanase inhibition | Cancer | All | Review detailing the role of heparanase in promoting tumor angiogenesis and metastasis |
| Goldshmidt et al Ref 14 | Cell surface expression and secretion of heparanase markedly promote tumor angiogenesis and metastasis | Proc Natl Acad Sci U S A. Jul. 23, 2002; 99(15): 10031-6 | Heparanase inhibition | Cancer | 10031, 10036 | Study showing that heparanase promotes angiogenesis and tumor metastasis in animal models. |
| Simizu et al Ref 15 | Heparanase as a molecular target of cancer chemotherapy | Cancer Sci. July 2004; 95(7): 553-8 | Heparanase inhibition | Cancer | 553, 557 | Review detailing the role of heparanase inhibitors in tumor angiogenesis and metastasis |
| Szlosarek et al Ref 16 | Tumour necrosis factor α: a potential target for the therapy of solid tumours | The Lancet Oncology September 2003; 4: 565-73 | TNFα inhibition | Cancer | 565 | Review highlighting the role TNFα as a tumor promoting agent and the use of TNF inhibitors in the treatment of cancer |

Compound/Composition-Coated Medical Devices

The compounds of the present invention can be used alone or in combination with other agents along with delivery devices to effectively prevent and treat the diseases described herein, though particular applications are found in vascular disease, and in particular, vascular disease caused by injury and/or by transplantation. Though this example focuses on vascular disease, provision of the compounds of the present invention with medical devices for treatment of the diseases and conditions capable of being treated with the compounds is contemplated by the present invention.

Various medical treatment devices utilized in the treatment of vascular disease can ultimately induce further complications. For example, balloon angioplasty is a procedure utilized to increase blood flow through an artery and is the predominant treatment for coronary vessel stenosis. However, the procedure typically causes a certain degree of damage to the vessel wall, thereby creating new problems or exacerbating the original problem at a point later in time. Although other procedures and diseases may cause similar injury, exemplary aspects of the present invention will be described with respect to the treatment of restenosis and related complications following percutaneous transluminal coronary angioplasty and other similar arterial/venous procedures, including the joining of arteries, veins and other fluid carrying conduits in other organs or sites of the body, such as the liver, lung, bladder, kidney, brain, prostate, neck and legs.

The local delivery of a compound of the present invention and, in some aspects, along with other therapeutic agents, from a stent prevents vessel recoil and remodeling through the scaffolding action of the stent. The activity of compound provided, with or without other therapeutic agents, helps determine for which application, to treat which disease, the coated medical device is being administered. For example, compound-coated stents can prevent multiple components of neointimal hyperplasia or restenosis as well as reduce inflammation and thrombosis. Local administration of a compound of the present invention and other therapeutic agents to stented coronary arteries may also have additional therapeutic benefit. For example, higher tissue concentrations of the compounds of the present invention and other therapeutic agents may be achieved utilizing local delivery rather than systemic administration. In addition, reduced systemic toxicity may be achieved utilizing local delivery rather than systemic administration while maintaining higher tissue concentrations. In utilizing local delivery from a stent rather than systemic administration, a single procedure may suffice with better patient compliance. An additional benefit of combination therapeutic agent and/or compound therapy can be to reduce the dose of each of the therapeutic agents, thereby limiting toxicity, while still achieving a reduction in restenosis, inflammation and thrombosis. Local stent-based therapy is therefore a means of improving the therapeutic ratio (efficacy/toxicity) of anti-restenosis, anti-inflammatory, and anti-thrombotic therapeutic agents.

Although exemplary aspects of the invention will be described with respect to the treatment of restenosis and other related complications, it is important to note that the local delivery of a compound of the present invention, alone or as part of a therapeutic agent combination, can be utilized to treat a wide variety of conditions utilizing any number of medical devices, or to enhance the function and/or life of the device. For example, intraocular lenses, placed to restore vision after cataract surgery is often compromised by the formation of a secondary cataract. The latter is often a result of cellular overgrowth on the lens surface and can be potentially minimized by combining one or more compounds of the present invention having activity that is effective in preventing unwanted cellular growth with the device. Other medical devices that often fail due to tissue in-growth or accumulation of proteinaceous material in, on and around the device, such as shunts for hydrocephalus, dialysis grafts, colostomy bag attachment devices, ear drainage tubes, leads for pace makers, and implantable defibrillators can also benefit from the combinations of the compounds of the present invention, possibly other pharmaceutical agents, and the devices. Other surgical devices, sutures, staples, anastomosis devices, vertebral disks, bone pins, suture anchors, hemostatic barriers, clamps, screws, plates, clips, vascular implants, tissue adhesives and sealants, tissue scaffolds, various types of dressings, bone substitutes, intraluminal devices, and vascular supports can also provide enhanced patient benefit using this compound-device combination approach. Essentially, any type of medical device can be coated in some fashion with at least one compound of the present invention, alone or as part of a therapeutic agent combination, which enhances treatment over the use of the device or therapeutic agent without combination with the compound.

As disclosed supra, the compounds of the present invention can be administered in combinational therapies with other therapeutic agents, and are not limited to only the other therapeutic agents disclosed herein. Thus, the present invention also contemplates, in addition to various medical devices; the coatings on these devices may be used to deliver a compound of the present invention in combination with other therapeutic agents. This illustrative list of therapeutic agents can be administered through pharmeutical means or in association with medical devices and such therapeutic agents include, but are not limited to, antiproliferative/antimitotic agents including natural products such as vinca alkaloids (e.g., vinblastine, vincristine, and vinorelbine), paclitaxel, epidipodophyllotoxins (e.g., etoposide, teniposide), antibiotics [e.g., dactinomycin (actinomycin D) daunorubicin, doxorubicin and idarubicin], anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) IIb/IIIa inhibitors and vitronectin receptor antagonists; antiproliferative/antimitotic alkylating agents such as nitrogen mustards (e.g., mechlorethamine, cyclophosphamide, and analogs, melphalan, chlorambucil), ethylenimines and methylmelamines (hexamethylmelamine and thiotepa), alkyl sulfonates-busulfan, nirtosoureas [carmustine (BCNU) and analogs, streptozocin], trazenes-dacarbazinine (DTIC); antiproliferative/antimitotic antimetabolites such as folic acid analogs (methotrexate), pyrimidine analogs (e.g., fluorouracil, floxuridine, and cytarabine), purine analogs and related inhibitors [mercaptopurine, thioguanine, pentostatin and 2-chlorodeoxyadenosine (cladribine)]; platinum coordination complexes (cisplatin, carboplatin), procarbazine, hydroxyurea, mitotane, aminoglutethimide; hormones (e.g., estrogen); anticoagulants (e.g., heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory agents such as adrenocortical steroids (e.g., cortisol, cortisone, fludrocortisone, prednisone, prednisolone, 6α-methylprednisolone, triamcinolone, betamethasone, and dexamethasone), non-steroidal agents (salicylic acid derivatives, i.e., aspirin; para-aminophenol derivatives, i.e., acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives, (Cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof, cell cycle inhibitors; mTOR inhibitors; and growth factor signal transduction kinase inhibitors.

Although any number of stents can be utilized in accordance with the present invention, for simplicity, a limited number of stents will be described in exemplary aspects of the present invention. The skilled artisan will recognize that any number of stents can be utilized in connection with the present invention. In addition, as stated above, other medical devices can be utilized. For example, though stents are described, sleeves outside the vessels are also contemplated, as are other medical devices that can provide a substrate for administration for at least one of the compounds of the present invention.

A stent is commonly used as a tubular structure left inside the lumen of a duct to relieve an obstruction. Typically, stents are inserted into the lumen in a non-expanded form and are then expanded autonomously, or with the aid of a second device in situ. A common method of expansion occurs through the use of a catheter-mounted, angioplasty balloon that is inflated within the stenosed vessel or body passageway in order to shear and disrupt the obstructions associated with the wall components of the vessel and to obtain an enlarged lumen.

A stent may resemble an expandable cylinder and may comprise a fenestrated structure for placement in a blood vessel, duct, or lumen to hold the vessel, duct, or lumen open, more particularly for protecting a segment of artery from restenosis after angioplasty. The stent can be expanded circumferentially and maintained in an expanded configuration that is circumferentially or radially rigid. The stent can be axially flexible and when flexed at a band, for example, the stent avoids any externally protruding component parts.

The stent can be fabricated utilizing any number of methods. For example, the stent can be fabricated from a hollow or formed stainless steel tube that can be machined using lasers, electric discharge milling, chemical etching, or other means. The stent is inserted into the body and placed at the desired site in an unexpanded form. In one aspect, expansion can be effected in a blood vessel by a balloon catheter, where the final diameter of the stent is a function of the diameter of the balloon catheter used. It should be appreciated that a stent in accordance with the present invention can be embodied in a shape-memory material including, for example, an appropriate alloy of nickel and titanium or stainless steel.

Structures formed from stainless steel can be made self-expanding by configuring the stainless steel in a predetermined manner, for example, by twisting it into a braided configuration. In this aspect, after the stent has been formed it can be compressed so as to occupy a space sufficiently small as to permit its insertion in a blood vessel or other tissue by insertion means, wherein the insertion means include a suitable catheter, or flexible rod. Upon emerging from the catheter, the stent can be configured to expand into the desired configuration where the expansion is automatic or triggered by a change in pressure, temperature, or electrical stimulation.

Furthermore, a stent can be modified to comprise one or more reservoirs. Each of the reservoirs can be opened or closed as desired. These reservoirs can be specifically designed to hold the compound or compound/therapeutic agent combination to be delivered. Regardless of the design of the stent, the compound or compound/therapeutic agent combination dosage can be applied with enough specificity and a sufficient concentration to provide an effective dosage in the effected area. In this regard, the reservoir size in the bands is preferably sized to adequately apply the compound or compound/therapeutic agent combination dosage at the desired location and in the desired amount.

In an alternative aspect, the entire inner and outer surface of the stent can be coated with the compound or compound/therapeutic agent combination in therapeutic dosage amounts. The coating techniques can vary depending on the compound or compound/therapeutic agent combination. Also, the coating techniques can vary depending on the material comprising the stent or other intraluminal medical device.

One or more compounds of the present invention and, in some instances, other therapeutic agents as a combination, can be incorporated onto or affixed to the stent in a number of ways. In one aspect, the compound is directly incorporated into a polymeric matrix and sprayed onto the outer surface of the stent. The compound elutes from the polymeric matrix over time and enters the surrounding tissue. The compound can remain on the stent for at least three days up to approximately six months, and, in another aspect, preferably between seven and thirty days.

Any number of non-erodible polymers may be utilized in conjunction with the compound, and such polymeric compositions are well known in the art. In one aspect, the polymeric matrix comprises two layers. The base layer comprises a solution of poly(ethylene-co-vinylacetate) and polybutylmethacrylate. The compound is incorporated into this base layer. The outer layer comprises only polybutylmethacrylate and acts as a diffusion barrier to prevent the compound from eluting too quickly. The thickness of the outer layer or topcoat determines the rate at which the compound elutes from the matrix. Essentially, the compound elutes from the matrix by diffusion through the polymer matrix. Polymers are permeable, thereby allowing solids, liquids and gases to escape therefrom. The total thickness of the polymeric matrix is in the range from about one micron to about twenty microns or greater. It is important to note that primer layers and metal surface treatments can be utilized before the polymeric matrix is affixed to the medical device. For example, acid cleaning, alkaline (base) cleaning, salinization and parylene deposition may be used as part of the overall process described above.

The poly(ethylene-co-vinylacetate), polybutylmethacrylate, and compound solution can be incorporated into or onto the stent in a number of ways. For example, the solution can be sprayed onto the stent or the stent can be dipped into the solution. Other methods include spin coating and plasma polymerization. In one aspect, the solution is sprayed onto the stent and then allowed to dry. In another aspect, the solution can be electrically charged to one polarity and the stent electrically charged to the opposite polarity. In this manner, the solution and stent will be attracted to one another. In using this type of spraying process, waste can be reduced and more precise control over the thickness of the coat may be achieved.

Drug-coated stents are manufactured by a number of companies including Johnson & Johnson, Inc. (New Brunswick, N.J.), Guidant Corp. (Santa Clara, Calif.), Medtronic, Inc. (Minneapolis, Minn.), Cook Group Incorporated (Bloomington, Ind.), Abbott Labs., Inc. (Abbott Park, Ill.), and Boston Scientific Corp. (Natick, Mass.). See e.g., U.S. Pat. No. 6,273, 913; U.S. Patent Application No. 20020051730; WO 02/26271; and WO 02/26139, each expressly entirely incorporated herein by reference.

Pharmaceutical Compositions

In one aspect, the present invention provides a composition comprising at least one compound as disclosed herein.

In another aspect, this invention provides a pharmaceutical composition, comprising:

at least one compound as disclosed herein; and optionally comprising a pharmaceutically acceptable additive selected from a carrier, an auxiliary, a diluent, an excipient, a preservative, a solvate, or any combination thereof.

In yet another aspect, this invention provides a pharmaceutical composition, comprising:

at least one compound as disclosed herein; and optionally comprising a pharmaceutically acceptable additive selected from a carrier, an auxiliary, a diluent, an excipient, a preservative, a solvate, or any combination thereof;

wherein the pharmaceutical composition is in the form of a tablet, a capsule, a syrup, a cachet, a powder, a granule, a solution, a suspension, an emulsion, a bolus, a lozenge, a suppository, a cream, a gel, a paste, a foam, a spray, an aerosol, a microcapsule, a liposome, or a transdermal patch.

In still another aspect, this invention provides a pharmaceutical composition, comprising:
- at least one compound as disclosed herein;
- optionally comprising a pharmaceutically acceptable additive selected from a carrier, an auxiliary, a diluent, an excipient, a preservative, a solvate, or any combination thereof; and
- further comprising an agent selected from a chemotherapeutic agent, an immunosuppressive agent, a cytokine, a cytotoxic agent, an anti-inflammatory agent, an antirheumatic agent, a cardiovascular agent, or any combination thereof.

Accordingly, in addition to the compounds disclosed herein, the pharmaceutical compositions of the present invention can further comprise at least one of any suitable auxiliary such as, but not limited to, diluent, binder, stabilizer, buffers, salts, lipophilic solvents, preservative, adjuvant, or the like. In one aspect of the present invention, pharmaceutically acceptable auxiliaries are employed. Examples and methods of preparing such sterile solutions are well known in the art and can be found in well known texts such as, but not limited to, REMINGTON'S PHARMACEUTICAL SCIENCES (Gennaro, Ed., 18th Edition, Mack Publishing Co. (1990)). Pharmaceutically acceptable carriers can be routinely selected that are suitable for the mode of administration, solubility and/or stability of the compound.

Pharmaceutical Compositions for Oral Administration

For oral administration in the form of a tablet or capsule, a compound can be combined with an oral, non-toxic pharmaceutically acceptable inert carrier such as ethanol, glycerol, water, and the like. Moreover, when desired or necessary, suitable binders, lubricants, disintegrating agents, and coloring agents may also be incorporated into the mixture. Suitable binders include, without limitation, starch; gelatin; natural sugars such as glucose or beta-lactose; corn sweeteners; natural and synthetic gums such as acacia, tragacanth, or sodium alginate, carboxymethylcellulose; polyethylene glycol; waxes; and the like. Lubricants used in these dosage forms include, without limitation, sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

Formulations of the present invention suitable for oral administration can be presented as discrete units such as capsules, cachets, or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, and the like.

Routes of Administration

The invention further relates to the administration of at least one compound disclosed herein by the following routes, including, but not limited to oral, parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, iontophoretic means, or transdermal means.

Dosages

More specifically, the pharmaceutical compositions can be administered in a single daily dose, or the total daily dosage can be administered in divided doses of two, three, or four times daily. In the case of oral administration, the daily dosage of the compositions can be varied over a wide range from about 0.0001 to about 1,000 mg per patient, per day. Alternatively, the range can be from about 0.001 mg/kg to about 10 mg/kg of body weight per day, about 0.1 to about 100 mg, about 1.0 to about 50 mg or about 1.0 to about 20 mg per day for adults (at about 60 kg).

The daily dosage of the pharmaceutical compositions may be varied over a wide range from about 0.01 to about 1000 mg per adult human per day. For oral administration, the pharmaceutical compositions can be provided in the form of tablets containing from about 0.1 mg to about 1000 mg of the compound or about 0.1, 0.2, 0.5, 1.0, 2.0, 5.0, 10.0, 15.0, 100, 150, 200, 250, 300, 350, 400, 450, 500, 550, 600, 650, 700, 800, 900, or 1000 milligrams of the active compound for the symptomatic adjustment of the dosage to the patient to be treated. An effective amount of the drug is ordinarily supplied at a dosage level of from about 0.1 mg/kg to about 20 mg/kg of body weight per day. In one aspect, the range is from about 0.2 mg/kg to about 10 mg/kg of body weight per day. In another aspect, the range is from about 0.5 mg/kg to about 10 mg/kg of body weight per day. The compounds may be administered on a regimen of about 1 to about 10 times per day.

In the case of injections, it is usually convenient to give by an intravenous route in an amount of about 0.01 to about 30 mg, about 0.1 to about 20 mg or about 0.1 to about 10 mg per day to adults (at about 60 kg). In the case of other animals, the dose calculated for 60 kg may be administered as well.

In addition, co-administration or sequential administration of the compounds of the present invention and other therapeutic agents can be desirable, such as chemotherapeutic agents, immunosuppressive agents, cytokines, cytotoxic agents, nucleolytic compounds, radioactive isotopes, receptors, and pro-drug activating enzymes, which can be naturally occurring or produced by recombinant methods. The combined administration includes co-administration, using separate formulations or a single pharmaceutical formulation, and consecutive administration in either order, wherein there is a time period while both (or all) active therapeutic agents simultaneously exert their biological activities.

It is to be understood that this invention is not limited to the particular methodology, syntheses, formulations, protocols, cell lines, constructs, and reagents described herein and as such can vary. It is also to be understood that the terminology used herein is for the purpose of describing particular aspects only, and is not intended to limit the scope of the present invention.

All publications, patents, and other references mentioned herein are provided for the purpose of describing and disclosing, for example, the constructs and methodologies that are described in these references, which might be used in connection with the presently described invention. The references provided or discussed in the text are provided solely for their disclosure prior to the filing date of the present application. Nothing herein is to be construed as an admission that the inventors are not entitled to antedate such disclosure by virtue of prior invention.

To the extent that any definition or usage provided by any document incorporated herein by reference conflicts with the definition or usage provided herein, the definition or usage provided herein controls.

For any particular compound disclosed herein, any general structure presented also encompasses all conformational isomers, regioisomers, stereoisomers and tautomers that can arise from a particular set of substituents. The general structure also emcompasses all enantiomers, diastereomers, and other optical isomers whether in enantiomeric or racemic forms, as well as mixtures of stereoisomers, as the context requires. The general structure also encompasses all salts, including pharmaceutically acceptable and non-pharmaceutically acceptable salts and prodrugs thereof.

When Applicants disclose or claim a range of any type, for example a range of temperatures, a range of numbers of atoms, a molar ratio, or the like, Applicants' intent is to disclose or claim individually each possible number that such a range could reasonably encompass, as well as any sub-ranges and combinations of sub-ranges encompassed therein. For example, when the Applicants disclose or claim a chemical moiety having a certain number of carbon atoms, Applicants' intent is to disclose or claim individually every possible number that such a range could encompass, consistent with the disclosure herein. For example, the disclosure that R is selected independently from an alkyl group having up to 20 carbon atoms, or in alternative language a $C_1$ to $C_{20}$ alkyl group, as used herein, refers to an R group that can be selected independently from a hydrocarbyl group having 1, 2, 3, 4, 5, 6, 7, 8, 9, 10, 11, 12, 13, 14, 15, 16, 17, 18, 19, or 20 carbon atoms, as well as any range between these two numbers for example a $C_3$ to $C_8$ alkyl group, and also including any combination of ranges between these two numbers for example a $C_3$ to $C_5$ and $C_7$ to $C_{10}$ hydrocarbyl group. In another example, by the disclosure that the molar ratio typically spans the range from about 0.1 to about 1.1, Applicants intend to recite that the molar ratio can be selected from about 0.1:1, about 0.2:1, about 0.3:1, about 0.4:1, about 0.5:1, about 0.6:1, about 0.7:1, about 0.8:1, about 0.9:1, about 1.0:1, or about 1.1:1.

Applicants reserve the right to proviso out or exclude any individual members of any such group, including any sub-ranges or combinations of sub-ranges within the group, that may be claimed according to a range or in any similar manner, if for any reason Applicants choose to claim less than the full measure of the disclosure, for example, to account for a reference that Applicants may be unaware of at the time of the filing of the application. Further, Applicants reserve the right to proviso out or exclude any individual substituents, compounds, ligands, structures, or groups thereof, or any members of a claimed group, if for any reason Applicants choose to claim less than the full measure of the disclosure, for example, to account for a reference that Applicants may be unaware of at the time of the filing of the application.

The following references disclose certain pyridine compounds.

TABLE 9

References disclosing pyridine compounds.

| Publication or Patent No. | Title | Patent Assignee |
| --- | --- | --- |
| US2004/0198728 | Pyridines and uses thereof | Hong (inventor) |
| WO 2005007648 | Preparation of biaryl piperazinyl-pyridine analogues as capsaicin receptor modulators | Neurogen Corporation, USA |
| WO 2005033105 | Preparation of pyridinyl and analogous vanilloid receptor ligands and their use in treating pain | Amgen Inc., USA |
| WO 2005030714 | Process for the production of compounds having 5- to 10-membered aromatic heterocycles with alkylmagnesium monoamides | Eisai Co., Ltd., Japan |
| WO 2005007646 | Preparation of arylaminotriazines and arylaminopyrimidines as capsaicin receptor modulators for the treatment of pain and other diseases | Neurogen Corporation, USA |
| GB 2404855 | Preparation of arylcarboxylates as antibacterials | Pantherix Ltd, UK |
| WO 2004094361 | Cobalt carbonyl and aminopyridine derivatives catalyzed process for producing β-hydroxyester | Daiso Co. Ltd., Japan |
| WO 2004089286 | Preparation of substituted pyrimidinamines and triazinamines as protein kinase inhibitors | IRM LLC, Bermuda |
| WO 2004085423 | Preparation of piperidine derivatives for the treatment of chemokine or H1 mediated disease state | Astrazeneca AB, Swed. |
| WO 2004062665 | Preparation of heteroaryl-substituted pyrrolo[2,3-b]pyridine derivatives as CRF receptor antagonists | SB Pharmco Puerto Rico Inc., USA; Neurocrine Biosciences Inc.; Glaxo Group Limited |
| WO 2004050643 | A preparation of heterocyclic non-nucleoside reverse transcriptase inhibitors, useful for the treatment of HIV-1 | Boehringer Ingelheim International G.m.b.H., Germany |
| WO 2004039795 | Preparation of aryl and heteroaryl amides, in particular benzamides and pyridinyl amides, as apolipoprotein B (Apo B) secretion inhibitors | Fujisawa Pharmaceutical Co., Ltd., Japan; Daiso Co., Ltd.; et al. |
| US 2004082780 | Preparation of (aryloxy)pyrimidine and (aryloxy)pyridazine as vanilloid receptor ligands | Amgen Inc., USA |
| WO 2004014366 | Preparation of tetrazole derivs. as matrix metalloproteinase inhibitors | Warner-Lambert Company Llc, USA |

TABLE 9-continued

References disclosing pyridine compounds.

| Publication or Patent No. | Title | Patent Assignee |
|---|---|---|
| US 2004204584 | Preparation of 2-acylaminobenzothiazole derivatives as adenosine receptor ligands | Hoffmann-La Roche Inc., Switz. |
| JP 2004359642 | Maleimides as monomers for heat-resistant polymers, and their manufacture | Nippon Shokubai Co., Ltd., Japan |
| JP 2004047229 | Photoelectric conversion devices using electrolyte solutions containing aminopyridines, and dye-sensitized solar cells using them | National Institute of Advanced Industrial Science and Technology, Japan |
| JP 2004018448 A2 20040122 JP 2002-174770 20020614 | Preparation of anhydrous salts of 2'-deoxyguanosine derivatives | Mitsui Chemicals Inc., Japan |
| WO 2004089910 | Preparation of arylpyrazoles as serotonin 5-HT2A and 5-HT2C receptor antagonists | Merck Patent GmbH, Germany |
| WO 2004000820 | Certain aromatic monocycles, particularly trisubstituted [1,3,5]triazine derivatives, as kinase modulators, and their pharmaceutical compositions and methods of use | Cellular Genomics, Inc., USA |
| WO 2003101989 | Preparation of pyrazolo[4,3-c]pyridinyl substituted pyrimidinamines as inhibitors of JAK and CDK2 protein kinases | Vertex Pharmaceuticals Incorporated, USA |
| WO 2003101959 | Preparation of pyrroles for the treatment of prostaglandin mediated diseases | Glaxo Group Limited, UK |
| WO 2003099771 | Preparation of diarylurea derivatives useful for the treatment of protein kinase dependent diseases | Novartis A.-G., Switz.; Novartis Pharma G.m.b.H. |
| U.S. Pat. No. 6864261 | Preparation of 1-(pyrid-2-yl)piperazines as metabotropic glutamate receptor inhibitor | Euro-Celtique, S.A., Luxembourg |
| WO 2003091226 | Preparation of triazole derivatives as tachykinin receptor antagonists | Eli Lilly and Company, USA |
| WO 2003087067 | Preparation of aryl-alkyne compounds as herbicides | Syngenta Participations A.-G., Switz. |
| WO 2003080060 | Substituted piperazine antithrombotic PAI-1 (plasminogen activator inhibitor-1) inhibitors, and their preparation, pharmaceutical compositions, and use in the treatment of thrombotic diseases. | Schering Aktiengesellschaft, Germany |
| WO 2003062392 | Methods using Edg receptor modulators for the treatment of Edg receptor-associated conditions | Ceretek LLC, USA |
| WO 2003051366 | Preparation of pyridine derivatives as protein kinase inhibitors | Abbott Laboratories, USA |
| WO 2003050087 | Preparation of pyridylalkynes as herbicides | Syngenta Participations Ag, Switz. |
| WO 2003048137 | Preparation of 2-phenylbenzoxazoles as metabotropic glutamate receptor-5 modulators for treatment of pain and CNS disorders | Merck & Co., Inc., USA |
| WO 2003045941 | Preparation of pyridine and pyrimidine derivatives as p38α kinase inhibitors | Celltech R & D Limited, UK |
| WO 2003029226 | Heterocyclyl-substituted phenoxyalkyl-, phenylthioalkyl-, phenylaminoalkyl- and phenylalkyl-sulfamoylcarboxamides as herbicides | Basf Aktiengesellschaft, Germany |
| WO 2003026664 | Preparation of 2-phenylamino-4-(5-pyrazolylamino)pyrimidines as kinase inhibitors, in particular, SRC kinase inhibitors | Bayer Corporation, USA |
| WO 2003022285 | Preparation of substituted 2-(4-phenoxyphenyl)pyridine derivatives and related compounds as sodium channel blockers for the treatment of neuronal damage and neurodegenerative conditions | Euro-Celtique S.A., Luxembourg |
| US 2004248739 | Preparation of pyridylpropynyloxyphenyl derivatives as herbicides | Syngenta Participations AG, Switz. |
| US 2003139435 | Preparation of pyridine and pyrimidine N-heterocyclic p38 kinase inhibitors for treating TNF-α mediated disorders | Bristol-Myers Squibb Company, USA; Pharmacopeia, Inc. |
| US 2003205696 | Carbazole-based materials for guest-host electroluminescent systems | Canon Kabushiki Kaisha, Japan |
| U.S. Pat. No. 6831175 | Preparation of heteroaryls for therapeutic use in pharmaceutical compositions as kinase | Abbott Laboratories, USA |

TABLE 9-continued

References disclosing pyridine compounds.

| Publication or Patent No. | Title | Patent Assignee |
|---|---|---|
| | inhibitors for treatment of hyperproliferative diseases, including cancer | |
| US 2003187026 | Preparation of pyridine derivatives as protein kinase inhibitors | USA |
| U.S. Pat. No. 6559167 | Preparation of benzimidazole derivatives as prodrugs of proton pump inhibitors | Regents of the University of California, USA; The United States Department of Veteran Affairs; Winston Pharmaceuticals, LLC |
| JP 2003344970 | Composition of bleachable dye and radical generator, silver halide photographic material containing it, and dye bleaching | Konica Minolta Holdings Inc., Japan |
| JP 2003335754 | Dibenzopyrrolidine derivatives for organic electroluminescent devices | Fuji Photo Film Co., Ltd., Japan |
| JP 2003335753 | Dibenzopyrrolidine derivatives for organic electroluminescent devices | Fuji Photo Film Co., Ltd., Japan |
| JP 2003221518 | Coloration compositions with good hue and light and ozone resistance | Fuji Photo Film Co., Ltd., Japan |
| JP 2003002834 | Pharmaceutical compositions containing heterocyclic compounds as α 1β 2 integrin-mediated adhesion inhibitors for treatment of inflammatory diseases | Tanabe Seiyaku Co., Ltd., Japan |
| CN 1405156 | Preparation of N-hydroxyamidines | Wuhan University, Peop. Rep. China |
| CN 1405154 | Preparation of N-hydroxylamine derivatives | Wuhan University, Peop. Rep. China |
| US 2004/0198728 | Pyridines and Uses Thereof | |
| US 2004122219 | Pyrazole azo dyes, their production and coupling agents therefor | Fuji Photo Film Co., Ltd., Japan |
| US 2004110757 | Preparation of aromatic carboxylic acids as Flt-1 ligands. | Chugai Seiyaku Kabushiki Kaisha, Japan |
| US 2003176416 | Aryl- and heteroaryl-substituted diazabicycloalkanes as cholinergic ligands for the nicotinic acetylcholine receptor | Neurosearch A/S, Den. |
| U.S. Pat. No. 6906067 | Preparation of s-triazines and pyrimidines for pharmaceutical use as cytokine, especially TNF-α inhibitors | Bristol-Myers Squibb Company, USA; Pharmaceopeia, Inc. |
| U.S. Pat. No. 6693295 | Novel indole derivative, material for light-emitting device and light-emitting device using the same | Fuji Photo Film Co., Ltd., Japan |
| JP 2002216969 | White- or blue-emitting organic electroluminescent (EL) elements with excellent emission efficiency and color purity | Toyota Central Research and Development Laboratories, Inc., Japan |
| JP 2002037777 | Aliphatic group-substituted aminopyridinium derivative for controlling of liquid crystal tilt angle | Fuji Photo Film Co., Ltd., Japan |
| U.S. Pat. No. 6673818 | Preparation of fluoro-substituted benzenesulfonyl pyrazoles and isoxazoles for the treatment of cyclooxygenase-2 mediated disorders such as inflammation | Pharmacia Corporation, USA |
| EP 1202608 | Organic light-emitting devices | Kabushiki Kaisha Toyota Chuo Kenkyusho, Japan |
| US 2002028329 | Light emitting element and azole compound | Fuji Photo Film Co., Ltd., Japan |
| U.S. Pat. No. 6767671 | Nonaqueous electrolytic solution for secondary battery | Mitsubishi Chemical Corporation, Japan |
| US 2004082586 | Preparation of 3,4-dihydro-2H-pyrroles as pesticides | Bayer A.-G., Germany |
| US 2004019190 | Thrombopoietin mimetics | SmithKline Beecham Corporation, USA; Glaxo Group Limited |

TABLE 9-continued

References disclosing pyridine compounds.

| Publication or Patent No. | Title | Patent Assignee |
|---|---|---|
| U.S. Pat. No. 6849618 | Preparation of uracil substituted N-sulfamoyl benzamides as herbicides | Basf Aktiengesellschaft, Germany |
| US 2004092552 | Preparation of 2-fluorobenzenesulfonyl-heterocycles with COX-1 and COX-2 inhibiting activity for pharmaceutical use in the treatment of inflammation | Pharmacia Corporation, USA |
| US 2001027196 | Preparation of pyrimidinamines and pyridinamines as adenosine receptor modulators for treatment of CNS disorders | F. Hoffmann La Roche A.-G., Switz. |
| U.S. Pat. No. 6897225 | Preparation of 3-(hetero)aryl-1,3-diazabicyclo[3.3.0]octane-2,4-diones and analogs as inhibitors of α1β2 mediated cell adhesion | Tanabe Seiyaku Co., Ltd., Japan |
| WO 2001027119 | Preparation of imidazopyridineamines and analogs as analgesics | Gruenenthal G.m.b.H., Germany |
| US 2004220235 | Method of inhibiting amyloid protein aggregation, treating Alzheimer's disease, and imaging amyloid deposits using [[(phenylalkyl)phenyl]amino]be nzoic acids and analogs | Warner-Lambert Company, USA; Yamanouchi Pharmaceutical Company, Ltd.; et al. |
| WO 2000043385 | Preparation of benzimidazolyltriazine derivatives as antitumor agents | Zenyaku Kogyo Kabushiki Kaisha, Japan |
| WO 2000021954 | Preparation of 1-benzyl-3-(pyrimidin-2-yl)indazoles and related compounds as stimulators of soluble guanylate cyclase. | Bayer Aktiengesellschaft, Germany |
| U.S. Pat. No. 6093734 | Preparation of benzimidazole derivatives as prodrugs of proton pump inhibitors | USA |
| JP 2000119256 | Pyrazolylacrylonitriles and their use as agrochemicals | Nissan Chemical Industries, Ltd., Japan |
| U.S. Pat. No. 6248892 | Procedure for the production of arylpyridines | Clariant G.m.b.H., Germany |
| WO 9957103 | Preparation of condensed imidazole derivative as therapeutic agents for liver disease | Nippon Chemiphar Co., Ltd., Japan; Zeria Pharmaceutical Co., Ltd. |
| WO 9920606 | Preparation of piperidine and piperazine glycoprotein IIb/IIIa antagonists | J. Uriach & Cia. S.A., Spain |
| U.S. Pat. No. 6251900 | Preparation of heterocyclic compounds as antitumor agents | Zenyaku Kogyo Kabushiki Kaisha, Japan |
| U.S. Pat. No. 5977138 | 1,4-Disubstituted piperidine ether muscarinic antagonists | Schering Corporation, USA |
| U.S. Pat. No. 5952349 | Preparation of arylaminopiperidines as muscarinic M2 antagonists for treating memory loss | Schering Corporation, USA |
| WO 9844925 | Calcilytic compounds | Smithkline Beecham Corporation, USA |
| U.S. Pat. No. 6841674 | Preparation of N-heterocyclic derivatives as NOS inhibitors | Berlex Laboratories, Inc., USA; Pharmacopeia, Inc.; et al. |
| U.S. Pat. No. 6043242 | Preparation of imidazopyridazines for control of Helicobacter bacteria | Byk Gulden Lomberg Chemische Fabrik G.m.b.H., Germany |
| WO 9825912 | Preparation of herbicidal 1H-tetrazole-1-carboxamides | E. I. Du Pont de Nemours & Co., USA; Rorer, Morris Padgett |
| U.S. Pat. No. 6020349 | Preparation of thiourea derivatives and related compounds as constrained somatostatin agonists and antagonists | Novo Nordisk A/S, Den. |
| U.S. Pat. No. 6040302 | Preparation of 1,4-disubstituted piperazines for the treatment of painful, hyperalgesic and/or inflammatory conditions | Novo Nordisk A/S, Den. |
| U.S. Pat. No. 6008234 | Benzamidine derivatives substituted by cyclic amino acid or cyclic hydroxy acid derivatives, and their use as anticoagulants | Schering A.-G., Germany |

TABLE 9-continued

References disclosing pyridine compounds.

| Publication or Patent No. | Title | Patent Assignee |
|---|---|---|
| WO 9806697 | Preparation of phenyl piperidin-4-yl ethers as muscarinic antagonists | Schering Corporation, USA |
| WO 9801425 | Preparation of 1,4-disubstituted piperidines as muscarinic antagonists | Schering Corp., USA |
| JP 10324671 | Amino alcohol esters as ceramide analogs and pharmaceuticals containing them for treatment of nerve diseases | Seikagaku Kogyo Co., Ltd., Japan |
| JP 10310583 | Pyridoneazo compound and thermal-transfer printing material using it | Mitsubishi Chemical Industries Ltd., Japan |
| JP 10260512 | Processing of photographic material using developer containing silver stain inhibitor | Fuji Photo Film Co., Ltd., Japan |
| JP 10207019 | Processing of silver halide photographic material using developer containing heterocyclic compound | Fuji Photo Film Co., Ltd., Japan |
| U.S. Pat. No. 6048675 | Processing of silver halide photographic materials with mercapto compounds | Fuji Photo Film Co., Ltd., Japan |
| JP 10153838 | Processing of silver halide photographic materials containing mercapto compounds | Fuji Photo Film Co., Ltd., Japan |
| U.S. Pat. No. 6573278 | Preparation of arysulfonamides and related compounds as cannabinoid CB1 and CB2 receptor agonists. | Bayer A.-G., Germany |
| WO 9826127 | Multicomponent system for altering, degrading, or bleaching lignin, lignin-containing materials, or similar substances, and method for its use | Consortium fuer Elektrochemische Industrie G.m.b.H., Germany |
| WO 9816224 | Pyrazolinones for the management of potency disorders | Merck Patent G.m.b.H., Germany |
| U.S. Pat. No. 6156903 | Preparation of novel pyridonecarboxylic acid derivatives as antibacterial agents | Wakunaga Pharmaceutical Co., Ltd., Japan; Yazaki, Akira; Niino, Yoshiko; Ohshita, Yoshihiro; Hirao, Yuzo; Amano, Hirotaka; Hayashi, Norihiro; Kuramoto, Yasuhiro |
| U.S. Pat. No. 5696282 | Process and catalysts for producing organosulfur compounds by the addition reaction of hydrogen sulfide or mercaptans with α, β-unsaturated carbonyl or nitrile compounds | Phillips Petroleum Co., USA |
| U.S. Pat. No. 6306884 | Preparation of benzamidine derivatives as anticoagulants | Berlex Laboratories, Inc., USA |
| JP 09194582 | Manufacture of polycarbonates using nitrogen compound catalysts | Idemitsu Petrochemical Co., Ltd., Japan |
| U.S. Pat. No. 6335444 | Preparation of diastereomeric 2-acylamino-3-morpholino-1-phenyl-1-propanols and analogs | Seikagaku Kogyo Kabushiki Kaisha (Seikagaku Corporation), Japan |
| WO 9715555 | Preparation of 1-phenylimidazoles as nitric oxide synthase inhibitors | Schering A.-G., Germany |
| U.S. Pat. No. 5990123 | Preparation of vasoconstrictive 2,3-dihydro-1,4-dioxinopyridines | Janssen Pharmaceutica N.V., Belg. |
| U.S. Pat. No. 5559135 | Preparation of endothelin antagonists bearing pyridylamide groups | Merck and Co., Inc., USA |
| U.S. Pat. No. 5929248 | Substituted aryl- and heteroarylphenyloxazolidinones | Upjohn Co., USA |
| U.S. Pat. No. 5559108 | Cephalosporin derivatives | Bristol-Myers Squibb Company, USA |
| U.S. Pat. No. 5514505 | Method for obtaining improved image contrast in migration imaging members | Xerox Corp., USA |
| JP 08175993 | Preparation and formulation of pyridine derivatives as antioxidants | Green Cross Corp, Japan |
| U.S. Pat. No. 5629134 | Chemical amplification positive-working resist material | Shinetsu Chemical Industry Co., Ltd., Japan; Nippon Telegraph & Telephone |
| GB 2297747 | Hydrazide for photographic material | Ilford A.G., Switz. |

TABLE 9-continued

References disclosing pyridine compounds.

| Publication or Patent No. | Title | Patent Assignee |
| --- | --- | --- |
| U.S. Pat. No. 5559108 | Cephalosporin derivatives | Bristol-Myers Company, USA |
| U.S. Pat. No. 5672708 | Preparation od N-arylaminoacrylic acids and their use as intermediates for the preparation of 4-quinolone-3-carboxylic acid derivatives | Bayer A.-G., Germany |
| WO 9602532 | Preparation of 7-piperazinyl-1,4-dihydro-4-oxo-1-[4-(1H-1,2,4-triazol-1-yl-methyl)phenyl]quinoline-3-carboxylic acids as virucides | Bayer A.-G., Germany |
| U.S. Pat. No. 5763438 | Preparation of 2-acylamino-3-piperidino-1-propanol derivatives and analogs for treatment of viral and nervous diseases | Seikagaku Corp., Japan |
| U.S. Pat. No. 6100268 | Preparation of vasoconstrictive dihydrobenzopyranpyrimidine derivatives | Janssen Pharmaceutica N.V., Belg. |
| U.S. Pat. No. 5801179 | Preparation of vasoconstrictive substituted aryloxyalkyl diaminoheterocyclyls | Janssen Pharmaceutica N.V., Belg. |
| U.S. Pat. No. 5451486 | Photographic contrast promoting agents | Sun Chemical Corp., USA |
| U.S. Pat. No. 5231094 | Pyrazolopyrimidine derivatives which are angiotensin II receptor antagonists | Laboratoires UPSA, Fr. |
| U.S. Pat. No. 5387747 | Triazolopyrimidine derivatives which are angiotensin II receptor antagonists, their methods of preparation and pharmaceutical compositions in which they are present | Laboratoires Upsa, Fr. |
| JP 07179771 | Preparation of trimethine dyes useful as intermediates for recording materials | Fuji Photo Film Co Ltd, Japan |
| JP 07099996 | Substrate composition for the determination of peroxidase | Fujirebio Kk, Japan |
| U.S. Pat. No. 5332582 | Cyclodextrin- and polymer-based drug delivery system | Insite Vision Inc, USA |
| U.S. Pat. No. 5336677 | Preparation of 4-(biphenylylamino)pyrimidines and analogs as angiotensin II antagonists | American Home Products Corp., USA |
| JP 06240163 | Manufacture of intermediates for trimethine color formers | Fuji Photo Film Co Ltd, Japan |
| U.S. Pat. No. 5374514 | Photothermographic materials. | Minnesota Mining and Manufacturing Co., USA |
| U.S. Pat. No. 5316890 | Silver halide photographic material | Fuji Photo Film Co., Ltd., Japan |
| U.S. Pat. No. 5510345 | Preparation of 1-(eburnaminine-14-carbonyl)-4-pyrimidinylpiperazines and analogs as lipid peroxidation inhibitors | Richeter Gedeon Vegyeszeti Gyar RT., Hung. |
| U.S. Pat. No. 5550240 | Preparation of piperazinylbis(alkylamino)pyrimidine derivatives as intermediates for lipid peroxidation inhibitors | Richter, Gedeon, Vegyeszeti Gyar Rt., Hung. |
| WO 9322311 | Fungicidal 1,3,4-oxadiazines and 1,3,4-thiadiazines | du Pont de Nemours, E. I., and Co., USA |
| WO 9311134 | Preparation of (3H,7H)thiazolo(3,4-a)pyridines having antiasthmatic and antiinflammatory activities on the respiratory tract | Boehringer Mannheim Italia S.p.A., Italy |
| U.S. Pat. No. 5336677 | Substituted aminopyrimidine angiotensin II receptor antagonists | American Home Products Corp., USA |
| JP 05132462 | Pyridinium salts and cationic polymerization initiators | Nippon Soda Co, Japan |
| JP 05132461 | Pyridinium salts and cationic polymerization initiators | Nippon Soda Co, Japan |
| U.S. Pat. No. 5149699 | Condensed pyrimidine derivatives and their use as angiotensine II antagonists | American Home Products Corp., USA |
| EP 525768 | Heterocyclyl group-substituted tetralones having antihypertensive and bronchodilating activity | Uriach, J., e Cia. S.A., Spain |
| WO 9217448 | Preparation of 3-methyleneisoindolin-1-one derivatives for treating ischemic cerebral disorders | Kyowa Hakko Kogyo Co., Ltd., Japan |
| U.S. Pat. No. 6559186 | Adrenergic agonists and antagonists for treatment of sympathetically maintained pain | USA |

TABLE 9-continued

References disclosing pyridine compounds.

| Publication or Patent No. | Title | Patent Assignee |
|---|---|---|
| WO 9300342 | Preparation of 1-thiazolylaminocarbonyl-4-arylpiperazines and analogs as bronchodilators | Boehringer Mannheim Italia S.p.A., Italy |
| EP 517542 | Organic electroluminescent devices | Sumitomo Chemical Co., Ltd., Japan |
| WO 9219615 | Preparation of pyrazoles, pyrazolines and tetrahydropyridazines as agrochemical fungicides | du Pont de Nemours, E. I., and Co., USA |
| U.S. Pat. No. 5942384 | Silver halide photographic material and its processing | Fuji Photo Film Co., Ltd., Japan |
| EP 493670 | Preparation of pyridinium betaines as enhancers of plant resistance against infection by microorganisms | Bayer A.-G., Germany |
| U.S. Pat. No. 5256408 | Aminosteroids for ophthalmic use | Insite Vision, Inc., USA |
| WO 9106542 | Preparation of pharmaceutically active amino-substituted heteroaryl amines | Upjohn Co., USA |
| U.S. Pat. No. 5023258 | Preparation of 1-(piperazinylphenoxy)-2-triazolylethanols as fungicides | Pfizer Inc., USA |
| U.S. Pat. No. 5527914 | Methine compounds as photographic sensitizers and silver halide emulsions containing them | Fuji Photo Film Co., Ltd., Japan |
| U.S. Pat. No. 5202224 | pyridine derivative photographic cyan couplers | Fuji Photo Film Co., Ltd., Japan |
| U.S. Pat. No. 5155166 | Use of 1-(1-pyrrolidinylcarbonyl)pyridinium salts to attach compounds to carboxylated particles and a kit containing same | Eastman Kodak Co., USA |
| U.S. Pat. No. 5654298 | Preparation of 4-aminopyridinium salts as bradycardiacs | Imperial Chemical Industries PLC, UK |
| U.S. Pat. No. 5179123 | Preparation of alkynoylbenzoic, -thiophenecarboxylic, -furancarboxylic, and -pyridinecarboxylic acids as leukotriene B4 (LTB4) synthesis inhibitors | G.D. Searle and Co., USA |
| EP 451585 | Preparation of 2-aryl-6-heteroarylpyridines as herbicides | Bayer A.-G., Germany |
| JP02235054 | Silver halide color photographic material with good image sharpner and safety light stability | Fuji Photo Film Co., Ltd., Japan |
| EP 376870 | Preparation of new organosilyl polyphosphate reagents for cyclization of aminomethylenemalonates in the preparation of quinolone and azaquinolone antibacterials | Centro Marga parala Investigacion S.A., Spain |
| EP 352946 | Triazolyl(hydroxypropoxy)phenylpiperazines as medical and agrochemical fungicides | Pfizer Ltd., UK; Pfizer Inc. |
| U.S. Pat. No. 4980350 | Preparation of piperazinylpyrimidines and analogs as hypoglycemic agents | Merck and Co., Inc., USA |
| WO 2005028467 | Preparation of 3,5-diaminopiperidine-substituted hetero/aromatic compounds as antibacterial agents | Anadys Pharmaceuticals, Inc., USA |
| US 2004110031 | Organic electroluminescent device and display | Japan |
| U.S. Pat. No. 5681954 | Preparation of piperazines having calmodulin inhibitory activity | Daiichi Pharmaceutical Co., Ltd., Japan |
| JP 08225535 | Preparation of 3-(piperazinoalkyl)indole derivatives as calmodulin antagonists | Daiichi Seiyaku Co, Japan |
| EP 624584 | Preparation of piperazine derivatives as calmodulin inhibitors. | Daiichi Pharmaceutical Co. Ltd., Japan |
| EP 263213 | Amino steroids useful for treating a variety of conditions, and a process for their preparation | Upjohn Co., USA |
| Heterocycles (1996), 43(1), 199-204 CODEN: HTCYAM; ISSN: 0385-5414 | Ring transformation of fused pyridazines. IV. Reaction of halo-substituted fused pyridazines with ynamines | Iwamoto, Ken-ichi; Suzuki, Sumiko; Oishi, Etuso; Miyashita, Akira; Higashino, Takeo |

Applicants reserve the right to proviso out, or to restrict from any claim currently presented, or from any claim that may be presented in this or any further application based upon this disclosure, including claims drawn any genus or subgenus disclosed herein, any compound or group of compounds disclosed in any reference provided herein.

Although methods, syntheses, and materials similar or equivalent to those described herein can be used in the practice or testing of this invention, typical methods, syntheses, and materials are described herein.

Acronyms and Abbreviations

The following abbreviations and acronyms are commonly used throughout this disclosure, including the Examples: DMF, dimethylformamide; BINAP, 2R,3S,2,2'-bis-(diphenylphosphino)-1,1'-binapthyl; DMSO, dimethylsulphoxide; NaH, sodium hydride; $CH_2Cl_2$ or DCM, dichloromethane; $CDCl_3$, deuterated chloroform or chloroform-d; $POCl_3$, phosphorus oxychloride; THF, tetrahydrofuran; $AlCl_3$, aluminum chloride; NaOH, sodium hydroxide; $Na_2CO_3$, sodium carbonate; MeOH, methanol; $NH_4OH$, ammonium hydroxide; $K_2CO_3$, potassium carbonate; TFA, trifluoroacetic acid; $SiO_2$, silicon dioxide or silica; $KH_2PO_4$, potassium dihydrogen phosphate; n-BuLi, n-butyllithium; $(PPh_3)_4Pd$, tetrakis (triphenylphosphine)palladium(0); $(PPh_3)_2PdCl_2$, bis(triphenylphosphine)palladium(II) chloride; HPLC, high performance liquid chromatography; TLC, thin layer chromatography; mL, milliliters; M.P., melting point; RT, room temperature, typically ranging from about 20° C. to about 40° C.; aq, aqueous; min, minutes; h or hr, hours; g, grams; atm, atmosphere; conc., concentrated; MS or Mass Spec, mass spectroscopy/spectrometry; NMR, nuclear magnetic resonance; TMS, tetramethylsilane; $R_f$, TLC retention factor; $R_t$, HPLC retention time; HPFC, high performance flash chromatography; IR, infrared spectroscopy/spectrum; $CH_3CN$, acetonitrile; $N_2$, nitrogen; mg, milligrams; mmol, millimoles; mol, moles; nm, nanometers; HRMS, high resolution mass spectroscopy; and ° C., degrees Centigrade.

Abbreviations especially frequent in the NMR data are as follows: MHz, megahertz; Hz, hertz; br, broad; apt, apparent; s, singlet; d, doublet; t, triplet; q, quartet; dq, doublet of quartets; dd, doublet of doublets; dt, doublet of triplets; and m, multiplet.

The precursor compounds such as halogenated pyridines, phenylboronic acid, and substituted phenylboronic acids were obtained from a variety of commercial sources, including, for example, Sigma-Aldrich Inc., Asymchem Laboratories, and Lancaster Synthesis, Inc.

The following experiments and Examples are merely illustrative, and compounds of the present invention are not limited by the following particular species. The skilled artisan will appreciate how the experiments and Examples may be further implemented as disclosed by variously altering the following examples, substituents, conditions, or reagents. In the following examples, in the disclosure of any measurements, including temperatures, pressures, times, weights, percents, concentrations, ranges, chemical shifts, frequencies, molar ratio, etc., it is to be understood that such measurements are respectively, "about."

EXAMPLES

Example 1

Synthesis of 2,6-dichloro-4-iodopyridine (B21)

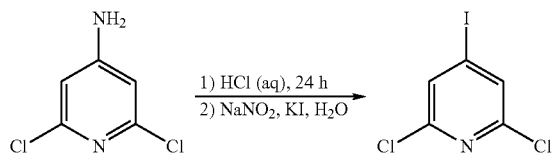

4-Amino-2,6-dichloropyridine (11.58 g, 71 mmol) was stirred in 100 mL of concentrated HCl at room temperature for 24 hour. The mixture was transferred to a 2 L Erlenmeyer flask and was cooled in an ice bath. Sodium nitrite (9.85 g, 142 mmol) in water (15 mL) was added drop wise. Potassium iodide (29.85 g, 178 mmol) in water (30 mL) was added slowly, and the reaction was allowed to stir for 5 minutes. (Water was used to rinse down the sides of the flask.) Tetrahydrofuran (60 mL) was added and the solution was neutralized by addition of solid sodium bicarbonate. The reaction mixture was extracted three times with diethyl ether. The combined organic fractions were washed with 10% sodium thiosulfate solution until it turned light orange in color. The organic layer was dried over magnesium sulfate and concentrated on the rotary evaporator, which yielded a light orange solid product (15.4 g, 80%). This material was typically used without further purification. A recrystallization may be performed as needed using 3:1 (hexanes:THF). The solid that was formed was filtered and quickly rinsed with cold acetone.

M.P.: 143-145° C.

HPLC: Inertsil ODS-3V C18, 30:70 [$KH_2PO_4$ (0.01M, pH 3.2):$CH_3CN$], 264 nm, $R_t$ 11.8 min, 95.6% purity.

$^1$H NMR (600 MHz, $CDCl_3$, TMS): δ 7.64 (s, 2H).

Reference: adapted from Mello, J. V.; Finney, N. S. *Org. Lett;* 2001, 26, 4263-4265.

Example 2

Synthesis of 2,6-di-chloro pyridine-1-oxide

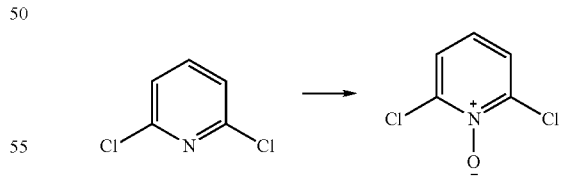

A mixture of 2,6-dichloropyridine (2 g, 13.6 mmol) in TFA (6 mL) and 30% $H_2O_2$ (2.5 mL) was prepared at 0° C., after which the mixture was heated to reflux at 90-100° C. After 7 hour at this temperature, the mixture was cooled to room temperature and neutralized with 1N NaOH solution to pH 8-9. The aqueous layer was extracted with petroleum ether (200 mL×3) and the organic layer was dried over sodium sulfate, filtered, and concentrated to dryness under vacuum. The residue was purified by column chromatography over 100-200 mesh silica gel, eluting with 20:80 acetone: hexanes, to afford the pure compound as a colorless solid (1.75 g, yield 80%).

M.P.: 137-138° C.

$^1$H NMR (200 MHz, CDCl$_3$) δ 7.35-7.49 (d, 2H, J=8.25 Hz), 7.08-7.18 (dd, 1H, J=8.56 Hz).

Mass Spec: (CI-MS) m/z: 164 (M$^+$+1, 100%).

Reference: Stan V. D Andrea et.al *Tetrahedron* 2000, 56, 5687-5698.

Example 3

Synthesis of 2,4,6-trichloropyridine

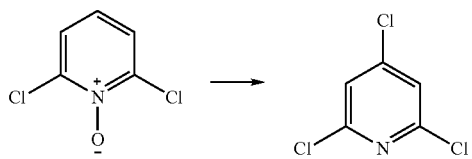

A mixture of 2,6-dichloropyridine-1-oxide (1.60 g, 9.81 mmol), obtained in step (i), distilled POCl$_3$ (10.0 mL), and dry LiCl was heated to reflux with stirring under a nitrogen atmosphere for 6 hour. After this time, the reaction mixture was cooled to 0° C., after which crushed ice was added slowly with stirring. Petroleum ether was added (50 mL) and 1N NaOH solution was added dropwise to the resulting reaction mixture until the pH was basic. The organic layer was separated, the aqueous layer was extracted with petroleum ether, and the combined organic layer was dried over sodium sulfate and concentrated under reduced pressure. The residue was purified by column chromatography over 100-200 mesh silica gel by elution with 10:90 ethyl acetate:hexanes, to provide the product as pure brown oil (yield 51%).

$^1$H NMR (200 MHz, CDCl$_3$) δ 7.29 (s, 2H).

Mass Spec: (CI-MS) m/z: 184 (M$^+$+2, 5%).

Reference: Stan V. D Andrea et.al *Tetrahedron* 2000, 56, 5687-5698.

Example 4

Synthesis of (2,6-dichloro-pyridin-4-yl)-p-tolyl-amine

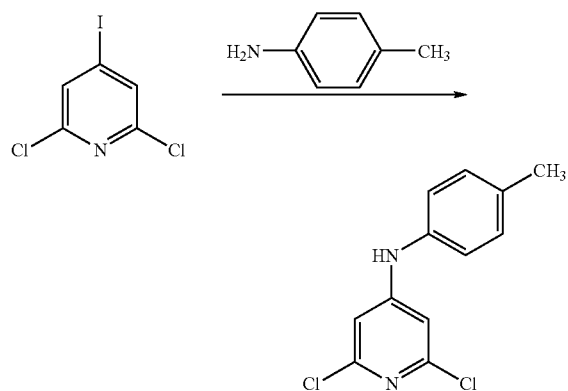

To 2,6-dichloro-4-iodopyridine (2.737 g, 10 mmol) dissolved in toluene (35 mL) was added p-toluidine (1.346 g, 12 mmol), tris(dibenzylideneacetone)dipalladium (180.3 mg, 0.2 mmol), 1,3-bis(diphenylphosphino)propane (162.3 mg, 0.4 mmol), and sodium-tert-butoxide (1.347 g, 14 mmol). The resulting mixture was allowed to stir at reflux for 12 hour. The sample was diluted in dichloromethane and filtered through Celite™. The Celite™ was washed with CH$_2$Cl$_2$; the filtrate was washed two times with water and one time with brine. The organic phase was dried over potassium carbonate and concentrated by rotary evaporation. The resulting sample was dried for 12 to 14 hours under vacuum. Purification (Biotage Horizon HPFC chromatography system, SiO$_2$, 80:20 hexanes:ethyl acetate) gave a light brown solid (149 mg, 6%).

M.P.: 94° C.

HPLC: Inertsil ODS-3V C18, 30:70 [KH$_2$PO$_4$ (0.01M, pH 3.2):CH$_3$CN], 264 nm, R$_t$ 12.1 min, 95.1% purity.

$^1$H NMR (300 MHz, CDCl$_3$, TMS) δ 2.37 (s, 3H), 6.15 (s, 1H), 6.63 (s, 2H), 7.07 (apt d, J=8.4 Hz, 2H), 7.21 (apt d, J=8.1 Hz, 2H).

Mass Spec: LC-MSD (ES+): m/z 253 (M+H, 70.89).

Example 5

Synthesis of 1-[4-(2,6-dichloro-pyridin-4-ylamino)-phenyl]-ethanone

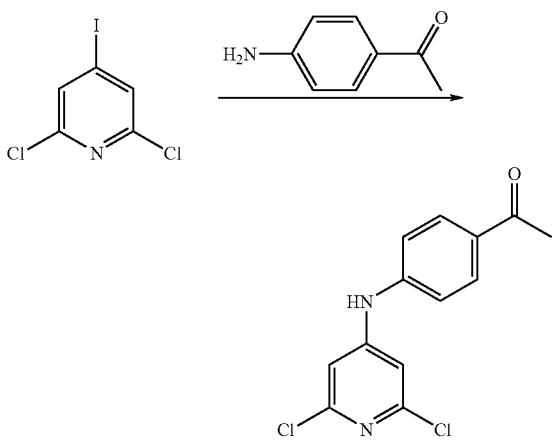

To 2,6-dichloro-4-iodopyridine (5.42 g, 20 mmol) dissolved in toluene (30 mL) and THF (10 mL) was added 4-amino-acetophenone (3.2412 g, 24 mmol), tris(dibenzylideneacetone)dipalladium (367.1 mg, 0.4 mmol), 1,3-bis (diphenyl-phosphino)propane (331.2 mg, 0.8 mmol), and sodium-tert-butoxide (2.69 g, 28 mmol). The resulting mixture was allowed to stir at reflux for 12-18 hours. The sample was diluted in dichloromethane and filtered through Celite™. The Celite™ was washed with dichloromethane; the filtrate was washed two times with water and one time with brine. The organic phase was dried over potassium carbonate and concentrated by rotary evaporation. The resulting sample was dried for 12-18 hours under vacuum. Recrystallization in dichloromethane gave a yellow solid (2.1 g, 37%).

M.P.: 226° C.

HPLC: Inertsil ODS-3V C18, 30:70 [KH$_2$PO$_4$ (0.01M, pH 3.2):CH$_3$CN], 264 nm, R$_t$ 6.5 min, 88.4% purity.

Example 6

Synthesis of 1-[4-(4-hydroxy-6'-phenyl-3,4,5,6-tetrahydro-2H-[1,2']bipyridinyl-4'-ylamino)-phenyl]-ethanone

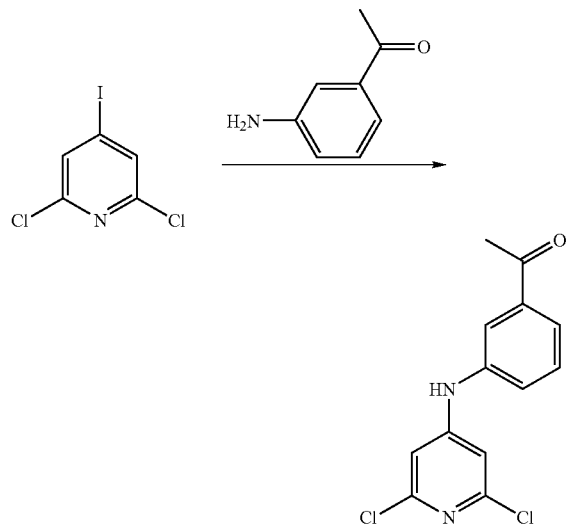

To 2,6-dichloro-4-iodopyridine (5.43 g, 20 mmol) and 3-aminoacetophenone (0.3.25 g, 24 mmol) dissolved in dry toluene (10 mL) and THF (2 mL) and tris(dibenzylideneacetone)dipalladium (0) (0.3627 g, 0.0.4 mmol), 1,3-bis(diphenylphospino)propane (0.3257 g, 0.8 mmol), sodium-tert-butoxide (2.68 g, 28 mmol) was added. The reaction mixture was stirred and refluxed for 12-18 hours under $N_2$. The reaction mixture was diluted with $CH_2Cl_2$ and filtered through Celite™, then rinsed with $CH_2Cl_2$. The filtrate was washed two times with water and one time with brine. The organic phase was collected and dried over potassium carbonate. The filtered sample was concentrated, and the resulting solid was dried for 12-18 hours under vacuum. Biotage Horizon HPFC system chromatography ($SiO_2$, 96:3:1 $CH_2Cl_2$:MeOH:$NH_4OH$) yielded a solid (1.2 g, 21%).

HPLC: Inertsil ODS-3V C18, 30:70 [$KH_2PO_4$(0.01M, pH 3.2):$CH_3CN$], 264 nm, $R_t$ 6.6 min, 98.3% purity.

$^1$H NMR: (300 MHz, $CDCl_3$, TMS): δ 2.63 (s, 3H), 6.47 (br s, 1H), 6.72 (s, 2H), 7.26-7.45 (m, 1H), 7.50 (t, J=7.8 Hz, 1H), 7.75-7.81 (m, 2H).

Example 7

Synthesis of benzo[1,3]dioxol-5-yl-(2,6-dichloro-pyridin-4-yl)-amine (B24)

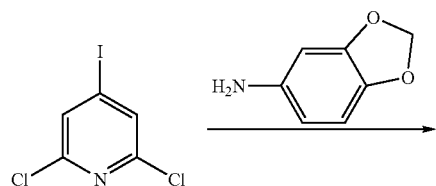

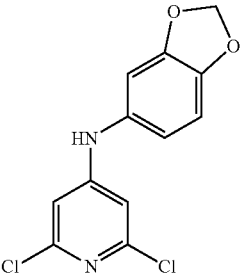

To 2,6-dichloro-4-iodopyridine (274.3 mg, 1 mmol) dissolved in toluene (15 mL) were added 3,4-(methylenedioxy)aniline (168.7 mg, 1.2 mmol), tris(dibenzylidene-acetone)-dipalladium (18.0 mg, 0.02 mmol), 1,3-bis(diphenylphosphino)propane (16.8 mg, 0.04 mmol), and sodium-tert-butoxide (134.0 mg, 1.4 mmol). The resulting mixture is allowed to stir at reflux for 12-18 hours. The sample was diluted in dichloromethane and filtered through Celite™. The Celite™ was washed with dichloromethane; the filtrate was washed two times with water and one time with brine. The organic phase was dried over sodium sulfate and concentrated by rotary evaporation. The resulting sample was dried for 12-18 hours under vacuum. Purification (Biotage Horizon HPFC chromatography system, $SiO_2$, 80:20 hexanes:ethyl acetate) gave a light brown solid product (190 mg, 67%).

M.P.: 129° C.

HPLC: Inertsil ODS-3V C18, 30:70 [$KH_2PO_4$ (0.01M, pH 3.2):$CH_3CN$], 264 nm, $R_t$ 8.1 min, 99.4% purity.

$^1$H NMR (600 MHz, $CDCl_3$, TMS): δ 6.011 (s, 2H), 6.09 (br s, 1H), 6.54 (s, 2H), 6.64 (dd, J=2.4, 8.1 Hz, 1H), 6.68 (d, J=1.8 Hz, 1H), 6.81. d, J=7.8 Hz, 1H).

Mass Spec: (TOF MS ES+): m/z 283 (M+H, 100).

Example 8

Synthesis of (2,6-dichloro-pyridin-4-yl)-(3-fluoro-phenyl)-amine (B25)

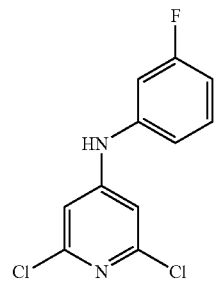

This compound was prepared by an analogous procedure to that disclosed in Example 7.

M.P.: 163° C.

HPLC: Inertsil ODS-3V C18, 30:70 [$KH_2PO_4$ (0.01M, pH 3.2):$CH_3CN$], 264 nm, $R_t$ 9.8 min, 94.5% purity.

$^1$H NMR (600 MHz, $CDCl_3$, TMS): δ 6.271 (s, 1H), 6.73 (s, 2H), 6.88-6.92 (m, 2H), 6.95-6.96 (m, 1H), 7.35 (q, J=7.8 Hz, 1H).

Mass Spec: (TOF MS ES+): m/z 257 (M+H, 100).

Example 9

Synthesis of (2,6-dichloro-pyridin-4-yl)-(3-methyl-sulfanyl-phenyl)-amine

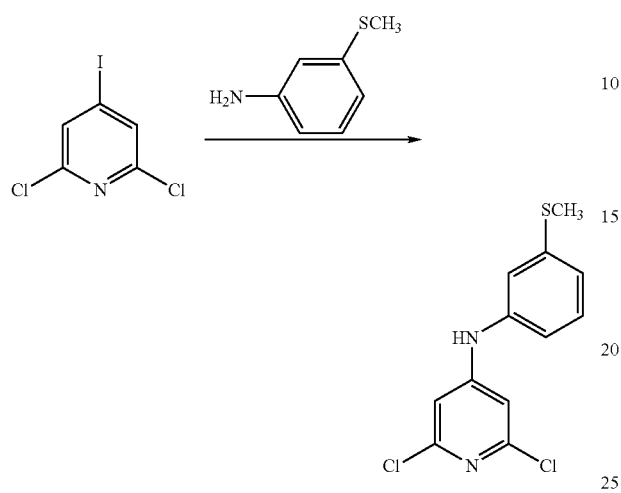

To 2,6-dichloro-4-iodopyridine (1.3715 g, 5 mmol) dissolved in toluene (30 mL) were added 3-methylthioaniline (0.73 mL, 6 mmol), tris(dibenzylidene-acetone)dipalladium (90.6 mg, 0.1 mmol), 1,3-bis(diphenylphosphino)propane (80.0 mg, 0.2 mmol), and sodium-tert-butoxide (672.1 mg, 7 mmol). The resulting mixture was allowed to stir at reflux for 12-18 hours. The sample was diluted in dichloromethane and filtered through Celite™. The Celite™ was washed with dichloromethane and the filtrate was washed two times with water and one time with brine. The organic phase was dried over potassium carbonate and concentrated by rotary evaporation. The resulting sample (9) was dried for 12-18 hours under vacuum. The sample was used without purification.

Example 10

Synthesis of thiocarbonic acid S-[3-(2,6-dichloro-pyridin-4-ylamino)-phenyl] ester-O-methyl ester

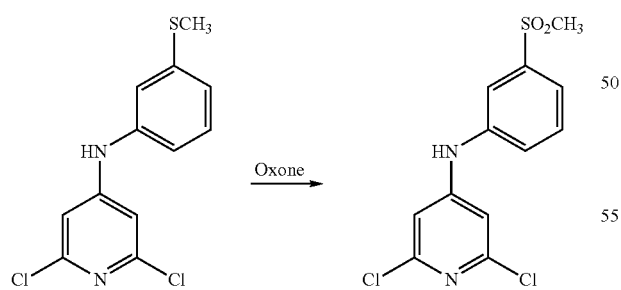

Unpurified (2,6-dichloro-pyridin-4-yl)-(3-methylsulfanyl-phenyl)-amine (1.8 g, 6.3 mmol) was dissolved in methanol (127 mL) and the resulting solution was cooled to 0° C. with an ice bath. A solution of oxone (17.52 g, 28.4 mmol) in water (285 mL) was added. The resulting mixture was allowed to warm to room temperature and was allowed to stir at room temperature for about 1.5 hours. The reaction mixture was diluted with water and extracted three times with dichloromethane. The organic phase was dried over sodium sulfate and concentrated by rotary evaporation. The resulting sample was dried for 12-18 hours under vacuum. Purification (Biotage Horizon HPFC chromatography system, SiO$_2$, 50:50 hexanes:ethyl acetate) gave a white solid product (905 mg, 45%).

M.P.: 162° C.

HPLC: Inertsil ODS-3V C18, 30:70 [KH$_2$PO$_4$ (0.01M, pH 3.2):CH$_3$CN], 264 um, R$_t$ 5.0 min, 93.8% purity.

$^1$H NMR (600 MHz, CDCl$_3$, TMS): δ 3.09 (s, 3H), 6.58 (s, 1H), 6.76 (s, 2H), 7.52-7.52 (m, 1H), 7.61 (apt t, J=7.9, 1H), 7.96 (apt t, J=1.6, 1H), 7.72-7.72 (m, 1H).

Mass Spec: (TOF MS ES+): m/z 317 (M+H, 100).

Example 11

Synthesis of 4-(2,6-dichloro-pyridin-4-yl)-morpholine

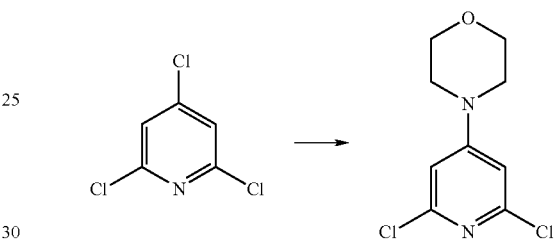

A mixture of morpholine (0.604 g, 6.04 mmol) in dry DMSO and NaH (0.251 g, 6.6 mmol) was stirred for 30 minutes at 0° C., after which time 2,4,6-trichloropyridine (1.0 g, 5.50 mmol) was added. This reaction mixture was stirred at room temperature for 4 hours, after which time ice cold water was added to quench the reaction (100 mL). The reaction mixture was then extracted with ethyl acetate, and the extract was washed with 3-4 times water. The organic layer was dried over sodium sulphate and concentrated under vacuum. The residue was purified by column chromatography over 100-200 mesh silica gel. Elution of the column with 20% acetone in hexanes gave the pure product as a colorless solid (0.565 g, yield 44%).

$^1$H NMR (200 MHz, CDCl$_3$): δ 6.58 (s, 2H), 3.83 (t, 4H, J=4.83 Hz), 3.28-3.35 (t, 4H, J=5.37 Hz).

Mass Spec: (CI-MS) m/z: 233 (M$^+$, 100%).

Example 12

Synthesis of 2,6-dichloro-4-pyrrolidino pyridine

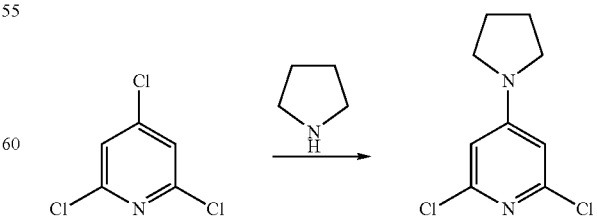

A mixture of pyrrolidine (0.910 g, 10.7 mmol) in dry DMSO and NaH (0.385 g, 16.0 mmol) was stirred for 30 minutes at 0° C., after which a sample of 2,4,6-trichloropyridine (1.75 g, 9.63 mmol) was added. This reaction mixture was stirred at room temperature for 4 hours, after which time ice cold water was added to quench the reaction. The reaction mixture was then extracted with ethyl acetate, and the extract was washed 3-4 times with water. The organic layer was dried over sodium sulphate and concentrated. The residue was purified by column chromatography over 100-200 mesh silica gel. Elution of the column with 20% acetone in hexanes gave the pure product as a colorless solid (yield: 75%).

$^1$H NMR (200 MHz, CDCl$_3$): δ 6.30 (s, 2H), 3.25-3.32 (t, 4H, J=13.34 Hz), 1.86-2.15 (m, 4H).

Mass Spec: (ES-MS) m/z: 216 (M$^+$, 100%).

Example 13

Synthesis of 2,6-dichloro-4-piperdino pyridine

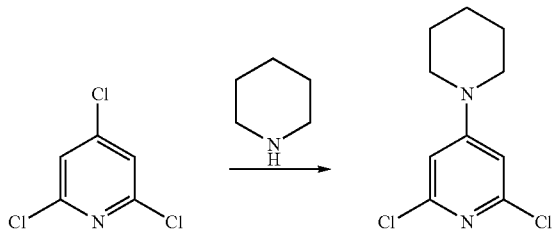

A mixture of piperidine (0.910 g, 10.7 mmol) in 25 mL of THF and 5 mL of 1N NaOH was stirred for 30 minutes at 0° C., after which time 2,4,6-trichloropyridine (1.63 g, 8.86 mmol) was added. The reaction mixture was then stirred at 30-40° C. for 12-18 hours, after which the reaction mixture was cooled and neutralized with 5% HCl (aq). This product was extracted with ethyl acetate, and the organic layer was dried over sodium sulfate and concentrated under reduced pressure. The residue was purified by column chromatography over 100-200 mesh silica gel by elution with 10:90 ethyl acetate: hexanes to afford the product as a pure colorless solid (yield 32%).

$^1$H NMR (200 MHz, CDCl$_3$): δ 6.56 (s, 2H), 3.34-3.37 (t, 4H, J=5.60 Hz), 1.54-1.75 (m, 6H).

Mass Spec: (CI-MS) m/z: 231 (M$^+$+1, 100%).

Reference: Stan V. D Andrea et al *Tetrahedron* 2000, 56, 5687-5698.

Example 14

Synthesis of 2',6'-dichloro-3,4,5,6-tetrahydro-2H-[1,4']bipyridinyl-4-ol

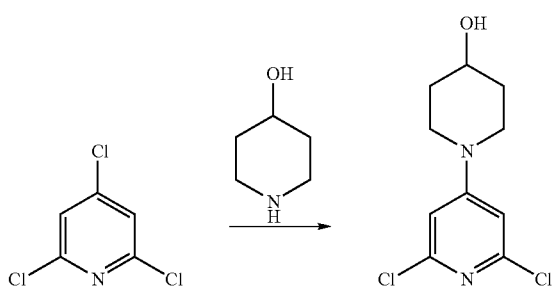

A solution of piperdine-4-ol (1.2 g, 12.0 mmol) in isopropylalcohol (30 mL) was prepared and 1N NaOH (8 mL) was added with stirring. After stirring 15 min at room temperature, 2,4,6-trichloropyridine (2.0 g, 10.0 mmol) was added, and the resulting reaction mixture was heated at 60° C. for 10 hours. After this time, water was added to the reaction mixture (100 mL), and the product was extracted with ethyl acetate (200 mL×3). The organic extract was washed with brine solution followed by water, after which the organic layer was dried over using sodium sulphate and concentrated under vacuum. The resulting product was purified by column chromatography using 230-400 mesh silica gel, eluted with 30:70 ethyl acetate:petroleum ether, to afford the desired compound as light yellow solid (1 g, yield 37%).

$^1$H NMR (200 MHz, CDCl$_3$): δ 6.58 (s, 1H), 4.05 (m, 1H), 3.7 (m, 2H), 3.19 (m, 2H), 2.0 (s, 1H), 1.8 (m, 2H), 1.6 (m, 2H).

Mass Spec: (ES-MS) m/z: 247 (M$^+$+1, 100%).

Example 15

Synthesis of (3-chloro-4-methoxy-phenyl)-(2,6-dichloro-pyridin-4-yl)-amine

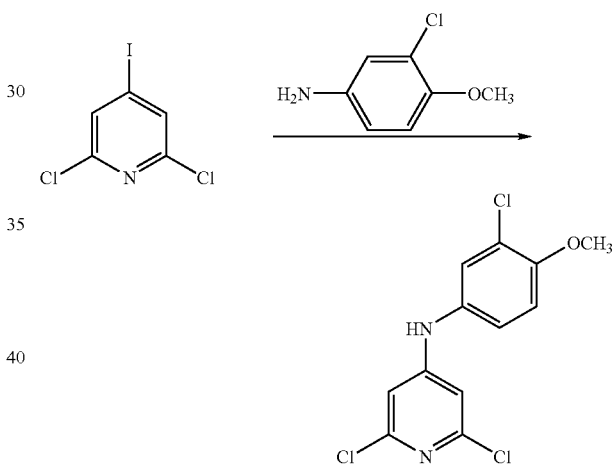

To tris(dibenzylideneacetone)dipalladium (0.1822 g, 0.2 mmol) and sodium tert-butoxide (1.5515 g, 15.9 mmol) in toluene (40 mL, anhydrous) under a nitrogen atmosphere was added a mixture of 2,6-dichloro-4-iodopyridine (2.4993, 9.13 mmol), 3-chloro-4-methoxy-phenylamine (1.8423 g, 10.5 mmol) and 1,3-bis(diphenyl-phospino)propane (0.1897, 0.45 mmol) in toluene (40 mL, anhydrous)-THF (2 mL, dry) by cannular transfer. The reaction mixture was heated at gentle reflux for approximately 3 h under nitrogen. The mixture was cooled and diluted with ethyl acetate followed by a brine wash. The organic layer was separated, dried over anhydrous potassium carbonate, filtered and then concentrated under vacuum. Purification (Biotage Horizon HPFC chromatography system, SiO$_2$, 70:30 hexanes:ethyl acetate) gave a solid (1.817 g, 65.6%).

HPLC: Inertsil ODS-3V C18, 30:70 [KH$_2$PO$_4$ (0.01M, pH 3.2):CH$_3$CN], 264 nm, R$_t$ 10.7 min, 98.4% purity.

$^1$H NMR (600 MHz, CDCl$_3$, TMS): δ 3.93 (s, 3H), 6.21 (s, 1H), 6.56 (s, 2H), 6.95 (d, J=9 Hz, 1H), 7.10 (dd, J=9, 3 Hz, 1H), 6.95 (d, J=3.6 Hz, 1H).

Mass Spec (TOF MS ES+): m/z 303 (M+H, 100).

Example 16

Synthesis of (2,6-dichloro-pyridin-4-yl)-(4-trifluoromethoxy-phenyl)-amine

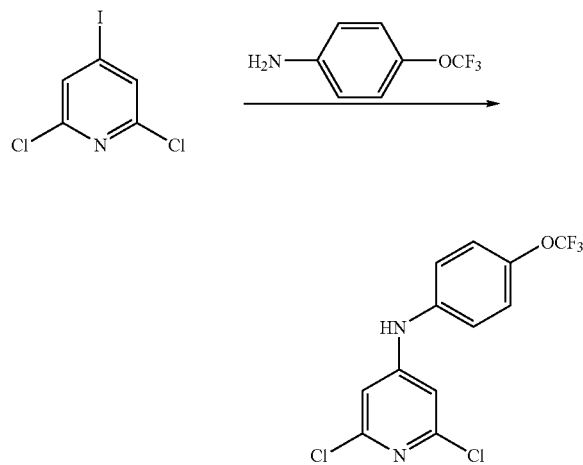

To 2,6-dichloro-4-iodopyridine (1.37 g, 5 mmol) dissolved in toluene (25 mL) was added 4-trifluoromethoxyaniline (0.80 mL, 6 mmol), tris(dibenzylidene-acetone)dipalladium (90.1 mg, 0.1 mmol), 1,3-bis(diphenylphosphino)propane (80.8 mg, 0.2 mmol), and sodium-tert-butoxide (672.7 mg, 7 mmol). The resulting mixture is allowed to stir at reflux overnight. The sample was diluted in dichloromethane and filtered through celite. The celite is washed with dichloromethane; the filtrate was washed two times with water and one time with brine. The organic phase was dried over sodium sulfate and concentrated by rotary evaporation. The resulting sample was dried overnight under vacuum. Purification (Biotage Horizon HPFC chromatography system, $SiO_2$, 70:30 hexanes:ethyl acetate) gave a light purple solid (1.186 g, 73%).

M.P.: 124° C.

HPLC: Inertsil ODS-3V C18, 30:70 [$KH_2PO_4$ (0.01M, pH 3.2):$CH_3CN$], 264 nm, $R_t$ 14.5 min, 96.0% purity.

$^1$H NMR (600 MHz, $CDCl_3$, TMS): δ 6.31 (s, 1H), 6.67 (s, 1H), 7.20-7.22 (m, 2H), 7.25-7.26 (m, 2H).

Mass Spec (TOF MS ES+): m/z 323 (M+H, 100).

Example 17

Synthesis of 1-[4-(2,6-dichloro-pyridin-4-ylamino)-phenyl]-ethanone

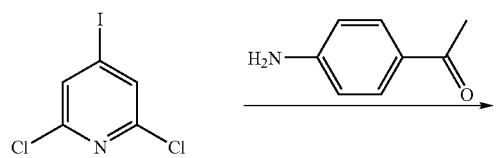

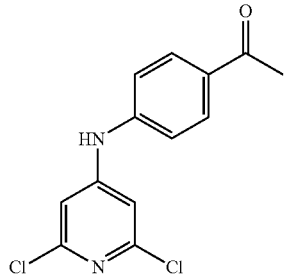

To 2,6-dichloro-4-iodopyridine (0.8177 g, 3 mmol) and 4-aminoacetophenone (0.4891 g, 3.6 mmol) dissolved in dry toluene (10 mL) and THF (2 mL) was added tris(dibenzylideneacetone)dipalladium(0) (0.0571 g, 0.06 mmol), 1,3-bis (diphenyl-phospino)propane (0.0499 g, 0.12 mmol), and sodium-tert-butoxide (0.4042 g, 4.2 mmol). The reaction mixture was stirred and refluxed for 12 to 14 hours under $N_2$. The reaction mixture was diluted with $CH_2Cl_2$ and filtered through Celite™, then rinsed with $CH_2Cl_2$. The filtrate was washed two times with water and one time with brine. The organic phase was collected and dried over potassium carbonate. The filtered sample was concentrated, and the resulting solid was dried for 12-18 hours under vacuum.

Biotage Horizon HPFC system chromatography ($SiO_2$, 96:3:1 $CH_2Cl_2$:MeOH:$NH_4OH$) yielded a light yellow (250 mg, 30%).

M.P.: 210° C.

HPLC: Inertsil ODS-3V C18, 30:70 [$KH_2PO_4$ (0.01M, pH 3.2):$CH_3CN$], 264 nm, $R_t$ 6.3 min, 84.7% purity.

$^1$H NMR (300 MHz, DMSO, TMS): δ 2.50 (s, 3H, overlaps with DMSO peak), 6.96 (s, 2H), 7.28 (d, J=8.7 Hz, 2H), 7.93 (d, J=8.7 Hz, 2H), 9.73 (s, 1H).

Mass Spec: : (TOF MS ES+): m/z 281 (M+, 100).

Example 18

Synthesis of 1-(2,6-dichloro-pyridin-4-yl)-4-methyl-piperazine (I)

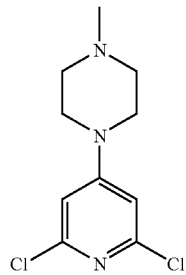

A mixture of N-methyl piperazine (0.604 g, 6.04 mmol) in dry DMSO (6 mL) was prepared and NaH (0.2637 g, 10.98 mmol) was added. The resulting mixture was stirred for 30 minutes at 0° C., after which time 2,4,6-trichloropyridine (1.0 g) was added. The reaction mixture was stirred at 20 to 40° C. for 4 hours. In the reaction mixture ice cold water was added and extracted with ethyl acetate giving 3-4 times water washing. The organic layer was dried and concentrated. The residue was purified by column chromatography using 100-200 mesh silica gel. Elution of the column with 20% acetone in hexanes gave the pure product as a colorless solid. Yield: 26%.

$^1$H NMR (200 MHz, CDCl$_3$): δ 6.62(s, 2H, J=13.67 Hz), 3.35-3.45 (t, 4H, J=10.34 Hz), 2.56-2.62 (t, 4H, J=10.00 Hz), 2.40 (s, 3H).

Mass Spec: (ES-MS) m/z: 216 (M$^+$, 100%).

Example 19

Synthesis of (3-chloro-4-methoxy-phenyl)-(2-chloro-6-phenyl-pyridin-4-yl)-amine (B23)

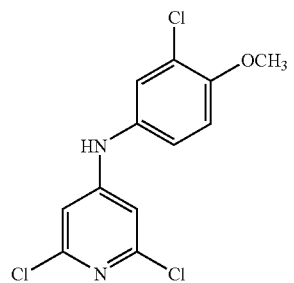
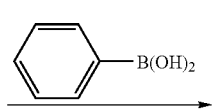

To (3-chloro-4-methoxy-phenyl)-(2,6-dichloro-pyridin-4-yl)-amine (0.459 g, 1.5 mmol) and phenylboronic acid (0.1861 g, 1.5 mmol) dissolved in acetonitrile (20 mL) and Na$_2$CO$_3$ (20 mL, 0.4 M) was added palladium(0) tetrakis triphenylphosphine (0.0891 g, 0.075 mmol). The reaction mixture was stirred and refluxed for 12-18 hours under N$_2$. The reaction mixture was diluted with CH$_2$Cl$_2$ and filtered through Celite™, then rinsed with CH$_2$Cl$_2$. The filtrate was washed one time with water and one time with brine. The organic phase was collected and dried over potassium carbonate. The filtered sample was concentrated, and the resulting solid was dried for 12-18 hours under vacuum. Biotage Horizon HPFC system chromatography (SiO$_2$, 100% CH$_2$Cl$_2$) yielded an off white solid product (182 mg, 52%).

M.P.: 128° C.

HPLC: Inertsil ODS-3V C18, 30:70 [KH$_2$PO$_4$(0.01M, pH 3.2):CH$_3$CN], 264 nm, R$_t$ 18.7 min, 96% purity.

$^1$H NMR: (600 MHz, CDCl$_3$, TMS, 55° C.): δ 3.92 (s, 3H), 6.00 (s, 1H), 6.60 (s, 1H), 6.94-6.95 (m, 2H), 7.11 (dd, J=2.4, 8.4 Hz, 1H), 7.25 (s, 1H), 7.36-7.42 (m, 3H), 7.86 (d, J=8.4 Hz, 2H).

Mass Spec: (TOF MS ES+): m/z 345 (M+H, 100).

Example 20

Synthesis of 2'-chloro-6'-phenyl-3,4,5,6-tetrahydro-2H-[1,4']bipyridinyl-4-ol

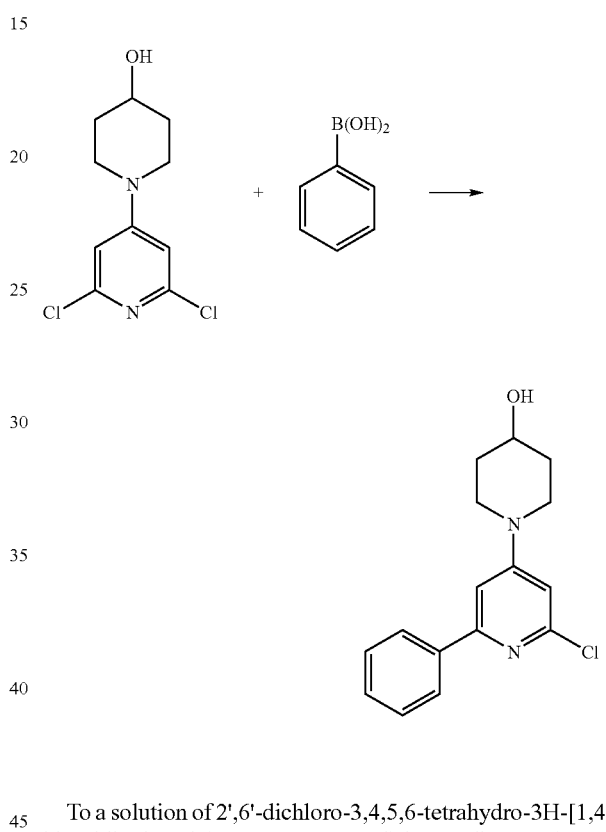

To a solution of 2',6'-dichloro-3,4,5,6-tetrahydro-3H-[1,4'] bipyridinyl-4-ol (100 mg, 0.4 mmol) in 1,4-dioxane (8 mL) were added 1N sodium carbonate solution (172 mg, 1.6 mmol) and tetrakis(triphenylphosphine)palladium(0) (46 mg, 0.04 mmol), followed by phenyl boronic acid (74 mg, 0.6 mmol). The resulting reaction mixture was refluxed for 4 hours, after which time water was added 100 mL to the reaction mixture, and the product was extracted with ethyl acetate. The organic layer was dried over sodium sulphate, filtered, and the filtrate was concentrated under vacuum. The resulting product was purified by column chromatography using 230-400 mesh silica gel (5% methanol in dichloromethane) to afford the desired compound as a yellow solid (50 mg, yield 45%.).

$^1$H NMR (400 MHz, CDCl$_3$): δ 7.91 (m, 2H), 7.45-7.38 (m, 3H), 6.99 (s, 1H), 6.64 (s, 1H), 4.01-3.95 (m, 1H), 3.78-3.699 (m, 2H), 3.23-3.168 (m, 2H), 2.02-1.95 (m, 2H), 1.67-1.59 (m, 2H).

Mass Spec: (CI-MS) (m/z): 289 (M$^+$+1, 100%).

IR (neat) cm$^{-1}$: 3329, 2926, 2854, 1599, 1526, 1434, 1367, 1224, 1145, 1074, 1042, 982, 810.

Example 21

Synthesis of 3-[6-chloro-4-(4-trifluoromethoxy-phenylamino)-pyridin-2-yl]-N-ethyl-benzamide

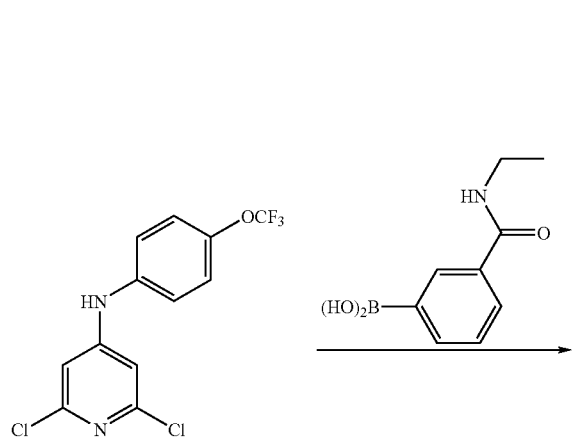

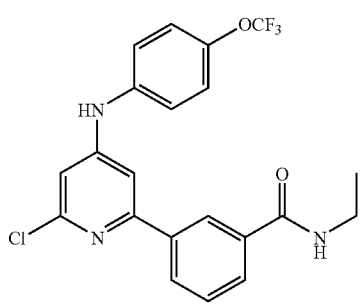

To (2,6-dichloro-pyridin-4-yl)-(4-trifluoromethoxy-phenyl)-amine (0.1002 g, 0.3 mmol) and 3-(N-ethylaminocarbonyl)phenyl boronic acid (0.1162 g, 0.6 mmol) dissolved in acetonitrile (10 mL) and Na$_2$CO$_3$ (10 mL, 0.4M) was added palladium (0) tetrakis(triphenylphosphine) (0.0179 g, 0.015 mmol). The reaction mixture was stirred and refluxed for 12-18 hours under N$_2$. The reaction mixture was diluted with CH$_2$Cl$_2$ and filtered through Celite™, then rinsed with CH$_2$Cl$_2$. The filtrate was washed two times with water and one time with brine. The organic phase was collected and dried over potassium carbonate. The filtered sample was concentrated, and the resulting solid was dried for 12-18 hours under vacuum. Biotage Horizon HPFC system chromatography (SiO$_2$, 50:50 hexanes:ethyl acetate) yielded a (36.5 mg, 32%).

HPLC: Inertsil ODS-3V C18, 30:70 [KH$_2$PO$_4$(0.01M, pH 3.2):CH$_3$CN], 264 nm, R$_t$ 11.6 min, 97.8% purity.

$^1$H NMR: (300 MHz, DMSO-d$_6$, TMS): δ 1.13 (t, J=6.9 Hz, 3H), 3.26-3.33 (m, 2H), 6.90 (s, 1H), 7.38-7.41 (br m, 4H), 7.56 (apt t, J=16.8 Hz, 1H), 7.90 (d, J=7.8 Hz, 1H), 8.05 (d, J=7.8 Hz, 1H), 8.35 (s, 1H), 8.62 (apt t, J=4.8 Hz, 1H), 9.38 (s, 1H).

Example 22

Synthesis of 1-[4-(2-chloro-6-morpholin-4-yl-pyridin-4-ylamino)-phenyl]-ethanone

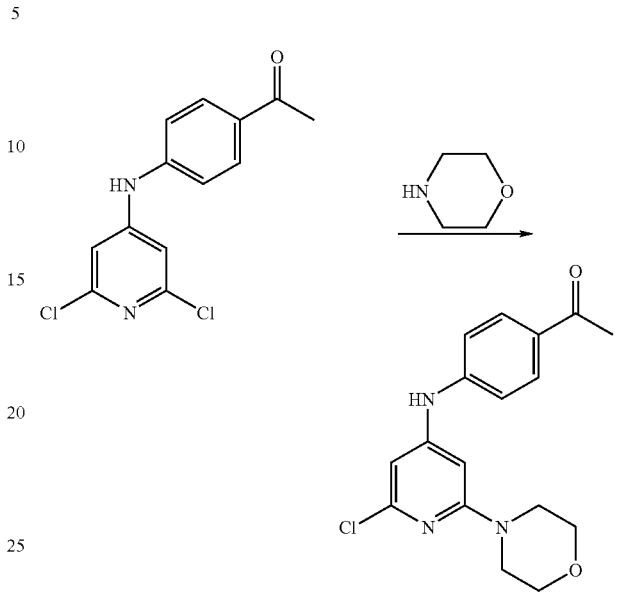

A portion of 1-[4-(2,6-Dichloro-pyridin-4-ylamino)-phenyl]-ethanone (600.1 mg, 2.13 mmol) was dissolved in morpholine (10 mL, 115 mmol). The resulting mixture was allowed to stir at reflux for 12-18 hours. The sample was allowed to cool to room temperature and was diluted in dichloromethane. The mixture was washed two times with water and one time with brine. The organic phase was dried over sodium sulfate and concentrated by rotary evaporation. The resulting sample was dried for 12-18 hours under vacuum. Purification (Biotage Horizon HPFC chromatography system, SiO$_2$, 98:2 dichloromethane:methanol) gave a brown solid (22, 554 mg, 78%).

M.P.: 174° C.

HPLC: Inertsil ODS-3V C18, 30:70 [KH$_2$PO$_4$ (0.01M, pH 3.2):CH$_3$CN], 264 nm, R$_t$ 5.9 min, 64.3% purity. (Used as is with no further purification.)

$^1$H NMR (300 MHz, CDCl$_3$, TMS): δ 2.57 (s, 3H), 3.41-3.47 (m, 4H), 3.76-3.781 (m, 4H), 6.12 (d, J=1.5 Hz, 1H), 6.34 (s, 1H), 6.413 (d, J=1.5 Hz, 1H), 7.13-7.26 (m, 2H), 7.90 7.97 (m, 2H).

Mass Spec: LC-MSD (ES+): m/z 332 (M+H, 40.1).

Example 23

Synthesis of 6'-chloro-4'-(4-trifluoromethoxy-phenylamino)-3,4,5,6-tetrahydro-2H-[1,2']bipyridinyl-4-ol

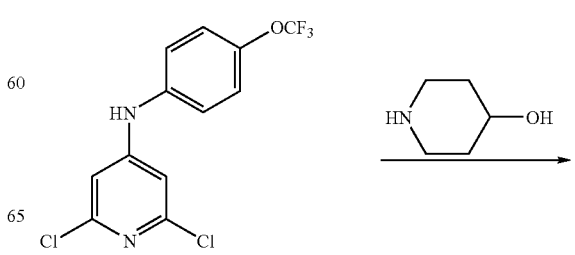

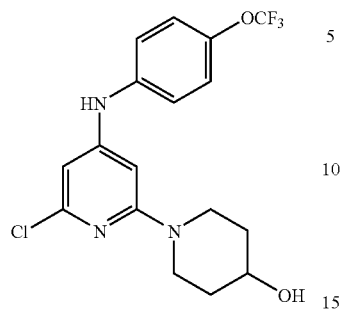
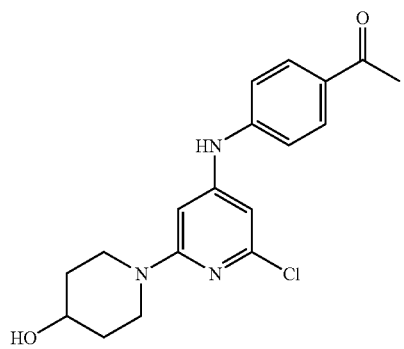

Portions of (2,6-Dichloro-pyridin-4-yl)-(4-trifluoromethoxy-phenyl)-amine (0.1987 g, 0.6 mmol) and 4-hydroxypiperidine (0.1258 g, 1.2 mmol) were dissolved in DMF (5 mL) followed by the addition of potassium carbonate (0.0998 g, 0.72 mmol). The reaction mixture was stirred and refluxed for 12-18 hours at 100° C. under $N_2$. The reaction was monitored by TLC, and after 18 hours, potassium carbonate (0.0491 g, 0.36 mmol) was added stirred and refluxed for another 12-18 hours under $N_2$. The reaction mixture was diluted with $CH_2Cl_2$. The filtrate was washed two times with water and one time with brine. The organic phase was collected and dried over potassium carbonate. The filtered sample was concentrated, and the resulting solid was dried for 12-18 hours under vacuum. Biotage Horizon HPFC system chromatography ($SiO_2$, 98:2 $CH_2Cl_2$:MeOH) yielded a solid (83 mg, 23%).

HPLC: Inertsil ODS-3V C18, 30:70 [$KH_2PO_4$(0.01M, pH 3.2):$CH_3CN$], 264 nm, $R_t$ 8.6 min, 98.9% purity.

$^1$H NMR: (300 MHz, $CHCl_3$, TMS): δ 1.50-1.61 (m, 3H) 1.92-1.97 (m, 2H), 3.07-3.15 (m, 2H), 3.92-3.99 (m, 3H), 5.91 (s, 1H), 6.21 (d, J=1.5 Hz, 1H), 7.14-7.22 (m, 4H), 7.15 (s, 2H), 7.23 (br s, 4H), 7.26 (s, 1H), 7.40-7.49 (m, 4H), 8.02-8.04 (br m, 4H).

Portions of 1-[4-(2,6-Dichloro-pyridin-4-ylamino)-phenyl]-ethanone (0.99 g, 3.5 mmol) and 4-hydroxypiperidine (0.7079 g, 7 mmol) were dissolved in DMF (10 mL) followed by the addition of potassium carbonate (0.5810 g, 4.2 mmol). The reaction mixture was stirred and refluxed for 12-18 hours at 100° C. under $N_2$. The reaction mixture was diluted with $CH_2Cl_2$. The filtrate was washed two times with water and one time with brine. The organic phase was collected and dried over potassium carbonate. The filtered sample was concentrated, and the resulting solid was dried for 12-18 hours under vacuum.

Biotage Horizon HPFC system chromatography ($SiO_2$, 98:2 $CH_2Cl_2$:MeOH) yielded a light yellow solid (552 mg, 49%).

M.P.: 80° C.

HPLC: Inertsil ODS-3V C18, 30:70 [$KH_2PO_4$(0.01M, pH 3.2):$CH_3CN$], 264 nm, $R_t$ 4.2 min, 97.1% purity.

$^1$H NMR: (300 MHz, $CHCl_3$, TMS): δ 1.51-1.62 (m, 3H), 1.91-1.99 (m, 2H), 2.58 (s, 3H), 3.10-3.19 (m, 3H), 3.89-4.01 (m, 3H), 6.15 (d, J=1.8 Hz, 1H), 6.22 (s, 1H), 6.35 (d, J=1.2 Hz, 1H), 7.14-7.17 (m, 2H), 7.93-7.96 (m, 2H).

Mass Spec: LC-MSD (ES+): m/z 346 (M+H, 100).

Example 24

Synthesis of 1-[4-(6'-chloro-4-hydroxy-3,4,5,6-tetrahydro-2H-[1,2']bipyridinyl-4'-ylamino)-phenyl]-ethanone Example 25

Synthesis of 1-[3-(6'-chloro-4-hydroxy-3,4,5,6-tetrahydro-2H-[1,2']bipyridinyl-4'-ylamino)-phenyl]-ethanone

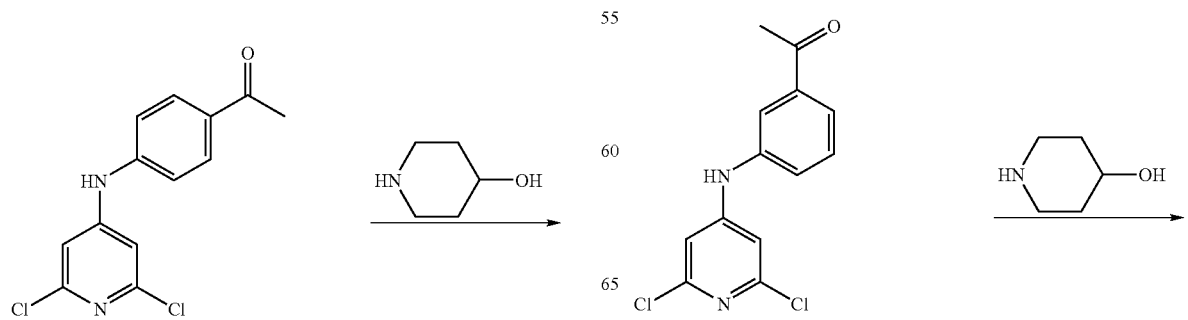

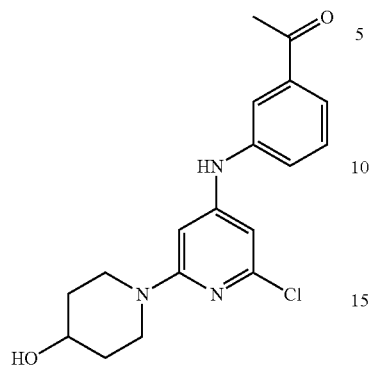

Samples of 1-[4-(4-hydroxy-6'-phenyl-3,4,5,6-tetrahydro-2H-[1,2']bipyridinyl-4'-ylamino)-phenyl]-ethanone (0.99 g, 3.5 mmol) and 4-hydroxypiperidine (0.7079 g, 7 mmol) were dissolved in DMF (10 mL) followed by the addition of potassium carbonate (0.5835 g, 4.2 mmol). The reaction mixture was stirred and refluxed for 12-18 hours at 100° C. under $N_2$. The reaction mixture was diluted with $CH_2Cl_2$. The filtrate was washed two times with water and one time with brine. The organic phase was collected and dried over potassium carbonate. The filtered sample was concentrated, and the resulting solid was dried for 12-18 hours under vacuum.

Biotage Horizon HPFC system chromatography ($SiO_2$, 96:3:1 $CH_2Cl_2$:MeOH:NH4OH) yielded a light brown solid (450 mg, 37%).

M.P.: 70° C.

HPLC: Inertsil ODS-3V C18, 30:70 [$KH_2PO_4$(0.01M, pH 3.2):$CH_3CN$], 264 nm, $R_t$ 4.5 min, 99.7% purity.

$^1$H NMR: (300 MHz, $CHCl_3$, TMS): δ 1.46-1.61 (m, 3H), 1.90-1.97 (m, 2H), 2.60 (s, 3H), 3.07-3.16 (m, 2H), 3.88-3.99 (m, 3H), 5.99 (s, 1H), 6.03 (d, J=1.5 Hz, 1H), 6.22 (d, J=1.5 Hz, 1H), 7.35-7.48 (m, 2H), 7.65-7.72 (m, 2H).

Mass Spec: LC-MSD (ES+): m/z 346 (M+H, 100).

Example 26

Synthesis of (2-chloro-6-morpholin-4-yl-pyridin-4-yl)-(4-trifluoromethoxy-phenyl)-amine

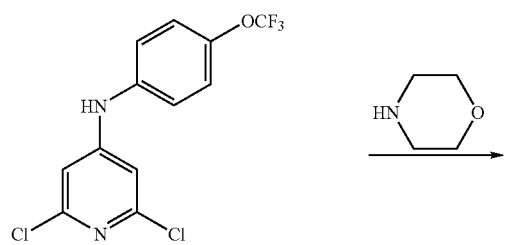

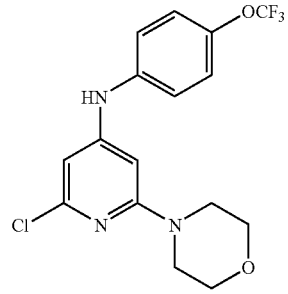

A portion of (2,6-dichloro-pyridin-4-yl)-(4-trifluoromethoxy-phenyl)-amine (0.0513 g, 0.15 mmol) was dissolved in morpholine (0.5 mL, 38 mmol). The reaction mixture was stirred and refluxed for 12-18 hours at 120° C. under $N_2$. The reaction mixture was diluted with ethyl acetate and washed with water two times and one time with brine. The organic phase was collected and dried over sodium sulfate. The filtered sample was concentrated, and the resulting solid was dried for 12-18 hours under vacuum. Flash chromatography ($SiO_2$, 70:30 hexanes:ethyl acetate) yielded a solid (36 mg, 61%).

HPLC: Inertsil ODS-3V C18, 30:70 [$KH_2PO_4$ (0.01M, pH 3.2):$CH_3CN$], 264 nm, $R_t$ 13.8 min, 98.5% purity.

$^1$H NMR: (300 MHz, $CHCl_3$, TMS): δ 3.44 (t, J=4.8 Hz, 4H), 3.77 (t, J=5.1 Hz, 4H), 5.94 (apt t, J=1.5 Hz, 2H), 6.26 (d, J=1.2 Hz, 1H), 7.19 (apt t, J=2.4 Hz, 4H).

Example 27

Synthesis of (6-chloro-4-pyrrolidin-1-yl-pyridin-2-yl)-(4-trifluoromethoxy-phenyl)-amine

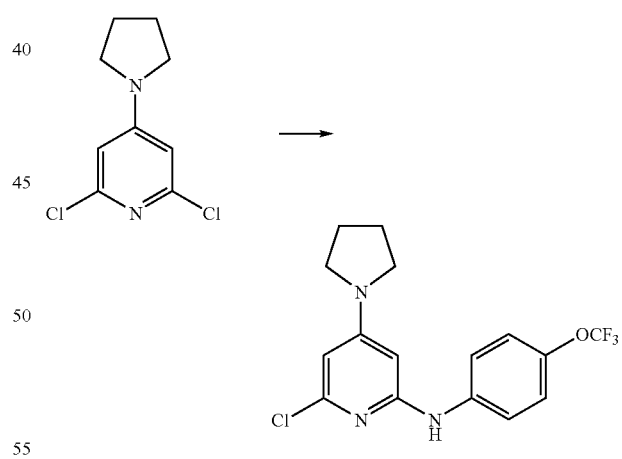

To a solution of 2,6-dichloro-4-pyrrolidino-pyridine (1.0 g, 4.62 mmol) in toluene (6 mL) were added potassium tert-butoxide (0.1556 g, 1.38 mmol), palladium(II)acetate (26 mg, 0.115 mmol), BINAP (36 mg, 0.057 mmol) and 4-trifluoromethoxyphenylamine (246 mg, 1.38 mmol), in a 10 mL reaction vessel. This reaction mixture was subjected the microwave radiation, in which the microwave power was 250 W, to attain a reaction temperature of 150° C. After this reaction proceeded for 30 min, water (200 mL) was added to the reaction mixture and the reaction product was extracted with ethyl acetate. The organic layer was dried over sodium sulphate, filtered, and the filtrate concentrated under vacuum. The product was purified through column chromatography using 230-400 mesh silica gel to afford the desired compound as light brown solid (220 mg, yield 14%).

$^1$H NMR (200 MHz, DMSO-$d_6$): δ 7.12-7.33 (m, 4H), 6.45 (s, 1H), 6.04 (s, 1H, J=1.66 Hz), 5.75 (s, 1H, J=1.66 Hz), 3.22-3.30 (m, 4H, J=13.34 Hz), 1.95-2.05 (m, 4H).

Mass Spec: (ES-MS) m/z: 358 (M$^+$+1, 100%).

Example 28

Synthesis of (6'-chloro-3,4,5,6-tetrahydro-2H-[1,4'] bipyridinyl-2'-yl]-(4-trifluoro-methoxyphenyl)-amine

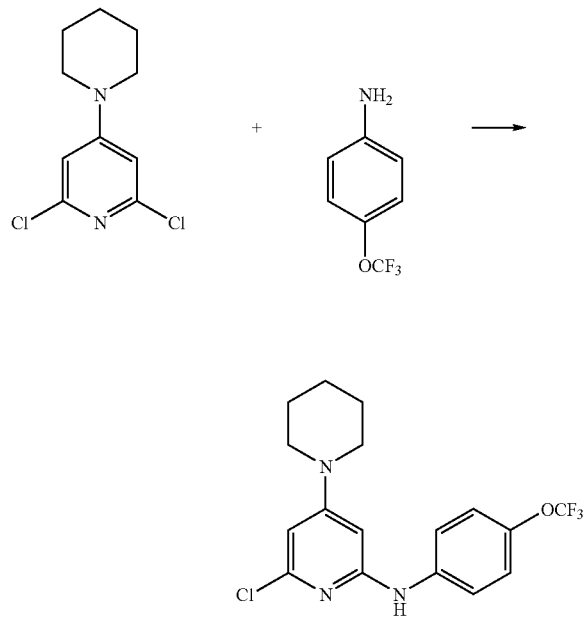

To a solution of 2',6'-dichloro-3,4,5,6-tetrahydro-2H-[1,4'] bipyridinyl (1 g, 4.3 mmol) in toluene (6 mL) were added potassium tert-butoxide (973 mg, 8.6 mmol), palladium(II) acetate (48 mg, 0.21 mmol), BINAP (135 mg, 0.21 mmol) and 4-trifluoro-methoxyphenylamine (769 mg, 4.3 mmol) in a 10 mL reaction vessel. This reaction mixture was subjected the microwave irradiation, in which the microwave power was 250 W, at a temperature of 150° C. After this reaction proceeded for 30 min, water was added to the reaction mixture and the reaction product was extracted with ethyl acetate. The organic layer was dried over sodium sulphate, filtered, and the filtrate concentrated under vacuum. The resulting product was purified through column chromatography using 230-400 mesh silica gel (18% ethylacetate in petroleum ether) to afford the desired compound as light yellow solid (820 mg, yield 51%).

$^1$H NMR (400 MHz, CDCl$_3$): δ 7.29-7.17(m, 4H), 6.61 (s, 1H), 6.27 (s, 1H), 6.04 (s, 1H), 3.28-3.26 (m, 4H), 1.66-1.59 (m, 6H).

Mass Spec: (CI-MS) m/z: 372 (MW$^+$+1, 100%).

Example 29

Synthesis of 4-(6'-chloro-3,4,5,6-tetrahydro-2H-[1, 4']bipyridinyl-2'-ylamino)-N-methyl-benzene-sulfonamide

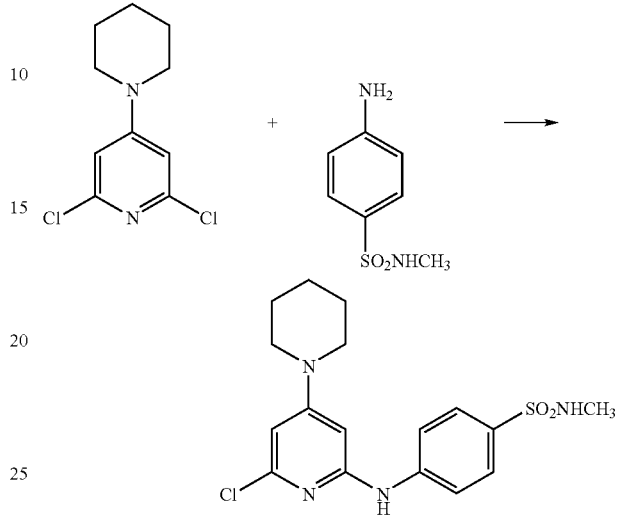

To a solution of 2',6'-dichloro-3,4,5,6-tetrahydro-2H-[1,4'] bipyridinyl (500 mg, 2.15 mmol) in toluene (6 mL) were added potassium tert-butoxide (486 mg, 4.3 mmol), palladium(II) acetate (24 mg, 0.1 mmol), BINAP (67 mg, 0.1 mmol), and 4-amino-N-methylbenzenesulfonamide (444 mg, 2.15 mmol) were taken in a 10 mL reaction vessel. This reaction mixture was subjected the microwave irradiation, in which the microwave power was 250 W, to attain a reaction temperature of 1 50° C. After this reaction proceeded for 30 min, water (200 mL) was added to the reaction mixture and the reaction product was extracted with ethyl acetate. The organic layer was dried over sodium sulphate, filtered, and the filtrate concentrated under vacuum. The product was purified through column chromatography using 230-400 mesh silica gel to afford the desired compound as light yellow solid (290 mg, yield, 35%).

Mass Spec: (ES-MS) m/z: 381 (M$^+$+1, 100%).

Example 30

Synthesis of 4-(6-chloro-4-pyrrolidin-1-yl-pyridin-2-ylamino)-N-methyl-benzenesulfonamide

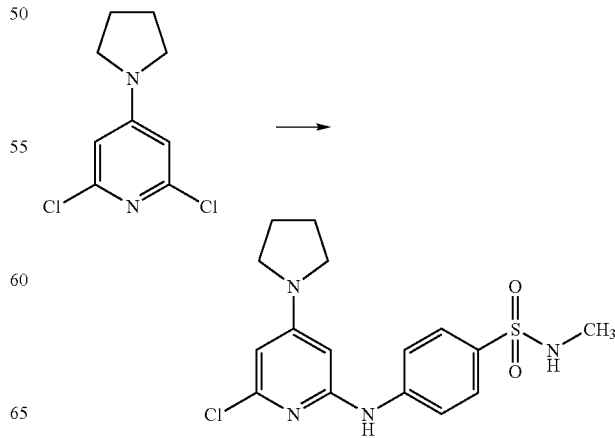

To a solution of 2,6-dichloro-4-pyrrolidino-pyridine (0.350 g, 1.62 mmol) in toluene (6 mL) were added potassium tert-butoxide (0.132 g, 1.18 mmol), palladium(II)-acetate (36.40 mg, 0.160 mmol), BINAP (32 mg, 0.514 mmol) and 4-amino-N-methyl-benzenesulfonamide (227 mg, 1.22 mmol) in a 10 mL reaction vessel. This reaction mixture was subjected the microwave irradiation, in which the microwave power was 250 W, to attain a reaction temperature of 150° C. After this reaction proceeded for 30 min, water (150 mL) was added to the reaction mixture and the reaction product was extracted with ethyl acetate. The organic layer was dried over sodium sulphate, filtered, and the filtrate concentrated under vacuum. The product was purified through column chromatography using 230-400 mesh silica gel (elution 20:80 acetone:petroleum ether) to afford the desired compound as a light brown solid (110 mg, yield 19%).

$^1$H NMR (200 MHz, DMSO-$d_6$): δ 9.31 (s, 1H), 7.74 (d, 2H, J=9.00 Hz), 7.64 (d, 2H), 7.46 (d, 2H, J=8.33 Hz), 7.18 (br s, 1H), 6.63 (s, 1H), 5.96 (s, 1H), 3.22-3.38 (m, 4H), 2.31-2.40 (d, 3H, J=5.00),1.99-2.06 (m, 4H).

Mass Spec: (ES-MS) m/z: 367 ((M$^+$+1, 50%).

Example 31

Synthesis of (6-chloro-4-morpholin-4-yl-pyridin-2-yl)-(4-trifluoromethoxy-phenyl)-amine

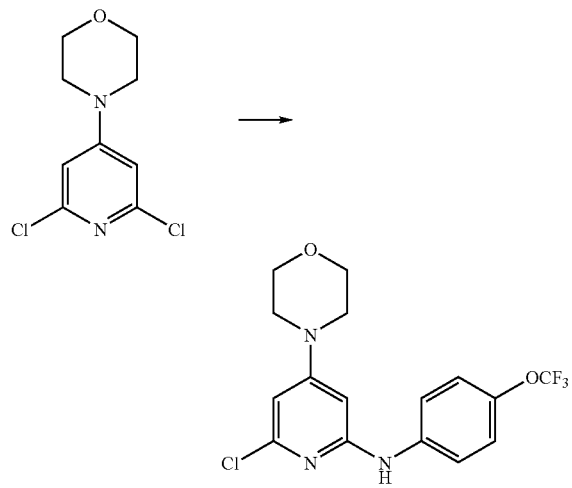

To a solution of 4-(2,6-dichloro-pyridin-4-yl)-morpholine (0.500 g, 2.15 mmol) in toluene (6 mL) were added potassium tert-butoxide (0.109 g, 0.973 mmol), palladium(II)acetate (24.13 mg, 0.107 mmol), BINAP (67.0 mg, 0.107 mmol) and 4-trifluoromethoxyphenylamine (456 mg, 2.58 mmol), in a 10 mL reaction vessel. This reaction mixture was subjected the microwave radiation, in which the microwave power was 250 W, to attain a reaction temperature of 150° C. After this reaction proceeded for 30 min, water (200 mL) was added to the reaction mixture and the reaction product was extracted with ethyl acetate. The organic layer was dried over sodium sulphate, filtered, and the filtrate concentrated under vacuum. The product was purified through column chromatography using 230-400 mesh silica gel (elution 30:70 ethyl acetate: petroleum ether) to afford the desired compound as a light yellow solid (140 mg, yield 18%).

$^1$H NMR (200 MHz, DMSO-$d_6$): δ7.15-7.32 (m, 4H), 6.45 (s, 2H), 6.28 (s, 1H), 3.77-3.82 (m, 4H), 3.19-3.25 (m, 4H).

Mass Spec: (ES-MS) m/z: 374 (M$^+$+1, 100%).

Example 32

Synthesis of (2-chloro-6-pyrrolidin-1-yl-pyridin-4-yl)-(4-trifluoromethoxy-phenyl)-amine

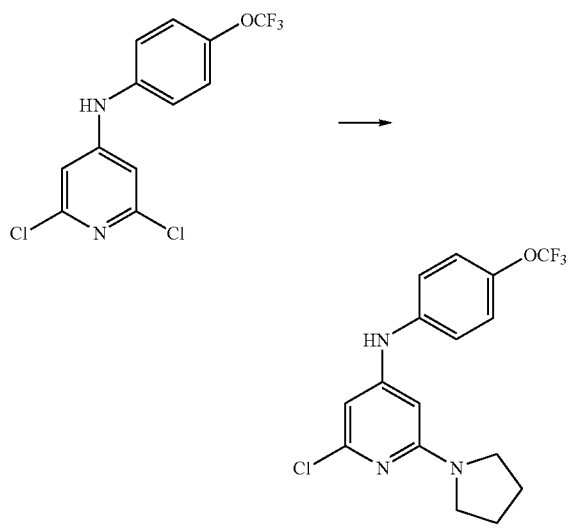

To (2,6-dichloro-pyridin-4-yl)-(4-trifluoromethoxy-phenyl)-amine (800.5 mg, 2.5 mmol) dissolved in pyrrolidine (16 mL, 192 mmol) was added potassium carbonate (1.041 g, 7.5 mmol). The resulting mixture is allowed to stir at 86° C. for 12 to 14 hours. The sample was allowed to cool to 20 to 40° C. and was diluted in dichloromethane. The mixture was washed two times with water and one time with brine. The organic phase was dried over potassium carbonate and concentrated by rotary evaporation. The resulting sample was dried for 12-18 hours under vacuum. Purification (Biotage Horizon KPFC chromatography system, SiO$_2$, 70:30 hexanes:ethyl acetate) gave a light brown solid (665 mg, 74%).

M.P.: 87° C.

HPLC: Inertsil ODS-3V C18, 30:70 [KH$_2$PO$_4$ (0.01M, pH 3.2):CH$_3$CN], 264 nm, R$_t$ 22.7 min, 98.4% purity.

$^1$H NMR (300 MHz, CDCl$_3$, TMS): δ 1.93-1.98 (m, 4H), 3.40 (t, J=6.6 Hz, 4H), 5.70, (d, J=1.8 Hz, 1H), 6.08 (s, 1H), 6.18 (d, J=1.5 Hz, 1H), 7.18 (s, 4H).

Mass Spec (TOF MS ES+): m/z 358 (M+H, 100).

Example 33

Synthesis of [2-chloro-6-(4-methyl-piperazin-1-yl)-pyridin-4-yl]-(4-trifluoromethoxy-phenyl)-amine

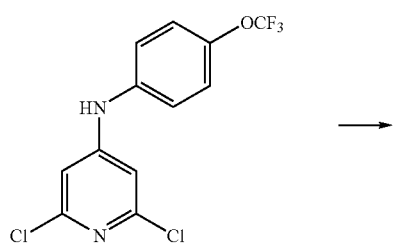

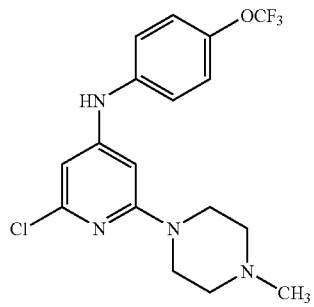

To (2,6-dichloro-pyridin-4-yl)-(4-trifluoromethoxy-phenyl)-amine (291.1 mg, 0.9 mmol) dissolved in dimethylformamide (5 mL) was added N-methylpiperazine (0.1 mL, 0.9 mmol) and potassium carbonate (152.1 mg, 1.1 mmol). After the resulting mixture was allowed to stir at 90° C. for 12 to 14 hours, a significant amount of starting material remained. Therefore, water (4-5 drops) was added, the temperature was raised to 110° C., and the reaction mixture was allowed to stir at 110° C. for 12 to 18 hours. The sample was diluted in dichloromethane, washed two times with water and one time with brine and filtered through Celite™. The organic phase was dried over potassium carbonate and concentrated by rotary evaporation. The resulting sample was dried for 12-18 hours under vacuum. Purification (Biotage Horizon HPFC chromatography system, SiO$_2$, 93:6:1 dichloromethane:methanol:ammonium hydroxide) gave the product as a solid (121 mg, 35%).

HPLC: Inertsil ODS-3V C18, 30:70 [KH$_2$PO$_4$ (0.01M, pH 3.2):CH$_3$CN], 264 nm, R$_t$ 2.9 min, 96.1% purity.

$^1$H NMR (600 MHz, CDCl$_3$, TMS): δ 2.33 (s, 3H), 2.47-2.48 (m, 4H), 3.48-3.49 (m, 4H), 5.96 (d, J=1.8 Hz, 1H), 5.98 (s, 1H), 6.23 (d, J=1.2 Hz, 1H), 7.16-7.27 (m, 4H).

Example 34

Synthesis of [6-chloro-4-(4-methyl-piperazin-1-yl)-pyridin-2-yl]-(4-trifluoromethoxy-phenyl)-amine

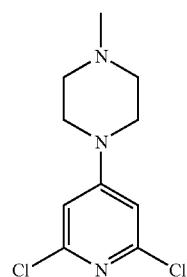

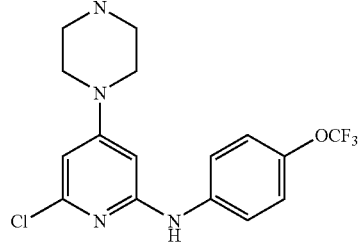

In a 10 mL reaction vessel, a solution of 1-(2,6-dichloro-pyridin-4-yl)-4-methyl-piperazine (0.250 g, 1.02 mmol) in toluene (6 mL) was prepared, and potassium tertiary butoxide (0.136 g, 1.22 mmol), palladium(II)acetate (22.80 mg, 0.101 mmol), BINAP (31.6 mg, 0.0508 mmol) and 4-trifluoromethoxy-phenylamine (216 mg, 1.22 mmol) were added to the solution. This reaction mixture was subjected the microwave irradiation, in which the microwave power was 250 W, to attain a temperature of 150° C. After this reaction proceeded for 30 min, water was added to the reaction mixture and the product extracted with ethyl acetate. The organic layer was dried over sodium sulphate, filtered and concentrated under vacuum and purified through column chromatography using 100-200 mesh silica gel (elution-20% acetone:petroleum ether) to afford the desired compound as light brown solid (98 mg, 25%).

$^1$H NMR (400 MHz, DMSO-d$_6$): δ 7.25-7.32 (d, 4H), 6.05-6.38 (s, 2H), 4.95(s, 1H), 3.25-3.32 (m, 4H), 2.02-2.35 (s, 3H).

Mass Spec: (ES-MS) m/z: 387 ((M$^+$+1,100%).

Example 35

Synthesis of (2,6-diphenyl-pyridin-4-yl)-p-tolyl-amine (B26)

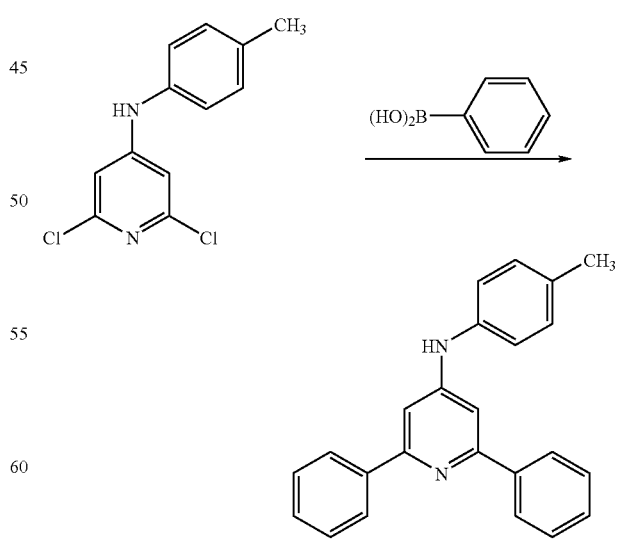

To a mixture of (2,6-dichloro-pyridin-4-yl)-p-tolyl-amine (100.4 mg, 0.4 mmol) dissolved in acetonitrile (6 mL) and 2 M Na$_2$CO$_3$ (6 mL) was added phenylboronic acid (122.5 mg, 1 mmol) and palladium tetrakis(triphenylphosphine) (46.3 mg, 0.04 mmol). The resulting mixture was allowed to stir at reflux for 12 hours. The sample was diluted in dichloromethane and filtered through Celite™. The Celite™ was washed with dichloromethane, and the filtrate was washed two times with water and one time with brine. The organic phase was dried over potassium carbonate and concentrated by rotary evaporation. The resulting sample was dried for 12-18 hours under vacuum. Purification (Biotage Horizon HPFC chromatography system, SiO₂, 70:30 hexanes:ethyl acetate) gave a brown solid (2,6-diphenyl-pyridin-4-yl)-p-tolyl-amine (116 mg, 86%).

M.P.: 125° C.

HPLC: Inertsil ODS-3V C18, 40:10:50 [KH₂PO₄ (0.01M, pH 3.2):CH₃CN:MeOH], 264 nm, R$_t$ 8.5 min, 91.4% purity.

¹H NMR (300 MHz, CDCl₃, TMS): δ 2.37 (s, 2H), 6.08 (s, 1H), 7.15-7.25 (m, 5H), 7.39-7.48 (m, 5H), 8.04-8.07 (m, 4H).

Mass Spec: (TOF MS ES+): m/z 337 (M+H, 100).

Example 36

Synthesis of (2,6-diphenyl-pyridin-4-yl)-(4-trifluoromethoxy-phenyl)-amine (B29)

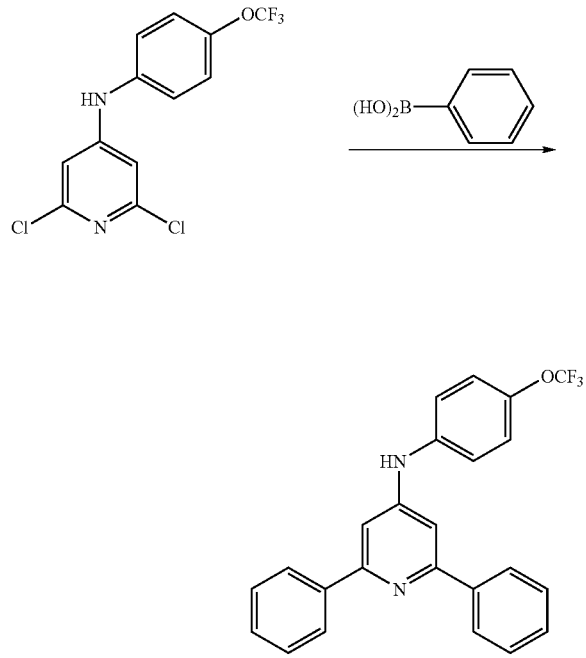

To (2,6-dichloro-pyridin-4-yl)-(4-trifluoromethoxy-phenyl)-amine (0.201 g, 0.6 mmol) and phenyl boronic acid (0.1476 g, 1.2 mmol) dissolved in acetonitrile (10 mL) and Na₂CO₃ (10 mL, 0.4M) was added palladium (0) tetrakis (triphenylphosphine) (0.0351 g, 0.03 mmol). The reaction mixture was stirred and refluxed for 12-18 hours under N₂. The reaction mixture was diluted with CH₂Cl₂ and filtered through Celite™, then rinsed with CH₂Cl₂. The filtrate was washed one time with water and one time with brine. The organic phase was collected and dried over potassium carbonate. The filtered sample was concentrated, and the resulting solid was dried for 12-18 hours under vacuum. Biotage Horizon HPFC system chromatography (SiO₂, 80:20 hexanes:ethyl acetate) yielded a pale brown solid (99 mg, 39%).

M.P.: 137° C.

HPLC: Inertsil ODS-3V C18, 30:70 [KH₂PO₄(0.01M, pH 3.2):CH₃CN], 264 nm, R$_t$ 13.4 min, 93.5% purity.

¹H NMR: (300 MHz, CDCl₃, TMS): δ 6.33 (s, 1H), 7.26-7.30 (m, 6H), 7.39-7.50 (m, 6H), 8.05 (dd, J=1.2, 7.9 Hz, 4H).

Mass Spec: (TOF MS ES+): m/z 407 (M+H, 100).

Example 37

Synthesis of [2,6-bis-(3-fluoro-phenyl)-pyridin-4-yl]-(4-trifluoromethoxy-phenyl)-amine (B28)

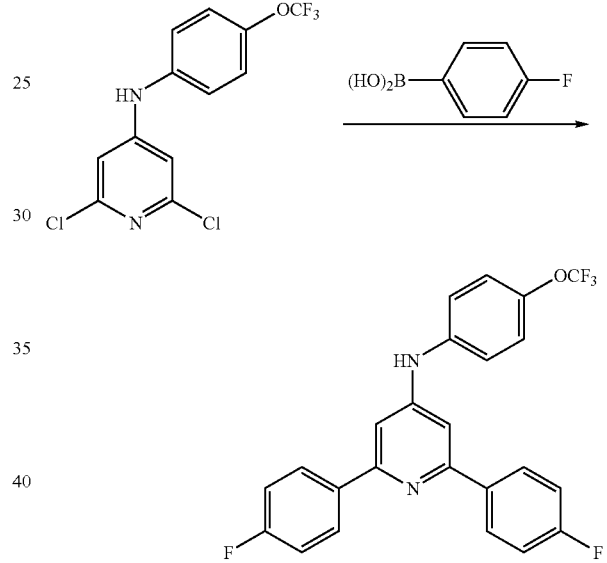

To (2,6-dichloro-pyridin-4-yl)-(4-trifluoromethoxy-phenyl)-amine (3.007 g, 9.3 mmol) dissolved in acetonitrile (40 mL) and 2 M Na₂CO₃ (40 mL, 80 mmol) was added 4-fluorophenyl boronic acid (3.256 g, 23.25 mmol) and palladium (0) tetrakis-(triphenylphosphine) (1.073 g, 0.93 mmol). The resulting mixture is allowed to stir at reflux for 12-18 hours. The sample was diluted in dichloromethane and filtered through Celite™. The Celite™ was washed with dichloromethane; the filtrate was washed two times with water and one time with brine. The organic phase was dried over potassium carbonate and concentrated by rotary evaporation. The resulting sample was dried for 12-18 hours under vacuum. Column chromatography (SiO₂, 70:30 hexanes:ethyl acetate) gave a white solid (3.291 g, 80%).

M.P.: 159° C.

HPLC: Inertsil ODS-3V C18, 30:70 [KH₂PO₄ (0.01M, pH 3.2):CH₃CN], 264 nm, R$_t$ 32.1 min, 98.3% purity.

¹H NMR (300 MHz, CDCl₃, TMS): δ 6.15 (s, 1H), 7.11-7.25 (m, 6H), 8.00-8.04 (m, 4H).

Mass Spec: (TOF MS ES+): m/z 443 (M+H, 100).

Example 38

Synthesis of [2,6-bis-(4-methanesulfonyl-phenyl)-pyridin-4-yl]-(4-trifluoromethoxy-phenyl)-amine (B30)

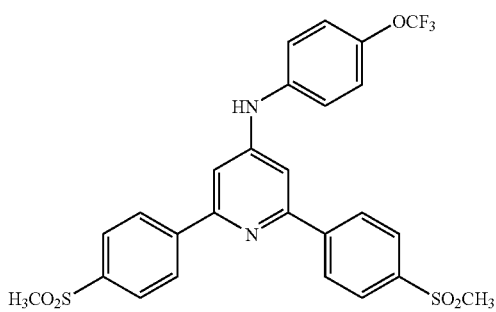

This compound was prepared by the process disclosed in Example 37.

M.P.: >270° C.

HPLC: Inertsil ODS-3V C18, 30:70 [$KH_2PO_4$ (0.01M, pH 3.2):$CH_3CN$], 264 nm, $R_t$ 8.6 min, 96.1% purity.

$^1$H NMR: (300 MHz, DMSO-$d_6$, TMS): δ 3.27 (s, 3H), 3.25 (s, 3H), 7.46 (quartet, J=9 Hz, 4H), 8.07 (d, J=8.4 Hz, 4H), 8.34 (d, J=8.1 Hz, 4H), 9.34 (s, 1H).

Mass Spec: (TOF MS ES+): m/z 563 (M+, 100); HRMS (TOF MS ES+) Calcd for $C_{26}H_{21}F_3N_2O_5S_2$, [M+H] 563.0922. Found 563.0911.

Example 39

Synthesis of [2,6-bis-(3-(methylsulfonyl)-phenyl)-pyridin-4-yl]-(4-trifluoromethoxy-phenyl)-amine (B31)

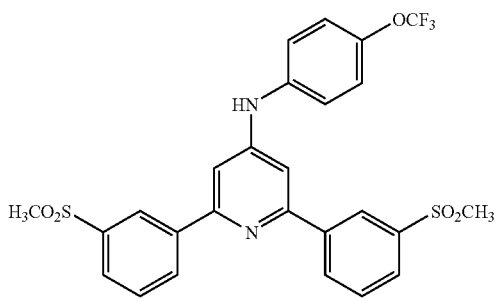

This compound was prepared by the process disclosed in Example 37.

M.P.: 231° C.

HPLC: Inertsil ODS-3V C18, 30:70 [$KH_2PO_4$ (0.01M, pH 3.2):$CH_3CN$], 264 nm, $R_t$ 8.9 min, 99.96% purity.

$^1$H NMR (300 MHz, DMSO-$d_6$, TMS): δ 3.32 (s, 6H), 5.76 (s, 1H), 7.38-7.47 (m, 4H), 7.59 (s, 1H), 7.83 (t, J=7.8 Hz, 2H), 8.03-8.48 (m, 4H), 8.59 (apt d, J=1.5 Hz, 2H), 9.36 (s, 1H).

Mass Spec: (TOF MS ES+): m/z 563 (M+H, 100); HRMS (TOF MS ES+) Calcd for $C_{26}H_{21}F_3N_2O_5S_2$, [M+H] 563.0922. Found 563.0920.

Example 40

Synthesis of 1-{3-[6-(3-acetyl-phenyl)-4-(4-trifluoromethoxy-phenylamino)-pyridin-2-yl]-phenyl}-ethanone (B33)

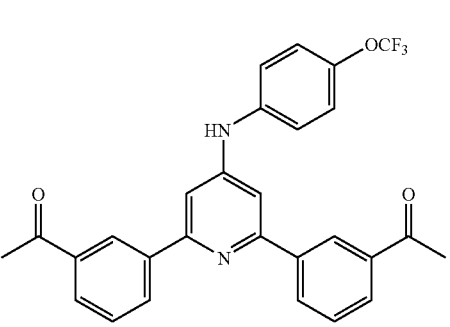

This compound was prepared by the process disclosed in Example 37.

M.P.: 160° C.

HPLC: Inertsil ODS-3V C18, 30:70 [$KH_2PO_4$(0.01M, pH 3.2):$CH_3CN$], 264 nm, $R_t$ 19.9 min, 99.6% purity.

$^1$H NMR: (300 MHz, $CHCl_3$, TMS): δ 2.68 (s, 6H), 6.42 (s, 1H), 7.24-7.30 (m, 6H), 7.57 (t, J=7.8 Hz, 2H), 8.00 (dt, J=1.8, 6.6 Hz, 2H), 8.26-8.29 (m, 1H), 8.62 (br s, 2H).

Mass Spec: (TOF MS ES+): m/z 491 (M+H, 100); HRMS (TOF MS ES+) Calcd for $C_{28}H_{21}F_3N_2O_3$, [M+H] 491.1582. Found 491.1582.

Example 41

Synthesis of 1-{4-[2,6-bis-(4-fluoro-phenyl)-pyridin-4-ylamino]-phenyl}-ethanone (B34)

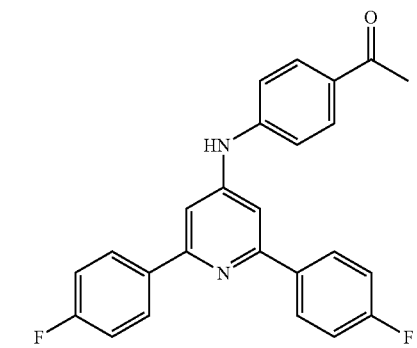

This compound was prepared by the process disclosed in Example 37.

M.P.: 220° C.

HPLC: Inertsil ODS-3V C18, 30:70 [$KH_2PO_4$(0.01M, pH 3.2):$CH_3CN$], 264 nm, $R_t$ 17.3 min, 95.6% purity.

$^1$H NMR: (300 MHz, $CHCl_3$, TMS): δ 2.60 (s, 3H), 6.49 (s, 1H), 7.13-7.20 (m, 4H), 7.26 (s, 2H), 7.32 (s, 2H), 7.99-8.08 (m, 6H).

Mass Spec: (TOF MS ES+): m/z 401 (M+, 100); HRMS (TOF MS ES+) Calcd for $C_{25}H_{18}F_2N_2O$, [M+H] 401.1465. Found 401.1466.

Example 42

Synthesis of [2,6-bis-(3-N,N-dimethyl-benzamide)-pyridin-2-yl]-(4-trifluoromethoxy-phenyl)-amine (B35)

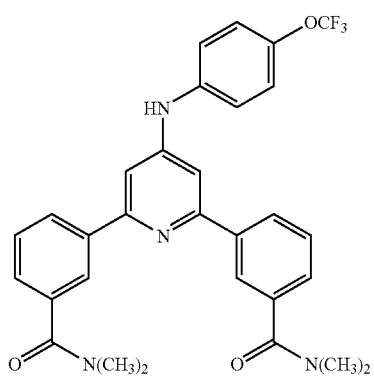

This compound was prepared by the process disclosed in Example 37.

M.P.: 175° C.

HPLC: Inertsil ODS-3V C18, 30:70 [$KH_2PO_4$ (0.01M, pH 3.2):$CH_3CN$], 264 nm, $R_t$ 4.8 min, 98.1% purity.

$^1$H NMR: (300 MHz, $CHCl_3$, TMS): δ 3.00 (br s, 6H), 3.15 (br s, 6H), 7.15 (s, 2H), 7.23 (br s, 4H), 7.26 (s, 1H), 7.40-7.49 (m, 4H), 8.02-8.04 (br m, 4H).

Mass Spec: (TOF MS ES+): m/z 549 (M+, 100).

Example 43

Synthesis of 3-{2,6-bis-(4-fluoro-phenyl)-pyridin-4-ylamino]-benzenethiol; compound with acetic acid methyl ester (B36)

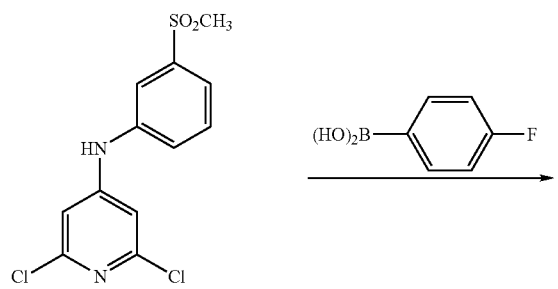

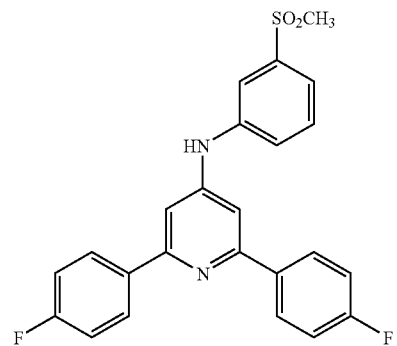

To thiocarbonic acid S-[3-(2,6-dichloro-pyridin-4-ylamino)-phenyl] ester-O-methyl ester (317.7 mg, 1 mmol) dissolved in acetonitrile (10 mL) and 0.4 M $Na_2CO_3$ (10 mL, 4 mmol) were added 4-fluorophenyl boronic acid (280.0 mg, 2 mmol) and palladium (0) tetrakis(triphenylphosphine) (58 mg, 0.05 mmol). The resulting mixture was allowed to stir at reflux for 12-18 hours. The sample was diluted in dichloromethane and filtered through Celite™. The Celite™ was washed with dichloromethane, and the filtrate was washed two times with water and one time with brine. The organic phase was dried over potassium carbonate and concentrated by rotary evaporation. The resulting sample was dried for 12-18 hours under vacuum. Purification (Biotage Horizon HPFC chromatography system, $SiO_2$, 98:2 dichloromethane:methanol) gave a white solid product (383 mg, 88%).

M.P.: 180° C.

HPLC: Inertsil ODS-3V C18, 40:10:50 [$KH_2PO_4$ (0.01M, pH 3.2):$CH_3CN$:MeOH], 264 nm, $R_t$ 11.2 min, 99.0% purity.

$^1$H NMR (300 MHz, $CDCl_3$, TMS): δ 3.10 (s, 3H), 6.49 (s, 1H), 7.12-7.18 (m, 4H), 7.242 (s, 2H), 7.55-7.64 (m, 3H), 7.79-7.80 (m, 1H), 8.01-8.06 (m, 4H).

Mass Spec: (TOF MS ES+): m/z 437 (M+H, 100); HRMS (TOF MS ES+) Calcd for $C_{24}H_{18}F_2N_2O_2S$, [M+H] 437.1135. Found 437.1138.

Example 44

Synthesis of [2,6-bis-(4-fluoro-phenyl)-pyridin-4-yl]-methyl-(4-trifluoromethoxy-phenyl)-amine (B29)

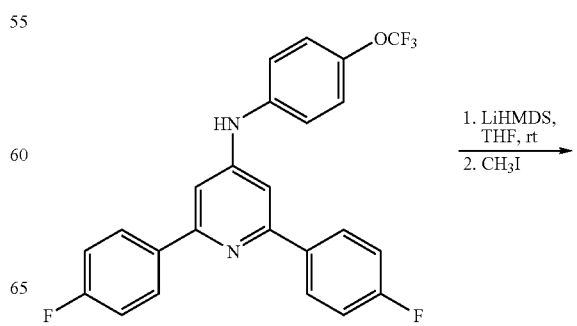

-continued

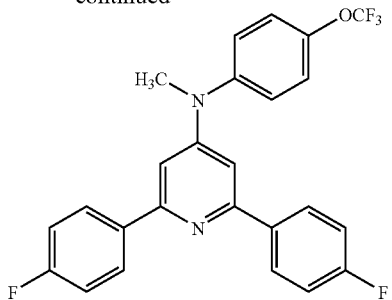

To [2,6-bis-(4-fluoro-phenyl)-pyridin-4-yl]-(4-trifluoromethoxy-phenyl)-amine in anhydrous THF (2 mL) under $N_2$ atmosphere was added lithium bis(trimethylsilyl)amide (0.2 mL, 1 M in THF, 0.2 mmol) at room temperature. The reaction was stirred for approximately 19 minutes, after which time iodomethane (0.012 mL, 0.2 mmol) was added, and the reaction was stirred for an additional 3 hours. Upon quenching with water, the mixture was diluted with dichloromethane and washed one time with brine. The organic layer was separated and dried over anhydrous potassium carbonate, filtered, and concentrated under vacuum. Biotage Horizon HPFC system chromatography ($SiO_2$, 20:80 ethyl acetate:hexanes) yielded a solid product (6 mg, 10%).

HPLC: Inertsil ODS-3V C18, 30:70 [$KH_2PO_4$ (0.01M, pH 3.2):$CH_3CN$], 264 nm, $R_t$ 30.5 min, 97% purity.

$^1$H NMR: (300 MHz, $CHCl_3$, TMS): δ 3.45 (s, 3H), 6.92 (s, 2H), 7.13 (apt t, J=8.7 Hz), 4H), 7.32 (s, 4 H), 7.96-8.00 (m, 4 H).

Example 45

Synthesis of 2,6-di(4-fluoro phenyl)-4-piperidino pyridine (B62)

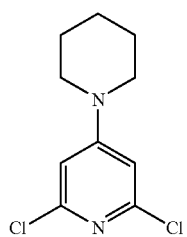 

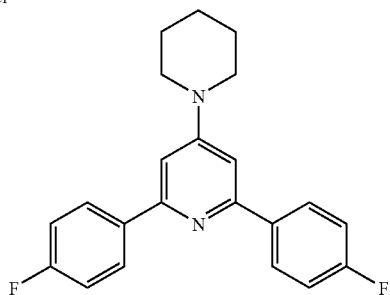

A mixture of 2,6-dichloro-4-piperdino pyridine (0.200 g, 1.09 mmol), 4-fluoro boronic acid (0.189 g, 1.30 mmol) and tetrakis(triphenylphosphine)Pd(0) [$Pd(PPh_3)_4$] (63 mg, 0.05 mmol), 1N $Na_2CO_3$ solution (2.2 mL), dioxane (15 mL) was prepared in a 10 mL vessel. This reaction was maintained in a CEM microwave at a pressure of 250 psi and a temperature of 200° C., and subjected the microwave radiationat 250 W for 30 minutes. Water was added (200 mL) to the reaction mixture and the product was extracted with ethyl acetate. The organic layer was dried over sodium sulfate and concentrated under reduced pressure. The residue was purified by column chromatography over 230-400 mesh silica gel by elution with 10:90 ethyl acetate:hexanes to afford the product as a pure colorless solid (purity 99%, yield 85%).

M.P.: 201-203° C.

$^1$H NMR (200 MHz, $CDCl_3$) δ: 7.90-8.06 (m, 4H), 7.08-7.24 (m, 6H), 3.24-3.56 (m, 4H), 1.55-1.75 (m, 6H).

Mass Spec (CI-MS): m/z 351 ($M^+$+1, 100%).

IR (neat) $cm^{-1}$: 2917, 1603, 1435, 1225, 1152, 987, 955, 824, 779, 562.

Example 46

Synthesis of 2',6'-bis-(4-trifluoromethoxy-phenyl)-3, 4,5,6-tetrahydro-2H-[1,4']bipyridinyl (B63)

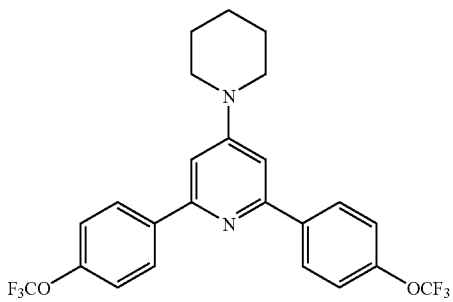

This compound was prepared by at least one of the processes disclosed in Examples 54-55, and could be prepared by both of the processes disclosed in these examples.

M.P.: 119-121° C.

$^1$H NMR (200 MHz, $CDCl_3$): δ 7.99-8.09 (m, 4H), 7.05-7.32 (m, 6H), 3.24-3.56 (m, 4H), 1.55-1.75 (m, 6H).

Mass Spec: (CI-MS) m/z: 483 ($M^+$+1, 100%).

IR (neat) $cm^{-1}$: 3431, 2943, 1603, 1445, 1272, 1151, 830.

Example 47

Synthesis of N-ethyl-3-[6-(3-methanesulfonyl-phenyl)-4-(4-trifluoromethoxy-phenylamino)-pyridin-2-yl]-benzamide (B32)

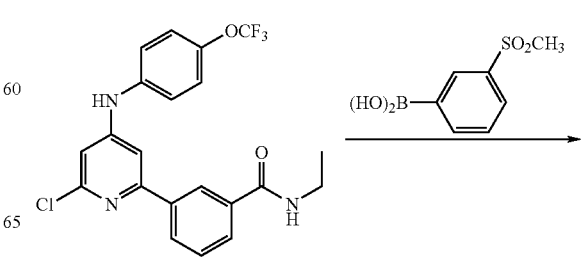

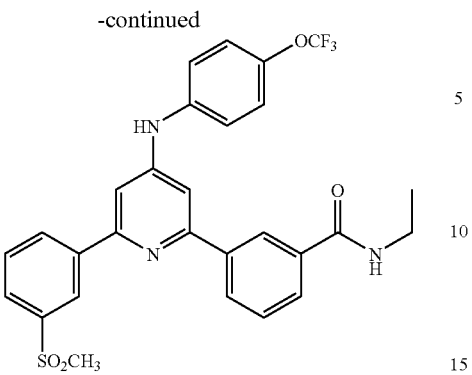

To 3-[6-chloro-4-(4-trifluoromethoxy-phenylamino)-pyridin-2-yl]-N-ethyl-benzamide (0.166 g, 0.4 mmol) and (3-methylsulfonylphenyl) boronic acid (0.1624 g, 0.8 mmol) dissolved in acetonitrile (8 mL) and Na₂CO₃ (8 mL, 2.0 M) was added palladium (0) tetrakis(triphenylphosphine) (0.0471 g, 0.04 mmol). The reaction mixture was stirred and refluxed for 12-18 hours under N₂. The reaction mixture was diluted with CH₂Cl₂ and filtered through Celite™, then rinsed with CH₂Cl₂. The filtrate was washed two times with water and one time with brine. The organic phase was collected and dried over potassium carbonate. The filtered sample was concentrated, and the resulting solid was dried for 12-18 hours under vacuum. Biotage Horizon HPFC system chromatography (SiO₂, 93:6:1 CH₂Cl₂:CH₃OH:NH₄OH) yielded a light yellow solid (70 mg, 33%).

M.P.: 85° C.

HPLC: Inertsil ODS-3V C18, 30:70 [KH₂PO₄(0.01M, pH 3.2):CH₃CN], 264 nm, R_t 8.3 min, 96.2% purity.

¹H NMR: (300 MHz, CHCl₃, TMS): δ 1.27 (t, J=7.2 Hz, 3H), 3.09 (s, 3H), 3.48-3.58 (m, 2H), 6.46 (t, J=5.4 Hz, 1H), 7.00 (s, 1H), 7.21-7.28 (m, 5H), 7.42-7.70 (m, 8H), 7.83 (br d, J=7.8 Hz, 1H), 7.95 (dt, J=0.9, 8.4 Hz, 1H), 8.10-8.13 (m, 1H), 8.25 (apt dt, J=1.2, 6.9 Hz, 1H), 8.40 (t, J=1.2 Hz, 1H), 8.56 (t, J=1.5 Hz, 1H).

Mass Spec: LC-MSD (ES+): m/z 556 (M+H, 100).

Example 48

Synthesis of 1-[3-(4-hydroxy-6'-phenyl-3,4,5,6-tetrahydro-2H-[1,2']bipyridinyl-4'-ylamino)-phenyl]-ethanone (B48)

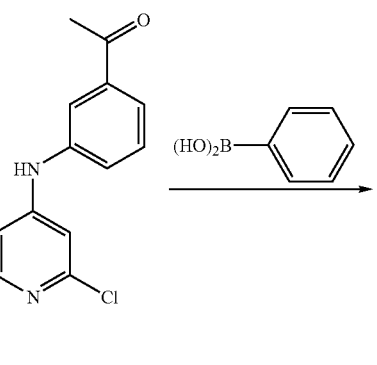

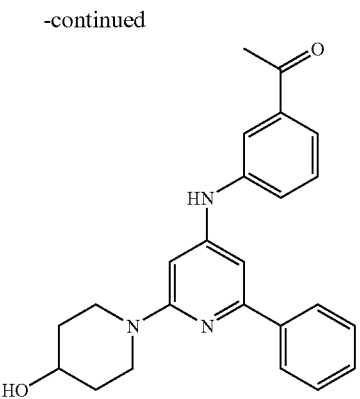

To 1-[3-(6'-chloro-4-hydroxy-3,4,5,6-tetrahydro-2H-[1,2']bipyridinyl-4'-ylamino)-phenyl]-ethanone (0.445 g, 1.2 mmol) and phenyl boronic acid (0.2954 g, 2.4 mmol) dissolved in acetonitrile (10 mL) and Na₂CO₃ (10 mL, 2.0 M) was added palladium(O) tetrakis triphenylphosphine (0.1386 g, 0.12 mmol). The reaction mixture was stirred and refluxed for 12-18 hours under N₂. The reaction mixture was diluted with CH₂Cl₂ and filtered through Celite™, then rinsed with CH₂Cl₂. The filtrate was washed two times with water and one time with brine. The organic phase was collected and dried over potassium carbonate. The filtered sample was concentrated, and the resulting solid was dried for 12-18 hours under vacuum. Flash chromatography (SiO₂, 93:6:1 CH₂Cl₂:MeOH:NH₄OH) yielding a light yellow solid (83 mg, 17%).

M.P.: 95° C.

HPLC: Inertsil ODS-3V C18, 30:70 [KH₂PO₄ (0.01M, pH 3.2):CH₃CN], 264 nm, R_t 2.9 min, 91.5% purity.

¹H NMR: (300 MHz, CHCl₃, TMS): δ 1.55-1.67 (m, 4H), 1.7-2.02 (m, 2H), 2.60 (s, 3H), 3.13-3.22 (m, 2H), 3.89-3.93 (m, 1H), 4.15 (dt, J=3.9, 13.5 Hz, 2H), 6.04 (s, 1H), 6.23 (d, J=1.5Hz, 1H), 6.74 (d, J=1.5Hz, 1H), 7.25-7.44 (m, 5H), 7.61-7.65 (m, 1H), 7.77-7.78 (m, 1H), 7.92-7.96 (m, 2H).

Mass Spec: LC-MSD (ES+): m/z 388 (M+H, 92.2).

Example 49

Synthesis of [2-(4-fluoro-phenyl)-6-morpholin-4-yl-pyridin-4-yl]-(4-trifluoromethoxy-phenyl)-amine (B49)

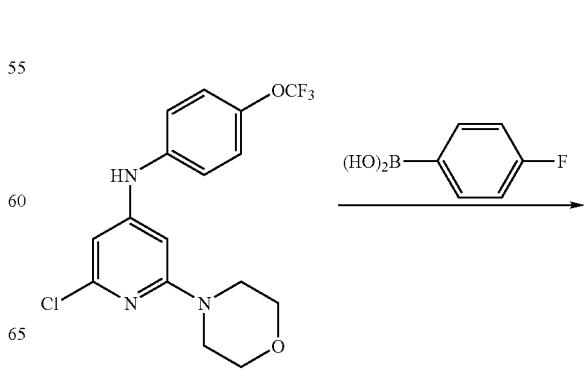

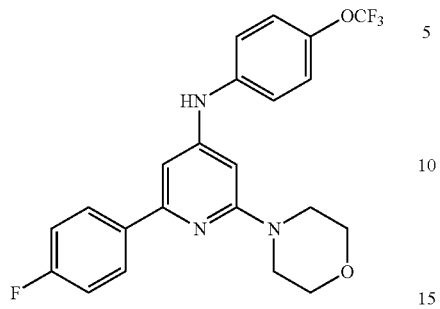

To (2-chloro-6-morpholin-4-yl-pyridin-4-yl)-(4-trifluoromethoxy-phenyl)-amine (0.03 g, 0.08 mmol) and 4-fluorophenyl boronic acid (0.0284 g, 0.16 mmol) dissolved in acetonitrile (5 mL) and Na$_2$CO$_3$ (5 mL, 0.4M) was added palladium (0) tetrakis-(triphenylphosphine) (0.0099 g, 0.008 mmol). The reaction mixture was stirred and refluxed for 12-18 hours under N$_2$. The reaction mixture was diluted with CH$_2$Cl$_2$ and filtered through Celite™, then rinsed with CH$_2$Cl$_2$. The filtrate was washed one time with water and one time with brine. The organic phase was collected and dried over potassium carbonate. The filtered sample was concentrated, and the resulting solid was dried for 12-18 hours under vacuum. Flash chromatography (SiO$_2$, 50:50 hexanes:ethyl acetate) yielded a pale yellow solid (30 mg, 86%).

M.P.: 192° C.

HPLC: Inertsil ODS-3V C18, 30:70 [KH$_2$PO$_4$ (0.01M, pH 3.2):CH$_3$CN], 264 nm, R$_t$ 13.6 min, 97.3% purity.

$^1$H NMR: (300 MHz, DMSO-d$_6$, TMS): δ 3.45-3.46 (br m, 4H), 3.72 (br s, 4H), 6.28 (s, 1H), 6.85 (s, 1H), 7.22-7.30 (m, 6H), 7.95-8.00 (m, 2H), 8.82 (s, 1H).

Mass Spec: (TOF MS ES+): m/z 434 (M+H, 100); HRMS (TOF MS ES+) Calcd for C$_{22}$H$_{19}$F$_4$N$_3$O$_2$, [M+H] 434.1491. Found 434.1481.

Example 50

Synthesis of [2-(3-methanesufonyl-phenyl)-6-morpholin-4-yl-pyridin-4-yl]-(4-trifluoro-methoxy-phenyl)-amine (B50)

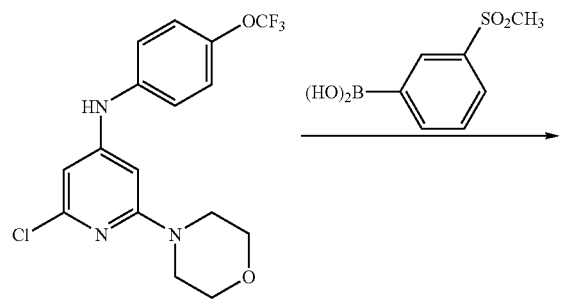

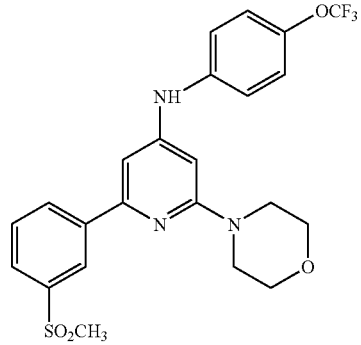

To (2-chloro-6-morpholin-4-yl-pyridin-4-yl)-(4-trifluoromethoxy-phenyl)-amine (0.1872 g, 0.5 mmol) and (3-methylsulfonyl phenyl) boronic acid (0.2011 g, 1.0 mmol) dissolved in acetonitrile (10 mL) and Na$_2$CO$_3$ (10 mL, 2.0 M) was added palladium (0) tetrakis(triphenylphoshine) (0.0581 g, 0.05 mmol). The reaction mixture was stirred and refluxed for 12-18 hours under N$_2$. The reaction was monitored by TLC, and after 18 h (3-methylsulfonylphenyl) boronic acid (0.2010 g, 1.0 mmol), Pd(PPh$_3$)$_4$ (0.0581 g, 0.05 mmol) was added stirred and refluxed for another 12-18 hours under N$_2$. The reaction mixture was diluted with CH$_2$Cl$_2$ and filtered through Celite™, then rinsed with CH$_2$Cl$_2$. The filtrate was washed two times with water and one time with brine. The organic phase was collected and dried over potassium carbonate. The filtered sample was concentrated, and the resulting solid was dried for 12-18 hours under vacuum. Biotage Horizon HPFC system chromatography (SiO$_2$, 50:50 hexanes:ethyl acetate) yielded a pale yellow solid (199 mg, 80%).

M.P.: 196° C.

HPLC: Inertsil ODS-3V C18, 30:70 [KH$_2$PO$_4$(0.01M, pH 3.2):CH$_3$CN], 264 nm, R$_t$ 8.4 min, 99.0% purity.

$^1$H NMR: (300 MHz, CHCl$_3$, TMS): δ 3.09 (s, 3H), 3.54 (t, J=4.8 Hz, 4H), 3.84 (t, J=4.8 Hz, 4H), 6.09 (s, 1H), 6.19 (d, J=1.8 Hz, 1H), 6.76 (d, J=1.5 Hz, 1H), 7.22 (s, 4H), 7.62 (t, J=7.8 Hz, 1H), 7.91-7.95 (m, 1H), 8.21-8.23 (m, 1H), 8.5 (t, J=1.8 Hz, 1H).

Mass Spec: LC-MSD (ES+): m/z 494 (M+H, 100).

Example 51

Synthesis of 19 -{3-[6-morpholin-4-yl-4-(4-trifluoromethoxy-phenylamino)-pyridin-2-yl]-phenyl}-ethanone (B51)

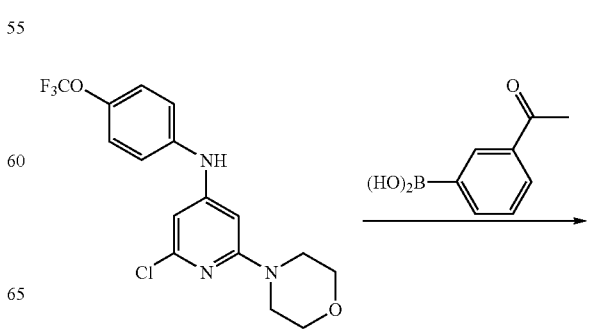

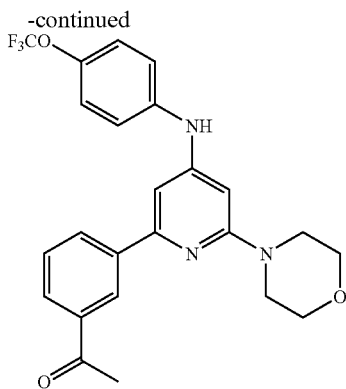

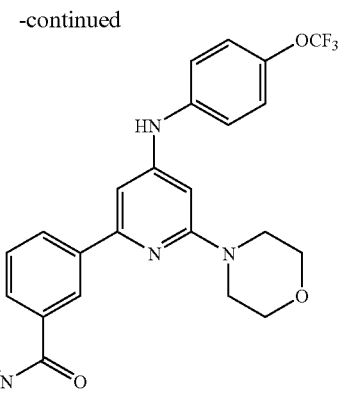

To (2-chloro-6-morpholin-4-yl-pyridin-4-yl)-(4-trifluoromethoxy-phenyl)-amine (0.1862 g, 0.5 mmol) and 3-acetylphenyl boronic acid (0.1621 g, 1.0 mmol) dissolved in acetonitrile (10 mL) and $Na_2CO_3$ (10 mL, 2.0 M) was added palladium (0) tetrakis(triphenylphosphine) (0.0579 g, 0.05 mmol). The reaction mixture was stirred and refluxed for 12-18 hours under $N_2$. The reaction was monitored by TLC after 18 h 3-acetyl phenyl boronic acid (0.0821 g, 0.5 mmol), palladium (0) tetrakis(triphenylphosphine) (0.0288 g, 0.025 mmol) was added stirred at reflux for 12-18 hours under $N_2$. The reaction mixture was diluted with $CH_2Cl_2$ and filtered through Celite™, then rinsed with $CH_2Cl_2$. The filtrate was washed two times with water and one time with brine. The organic phase was collected and dried over potassium carbonate. The filtered sample was concentrated, and the resulting solid was dried for 12-18 hours under vacuum. Biotage Horizon HPFC system chromatography ($SiO_2$, 70:30 hexanes:ethyl acetate) yielded a pale brown solid (160 mg, 70%).

M.P.: 122° C.

HPLC: Inertsil ODS-3V C18, 30:70 [$KH_2PO_4$ (0.01M, pH 3.2):$CH_3CN$], 264 nm, $R_t$ 10.6 min, 99.4% purity.

$^1$H NMR: (300 MHz, $CHCl_3$, TMS): δ 2.65 (s, 3H), 3.55 (apt t, J=4.8 Hz, 4H), 3.84 (apt t, J=5.1 Hz, 4H), 6.05 (s, 1H), 6.18 (d, J=1.5Hz, 1H), 6.79 (d, J=1.5 Hz, 1H), 7.21 (s, 4H), 7.52 (t, J=7.8 Hz, 1H), 7.95 (dd, J=1.5, 6.6 Hz, 1H), 8.06 (dd, J=1.5, 7.7 Hz, 1H), 8.50-8.519 (m, 1H).

Mass Spec: (TOF MS ES+): m/z 458 (M+H, 100); HRMS (TOF MS ES+) Calcd for $C_{24}H_{22}F_3N_3O_3$, [M+H] 458.1691. Found 458.1686.

Example 52

Synthesis of {3-[6-morpholin-4-yl-4-(4-trifluoromethoxy-phenylamino)-pyridin-2-yl]-phenyl}-pyrrolidin-1-yl-methanone (B52)

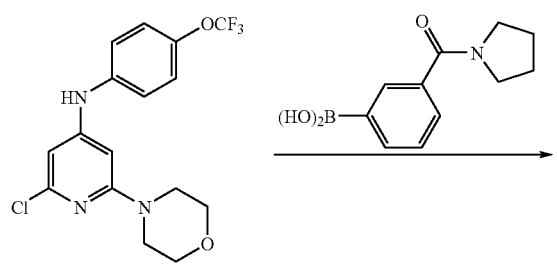

To (2-chloro-6-morpholin-4-yl-pyridin-4-yl)-(4-trifluoromethoxy-phenyl)-amine (0.1806 g, 0.5 mmol) and 3-(pyrrolidine-1-carbonyl)phenyl boronic acid (0.2185 g, 1.0 mmol) dissolved in acetonitrile (10 mL) and $Na_2CO_3$ (10 mL, 2.0 M) was added palladium (0) tetrakis(triphenylphosphine) (0.0581 g, 0.05 mmol). The reaction mixture was stirred and refluxed for 12-18 hours under $N_2$. The reaction was monitored by TLC, and after 18 h 3-(pyrrolidine-1-carbonyl)phenyl boronic acid (0.108 g, 0.5 mmol), palladium (0) tetrakis (triphenylphoshine) (0.0291 g, 0.025 mmol) was added stirred at reflux for 12-18 hours under $N_2$. The reaction mixture was diluted with $CH_2Cl_2$ and filtered through Celite™, then rinsed with $CH_2Cl_2$. The filtrate was washed two times with water and one time with brine. The organic phase was collected and dried over potassium carbonate. The filtered sample was concentrated, and the resulting solid was dried for 12-18 hours under vacuum. Biotage Horizon HPFC system chromatography ($SiO_2$, 98:2 $CH_2Cl_2$:MeOH) yielded a pale brown solid (185 mg, 75%),

M.P.: 179° C.

HPLC: Inertsil ODS-3V C18, 30:70 [$KH_2PO_4$ (0.01M, pH 3.2):$CH_3CN$], 264 nm, $R_t$ 6.2 min, 96.8% purity.

$^1$H NMR: (300 MHz, $CHCl_3$, TMS): δ 1.62 (br s, 1H), 1.86 (pentet, J=6.6 Hz, 2H), 1.97 (pentet, J=6.9 Hz, 2H), 3.44 (t, J=6.3 Hz, 2H), 3.52 (br t, J=4.8 Hz, 3H), 3.67 (t, J=6.9 Hz, 2H), 3.82 (t, J=5.1 Hz, 3H), 6.14 (d, J=1.8 Hz, 1H), 6.21 (s, 1H), 6.74 (d, J=1.5 Hz, 1H), 7.19 (s, 3H), 7.40-7.55 (m, 3H), 7.63-7.70 (m, 1H), 7.97 (apt d, J=7.5 Hz, 1H), 8.07 (s, 1H).

Mass Spec: (TOF MS ES+): m/z 513 (M+H, 100).

Example 53

Synthesis of thiocarbonic acid O-methyl ester S-{3-[6-pyrrolidin-1-yl-4-(4-trifluoromethoxy-phenylamino)-pyridin-2-yl]-phenyl}ester (B37)

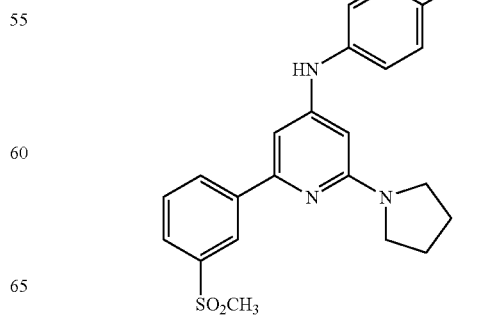

This compound was prepared by a method analogous to that disclosed in Example 52.

M.P.: 149° C.

HPLC: Inertsil ODS-3V C18, 40:10:50 [$KH_2PO_4$ (0.01M, pH 3.2):$CH_3CN$:MeOH], 264 nm, $R_t$ 4.0 min, 98% purity.

$^1$H NMR (300 MHz, $CDCl_3$, TMS): δ 1.97-2.02 (m, 4H), 3.10 (s, 1H), 3.51 (br s, 4H), 5.92 (d, J=1.5 Hz, 1H), 6.65 (d, J=1.5 Hz, 1H), 7.17-7.21 (m, 4H), 7.58 (t, J=7.8 Hz, 1H), 7.90 (apt d, J=7.8 Hz, 1H), 8.19 (apt d, J=7.8 Hz, 1H), 8.49 (s, 1H).

Mass Spec: (TOF MS ES+): m/z 478 (M+H).

Example 54

Synthesis of 1-{3-[6-pyrrolidin-1-yl-4-(4-trifluoromethoxy-phenylamino)-pyridin-2-yl]-phenyl}-ethanone (B38)

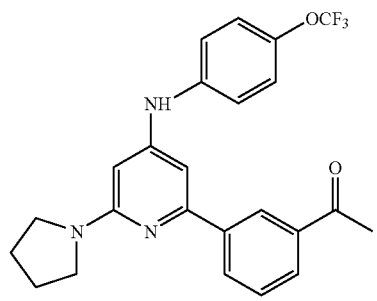

This compound was prepared by a method analogous to that disclosed in Example 52.

M.P.: 95° C.

HPLC: Inertsil ODS-3V C18, 30:70 [$KH_2PO_4$ (0.01M, pH 3.2):$CH_3CN$], 264 nm, $R_t$ 3.6 min, 95.2% purity.

$^1$H NMR: (300 MHz, $CHCl_3$, TMS): δ 1.97-2.01 (m, 4H), 2.65 (s, 3H), 3.51 (t, J=6.6 Hz, 4H), 5.93 (d, J=1.8 Hz, 1H), 6.05 (s, 1H), 6.66 (d, J=1.5 Hz, 1H), 7.20 (apt s, 3H), 7.49 (t, J=7.8 Hz, 2H), 7.93 (dt, J=1.5, 7.8 Hz, 1H), 8.18 (dt, J=1.5, 7.8 Hz, 1H), 8.56 (t, J=1.5 Hz, 1H).

Mass Spec: LC-MSD (ES+): m/z 442 (M+H, 100).

Example 55

Synthesis of [2-(4-fluoro-phenyl)-6-(4-methyl-piperazin-1-yl)-pyridin-4-yl]-(4-trifluoromethoxy-phenyl)-amine (B39)

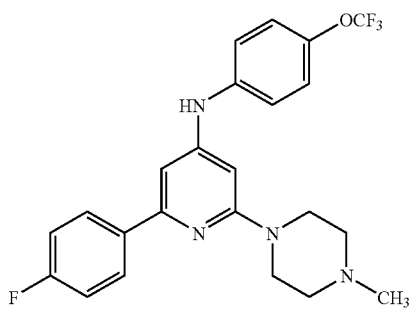

This compound was prepared by a method analogous to that disclosed in Example 52.

M.P.: 142° C.

HPLC: Inertsil ODS-3V C18, 40:10:50 [$KH_2PO_4$ (0.01M, pH 3.2):$CH_3CN$:MeOH], 264 nm, $R_t$ 6.3 min, 96.7% purity.

$^1$H NMR (600 MHz, $CDCl_3$, TMS): δ 2.34 (s, 3H), 2.51-2.53 (m, 4H), 3.58-3.60 (m, 4H), 5.91 (s, 1H), 6.125 (s, 1H), 6.66 (s, 1H), 7.06-7.09 (t, J=8.4 Hz, 2H), 7.19 (apt s, 4H), 7.90-7.92 (m, 2H).

Mass Spec: LC-MSD (ES+): m/z 447 (M+H, 98.5).

Example 56

Synthesis of (6-phenyl-4-pyrrolidin-1-yl-pyridin-2-yl)-(4-trifluoromethoxy-phenyl)-amine (B64)

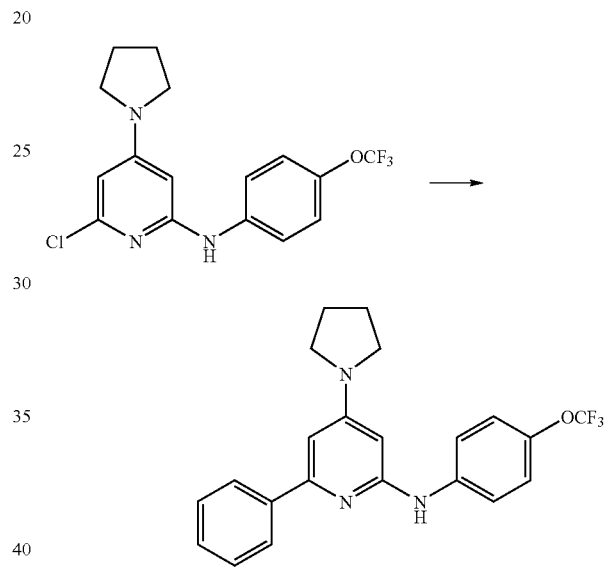

To a solution of (6-chloro-4-pyrrolidin-1-yl-pyridin-2-yl)-(4-trifluoromethoxy-phenyl)-amine (120 mg, 0.336 mmol) in 1,4-dioxane (8 mL) was added potassium-tert-butoxide (75 mg, 0.670 mmol) and tetrakis(triphenylphosphine)palladium (0) (20 mg, 0.017 mmol), followed by phenyl boronic acid (102 mg, 0.836 mmol). The resulting reaction mixture was refluxed for 10 hours, after which time water was added 100 mL to the reaction mixture, and the product was extracted with ethyl acetate (100 mL×3). The organic layer was dried over sodium sulphate, filtered, and the filtrate was concentrated under vacuum. The resulting product was purified by column chromatography using 230-400 mesh silica gel (20:80 acetone:petroleum ether) to afford the desired compound (75 mg, purity 99%, yield 6%.).

M.P.: 141-143° C.

$^1$H NMR (200 MHz, $CDCl_3$): δ 7.90-7.96 (d, 2H, J=9.67 Hz), 7.40-7.48 (m, 5H), 7.15 (d, 2H, J=25.34), 6.50 (s, 1H), 6.47 (s, 1H), 5.90 (s, 1H), 3.20-3.39 (t, 4H, J=13.00 Hz), 1.99-2.06 (m, 4H).

Mass Spec: (CI-MS) m/z: 400 (M$^+$+1, 100%).

IR (neat) cm$^{-1}$: 2924, 2599, 1555, 1505, 1268, 1157, 983, 814.

Example 57

Synthesis of [6'-(4-fluorophenyl)-3,4,5,6-tetrahydro-2H-[1,4']bipyridinyl-2'-yl]-(4-trifluoromethoxyphenyl)-amine (B56)

Example 58

Synthesis of (6'phenyl-3,4,5,6-tetrahydro-2H-[1,4'] bipyridinyl-2'-yl)-(4-trifluoro-methoxyphenyl)-amine (B58)

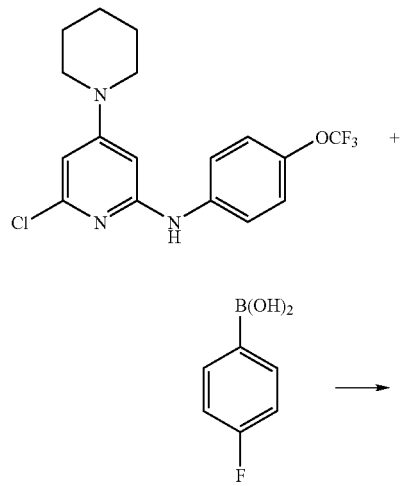

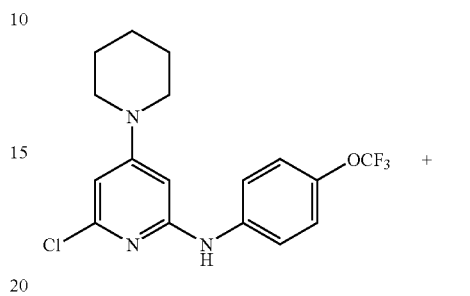

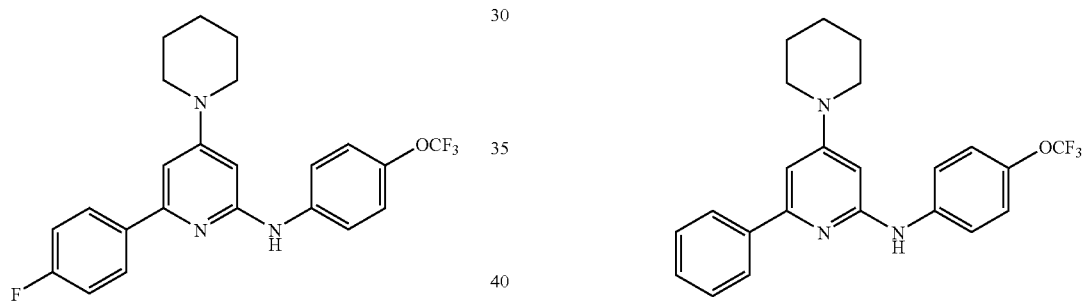

To a solution of (6'-chloro-3,4,5,6-tetrahydro-2H[1,4']bipyridinyl-2'-yl)-(4-trifluoromethoxyphenyl)-amine (200 mg, 0.53 mmol) in 1,4-dioxane (8 mL) were added potassium carbonate (148 mg, 1.06 mmol), and tetrakis(triphenylphosphine)palladium(0) (62 mg, 0.053 mmol), followed by 4-fluorophenyl boronic acid (150 mg, 1.6 mmol). This reaction mixture was refluxed for 8 hours, after which time water was added (10 mL) to the reaction mixture, and the product was extracted with ethyl acetate. The organic layer was dried over sodium sulphate, filtered, and the filtrate was concentrated under vacuum. The resulting product was purified through column chromatography using 230-400 mesh silica gel (15% ethyl acetate in petroleum ether) to afford the desired compound as colorless gummy mass (130 mg, yield 60%).

$^1$H NMR (400 MHz, CDCl$_3$): δ 7.91-7.86 (m, 2H), 7.4 (d, 2H, J=3.22 Hz), 7.17-7.08 (m, 4H), 6.74-6.71 (br s, 1 H), 6.67 (s, 1H), 6.14 (s, 1H), 3.34-3.33 (m, 4H), 1.66 (m, 6 H).

Mass Spec: (ES-MS) m/z: 432 (M$^+$+1, 100%).

IR (neat) cm$^{-1}$: 3408, 2935, 1607, 1590, 1449, 1261, 1157, 1018, 921, 844, 812.

To a solution of (6'-chloro-3,4,5,6-tetrahydro-2H[1,4']bipyridinyl-2'-yl)-(4-trifluoromethoxyphenyl)-amine (170 mg, 0.45 mmol) in 1,4-dioxane (8 mL) were added potassium carbonate (101 mg, 0.9 mmol), and tetrakis(triphenylphosphine)palladium(0) (52 mg, 0.045 mmol), followed by phenyl boronic acid (111 mg, 0.9 mmol). This reaction mixture was refluxed for 8 hours, after which time water was added (10 mL) to the reaction mixture, and the product was extracted with ethyl acetate (100 mL×3). The organic layer was dried over sodium sulphate, filtered, and the filtrate was concentrated under vacuum. The resulting product was purified through column chromatography using 230-400 mesh silica gel (15% ethyl acetate in petroleum ether) to afford the desired compound as light yellow solid (120 mg, yield 65%).

M.P.: 107-108° C.

$^1$H NMR (400 MHz, CDCl$_3$): δ 7.93 (d, 2H), 7.45-7.349 (m, 5H), 7.169 (d, 2H), 6.75 (s, 1H), 6.5 (s, 1H), 6.16 (s, 1H), 3.348-3.335 (m, 4H), 1.66 (m, 6H).

Mass Spec: (ES-MS) m/z: 414 (M$^+$+1, 100%).

IR (neat) cm$^{-1}$: 2940, 1597, 1556, 1506, 1451, 1263, 1223, 1152, 986, 922.

Example 59

Synthesis of [6'-(3-methanesulfonylphenyl)-3,4,5,6-tetrahydro-2H-[1,4']bipyridinyl-2'-yl]-(4-trifluoromethoxyphenyl)-amine (B59)

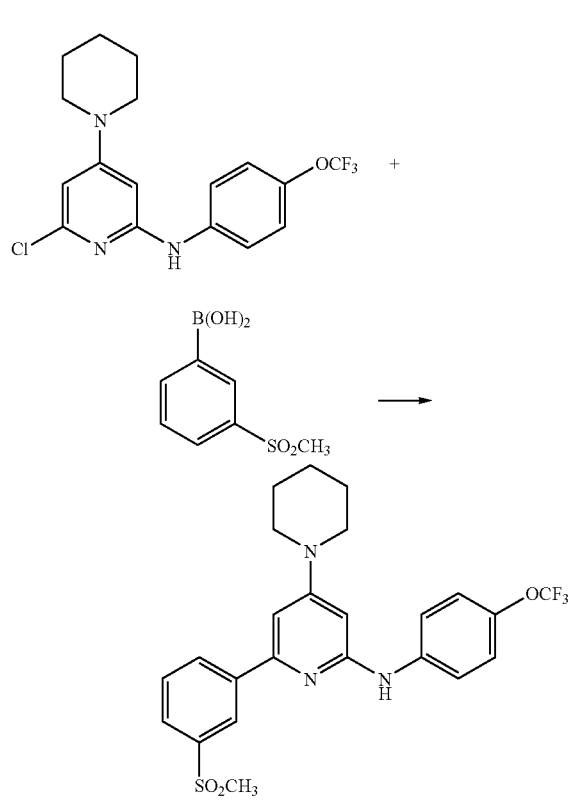

To a solution of (6'-chloro-3,4,5,6-tetrahydro-2H[1,4']bipyridinyl-2'-yl)-(4-trifluoromethoxyphenyl)-amine (200 mg, 0.53 mmol) in 1,4-dioxane (8 mL) were added sodium carbonate (1N solution; 228 mg, 2.12 mmol), and tetrakis(triphenylphosphine) palladium(0) (62 mg, 0.053 mmol), followed by 3-(methanesulphonyl)-phenyl boronic acid (215 mg, 1.06 mmol). This reaction mixture was refluxed for 12 hours, after which time water was added (10 mL) to the reaction mixture, and the product was extracted with ethyl acetate. The organic layer was dried over sodium sulphate, filtered, and the filtrate was concentrated under vacuum. The resulting product was purified through column chromatography using 230-400 mesh silica gel (15% ethyl acetate in petroleum ether) to afford the desired compound as a colorless solid (132 mg, yield 50%).

M.P.: 176-177° C.

$^1$H NMR (400 MHz, CDCl$_3$): δ 8.5 (s, 1H), 8.269 (d, 1H, J=5.1 Hz), 7.95 (d, 1H), 7.65 (t, 2H, J=8.32 Hz), 7.44-7.40 (d, 2H, J=3.49 Hz), 7.19 (d, 2H), 6.78 (s, 1H), 6.45 (s, 1H), 6.17 (s, 1H), 3.36 (m, 4H), 1.68 (m, 6H).

Mass Spec: (ES-MS) m/z: 492 (M$^+$+1, 100%), 493 (M$^+$+2, 38%).

IR (neat) cm$^{-1}$: 3362, 2926, 1619, 1595, 1533, 1506, 1464, 1416, 1296, 1251, 1244, 1196, 1149, 1128, 966, 824, 795.

Example 60

Synthesis of 4-[6'-(4-fluorophenyl)-3,4,5,6-tetrahydro-2H-[1,4']bipyridinyl-2'-ylamino]-N-methyl-benzenesulfonamide (B60)

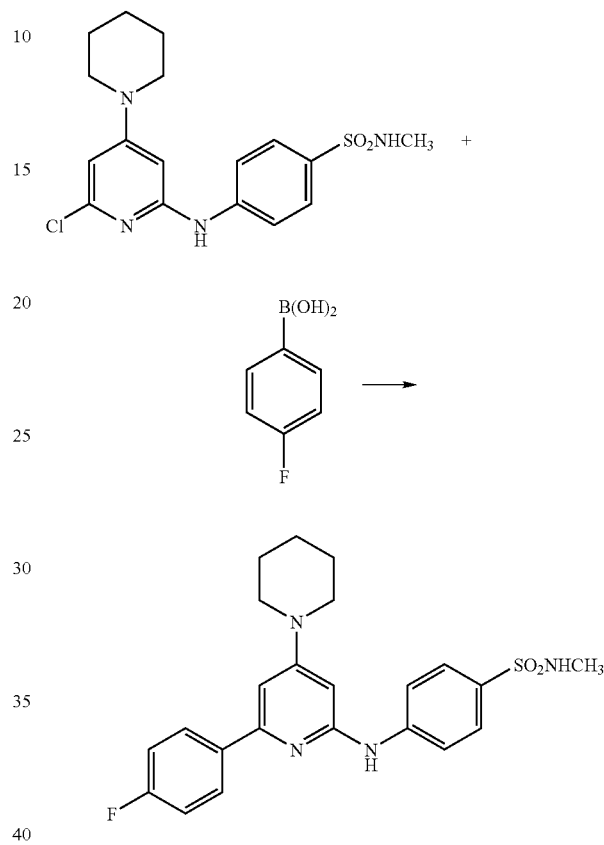

To a solution of 4-(6'-chloro-3,4,5,6-tetrahydro-2H-[1,4']bipyridinyl-2'-ylamino)-N-methyl-benzenesulfonamide (70 mg, 0.18 mmol) in 1,4-dioxane (8 mL) was added sodium carbonate (1N, 80 mg, 0.72 mmol), and tetrakis(triphenylphosphine)palladium(0) (21 mg, 0.018 mmol), followed by 4-fluorophenyl boronic acid (49 mg, 0.36 mmol). This reaction was refluxed for 8 hours, after which time water (100 mL) added to the reaction mixture, and the product was extracted with ethyl acetate (100 mL×3). The organic layer was dried over sodium sulphate, filtered, and the filtrate was and concentrated under vacuum. The resulting product was purified through column chromatography using 230-400 mesh silica gel (5% methanol in dichloromethane) to afford the desired compound as A yellow solid (48 mg, Yield 60%). Purity: 98.2%.

M.P.: 191-192° C.

$^1$H NMR (400 MHz, CDCl$_3$): δ 7.91-7.88 (m, 2H), 7.7 (d, 2H, J=6.9 Hz), 7.578 (d, 2H), 7.13-7.096 (t, 2H), 6.8 (br s, 1H), 6.75 (s, 1H), 6.2 (s, 1H), 4.39 (br s, 1H), 3.38 (m, 4H), 2.63 (s, 3H), 1.68 (m, 6H).

Mass Spec: (CI-MS) m/z: 441 (M$^+$+1, 100%).

IR (neat) cm$^{-1}$: 3387, 2934, 1613, 1584, 1508, 1462, 1331, 1223, 1153, 1093, 819.

Example 61

Synthesis of N-methyl-4-[4-Pyrrolidin-1-yl-6-(4-trifluoromethoxy-phenyl)-pyridin-2-ylamino]-benzenesulfonamide (B6)

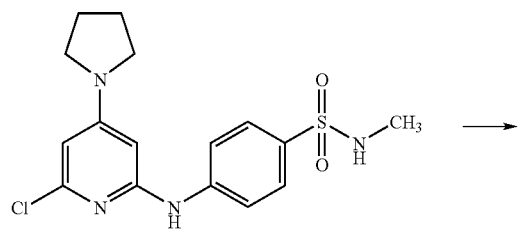

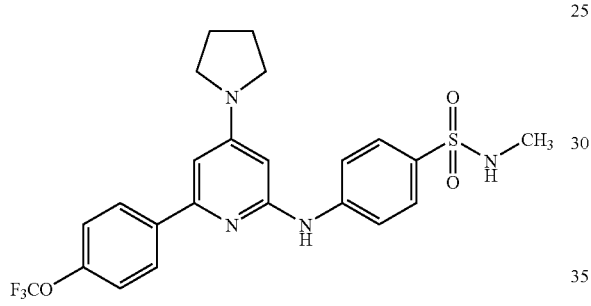

To a solution of 4-(6-chloro-4-pyrrolidin-1-yl-pyridin-2-ylamino)-N-methyl-benzenesulfonamide (100 mg, 0.27 mmol) in 1,4-dioxane (8 mL) was added 1N sodium carbonate solution (0.3 mL) and tetrakis(triphenylphosphine)palladium(0) (15.8 mg, 0.013 mmol), followed by 4-trifluoromethoxyphenyl boronic acid (67.2 mg, 0.32 mmol). The resulting reaction mixture was refluxed for 8 hours, after which time water was added (100 mL) to the reaction mixture, and the product was extracted with ethyl acetate (100 mL×3). The organic layer was dried over sodium sulphate, filtered, and the filtrate was concentrated under vacuum. The resulting product was purified by column chromatography using 230-400 mesh silica gel (20:80 acetone:petroleum ether) to afford the desired compound pale yellow solid (46 mg, yield 34%.).

M.P.: 83-85° C.

$^1$H NMR (200 MHz, DMSO-$d_6$): δ 9.31 (s, 1H), 8.18 (d, 2H, J=8.67 Hz), 7.94 (d, 2H, J=8.67 Hz), 7.64 (d, 2H, J=8.67 Hz), 7.46 (d, 2H, J=8.33 Hz), 7.12 (br s, 1H), 6.70 (s, 1H), 5.96 (s, 1H), 3.22-3.39 (m, 4H), 2.40 (d, 3H, J=5.00 Hz), 1.99-2.06 (m, 4H).

Mass Spec: (ES-MS) m/z: 493 (M$^+$+1, 100%).

IR (neat) cm$^{-1}$: 3254, 2925, 1618, 1600, 1524, 1326, 1220, 1153, 1092, 979, 917, 856.

Example 62

Synthesis of [6-(3-methanesulfonyl-phenyl)-4-morpholin-4-yl-pyridin-2-yl]-(4-trifluoromethoxy-phenyl)-amine (B68)

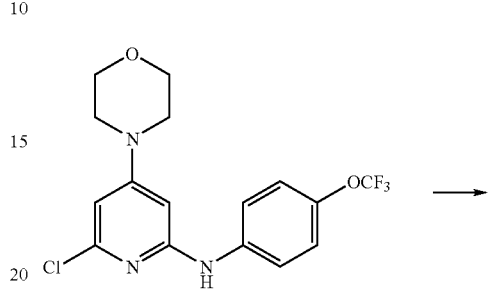

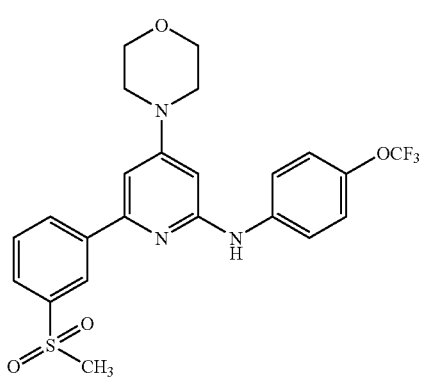

To a solution of (6-chloro-4-morpholin-4-yl-pyridin-2-yl)-(4-trifluoromethoxy-phenyl)-amine (75 mg, 0.20 mmol) in 1,4-dioxane (8 mL) were added 2N sodium carbonate solution (0.5 mL) and tetrakis(triphenylphosphine)palladium(0) (11.6 mg, 0.010 mmol), followed by 3-methanesulfonyl phenyl boronic acid (48 mg, 0.24 mmol). The resulting reaction mixture was refluxed for 8 hours, after which time water was added (100 mL) to the reaction mixture, and the product was extracted with ethyl acetate (100 mL×3). The organic layer was dried over sodium sulphate, filtered, and the filtrate was concentrated under vacuum. The resulting product was purified by column chromatography using 230-400 mesh silica gel (elution 2:98 methanol:DCM) to afford the desired compound pale yellow solid (30 mg, yield 30%.).

M.P.: 233-235° C.

$^1$H NMR (200 MHz, DMSO-$d_6$): δ 9.12 (s, 1H), 8.45 (d, 2H), 7.74-7.96 (m, 4H), 7.27 (d, 2H, J=11.00 Hz), 7.15 (s, 1H), 6.25 (s, 1H), 3.60-3.85 (m, 4H), 3.15-3.42 (m, 4H), 3.25 (s, 3H).

Mass Spec: (ES-MS) m/z: 494 (M$^+$+1, 100%).

IR (neat) cm$^{-1}$: 3386, 2920, 1615, 1450, 1302, 1153, 1015, 959, 832.

Example 63

Synthesis of N-methyl-4-[4-morpholin-4-yl-6-(4-trifluoromethoxy-phenylamino)-pyridin-2-yl]-benzenesulfonamide (B69)

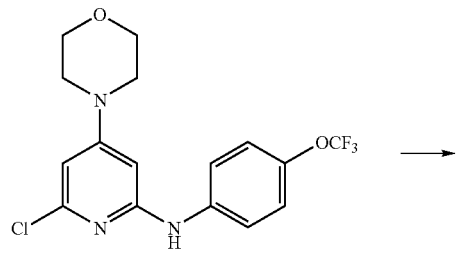

↓

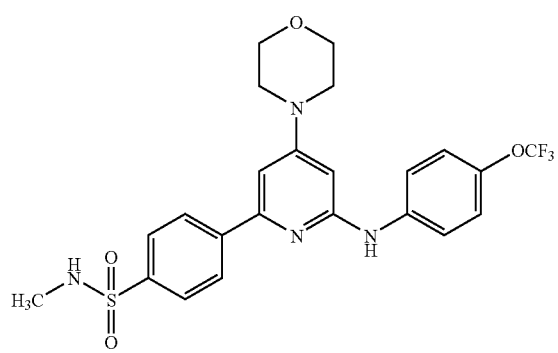

To a solution of (6-chloro-4-morpholin-4-yl-pyridin-2-yl)-(4-trifluoromethoxy-phenyl)-amine (50 mg, 0.13 mmol) in 1,4-dioxane (8 mL) were added 2N sodium carbonate solution (0.5 mL), and tetrakis(triphenylphosphine)palladium(0) (7.74 mg, 0.0067 mmol), followed by 3-methyl-4-boron benzenesulfonamide (34.6 mg, 0.16 mmol). The resulting reaction mixture was refluxed for 8 hours, after which time water was added (100 mL) to the reaction mixture, and the product was extracted with ethyl acetate. The organic layer was dried over sodium sulphate, filtered, and the filtrate was concentrated under vacuum. The resulting product was purified by column chromatography using 230-400 mesh silica gel (elution 2:98 methanol:DCM) to afford the desired compound colorless solid (25 mg, yield 36%.).

M.P.: 234-236° C.

$^1$H NMR (200 MHz, DMSO-d$_6$): δ 9.12 (s, 1H), 8.26 (d, 2H, J=8.60 Hz), 7.74-7.87 (m, 4H), 7.47 (d, 1H), 7.25 (d, 2H), 7.15 (s, 1H), 6.24 (s, 1H), 3.78-3.82 (m, 4H), 2.28-2.38 (m, 4H), 2.56 (d, 3H, J=1.60 Hz).

Mass Spec: (CI-MS) m/z: 508 (M$^+$, 100%).

IR (neat) cm$^{-1}$: 3374, 2925, 1770, 1597, 1450, 1265, 1162, 929.

Example 64

Synthesis of [6-(4-fluoro-phenyl)-4-pyrrolidin-1-yl-pyridin-2-yl]-(4-trifluoromethoxy-phenyl)-amine (B65)

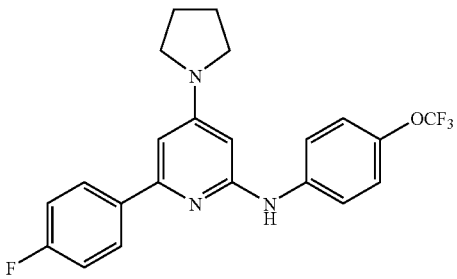

This compound was prepared by a process analogous to that disclosed in Example 63.

M.P.: 83-85° C.

$^1$H NMR (200 MHz, CDCl$_3$) δ 7.90-7.96 (d, 2H, J=9.67 Hz), 7.40-7.48 (m, 4H), 6.40 (s, 1H), 5.90 (s, 1H), 5.30 (s, 1H), 3.22-3.39 (t, 4H, J=13.00 Hz), 1.99-2.06 (m, 4H).

Mass Spec: (ES-MS) m/z: 418 (M$^+$+1, 100%).

IR (neat) cm$^{-1}$: 2925, 2854, 1613, 1459, 1352, 1262, 1156, 981, 843, 808.

Example 65

Synthesis of N-methyl-4-[4-(4-methyl-piperazin-1-yl)-6-(4-trifluoromethoxy-phenyl-amino)-pyridin-2-yl]-benzenesulfonamide (B67)

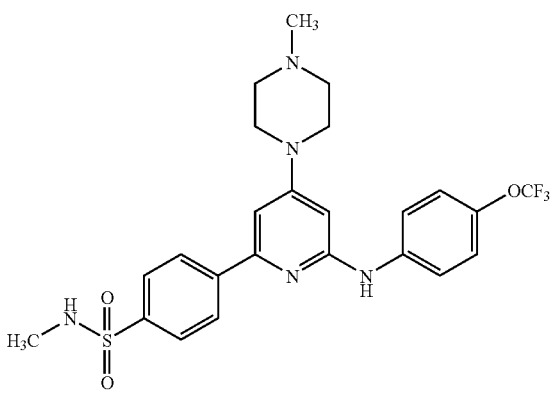

This compound was prepared by a process analogous to that disclosed in Example 63.

M.P.: 184-186° C.

$^1$H NMR (200 MHz, CDCl$_3$) δ 8.01 (d, 4H, J=8.67 Hz), 7.17-7.45 (d, 4H, J=9.00 Hz), 6.740 (s, 1H), 6.70 (s, 1H), 6.20 (s, 1H), 4.90 (m, 1H), 3.25-3.42 (m, 4H), 2.46-2.68 (m, 4H), 2.24 (s, 3H), 1.25 (d, 3H, J=7.04 Hz).

Mass Spec: (ES-MS) m/z: 522(M$^+$+1, 100%).

IR (neat) cm$^{-1}$: 3380, 2925, 1595, 1506, 1452, 1261, 1160, 813.

Example 66

Synthesis of (4-trifluoromethoxy-phenyl)-[6'(4-trifluoromethoxy-phenyl)-3,4,5,6-tetrahydro-2H-[1,4']bipyridinyl-2'-yl]-amine (B57)

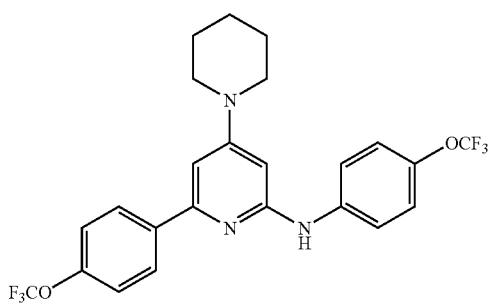

This compound was prepared by a process analogous to that disclosed in Example 63.

$^1$H NMR (400 MHz, CDCl$_3$): δ 7.95 (d, 2H, J=4.83 Hz), 7.4 (d, 2H, J=4.83 Hz), 7.28 (d, 2H), 7.17 (d, 2H, J=8.32 Hz), 6.7 (s, 1H), 6.49 (s, 1H), 6.15 (s, 1H), 3.35 (m, 4H), 1.66 (m, 6H).

Mass Spec: (ES-MS) m/z: 498 (M$^+$+1, 100%).

IR (neat) cm$^{-1}$: 2938, 1607, 1550, 1506, 1449, 1260, 1203, 1162, 1017, 921, 807.

Example 67

Synthesis of 1-[4-(4-hydroxy-6'-phenyl-3,4,5,6-tetrahydro-2H-[1,4']bipyridinyl-2'ylamino)-phenyl]-ethanone (B44)

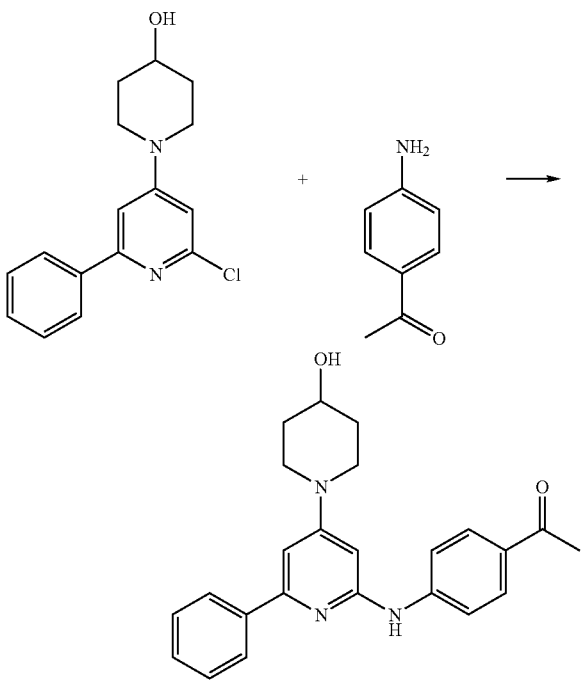

To a solution of 2'-chloro-6'-phenyl-3,4,5,6-tetrahydro-2H-[1,4']bipyridinyl-4-ol (40 mg, 0.13 mmol) in toluene (4 mL) were added potassium tert-butoxide (31 mg, 0.26 mmol), palladium(II)acetate (3 mg, 0.156 mmol), BINAP (4 mg, 0.0065 mmol) and 1-(4-aminophenyl)-ethanone (22 mg, 0.156 mmol) in a 10 mL reaction vessel. This reaction mixture was subjected the microwave radiation, in which the microwave power was 250 W, to attain a reaction temperature of 150° C. After this reaction proceeded for 30 min, water (5 mL) was added to the reaction mixture and the reaction product was extracted with ethyl acetate. The organic layer was dried over sodium sulphate, filtered, and the filtrate concentrated under vacuum. The product was purified through column chromatography using 230-400 mesh silica gel (5% methanol in dichloromethane) to afford the desired compound as a yellow solid (29 mg, yield 55%, purity 96%).

M.P.: 150-152° C.

$^1$H NMR (400 MHz, CDCl$_3$): δ 7.94-7.92 (m, 4H), 7.5-7.39 (m, 5H), 6.82 (m, 2H), 6.29 (s, 1H), 3.98-3.94 (m, 1H), 3.78 (m, 2H), 3.19 (m, 2H), 2.56 (s, 3H), 2.01 (m, 2H), 1.69 (m, 2H).

Mass Spec: (ES-MS) m/z: 388 (M$^+$+1, 100%).

Example 68

Synthesis of 1-[4-(2-morpholin-4-yl-6-phenyl-pyridin-4-ylamino)-phenyl]-ethanone (B45)

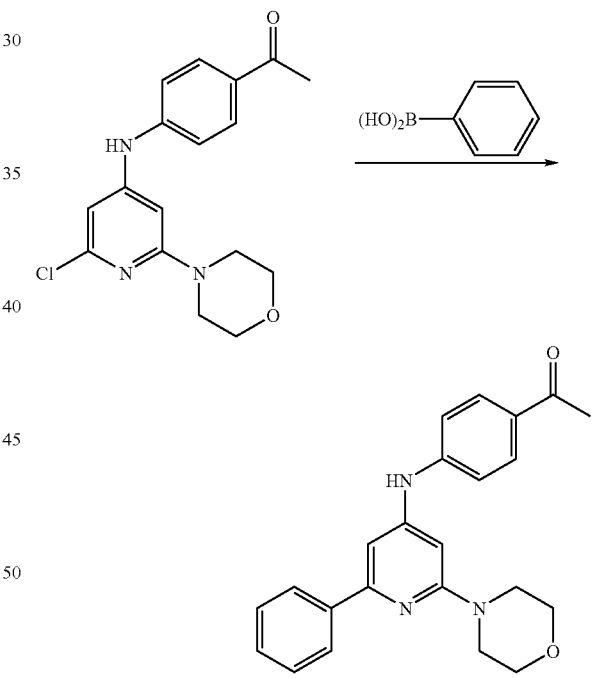

To 1-[4-(2-chloro-6-morpholin-4-yl-pyridin-4-ylamino)-phenyl]-ethanone (251.7 mg, 0.75 mmol) dissolved in acetonitrile (10 mL) and 2 M Na$_2$CO$_3$ (10 mL, 20 mmol) was added phenyl boronic acid (184.9 mg, 1.5 mmol) and palladium tetrakis(triphenylphosphine) (87.3 mg, 0.075 mmol). The resulting mixture was allowed to stir at reflux for 12-18 hours. The sample was diluted in dichloromethane and filtered through Celite™. The Celite™ was washed with dichloromethane; the filtrate was washed two times with water and one time with brine. The organic phase was dried over potassium carbonate and concentrated by rotary evaporation. The resulting sample was dried for 12-18 hours under vacuum.

Column chromatography (SiO$_2$, 96:3:1 dichloro-methane:methanol:ammonium hydroxide) gave a light yellow solid (78 mg, 28%).

M.P.: 148° C.

HPLC: Inertsil ODS-3V C18, 30:70 [KH$_2$PO$_4$ (0.01M, pH 3.2):CH$_3$CN], 264 nm, R$_t$ 7.1 min, 94.8% purity.

$^1$H NMR (300 MHz, CDCl$_3$, TMS): δ 2.57 (s, 3H), 3.57 (t, J=5.1 Hz, 4H), 3.84 (t, J=4.5 Hz, 4H), 6.29 (d, J=1.2 Hz, 1H), 6.54 (br s, 1H), 6.91 (d, J=1.5 Hz, 1H), 7.20 (apt d, J=8.7 Hz, 2H), 7.37-7.45 (m, 3H), 7.92-7.96 (m, 4H) [D$_2$O exchange; peak at 6.54 for 1H disappeared].

Mass Spec: LC-MSD (ES+): m/z 374 (M+H, 94.49).

Example 69

Synthesis of 6'-(4-fluoro-phenyl)-4'-(4-trifluoromethoxy-phenylamino)-3,4,5,6-tetra-hydro-2H-[1,2']bipyridinyl-4-ol (B46)

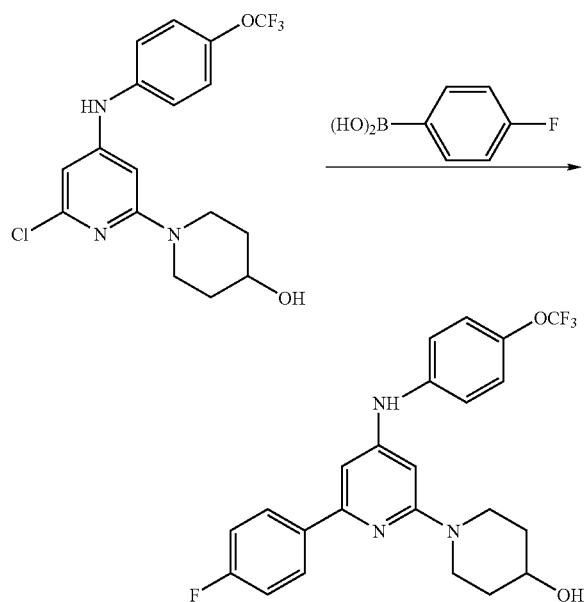

6'-Chloro-4'-(4-trifluoromethoxy-phenylamino)-3,4,5,6-tetrahydro-2H-[1,2']bipyridinyl-4-ol (0.080 g, 0.2 mmol) and 4-fluorophenyl boronic acid (0.0562 g, 0.4 mmol) dissolved in acetonitrile (5 mL) and Na$_2$CO$_3$ (5 mL, 2.0 M) was added palladium (0) tetrakis(triphenylphosphine) (0.0235 g, 0.02 mmol). The reaction mixture was stirred and refluxed for 12-18 hours under N$_2$. The reaction was monitored by TLC, and after 18 h 4-fluorophenyl boronic acid (0.0381 g, 0.4 mmol), palladium (0) tetrakis (triphenylphosphine) (0.012 g, 0.01 mmol) was added stirred and refluxed for 12-18 hours under N$_2$. The reaction mixture was diluted with CH$_2$Cl$_2$ and filtered through Celite™, then rinsed with CH$_2$Cl$_2$. The filtrate was washed two times with water and one time with brine. The organic phase was collected and dried over potassium carbonate. The filtered sample was concentrated, and the resulting solid was dried for 12-18 hours under vacuum. Biotage Horizon HPFC system chromatography (SiO$_2$, 93:6:1 CH$_2$Cl$_2$:MeOH:NH$_4$OH) yielded a pale brown solid (34 mg, 37%).

M.P. 134° C.

HPLC: Inertsil ODS-3V C18, 30:70 [KH$_2$PO$_4$ (0.01M, pH 3.2):CH$_3$CN], 264 nm, R$_t$ 4.6 min, 96.1% purity.

$^1$H NMR (300 MHz, CHCl$_3$, TMS): δ 1.48-1.59 (m, 3H), 1.89-1.94 (m, 2H), 3.03-3.01 (m, 2H), 3.81-3.87 (m, 1H), 4.03-4.07 (m, 2H), 5.90 (s, 1H), 6.09 (s, 1H), 6.57 (s, 1H), 7.01 (apt t, J=8.4 Hz, 2H), 7.12 (s, 3H), 7.82-7.87 (m, 2H).

Mass Spec: (TOF MS ES+): m/z 448 (M+, 100); HRMS (TOF MS ES+) Calcd for C$_{23}$H$_{21}$F$_4$N$_3$O$_2$, [M+H] 448.1648. Found 448.1640.

Example 70

Synthesis of 1-[4-(4-hydroxy-6'-phenyl-3,4,5,6-tetrahydro-2H-[1,2']bipyridinyl-4'-ylamino)-phenyl]-ethanone (B47)

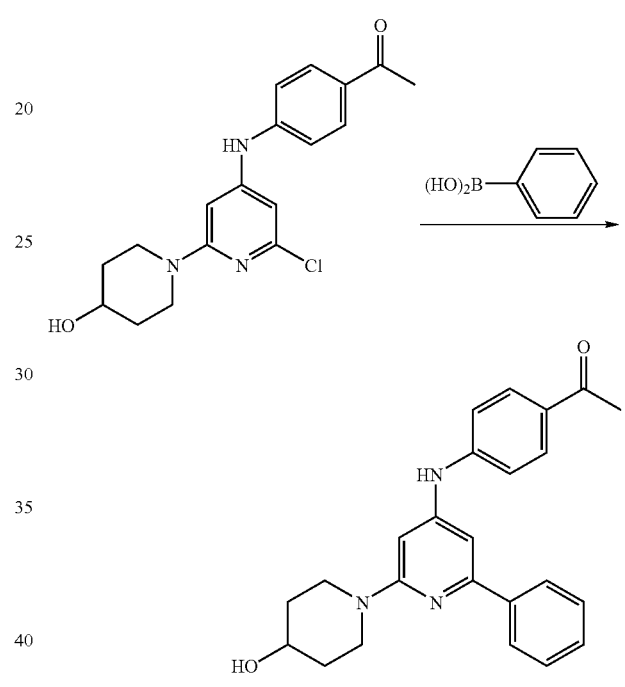

1-[4-(6'-chloro-4-hydroxy-3,4,5,6-tetrahydro-2H-[1,2'] bipyridinyl-4'-ylamino)-phenyl]-ethanone (0.497 g, 1.4 mmol) and phenylboronic acid (0.3421 g, 2.8 mmol) dissolved in acetonitrile (15 mL), THF (5 mL) and Na$_2$CO$_3$ (20 mL, 2.0 M) was added palladium(0) tetrakis(triphenylphosphine) (0.1621 g, 0.14 mmol). The reaction mixture was stirred and refluxed for 12-18 hours under N$_2$. The reaction mixture was diluted with CH$_2$Cl$_2$ and filtered through Celite™, then rinsed with CH$_2$Cl$_2$. The filtrate was washed two times with water and one time with brine. The organic phase was collected and dried over potassium carbonate. The filtered sample was concentrated, and the resulting solid was dried for 12-18 hours under vacuum. Flash chromatography (SiO$_2$, 93:6:1 CH$_2$Cl$_2$:MeOH:NH$_4$OH) yielded a pale brown solid (188 mg, 34%).

M.P.: 70° C.

HPLC: Inertsil ODS-3V C18, 40:10:50 [KH$_2$PO$_4$(0.01M, pH 3.2):CH$_3$CN], 264 nm, R$_t$ 4.1 min, 97.4% purity.

$^1$H NMR: (300 MHz, CHCl$_3$, TMS): δ 1.57-1.68 (m, 3H), 1.69-2.04 (m, 2H), 2.57 (s, 3H), 3.16-3.25 (m, 2H), 3.93 (octet, J=4.2 Hz, 1H), 4.16 (dt, J=4.5, 13.5 Hz, 2H), 6.23 (s, 1H), 6.33 (d, J=1.8 Hz, 1H), 6.85 (d, J=1.8 Hz, 1H), 7.16-7.21 (m, 2H), 7.34-7.45 (m, 3H), 7.92-7.81 (m, 4H).

Mass Spec: LC-MSD (ES+): m/z 388 (M+H, 100).

Example 71

Synthesis of 2',6'-bis-(4-trifluoromethoxy-phenylamino)-3,4,5,6-tetrahdro-2H[1,4']bipyridinyl-4-ol (B71)

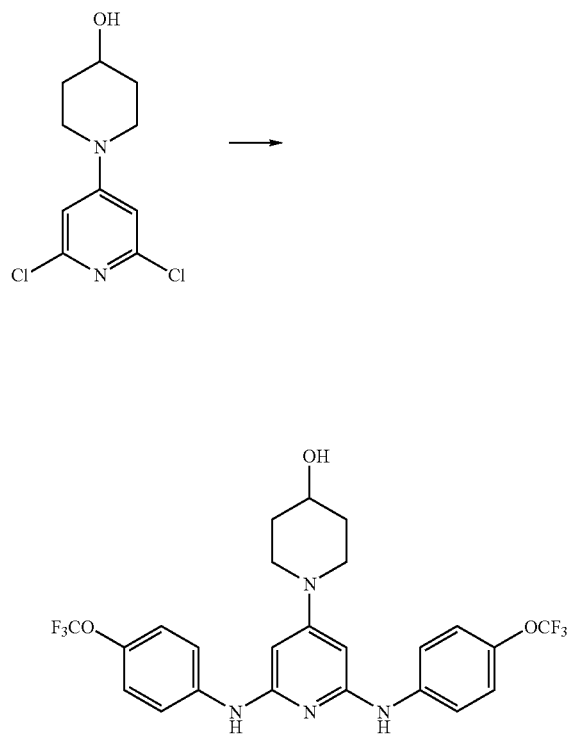

To a solution of 2',6'-dichloro-3,4,5,6-tetrahydro-2H-[1,4']bipyridinyl-4-ol (280 mg, 1.1 mmol) in toluene (6 mL) were added potassium tert-butoxide (254 mg, 2.2 mmol), palladium(II)acetate (25 mg, 0.11 mmol), BINAP (49 mg, 0.079 mmol) and 4-trifluoromethoxyphenylamine (0.2 mL, 1.134 mmol), in a 10 mL reaction vessel. This reaction mixture was irradiated with microwave radiation at 250 W, to attain a reaction temperature of 160° C. After this reaction proceeded for 15 min, water (5-6 mL) was added to the reaction mixture and the reaction product was extracted with ethyl acetate. The organic layer was dried over sodium sulphate, filtered, and the filtrate concentrated under vacuum. The product was purified through column chromatography using 230-400 mesh silica gel, eluting with 3:97 MeOH:CHCl$_3$, to afford the desired compound as a colorless solid (100 mg, yield 16.7%, purity 96%).

M.P.: 119-120° C.

$^1$H NMR (200 MHz, CDCl$_3$): δ 7.3 (d, 4H), 7.2 (m, 4H), 6.39 (s, 1H), 5.79 (s, 2H), 3.9 (m, 1H, J=4.3 Hz), 3.6 (m, 2H), 3.0 (m, 2H), 1.8 (m, 2H), 1.6 (m, 2H).

Mass Spec: (ES-MS) m/z: 529 (M$^+$+1, 100%).

IR (neat) cm$^{-1}$: 3408, 2929, 1602, 150, 1266, 1201, 1051, 793.

Example 72

Synthesis of 2,6-dichloro-4-(4-methanesulfonyl-phenyl)-pyridine

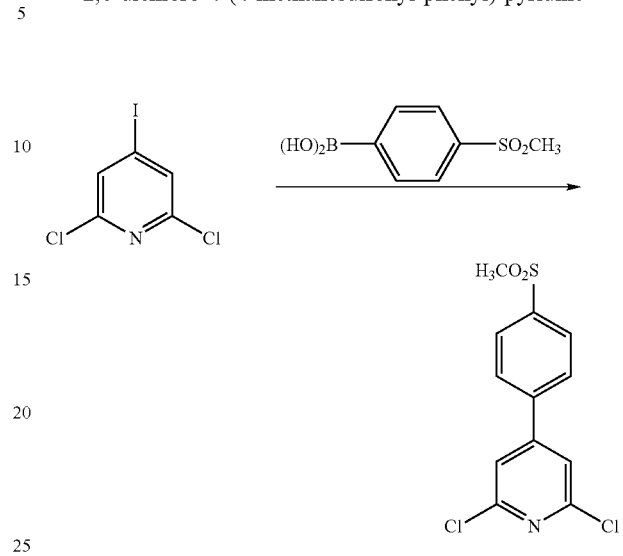

To 2,6-dichloro-4-iodopyridine (0.8296 g, 3 mmol) and 4-methanesulfonylphenyl boronic acid (0.6124 g, 3 mmol) dissolved in acetonitrile (30 mL) and Na$_2$CO$_3$ (30 mL, 0.4M) was added palladium (0) tetrakis(triphenylphosphine) (0.1733 g, 0.15 mmol). The reaction mixture was stirred and refluxed for 12-18 hours under N$_2$. The reaction mixture was diluted with CH$_2$Cl$_2$ and filtered through Celite™, then rinsed with CH$_2$Cl$_2$. The filtrate was washed two times with water and one time with brine. The organic phase was collected and dried over potassium carbonate. The filtered sample was concentrated, and the resulting solid was dried for 12-18 hours under vacuum. Biotage Horizon HPFC system chromatography (SiO$_2$, 50:50 hexanes:ethyl acetate) yielded a off white solid (640 mg, 70%).

M.P.: 165° C.

HPLC: Inertsil ODS-3V C18, 30:70 [KH$_2$PO$_4$ (0.01M, pH 3.2):CH$_3$CN], 264 nm, R$_t$ 6.2 min, 99.4% purity.

$^1$H NMR: (600 MHz, CDCl$_3$, TMS, 55° C.): δ 3.09 (s, 3H), 7.47 (s, 4H), 7.76-7.78 (m, 2H), 8.07-8.08 (m, 2H).

Mass Spec: (EI+): m/z 301 (M+, 100).

Example 73

Synthesis of [4-(2,6-dichloro-pyridin-4-yl)-phenyl]-morpholin-4-yl-methanone (B73)

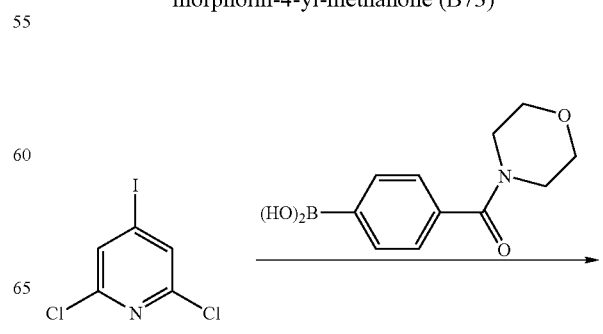

-continued

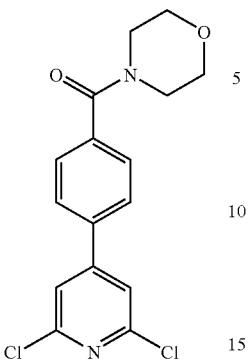

To 2,6-dichloro-4-iodopyridine (0.8238 g, 3 mmol) and [(4-morpholine-4-carbonyl)-phenyl]boronic acid (0.7051 g, 3 mmol) dissolved in acetonitrile (23 mL), THF (7 mL), and $Na_2CO_3$ (30 mL, 0.4M) was added palladium (0) tetrakis (triphenylphosphine) (0.1758 g, 0.15 mmol). The reaction mixture was stirred and refluxed for 2.5 h under $N_2$. The reaction mixture was diluted with $CH_2Cl_2$ and filtered through Celite™, then rinsed with $CH_2Cl_2$. The filtrate was washed one time with water and one time with brine. The organic phase was collected and dried over potassium carbonate. The filtered sample was concentrated, and the resulting solid was dried for 12-18 hours under vacuum. Biotage Horizon HPFC system chromatography ($SiO_2$, 50:50 hexanes:ethyl acetate) yielded a pale yellow product (570 mg, 56%).

M.P.: 187° C.

HPLC: Inertsil ODS-3V C18, 30:70 [$KH_2PO_4$(0.01M, pH 3.2):$CH_3CN$], 264 nm, $R_t$ 5.6 min, 99.2% purity.

$^1$H NMR: (600 MHz, $CDCl_3$, TMS, 55° C.): δ 3.44 (br s, 2H), 3.64 (br s, 2H), 3.79 (br s, 4H), 7.45 (s, 2H), 7.54 (d, J=8.4 Hz, 2H), 7.63 (apt d, J=8.4 Hz, 2H).

MS (EI+): m/z 337 (M+1, 30), 250 (100).

Examples 74

Synthesis of 2,6-dichloro-4-phenyl-pyridine (B74)

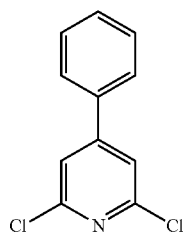

This compound was prepared by a procedure analogous to that disclosed in Example 73.

M.P.: 35° C.

HPLC: Inertsil ODS-3V C18, 30:70 [$KH_2PO_4$ (0.01M, pH 3.2):$CH_3CN$], 264 nm, $R_t$ 15.6 min, 97.3% purity.

$^1$H NMR (600 MHz, $CDCl_3$, TMS): δ 7.54 (s, 1H), 7.48-7.50 (m, 3H), 7.56-7.58 (m, 2H).

Mass Spec: (EI+): m/z 223 (M+H, 100).

Example 75

Synthesis of 2,6-dichloro-4-(4-fluoro-phenyl)-pyridine (B75)

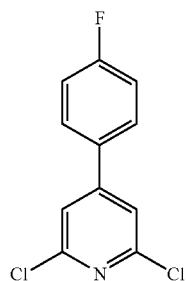

This compound was prepared by a procedure analogous to that disclosed in Example 73.

M.P.: 147° C.

HPLC: Inertsil ODS-3V C18, 30:70 [$KH_2PO_4$(0.01M, pH 3.2):$CH_3CN$], 264 nm, $R_t$ 13.8 min, 92.4% purity.

$^1$H NMR: (600 MHz, $CDCl_3$, TMS, 55° C.): δ 7.17-7.20 (m, 2H), 7.41 (s, 2H), 7.56-7.59 (m, 2H).

Mass Spec: (EI+): m/z 241 (M+1, 100).

Example 76

Synthesis of 2,6-dichloro-4-(4-methanesulfonyl-phenyl)-pyridine (B76)

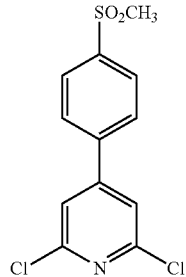

This compound was prepared by a procedure analogous to that disclosed in Example 73.

M.P.: 165° C.

HPLC: Inertsil ODS-3V C18, 30:70 [$KH_2PO_4$ (0.01M, pH 3.2):$CH_3CN$], 264 nm, $R_t$ 6.2 min, 99.4% purity.

$^1$H NMR: (600 MHz, $CDCl_3$, TMS, 55° C.): δ 3.09 (s, 3H), 7.47 (s, 4H), 7.76-7.78 (m, 2H), 8.07-8.08 (m, 2H).

Mass Spec: (EI+): m/z 301 (M+, 100).

Example 77

Synthesis of 2,6-dichloro-4-(4-fluoro-phenyl)-pyridine (13)

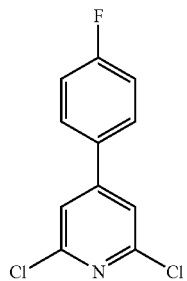

This compound was prepared by a procedure analogous to that disclosed in Example 73.

M.P.: 147° C.

HPLC: Inertsil ODS-3V C18, 30:70 [$KH_2PO_4$ (0.01M, pH 3.2):$CH_3CN$], 264 nm, $R_t$ 13.8 min, 92.4% purity.

$^1$H NMR (600 MHz, $CDCl_3$, TMS, 55° C.): δ 7.17-7.20 (m, 2H), 7.41 (s, 2H), 7.56-7.59 (m, 2H).

Mass Spec (EI+): m/z 241 (M+1, 100).

Example 78

Synthesis of [4-(2,6-dichloro-pyridin-4-yl)-phenyl]-morpholin-4-yl-methanone (17)

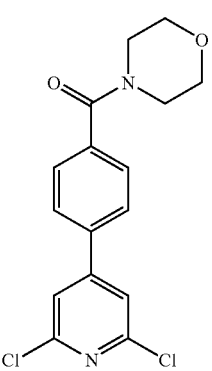

This compound was prepared by a procedure analogous to that disclosed in Example 73.

M.P.: 187° C.

HPLC: Inertsil ODS-3V C18, 30:70 [$KH_2PO_4$ (0.01M, pH 3.2):$CH_3CN$], 264 nm, $R_t$ 5.6 min, 99.2% purity.

$^1$H NMR (600 MHz, $CDCl_3$, TMS, 55° C.): δ 3.44 (br s, 2H), 3.64 (br s, 2H), 3.79 (br s, 4H), 7.45 (s, 2H), 7.54 (d, J=8.4 Hz, 2H), 7.63 (apt d, J=8.4 Hz, 2H).

MS (EI+): m/z 337 (M+1, 30), 250 (100).

Example 79

Synthesis of 2,6-dichloro-4-(4-trifluoromethoxy-phenyl)-pyridine (19)

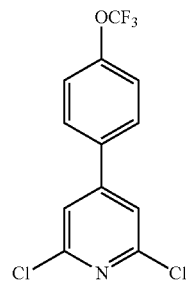

This compound was prepared by a procedure analogous to that disclosed in Example 73.

Example 80

Synthesis of 2,6-dichloro-4-phenyl-pyridine (27)

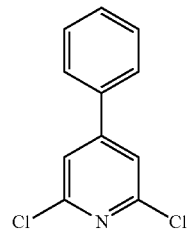

This compound was prepared by a procedure analogous to that disclosed in Example 73.

M.P.: 35° C.

HPLC: Inertsil ODS-3V C18, 30:70 [$KH_2PO_4$ (0.01M, pH 3.2):$CH_3CN$], 264 nm, $R_t$ 15.6 min, 97.3% purity.

$^1$H NMR (600 MHz, $CDCl_3$, TMS): δ 7.54 (s, 1H), 7.48-7.50 (m, 3H), 7.56-7.58 (m, 2H).

MS (EI+): m/z 223 (M+H, 100).

Example 81

Synthesis of 1-[4,6-bis-(4-fluoro-phenyl)-pyridin-2-yl]-4-methyl-piperazine (B40)

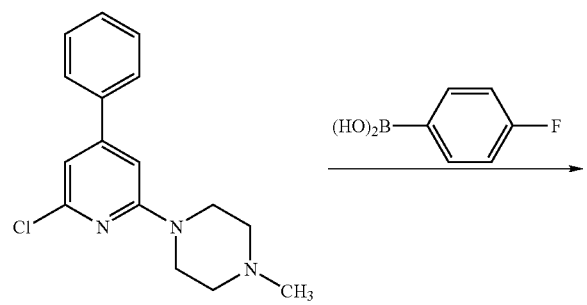

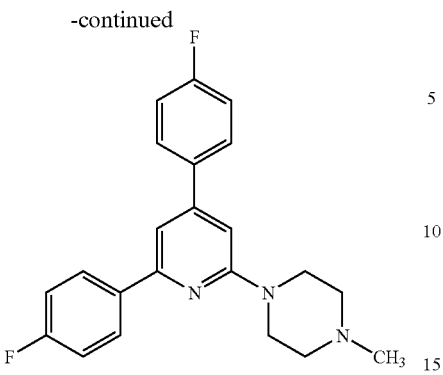

1-[6-Chloro-4-(4-fluoro-phenyl)-pyridin-2-yl]-4-methyl-piperazine (0.157 g, 0.5 mmol) and 4-fluorophenyl boronic acid (0.0862 g, 0.6 mmol) were dissolved in acetonitrile (5 mL) and Na$_2$CO$_3$ (5 mL, 0.4M) followed by addition of palladium (0) tetrakis(triphenylphoshine) (0.0292 g, 0.025 mmol). The reaction mixture was allowed to stir and reflux for 12-18 hours. The reaction mixture was diluted with CH$_2$Cl$_2$ and filtered through Celite™, then rinsed with CH$_2$Cl$_2$. The filtrate was washed one time with water and one time with brine. The organic phase was collected and dried over potassium carbonate. The filtered sample was concentrated, and the resulting solid was dried for 12-18 hours under vacuum. Biotage Horizon HPFC system chromatography (SiO$_2$, 93:6:1 CH$_2$Cl$_2$:MeOH:NH$_4$OH) yielded a pale brown solid product (125 mg, 67%).

M.P.: 102° C.

HPLC: Inertsil ODS-3V C18, 40:10:50 [KH$_2$PO$_4$ (0.01M, pH 3.2):CH$_3$CN:MeOH], 264 nm, R$_t$ 5.1 min, 96.5% purity.

$^1$H NMR: (600 MHz, CDCl$_3$, TMS, 55° C.): δ 2.38 (s, 3H), 2.58 (t, J=4.8 Hz, 4H), 3.73 (t, J=4.8 Hz, 4H), 6.72 (s, 1H), 7.11-7.18 (m, 4H), 7.21 (s, 1H), 7.6-7.63 (m, 2H), 8.03-8.06 (m, 2H).

Mass Spec: (TOF MS ES+): m/z 366 (M+H, 100); HRMS (TOF MS ES+) Calcd for C$_{22}$H$_{22}$F$_2$N$_3$, [M+H] 366.1782. Found 366.1793.

Example 82

Synthesis of 6'-(4-fluoro-phenyl)-4'-(4-methane-sulfonyl-phenyl)-3,4,5,6-tetrahydro-2H-[1,2']bipyridinyl-4-ol (B55)

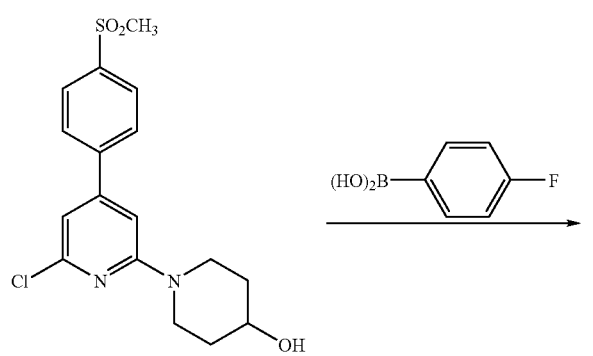

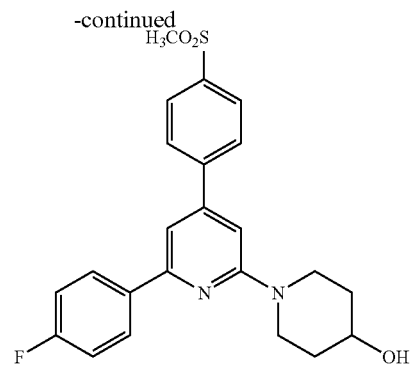

To 6'-chloro-4'-(4-methanesulfonyl-phenyl)-3,4,5,6-tetrahydro-2H-[1,2']bi-pyridinyl-4-ol (0.2197 g, 0.6 mmol) and 4-fluorophenyl boronic acid (0.1040 g, 0.72 mmol) dissolved in acetonitrile (4 mL) and THF (6 mL) and Na$_2$CO$_3$ (10 mL, 0.4M) was added palladium (0) tetrakis(triphenylphosphine) (0.0352 g, 0.03 mmol). The reaction mixture was stirred and refluxed for 12-18 hours under N$_2$. The reaction mixture was diluted with CH$_2$Cl$_2$ and filtered through Celite™, then rinsed with CH$_2$Cl$_2$. The filtrate was washed two times with water and one time with brine. The organic phase was collected and dried over potassium carbonate. The filtered sample was concentrated, and the resulting solid was dried for 12-18 hours under vacuum. Biotage Horizon HPFC system chromatography (SiO$_2$, 98:2 CH$_2$Cl$_2$:MeOH) yielded a yellow solid (235 mg, 92%).

M.P.: 111° C.

HPLC: Inertsil ODS-3V C18, 30:70 [KH$_2$PO$_4$(0.01M, pH 3.2):CH$_3$CN], 264 nm, R$_t$ 6.1 min, 97.3% purity;

$^1$H NMR: (600 MHz, CDCl$_3$, TMS, 55° C.): δ 1.61-1.67 (m, 3H), 2.01-2.04 (m, 2H), 3.09 (s, 3H), 3.97 (septet, J=3.6 Hz, 1H), 3.28-3.32 (m, 2H), 4.24 (dt, J=4.2, 13.8 Hz, 2H), 6.75 (dt, J=4.2, 13.8 Hz, 2H), 7.11-7.14 (m, 2H), 7.15 (s, 1H), 7.8 (d, J=9.0 Hz, 2H) 8.01-8.04 (m, 4H).

Mass Spec: (TOF MS ES+): m/z 427 (M+H, 100); HRMS (TOF MS ES+) Calcd for C$_{23}$H$_{23}$FN$_2$O$_3$S, [M+H] 427.1491. Found 427.1497.

Examples 83

Synthesis of 1-[4-(4-fluoro-phenyl)-6-(4-methane-sulfonyl-phenyl)-pyridin-2-yl]-4-methyl-piperazine (B41)

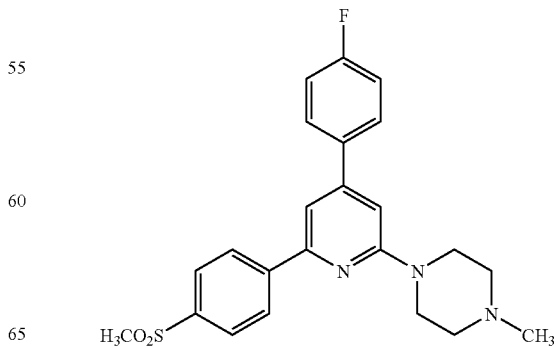

This compound was prepared by a procedure analogous to that disclosed in Example 82.

M.P. 151° C.

HPLC: Inertsil ODS-3V C18, 40:10:50 [KH$_2$PO$_4$ (0.01M, pH 3.2):CH$_3$CN:MeOH], 264 nm, R$_t$ 3.2 min, 97.1% purity.

$^1$H NMR: (600 MHz, CDCl$_3$, TMS, 55° C.): δ 2.39 (s, 3H), 2.59 (t, J=4.8 Hz, 4H), 3.09 (s, 3H), 3.75 (t, J=4.8 Hz, 4H), 6.81 (s, 1H), 7.18 (apt t, J=9.0 Hz, 2H), 7.3 (s, 1H), 7.61-7.63 (m, 2H), 8.02 (d, J=9.0 Hz, 2H), 8.24 (d, J=9.0 Hz, 2H).

Mass Spec: HRMS (TOF MS ES+) Calcd for C$_{23}$H$_{24}$FN$_3$O$_2$S$_3$, [M+H] 426.1651. Found 426.1648.

Example 84

Synthesis of 1-[6-(4-fluoro-phenyl)-4-(4-methane-sulfonyl-phenyl)-pyridin-2-yl]-4-methyl-piperazine (B42)

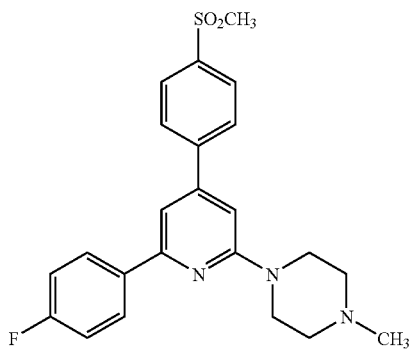

This compound was prepared by a procedure analogous to that disclosed in Example 82.

M.P.: 202° C.

HPLC: Inertsil ODS-3V C18, 40:10:50 [KH$_2$PO$_4$ (0.01M, pH 3.2):CH$_3$CN:MeOH], 264 nm, R$_t$ 3.3 min, 99.4% purity.

$^1$H NMR: (600 MHz, CDCl$_3$, TMS, 55° C.): δ 2.37(s, 3H), 2.57 (apt t, J=6.0 Hz, 4H), 3.09 (s, 3H), 3.73 (apt t, J=4.2 Hz, 4H), 6.73 (br s, 1H), 7.11-7.14 (m, 2H), 7.20 (br s, 1H), 7.80-7.81 (m, 2H), 8.02-8.04 (m, 4H).

Mass Spec: (TOF MS ES+): m/z 426 (M+H, 100); HRMS (TOF MS ES+) Calcd for C$_{23}$H$_{24}$FN$_3$O$_2$S, [M+H] 426.1651. Found 426.1662.

Example 85

Synthesis of {4-[2-(4-fluoro-phenyl)-6-(4-methyl-piperazin-1-yl)-pyridin-4-yl]-phenyl}-morpholin-4-yl-methanone (B43)

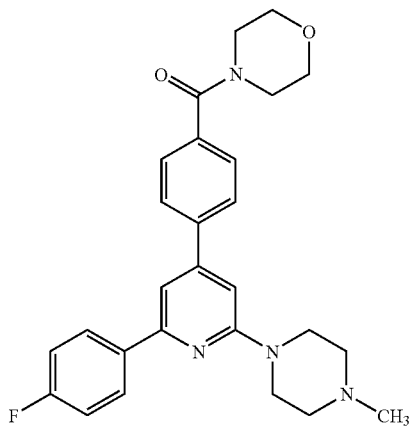

This compound was prepared by a procedure analogous to that disclosed in Example 82.

M.P.: 151° C.

HPLC: Inertsil ODS-3V C18, 40:10:50 [KH$_2$PO$_4$ (0.01M, pH 3.2):CH$_3$CN:MeOH], 264 nm, R$_t$ 0.1 min, 98.6% purity.

$^1$H NMR (600 MHz, CDCl$_3$, TMS, 55° C.): δ 2.86 (s, 3H), 2.58 (apt t, J=5.4 Hz, 4H), 3.51 (br s, 2H), 3.66 (br s, 2H), 3.74 (apt t, J=4.8 Hz, 4H), 3.81 (br s, 4H), 6.75 (s, 1H), 7.14 (d, J=8.4 Hz, 2H), 7.23 (s, 1H), 7.52 (d, J=7.8 Hz, 2H), 7.69 (d, J=8.4 Hz, 2H), 8.05 (dd, J=8.1, 5.4 Hz, 2H).

Mass Spec: (TOF MS ES+): m/z 461 (M+H, 100); HRMS (TOF MS ES+) Calcd for C$_{27}$H$_{29}$FN$_4$O$_2$, [M+H] 461.2353. Found 461.2373.

Example 86

Synthesis of 1-[6-(4-fluoro-phenyl)-4-(4-trifluoromethoxy-phenyl)-pyridin-2-yl]-4-methyl-piperazine (B44)

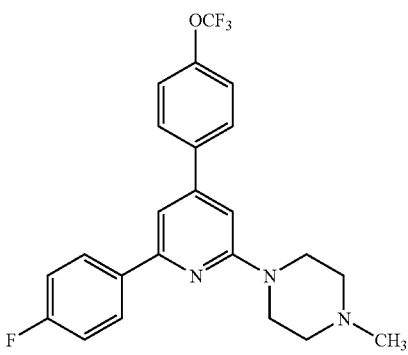

This compound was prepared by a procedure analogous to that disclosed in Example 82.

HPLC: Inertsil ODS-3V C18, 30:70 [KH$_2$PO$_4$ (0.01M, pH 3.2):CH$_3$CN], 264 nm, R$_t$ 3.0 min, 95.7% purity.

$^1$H NMR: (600 MHz, CDCl$_3$, TMS, 55° C.): δ 2.63 (s, 3H), 2.81 (apt t, J=4.8 Hz, 4H), 3.92 (apt t, J=5.4 Hz, 4H), 6.89 (s, 1H), 7.07 (s, 1H), 7.59 (d, J=7.8 Hz, 2H), 7.85-7.87 (m, 2H).

Mass Spec: (TOF MS ES+): m/z 372 (M+H, 100).

Example 87

Synthesis of 4',6'-bis-(4-fluoro-phenyl)-3,4,5,6-tetrahydro-2H-[1,2']bipyridinyl-4-ol (B54)

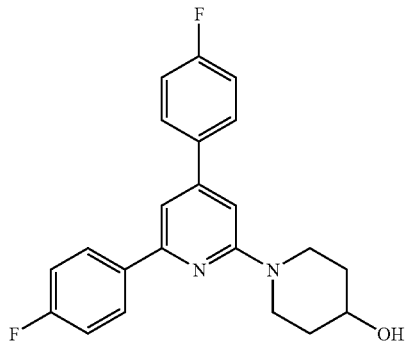

This compound was prepared by a procedure analogous to that disclosed in Example 82.

M.P.: 127° C.

HPLC: Inertsil ODS-3V C18, 30:70 [KH$_2$PO$_4$ (0.01M, pH 3.2):CH$_3$CN], 264 nm, R$_t$ 14.3 min, 97.2% purity.

$^1$H NMR: (600 MHz, CDCl$_3$, TMS, 55° C.): δ 1.49 (apt s, 1H), 1.61-1.67 (m, 2H), 2.01-2.04 (m, 2H), 3.25-3.29 (m, 2H), 3.95 (br s, 1H), 4.25 (dt, J=4.2, 13.2 Hz, 2H), 6.73 (s, 1H), 7.10-7.16 (m, 5H), 7.58-7.60 (m, 2H), 8.01-8.04 (m, 2H).

Mass Spec: (ES+): m/z 367 (M+H, 100); HRMS (TOF MS ES+) Calcd for C$_{22}$H$_{20}$F$_2$N$_2$O, [M+H] 367.1622. Found 367.1615.

Example 88

Synthesis of 2,4,6-tris-(4-fluoro-phenyl)-pyridine (B22)

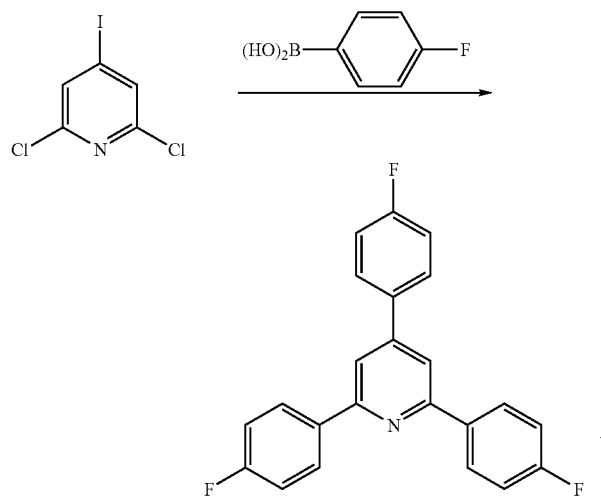

2,6-Dichloro-4-iodopyridine (0.13629 g, 0.5 mmol) and 4-fluorophenyl boronic acid (0.2098 g, 1.5 mmol) were dissolved in acetonitrile (20 mL) and Na$_2$CO$_3$ (20 mL, 0.4M) followed by addition of palladium (0) tetrakis(triphenylphosphine) (0.086 g, 0.075 mmol) to the mixture. The reaction mixture was allowed to stir and reflux for 12-18 hours. The reaction mixture was diluted with CH$_2$Cl$_2$ and filtered through Celite™, then rinsed with CH$_2$Cl$_2$. The filtrate was washed one time with water and one time with brine. The organic phase was collected and dried over potassium carbonate. The filtered sample was concentrated, and the resulting solid was dried for 12-18 hours under vacuum. Biotage Horizon HPFC system chromatography (SiO$_2$, 90:10 hexanes:ethyl acetate) yielded a dark brown solid product (169 mg, 94%).

M.P.: 198° C.

HPLC: Inertsil ODS-3V C18, 30:70 [KH$_2$PO$_4$ (0.01M, pH 3.2):CH$_3$CN], 264 nm, R$_t$ 71.8 min, 96.7% purity.

$^1$H NMR: (600 MHz, CDCl$_3$, TMS, 55° C.): δ 7.17-7.25 (m, 6H), 7.68-7.71 (m, 2H), 7.68 (s, 2H), 8.14-8.17 (m, 4H).

Mass Spec: (EI+): m/z 361 (M+, 100).

Example 89

Synthesis of 6'-chloro-4'-(4-methanesulfonyl-phenyl)-3,4,5,6-tetrahydro-2H-[1,2']-bipyridinyl-4-ol

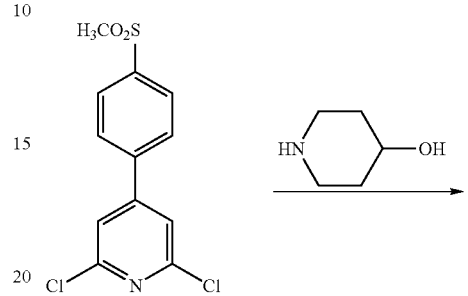

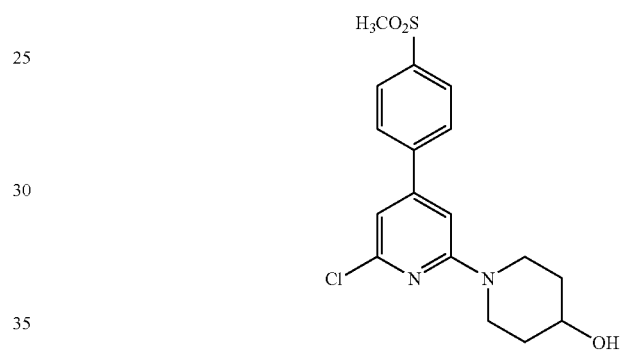

2,6-Dichloro-4-(4-methanesulfonyl-phenyl)-pyridine (0.3015 g, 1 mmol) and 4-hydroxypiperidine (0.1024 g, 1 mmol) were dissolved in DMF (5 mL) and potassium carbonate (0.1702 g, 1.2 mmol) was added. The reaction mixture was stirred and refluxed for 12-18 hours at 90° C. under N$_2$. The reaction mixture was diluted with CH$_2$Cl$_2$. The filtrate was washed three times with water and one time with brine. The organic phase was collected and dried over potassium carbonate. The filtered sample was concentrated, and the resulting solid was dried for 12-18 hours under vacuum. Biotage Horizon HPFC system chromatography (SiO$_2$, 93:6:1 CH$_2$Cl$_2$:MeOH:NH4OH) yielded a pale yellow solid (185 mg, 51%).

M.P.: 169° C.

HPLC: Inertsil ODS-3V C18, 30:70 [KH$_2$PO$_4$ (0.01M, pH 3.2):CH$_3$CN], 264 nm, R$_t$ 4.5 min, 96.5% purity.

$^1$H NMR: (600 MHz, CDCl$_3$, TMS, 55° C.): δ 1.53 (br s, 1H), 1.58-1.63 (m, 2H), 1.96-2.04 (m, 2H), 3.08 (s, 3H), 3.25-3.30 (m, 2H), 3.95-3.98 (m, 1H), 4.08 (dt, J=4.8, 9 Hz, 2H), 6.63 (d, J=1.2 Hz), 6.75 (d, J=1.2 Hz), 7.71-7.72 (m, 2H), 8.00-8.02 (m, 2H).

Mass Spec: (TOF MS ES+): m/z 367 (M+H, 100); HRMS (TOF MS ES+) Calcd for C$_{17}$H$_{19}$ClN$_2$O$_3$S, [M+H] 367.0883. Found 367.0883.

Example 90

Synthesis of 6'-chloro-4'-phenyl-3,4,5,6-tetrahydro-2H-[1,2']bipyridinyl-4-ol (B53)

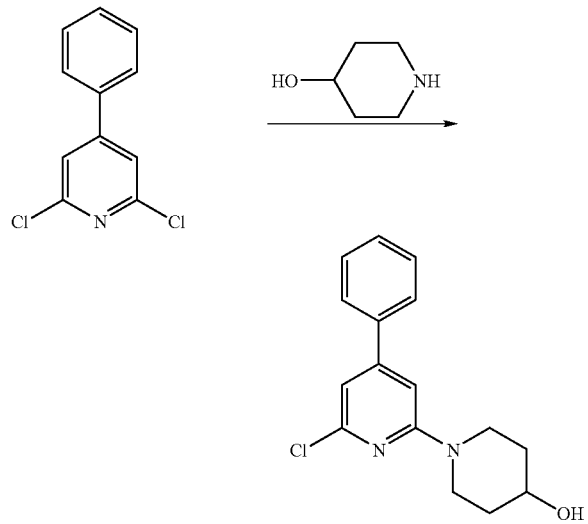

To 2,6-dichloro-4-phenyl-pyridine (448.7 mg, 2 mmol) dissolved in N,N-dimethylformamide (10 mL) was added 4-hydroxypiperidine (202.7 mg, 2 mmol) and potassium carbonate (332.5 mg, 2.4 mmol). The resulting mixture is allowed to stir at 90° C. for 12-18 hours. The sample was diluted in dichloromethane, washed two times with water, and washed one time with brine. The organic phase was dried over sodium sulfate and concentrated by rotary evaporation. The resulting sample was dried for 12-18 hours under vacuum. Purification (Biotage Horizon HPFC chromatography system, $SiO_2$, 50:50 hexanes:ethyl acetate) gave a beige solid product (377 mg, 65%).

M.P.: 82° C.

HPLC: Inertsil ODS-3V C18, 30:70 [$KH_2PO_4$ (0.01M, pH 3.2):$CH_3CN$], 264 nm, $R_t$ 8.8 min, 99.4% purity.

$^1$H NMR (600 MHz, $CDCl_3$, TMS): δ 1.59-1.63 (m, 2H), 1.97-2.00 (m, 2H), 3.22-3.26 (m, 2H), 3.95 (br s, 1H), 4.10 (apt dt, J=4.2, 9.0 Hz, 2H).

Mass Spec: (TOF MS ES+): m/z 289 (M+H).

Example 91

Synthesis of 1-[6-chloro-4-(4-fluoro-phenyl)-pyridin-2-yl]-4-methyl-piperazine

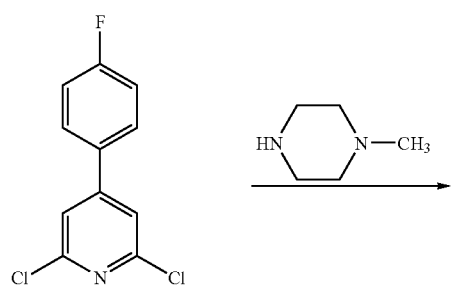

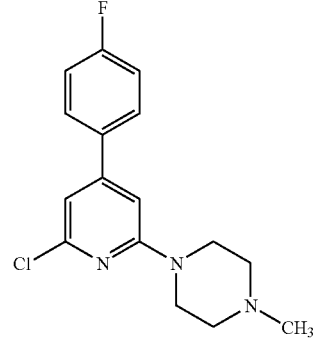

A solution of 2,6-dichloro-4-(4-fluorophenyl)-pyridine (0.480 g, 2 mmol) and 1-methylpiperizine (0.22 mL, 2 mmol) was prepared in DMF (10 mL) and potassium carbonate (0.3420 g, 2.4 mmol) was added to this solution. The reaction mixture was stirred and refluxed for 12-18 hours at 90° C. under an inert atmosphere ($N_2$). The reaction mixture was then diluted with $CH_2Cl_2$ and filtered. The filtrate was washed three times with water and one time with brine. The organic phase was collected and dried over potassium carbonate. This sample was filtered, the filtrate was concentrated, and the resulting solid was dried for 12-18 hours under vacuum. Biotage Horizon HPFC system chromatography ($SiO_2$, 93:6:1 $CH_2Cl_2$:MeOH:$NH_4OH$) yielded a pale green solid (173 mg, 29%).

M.P.: 60° C.

HPLC: Inertsil ODS-3V C18, 40:10:50 [$KH_2PO_4$ (0.01M, pH 3.2):$CH_3CN$:MeOH], 264 nm, $R_t$ 3.6 min, 98.9% purity.

$^1$H NMR: (600 MHz, $CDCl_3$, TMS, 55° C.): δ 2.33 (s, 3H), 2.5 (t, J=4.8 Hz, 4H), 3.61 (dt, J=5.4 Hz, 4H), 6.58 (s, 1H), 6.76 (s, 1H), 7.10-7.14 (m, 2H), 7.5-7.53 (m, 2H).

Mass Spec: (TOF MS ES+): m/z 306 (M+H, 100); HRMS (TOF MS ES+) Calcd for $C_{16}H_{17}ClFN_3$, [M+H] 306.1173. Found 306.1165.

Example 92

Synthesis of 1-[6-chloro-4-(4-methanesulfonyl-phenyl)-pyridin-2-yl]-4-methyl-piperazine (16)

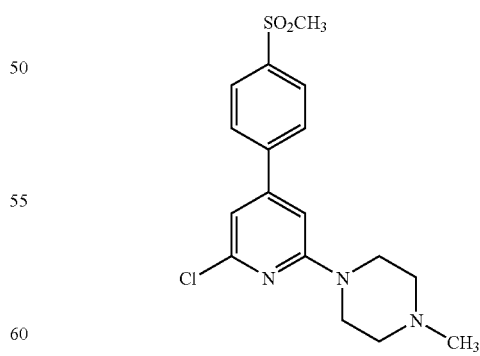

This compound was prepared by a procedure analogous to that disclosed in Example 91.

M.P.: 125° C:

HPLC: Zorbax Eclipse C18, 30:70 [Formic acid (0.01M):$CH_3CN$], 264 nm, $R_t$ 0.9 min, 100% purity.

¹H NMR: (600 MHz, CDCl₃, TMS, 55° C.): δ 2.35 (s, 3H), 2.52 (apt t, J=5.4 Hz, 4H), 3.09 (s, 3H), 4.8 (apt t, J=4.8 Hz, 4H), 6.62 (s, 1H), 6.79 (s, 1H), 7.73 (d, J=8.4 Hz, 2H), 8.02 (d, J=7.8 Hz, 2H).
Mass Spec: (TOF MS ES+): m/z 366 (M+H, 100).

Example 93

Synthesis of {4-[2-chloro-6-(4-methyl-piperazin-1-yl)-pyridin-4-yl]-phenyl}-morpholin-4-yl-methanone (18)

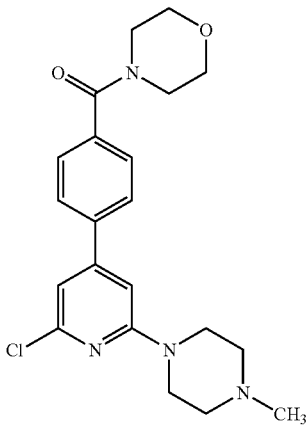

This compound was prepared by a procedure analogous to that disclosed in Example 91.
M.P.: 137° C.
HPLC: Inertsil ODS-3V C18, 40:10:50 [KH₂PO₄ (0.01M, pH 3.2):CH₃CN:MeOH], 264 nm, R_t 2.4 min, 99.8% purity;
¹H NMR (600 MHz, CDCl₃, TMS, 55° C.): δ 2.64 (s, 3H), 2.81 (t, J=5.4 Hz, 4H), 2.8-4.09 (br m, 12H), 6.92 (s, 1H), 7.09 (s, 1H), 7.78 (d, J=9 Hz, 2H), 7.89 (d, J=8.4 Hz, 2H).
Mass Spec: (TOF MS ES+): m/z 401 (M+H, 100).

Example 94

Synthesis of 1-[6-chloro-4-(4-trifluoromethoxy-phenyl)-pyridin-2-yl]-4-methyl-piperazine (20)

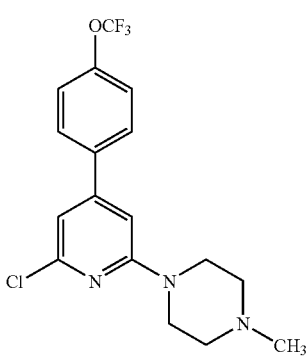

This compound was prepared by a procedure analogous to that disclosed in Example 91.
HPLC: Inertsil ODS-3V C18, 30:70 [KH₂PO₄ (0.01M, pH 3.2):CH₃CN], 264 nm, R_t 3.0 min, 95.7% purity.

¹H NMR: (600 MHz, CDCl₃, TMS, 55° C.): δ 2.63 (s, 3H), 2.81 (apt t, J=4.8 Hz, 4H), 3.92 (apt t, J=5.4 Hz, 4H), 6.89 (s, 1H), 7.07 (s, 1H), 7.59 (d, J=7.8 Hz, 2H), 7.85-7.87 (m, 2H).
Mass Spec: (TOF MS ES+): m/z 372 (M+H, 100).

Example 95

Synthesis of 6'-chloro-4'-(4-fluoro-phenyl)-3,4,5,6-tetrahydro-2H-[1,2']bipyridinyl-4-ol (28)

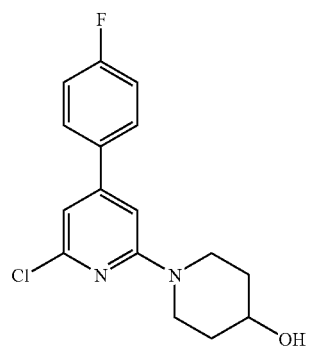

This compound was prepared by a procedure analogous to that disclosed in Example 91.
M.P.: 145° C.
HPLC: Inertsil ODS-3V C18, 30:70 [KH₂PO₄ (0.01M, pH 3.2):CH₃CN], 264 nm, R_t 8.5 min, 99.4% purity.
¹H NMR: (600 MHz, CDCl₃, TMS, 55° C.): δ 1.49 (apt s, 1H), 1.56-1.62 (m, 2H), 1.95-1.99 (m, 2H), 3.21-3.26 (m, 2H), 3.94 (septet, J=3.6 Hz, 1H), 4.08 (dt, J=4.8, 13.2 Hz, 2H), 6.60 (s, 1H), 6.73 (d, J=1.2 Hz, 1H), 7.10-7.14 (m, 2H), 7.49-7.53 (m, 2H).
Mass Spec: (ES+): m/z 307 (M+100).

Example 96

Synthesis of 1-[4,6-bis-(4-fluoro-phenyl)-pyridin-2-yl]-4-methyl-piperazine (B40)

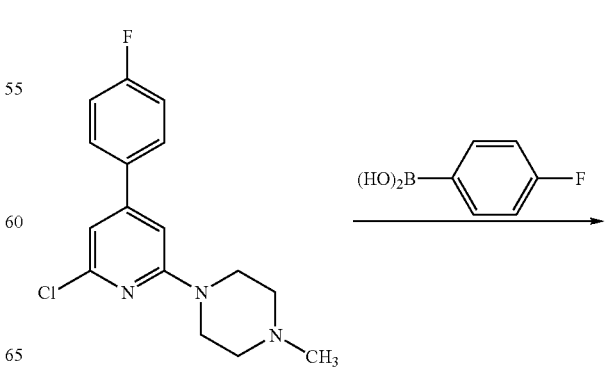

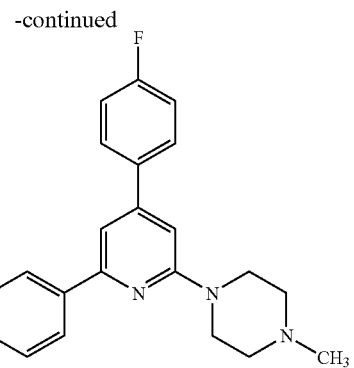

To 1-[6-chloro-4-(4-fluoro-phenyl)-pyridin-2-yl]-4-methyl-piperazine (0.157 g, 0.5 mmol) and 4-fluorophenyl boronic acid (0.0862 g, 0.6 mmol) dissolved in acetonitrile (5 mL) was added Na$_2$CO$_3$ (5 mL, 0.4M) followed by addition of palladium (0) tetrakis(triphenylphoshine) (0.0292 g, 0.025 mmol). This reaction was allowed to stir and reflux for 12-18 hours. The resulting mixture was diluted with CH$_2$Cl$_2$ and filtered through Celite™, then rinsed with CH$_2$Cl$_2$. The filtrate was washed one time with water and one time with brine. The organic phase was collected and dried over potassium carbonate. This sample was filtered, the filtrate was concentrated, and the resulting solid was dried for 12-18 hours under vacuum. Biotage Horizon HPFC system chromatography (SiO$_2$, 93:6:1 CH$_2$Cl$_2$:MeOH:NH$_4$OH) yielded a pale brown solid (125 mg, 67%).

M.P.: 102° C.

HPLC: Inertsil ODS-3V C18, 40:10:50 [KH$_2$PO$_4$ (0.01M, pH 3.2):CH$_3$CN:MeOH], 264 nm, R$_t$ 5.1 min, 96.5% purity.

$^1$H NMR: (600 MHz, CDCl$_3$, TMS, 55° C.): δ 2.38 (s, 3H), 2.58 (t, J=4.8 Hz, 4H), 3.73 (t, J=4.8 Hz, 4H), 6.72 (s, 1H), 7.11-7.18 (m, 4H), 7.21 (s, 1H), 7.6-7.63 (m, 2H), 8.03-8.06 (m, 2H).

Mass Spec: (TOF MS ES+): m/z 366 (M+H, 100); HRMS (TOF MS ES+) Calcd for C$_{22}$H$_{21}$F$_2$N$_3$, [M+H] 366.1782. Found 366.1793.

Example 97

Synthesis of 4-(3-fluoro-4-methoxy-phenyl)-pyridine (B1)

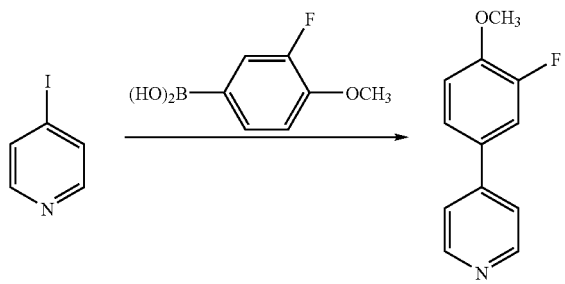

4-Iodopyridine (0.1031 g, 0.5 mmol) and 3-fluoro-4-methoxy phenyl boronic acid were (0.0852 g, 0.5 mmol) were dissolved in acetonitrile (5 mL) and Na$_2$CO$_3$ (5 mL, 0.4M) and then Pd(PPh$_3$)$_4$ (0.0291 g, 0.025 mmol) were added. The reaction mixture was stirred at reflux for 2.5 hours. The resulting suspension was filtered, and the filtrate was concentrated to about half the original volume. The precipitate was collected and washed with CH$_2$Cl$_2$ and water. The organic phase was collected and dried over potassium carbonate. The filtered sample was concentrated, and the resulting solid was dried for 12-18 hours under vacuum. Purification (Biotage Horizon HPFC chromatography system, SiO$_2$, 50:50 hexanes:ethyl acetate) yielded a light yellow solid (25 mg, 20%).

HPLC: Inertsil ODS-3V C18, 30:70 [KH$_2$PO$_4$ (0.01M, pH 3.2):CH$_3$CN], 264 nm, R$_t$ 4.0 min, 99.4% purity.

M.P.: 57° C.

$^1$H NMR (600 MHz, CDCl$_3$, 55° C.): δ 3.95 (s, 3H), 7.06 (t, J=8.4 Hz, 1H), 7.38-7.40 (m, 2H), 7.43-7.44 (m, 2H), 8.63 (d, J=5.6 Hz, 2H).

Mass Spec: m/z (EI) 203 (M+, 100).

Example 98

Synthesis of 2,6-bis-(3-fluoro-4-methoxy-phenyl)-pyridine (B12)

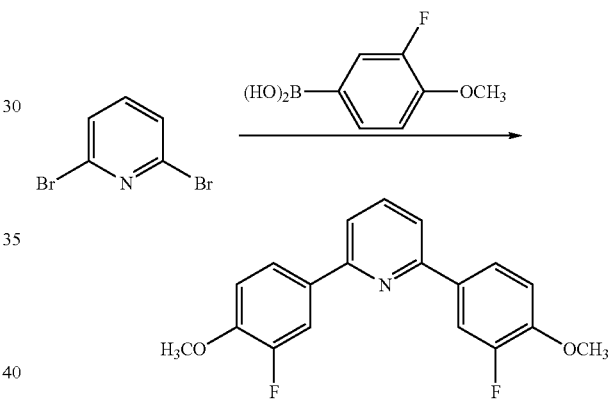

To 2,6-dibromopyridine (0.2405 g, 1.0 mmol) and 3-fluoro-4-methoxy phenyl boronic acid (0.3392 g, 2.0 mmol) dissolved in dimethoxy ethane (15 mL) and 2 M sodium carbonate (5 mL) was added tetrakis(triphenylphosphine)palladium(0) (0.0995 g, 0.086 mmol). The reaction mixture was stirred at reflux for 12-18 hours under nitrogen. The reaction was cooled, the reaction volatiles were evaporated, and dichloromethane and water were added to the residue. The organic extract layer was collected and dried over potassium carbonate, filtered, and the filtrate concentrated under vacuum. The resulting solid was collected and dried for 12-18 hours under vacuum. Purification (Biotage Horizon HPFC chromatography system, SiO$_2$, 70:30 hexanes:ethyl acetate) yielded a yellow solid (310 mg, 93%); HPLC: Inertsil ODS-3V C18, 30:70 [KH$_2$PO$_4$ (0.01M, pH 3.2):CH$_3$CN], 264 nm, R$_t$ 20.7 min, 98.0% purity; to give the product as a yellow solid (yield, 93%).

M.P.: 108° C.

$^1$H NMR (600 MHz, CDCl$_3$, 55° C.): δ 3.95 (s, 6H), 7.05 (t, J=8.4 Hz, 2H), 7.56 (d, J=13.2 Hz, 2H), 7.74 (t, J=7.8 Hz, 1H), 7.84 (d, J=7.84 Hz, 2H), 7.92 (dd, J=13.2, 1.8 Hz, 2H).

Mass Spec: (EI) m/z: 327 (M+, 100).

Example 99

Synthesis of (6-chloro-pyridine-2-yl)-(4-fluoro-phenyl)-amine

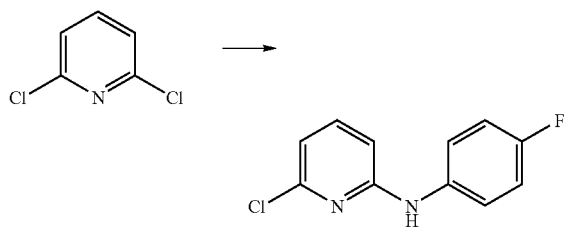

A solution of 2,6-dichloropyridine (2 g, 13.5 mmol) in toluene (24 mL) was prepared and 4-flouro-phenylamine (1.43 mL, 14.8 mmol) and potassium tert-butoxide (6.05 g, 54 mmol) were added to the mixture. This reaction mixture was subjected to microwave radiation at 1000 W for 1 minute, after which the mixture was cooled to room temperature. The reaction product was extracted into the ethyl acetate, which was washed with water. The organic layer was dried over sodium sulphate, filtered, and concentrated under vacuum. The product was purified by column chromatography using 230-400 mesh silica gel, eluting with 6:94 ethyl acetate: petroleum ether, to afford the desired compound as light yellow solid (1.24 g, yield, 41.6%).

$^1$H NMR (200 MHz, DMSO-d$^6$): δ 9.33 (s, 1H), 7.58 (m, 3H), 6.77 (d, 2H, J=7.2 Hz), 6.75 (d, 2H, J=8.0 Hz).

Mass Spec: (ES-MS) m/z: 223 (M$^+$+1, 100%).

IR (neat) cm$^{-1}$: 3258, 3173, 3063, 1595, 1418, 1214, 1160, 1096, 787.

Example 100

Synthesis of (4-fluoro-phenyl)-[6-trifluoromethoxyphenyl)-pyridin-2-yl]-amine (B70)

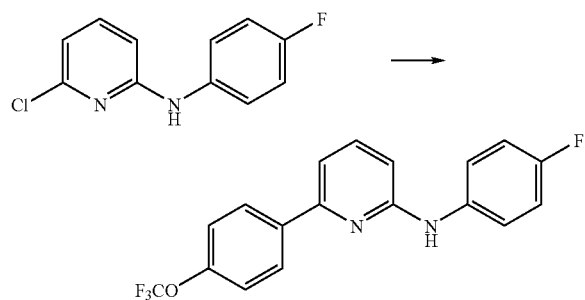

To a solution of (6-chloro-pyridine-2-yl)-(4-fluoro-phenyl)amine (2 g, 9 mmol) in 1,4-dioxane (25 mL) was added potassium carbonate (4.98 g, 36 mol) and tetrakis (triphenylphosphine)palladium(0) (11.6 mg, 0.45 mmol) followed by 4-trifluoro methoxy phenylboronicacid (2.04 g, 9.0 mmol). This reaction mixture was refluxed for 12 hours, after which water added to the mixture (200 mL) and the product was extracted with ethyl acetate. The organic layer was dried over sodium sulphate, filtered, and the filtrate was concentrated under vacuum. The resulting product was purified through column chromatography using 230-400 mesh silica gel, eluting with 20:80 ethyl acetate:DCM, to afford the desired compound as a light yellow solid (1.78 g, yield 56.7%, purity 98.62%).

M.P.: 72-74° C.

$^1$H NMR(400 MHz, DMSO-d$_6$): δ 9.16 (s, 1H), 8.15 (d, 2H, J=6.8, 2.1 Hz due to flourocoupling), 7.75 (d, 2H, J=7.9, 2.1 Hz due to fluorocoupling), 7.74 (t, 1H, J=3.0 Hz), 7.3 (d, 1H, J=6.98 Hz), 7.4 (d, 1H, J=8.8 Hz), 7.12 (d, 2H, J=4.9, 2.4 Hz due to fluoro coupling), 6.83 (d, 2H, J=6.7, 2.4 Hz due to fluoro coupling).

Mass Spec: CI-MS m/z: 349 (M$^+$+1, 100%).

IR (neat) cm$^{-1}$: 3417, 2927, 1578, 1509, 1455, 1220, 1165, 1016, 829, 790.

Example 101

Synthesis of 2-chloro-4-(3-fluoro-4-methoxy-phenyl)-pyridine (B2)

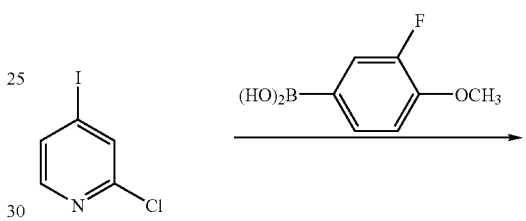

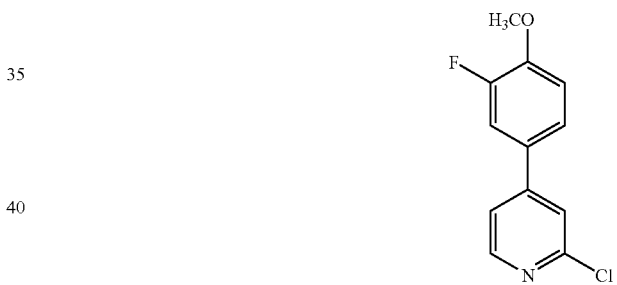

2-Chloro-4-iodopyridine (2.392 g, 10 mmol) and 3-fluoro-4-methoxy phenyl boronic acid (1.710 g, 10 mmol) were dissolved in acetonitrile (60 mL) and 0.4 M sodium carbonate (60 mL), followed by the addition of tetrakis(triphenylphosphine)palladium(0) (0.577 g, 5.0 mmol). The reaction mixture was stirred at reflux for 2.5 hour. The resulting suspension was filtered and the filtrate was concentrated to about half its original volume. The precipitate that formed was collected and washed with dichloromethane and water. The organic phase was collected and dried over potassium carbonate. The filtered sample was concentrated, and the resulting solid was dried for 12-18 hours under vacuum. Purification (Biotage Horizon HPFC chromatography system, SiO$_2$, 80:20 hexanes:ethyl acetate) yielding an off-white solid (2.03 g, 86%); HPLC: Inertsil ODS-3V C18, 30:70 [KH$_2$PO$_4$ (0.01M, pH 3.2):CH$_3$CN], 264 nm, R$_t$ 7.9 min, 99% purity.

M.P.: 104° C.

$^1$H NMR (600 MHz, CDCl$_3$): δ 3.94 (s, 3H), 7.05 (t, J=8.4 Hz, 1H), 7.33-7.36 (m, 3H), 7.46 (s, 1H), 8.38 (d, J=4.8 Hz, 1H).

Mass Spec: m/z (EI) 237(M+, 100).

Example 102

Synthesis of 2-chloro-4-phenyl-pyridine (B4)

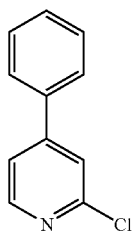

This compound was prepared by a procedure analogous to that disclosed in Example 101. The filtered sample was concentrated, and the resulting solid was dried overnight under vacuum. Biotage Horizon HPFC chromatography system (SiO$_2$, 80:20 hexanes:ethyl acetate) yielded an off-white solid (260 mg, 63%); HPLC: Inertsil ODS-3V C18, 30:70 [KH$_2$PO$_4$ (0.01M, pH 3.2):CH$_3$CN], 264 nm, R$_t$ 8.7 min, 99.9% purity.

M.P.: 61° C.

$^1$H NMR (600 MHz, CDCl$_3$, 55° C.): δ 7.41 (dd, J=4.8, 0.6 Hz, 1H), 7.44-7.49 (m, 3H), 7.53 (s, 1H), 7.60 (d, J=7.2 Hz, 2H), 8.42 (d, J=5.4 Hz, 1H).

Mass Spec: m/z (EI): 189 (M+, 100).

Example 103

Synthesis of 2-chloro-4-(3,4-difluoro-phenyl)-pyridine (B6)

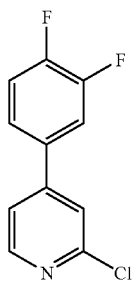

This compound was prepared by a procedure analogous to that disclosed in Example 101. Purification (Biotage Horizon HPFC chromatography system, SiO$_2$, 80:20 hexanes:ethyl acetate) yielded a light yellow solid (94 mg, 82%); HPLC: Inertsil ODS-3V C18, 30:70 [KH$_2$PO$_4$ (0.01M, pH 3.2):CH$_3$CN], 264 nm, R$_t$ 8.9 min, 98.9% purity.

M.P.: 167° C.

$^1$H NMR (600 MHz, CDCl$_3$): δ 7.25-7.30 (m, 1H), 7.33-7.35 (m, 2H), 7.40-7.43 (m, 1H), 7.46 (apt s, 1H), 8.43 (d, J=5.4 Hz, 1H).

Mass Spec: EI (m/z) 225 (M+, 100).

Example 104

Synthesis of 2-chloro-4-(4-methanesulfonyl-phenyl)-pyridine (B8)

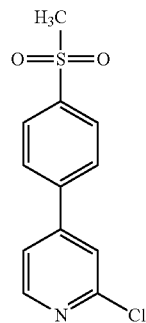

This compound was prepared by a procedure analogous to that disclosed in Example 101. Purification (Biotage Horizon HPFC chromatography system, SiO$_2$, 50:50 hexanes: ethyl acetate) yielded a off white solid (79 mg, 58%); HPLC: Inertsil ODS-3V C18, 30:70 [KH$_2$PO$_4$ (0.01M, pH 3.2):CH$_3$CN], 264 nm, R$_t$ 4.4 min, 99.8% purity.

M.P.: 112° C.

$^1$H NMR (600 MHz, CDCl$_3$): δ 3.09 (s, 3H), 7.43 (dd, J=5.4, 1.8 Hz, 1H), 7.55 (apt s, 1H), 7.78-7.80 (m, 2H), 8.06-8.07 (m, 2H), 8.50 (d, J=5.4 Hz, 1H).

Mass Spec: EI (m/z) 267 (M+, 100).

Example 105

Synthesis of 2-chloro-4-(3-methanesulfonyl-phenyl)-pyridine (B9)

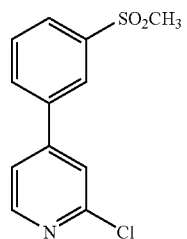

This compound was prepared by a procedure analogous to that disclosed in Example 101. The filtered sample was concentrated, and the resulting solid was dried overnight under vacuum. Purification (Biotage Horizon HPFC chromatography system, SiO$_2$, 50:50 hexanes:ethyl acetate) yielded a light brown solid (72 mg, 53%); HPLC: Inertsil ODS-3V C18, 30:70 [KH$_2$PO$_4$ (0.01M, pH 3.2):CH$_3$CN], 264 nm, R$_t$ 4.5 min, 99.7% purity.

M.P.: 130° C.

$^1$H NMR (600 MHz, CDCl$_3$, 55° C.): δ 3.00 (s, 3H), 7.44 (dd, J=5.4, 1.2 Hz, 1H), 7.56 (app d, J=0.6 Hz, 1H), 7.71 (t, J=7.2 Hz, 1H), 7.86-7.88 (m, 1H), 8.02-8.04 (m, 1H), 8.171-8.177 (m, 1H), 8.48 (d, J=5.4 Hz, 1H).

Mass Spec: EI (m/z): 267 (M+, 100).

Example 106

Synthesis of 4-benzo[1,3]dioxol-5-yl-2-chloro-pyridine (B10)

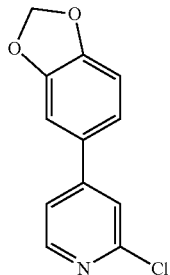

This compound was prepared by a procedure analogous to that disclosed in Example 101. Purification by column chromatography (Biotage Horizon HPFC system, $SiO_2$, 80:20 hexanes:ethyl acetate) gave a colorless solid (0.275 g, 78%); HPLC: Inertsil ODS-3V C18, 30:70 [$KH_2PO_4$ (0.01M, pH 3.2):$CH_3CN$], 264 nm, $R_t$ 7.475 min, 99.86% purity.

M.P.: 148-149° C.

$^1$H NMR (600 MHz, $CDCl_3$): δ 6.03 (s, 2H), 6.9 (d, J=7.8 Hz, 1H), 7.07 (d, J=1.2 Hz, 1H), 7.10 (dd, J=7.8, 1.8 Hz, 1H), 7.33 (dd, J=5.4, 1.2 Hz, 1H), 7.45 (d, J=1.2 Hz, 1H), 8.37 (d, J=4.8 Hz, 1H).

Mass Spec: EI (m/z) 233 (M+H, 100), 232 (64), 234(40), 235(42), 140 (23), 113 (11), 99(23).

Example 107

Synthesis of 2-chloro-4-(4-trifluoromethoxy-phenyl)-pyridine (3)

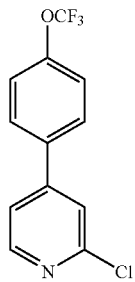

This compound was prepared by a procedure analogous to that disclosed in Example 101. Biotage Horizon HPFC system chromatography ($SiO_2$, 80:20 hexanes:ethyl acetate) yielded a pale yellow solid (1.02 g, 74%).

M.P.: 44° C.

HPLC: Inertsil ODS-3V C18, 30:70 [$KH_2PO_4$ (0.01M, pH 3.2):$CH_3CN$], 264 nm, $R_t$ 12.8 min, 99.9% purity.

$^1$H NMR (600 MHz, $CDCl_3$, TMS, 55° C.): δ 7.33 (d, J=7.8 Hz, 2H), 7.39 (dd, J=4.8, 1.8 Hz, 1H), 7.5 (apt d, J=1.2 Hz, 1H), 7.61-7.64 (m, 2H), 8.44 (d, J=5.4 Hz, 1H).

Mass: (EI+): m/z 273 (M+, 100).

Example 108

Synthesis of 4-(3-fluoro-4-methoxy-phenyl)-2-phenyl-pyridine (B3)

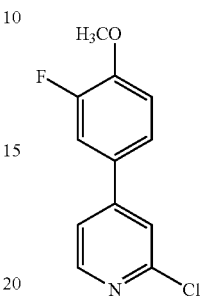 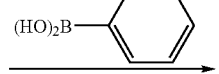

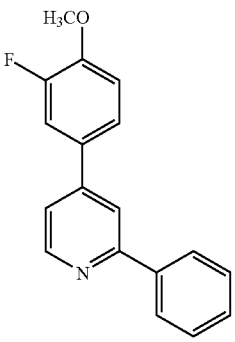

2-Chloro-4-(3-chloro-4-methoxy-phenyl)-pyridine (0.118 g, 0.5 mmol) and phenyl boronic acid (0.0655 g, 0.5 mmol) were dissolved in acetonitrile (5 mL), and 0.4M sodium carbonate (5 mL) and tetrakis(triphenylphosphine)palladium(0) (0.0288 g, 0.025 mmol) were added thereto. The reaction mixture was stirred at reflux for 12-18 hours. The resulting suspension was filtered and the filtrate was concentrated to about half its original volume. The precipitate was collected and washed with dichloromethane and water, and the organic phase was collected and dried over potassium carbonate. The filtered sample was then concentrated, and the resulting solid was dried for 12-18 hours under vacuum. Purification (Biotage Horizon HPFC chromatography system, $SiO_2$, 80:20 hexanes:ethyl acetate) yielded an off-white solid (90 mg, 65%); HPLC: Inertsil ODS-3V C18, 30:70 [$KH_2PO_4$ (0.01M, pH 3.2):$CH_3CN$], 264 nm, $R_t$ 11.3 min, 98.9% purity; to give the product as an off-white solid (yield 65%).

M.P.: 84° C.

$^1$H NMR (600 MHz, $CDCl_3$, 55° C.): δ 3.95 (s, 3H), 7.07 (t, J=8.4 Hz, 1H), 7.37 (dd, J=5.4, 1.8 Hz, 1H), 7.41-7.45 (m, 3H), 7.48 (t, J=7.2 Hz, 2H), 7.85 (s, 1H), 8.04 (d, J=7.2 Hz, 2H), 8.70 (d, J=5.4 Hz, 1H).

Mass Spec: EI (m/z): 279 (M+, 100).

Example 109

Synthesis of 2-(3-fluoro-4-methoxy-phenyl)-4-phenyl-pyridine (B5)

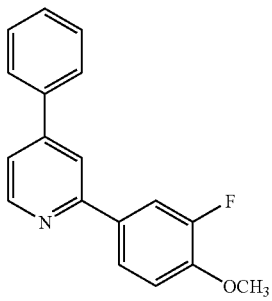

This compound was prepared by a procedure analogous to that disclosed in Example 108. Purification (Biotage Horizon HPFC chromatography system, $SiO_2$, 80:20 hexanes:ethyl acetate) yielded a white solid (95 mg, 53%); HPLC: Inertsil ODS-3V C18, 30:70 [$KH_2PO_4$(0.01M, pH 3.2):$CH_3CN$], 264 nm, $R_t$ 13.2 min, 98.9% purity.

M.P.: 58° C.

$^1$H NMR (600 MHz, CDCl$_3$, 55° C.): δ 3.95 (s, 3H), 7.06 (t, J=9 Hz, 1H), 7.41 (dd, J=5.4, 1.2 Hz, 1H), 7.44-7.46 (m, 1H), 7.49-5.51 (m, 2H), 7.67-7.68 (m, 2H), 7.80-7.82 (m, 1H), 7.83-7.86 (m, 2H), 8.70 (d, J=5.4 Hz, 1H).

Mass Spec: EI (m/z): 279 (M+, 100).

Example 110

Synthesis of 4-(3,4-difluoro-phenyl)-2-phenyl-pyridine (B7)

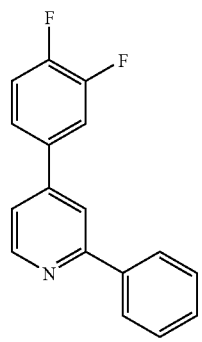

This compound was prepared by a procedure analogous to that disclosed in Example 108. Purification (Biotage Horizon HPFC chromatography system, $SiO_2$, 100% $CH_2Cl_2$) yielded a white solid (42 mg, 51%); HPLC: Inertsil ODS-3V C18, 30:70 [$KH_2PO_4$ (0.01M, pH 3.2):$CH_3CN$], 264 nm, $R_t$ 14.3 min, 99.7% purity.

M.P.: 92° C.

$^1$H NMR (600 MHz, CDCl$_3$): δ 7.27-7.31 (m, 1H), 7.37 (dd, J=5.4, 2.4 Hz, 1H), 7.40-7.45 (m, 2H), 7.48-7.51 (m, 3H), 7.841-7.843 (m, 1H), 8.02-8.03 (m, 2H), 8.74 (d, J=4.8 Hz, 1H).

Mass Spec: EI (m/z): 267 (M+, 100).

Example 111

Synthesis of 4-benzo[1,3]dioxol-5-yl-2-phenyl-pyridine (B11)

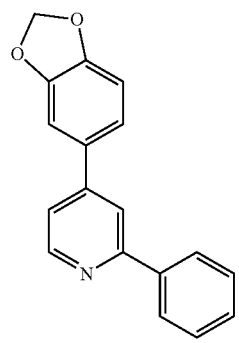

This compound was prepared by a procedure analogous to that disclosed in Example 108. Purification by column chromatography (Biotage Horizon HPFC system, $SiO_2$, 80:20 hexanes:ethyl acetate) gave a colorless solid (0.110 g, 62.5%); HPLC: Inertsil ODS-3V C18, 30:70 [$KH_2PO_4$ (0.01M, pH 3.2):$CH_3CN$], 264 nm, $R_t$ 10.2 min, 97.72% purity.

M.P.: 87-88° C.

$^1$H NMR (600 MHz, CDCl$_3$): δ 6.04 (s, 2H), 6.94 (d, J=7.8 Hz, 1H), 7.17 (apt d, J=1.8 Hz, 1H), 7.20 (dd, J=8.4, 2.4 Hz, 1H), 7.37 (dd, J=7.1, 1.8 Hz, 1H), 7.42-7.46 (m, 1H, 7.49 (t, J=10.2 Hz, 2H), 7.85 (s, 1H), 8.03 (d, J=7.2 Hz, 2H), 8.7 (d, J=5.4 Hz, 1H).

Mass Spec: EI (m/z): 275 (M+, 100).

Example 112

Synthesis of (3-chloro-4-methoxy-phenyl)-(2-chloropyridin-4-yl)-amine

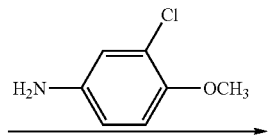

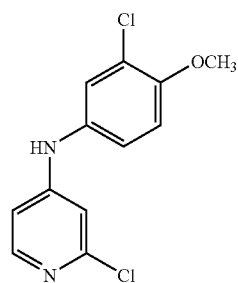

To 2-chloro-4-iodo pyridine (1.4429 g, 6 mmol) and 3-chloro-p-anisidine (1.13 g, 7.2 mmol) dissolved in dry toluene (20 mL) were added tris(dibenzylideneacetone)dipalladium (0) (0.1095 g, 0.12 mmol), 1,3-bis(diphenylphospino)propane (0.0991 g, 0.24 mmol), and sodium-tert-butoxide (0.8093 g, 8.4 mmol). The reaction mixture was stirred at reflux for 12-18 hours under $N_2$. The reaction mixture was diluted with $CH_2Cl_2$ and filtered through Celite™, then rinsed with $CH_2Cl_2$. The filtrate was washed two times with water and one time with brine. The organic phase was collected and dried over potassium carbonate. The filtered sample was concentrated, and the resulting solid was dried for 12-18 hours under vacuum. Biotage Horizon HPFC system chromatography ($SiO_2$, 50:50 hexanes:ethyl acetate) yielded a brown solid (780 mg, 48%).

M.P.: 135° C.

HPLC: Inertsil ODS-3V C18, 30:70 [$KH_2PO_4$ (0.01M, pH 3.2):$CH_3CN$], 264 nm, $R_t$ 6.2 min, 99.2% purity.

$^1$H NMR: (300 MHz, $CDCl_3$, TMS,): δ 3.92 (s, 3H), 6.02 (s, 1H), 6.57 (dd, J=2.1, 5.7 Hz, 1H), 6.65 (d, J=2.1 Hz, 1H), 6.95 (d, J=8.7 Hz, 1H), 7.09 (dd, J=2.4, 6.3 Hz, 1H), 7.25 (t, J=2.7 Hz, 1H), 8.01 (t, J=5.7 Hz, 1H).

Mass Spec: LC-MSD (ES+): m/z 269 (M+H, 100).

Example 113

Synthesis of (2-chloro-pyridin-4-yl)-(4-fluoro-3-methoxy-phenyl)-amine (B18)

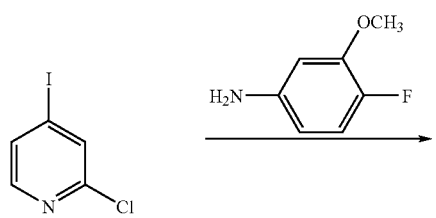

2-Chloro-4-iodopyridine (340.4 mg, 1.42 mmol) was dissolved in anhydrous toluene (15 mL), after which 4-fluoro-3-methoxyaniline (241.4 mg, 1.7 mmol), tris(dibenzylidineacetone)dipalladium(0) (26.5 mg, 0.028 mmol), 1,3-bis(diphenylphosphino)propane (23 mg, 0.06 mmol), and sodium-tert-butoxide (191.9 mg, 2.0 mmol) were added to the solution. This reaction mixture was stirred at reflux for 12-18 hours, after which the reaction was diluted in dichloromethane and filtered through Celite™. The Celite™ was washed with dichloromethane, and the resulting solution was concentrated to afford the product. This solid was collected and dried for 12-18 hours under vacuum. Purification (Biotage Horizon HPFC chromatography system, $SiO_2$, 90:9:1 dichloromethane:methanol:ammonium hydroxide) yielded a light brown solid (18, 169 mg, 47%); HPLC: Inertsil ODS-3V C18, 30:70[$KH_2PO_4$ (0.01M, pH 3.2): $CH_3CN$], 264 nm, $R_t$ 5.2 min, 93.6% purity.

M.P.: 89° C.

$^1$H NMR (600 MHz, $CDCl_3$): δ 3.68 (s, 3H), 6.08 (s, 1H), 6.60 (dd, J=5.6, 2.4 Hz, 1H), 6.69 (d, J=1.8 Hz, 1H), 6.71 (dt, J=8.4, 3.6 Hz, 1H), 6.78 (dd, J=7.8, 1.8 Hz, 1H) 7.08 (dd, J=10.8, 8.4 Hz, 1H), 8.01 (d, J=6 Hz, 1H).

Mass Spec: ES (m/z): 256 (45.9), 255 (24.4), 253 (M+H, 100).

Example 114

Synthesis of (2-chloro-pyridin-4-yl)-(3-fluoro-4-methoxy-phenyl)-amine (30)

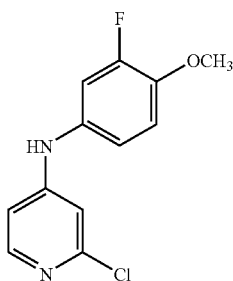

This compound was prepared by a procedure analogous to that disclosed in Example 113.

Example 115

Synthesis of 3-chloro-4-methoxy-phenyl)-(2-phenyl-pyridin-4-yl)-amine (B19)

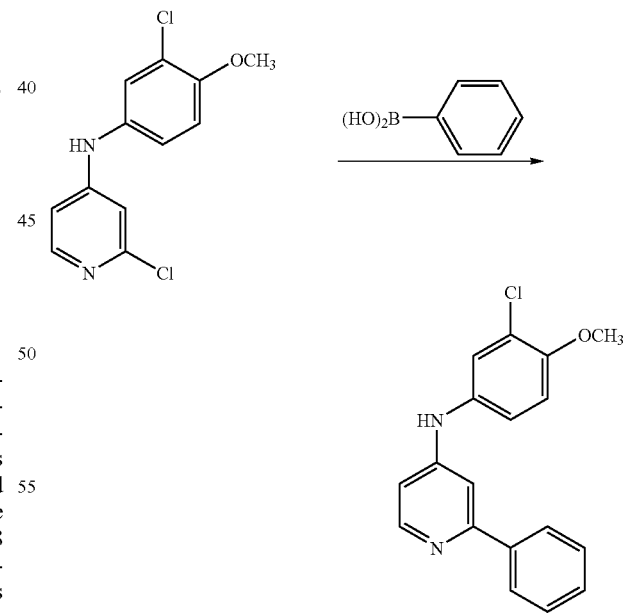

To (3-chloro-4-methoxy-phenyl)-(2-chloro-pyridin-4-yl)-amine (0.3241 g, 1.2 mmol) and phenyl boronic acid (0.1762 g, 1.44 mmol) dissolved in acetonitrile (15 mL) and $Na_2CO_3$ (15 mL, 0.4M) was added palladium (0) tetrakis(triphenylphosphine) (0.0699 g, 0.06 mmol). The reaction mixture was stirred and refluxed for 12-18 hours under $N_2$. The reaction was monitored by TLC; then additional palladium (0) tetrakis(triphenylphosphate) (0.0699 g, 0.06 mmol) was added and refluxed for 12-18 hours. The reaction mixture was diluted with CH$_2$Cl$_2$ and filtered through Celite™, then rinsed with CH$_2$Cl$_2$. The filtrate was washed one time with water and one time with brine. The organic phase was collected and dried over potassium carbonate. The filtered sample was concentrated, and the resulting solid was dried for 12-18 hours under vacuum. Biotage Horizon HPFC system chromatography (SiO$_2$, 50:50 hexanes:ethyl acetate) yielded a white solid product (270 mg, 72% yield).

M.P.: 160° C.

HPLC: Inertsil ODS-3V C18, 30:70 [KH$_2$PO$_4$(0.01M, pH 3.2):CH$_3$CN], 264 nm, R$_t$ 3.3 min, 97.4% purity.

$^1$H NMR: (300 MHz, CDCl$_3$, TMS,): δ 3.92 (s, 3H), 5.99 (s, 1H), 4.43 (dd, J=2.0, 5.7 Hz, 1H), 6.95(d, J=8.7 Hz, 1H), 7.08-7.15 (m, 2H), 7.29 (dd, J=2.7 Hz, 1H), 7.38-7.43 (m, 3H), 7.86-7.90 (m, 2H), 8.36 (d, J=5.7 Hz, 1H).

Mass Spec: HRMS (TOF MS ES+), calcd for C$_{18}$H$_{15}$ClN$_2$O [M+H] 311.0951. Found 311.0948.

Example 116

Synthesis of N$^2$-cyclohexylmethyl-N$^4$-(3-fluoro-4-methoxy-phenyl)-pyridine-2,4-diamine (B72)

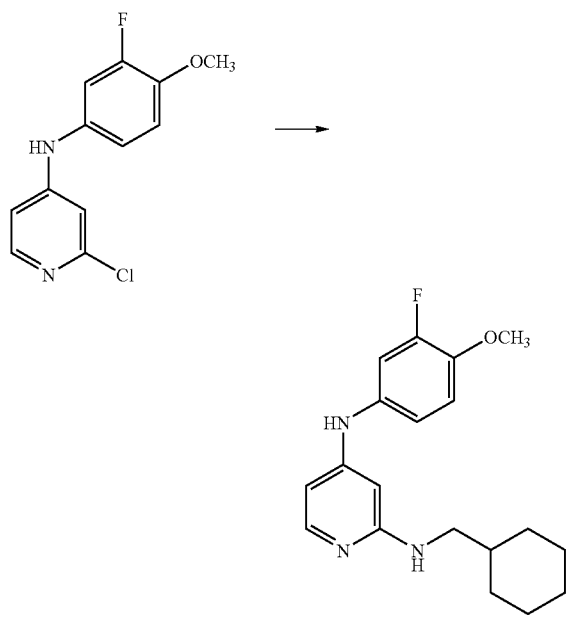

In a dry round bottom flask, tris(dibenzylideneacetone)dipalladium (18.7 mg, 0.16 mmol), sodium-tert-butoxide (144.0 mg, 1.5 mmol) and (2-chloro-pyridin-4-yl)-(3-fluoro-4-methoxy-phenyl)-amine (238.8 mg, 0.95 mmol) were dissolved in 10 mL of anhydrous toluene. Nitrogen was blown over the mixture for about 10 minutes. The ligand, 2,8,9-triisobutyl-2,5,8,9-tetraaza-1-phosphabicyclo-[3.3.3]undecane (0.03 mL, 0.08 mmol) and cyclohexanemethylamine (0.16 mL, 1.3 mmol) were dissolved in 3 mL of dry toluene. The ligand/amine mixture was added to the reaction flask, and the resulting mixture was allowed to stir at reflux for 12-18 hours. The reaction mixture was diluted with dichloromethane and filtered through Celite™. The Celite™ was washed with dichloromethane and the sample was concentrated by rotary evaporation. The resulting solid was dried for 12-18 hours under vacuum. Flash column chromatography (SiO$_2$, 50:50 hexanes:ethyl acetate) gave a light yellow solid (94 mg, 30%).

M.P.: 58° C.

HPLC: Inertsil ODS-3V C18, 30:70 [KH$_2$PO$_4$ (0.01M, pH 3.2):CH$_3$CN], 264 um, R$_t$ 3.5 min, 98.8% purity.

$^1$H NMR (600 MHz, CDCl$_3$, TMS): δ 0.96-1.03 (m, 2H), 1.15-1.26 (m, 3H), 1.57-1.83 (m, 6H), 3.14 (t, J=6.0 Hz, 2H), 3.92 (s, 3H), 4.65 (br s, 1H), 6.45 (s, 1), 6.70 (d, J=5.4 Hz, 1H), 7.00-7.03 (m, 1H), 7.29-7.34 (m, 2H), 8.07 (d, J=5.4 Hz, 1H).

Mass Spec: (TOF MS ES+): m/z 316 (44.3), 315 (M+H, 100).

Example 117

Synthesis of (3-fluoro-4-methoxy-phenyl)-(4-phenyl-pyridin-2-yl)-amine

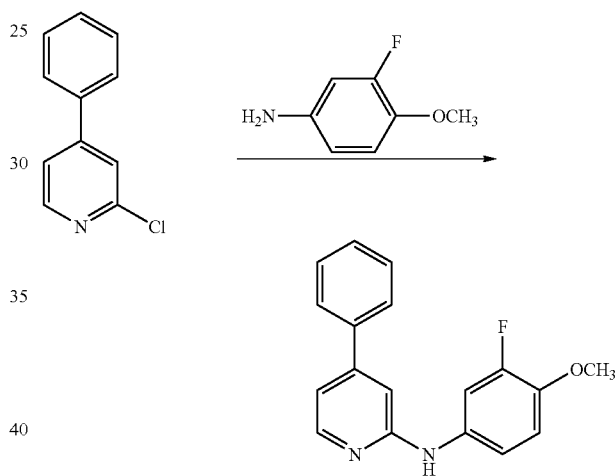

To a dry 50 mL round bottomed flask were added tris(dibenzylidineacetone)dipalladium(0) (0.019 g, 0.021 mmol) and sodium-tert-butoxide (0.151 g, 1.57 mmol), under a nitrogen atmosphere. 2,8,9-Triisobutyl-2,5,8,9-tetraaza-1-phospha-bicyclo[3.3.3]undecane (0.028 g, 0.084 mmol), 2-chloro-4-phenyl pyridine (0.2 g, 1.05 mmol), and 3-fluoro-p-anisidine (0.177 g, 1.26 mmol) were added to the reaction consecutively, followed by dry toluene (8 mL). This reaction mixture was heated at 80° C. for 15 hours, and then at reflux for an additional 22 hours. The crude reaction mixture was filtered through Celite™, which was washed with toluene. The resulting organic layer was concentrated to dryness and the product was purified by column chromatography (Biotage Horizon HPFC system, SiO$_2$, 80:20 hexanes:ethyl acetate) gave a pale brown solid (0.142 g, 46%); HPLC: Inertsil ODS-3V C18, 30:70 [KH$_2$PO$_4$ (0.01M, pH 3.2):CH$_3$CN], 264 nm, R$_t$ 8.3 min, 99.3% purity.

M.P.: 139-140° C.

$^1$H NMR (600 MHz, CDCl$_3$): δ 3.89 (s, 3H), 6.61 (s, 1H), 6.91 (s, 1H), 6.94-6.96 (m, 2H), 7.05 (apt d, J=9 Hz, 1H), 7.26 (dd, J=7.2, 3 Hz, 1H), 7.41-7.46 (m, 3H), 7.56 (d, J=6.6 Hz, 2H), 8.23 (d, J=5.4 Hz, 1H).

Mass Spec: ES (m/z): 295 (M+H, 100).

Example 118

Synthesis of cycloheptyl-[4-(3-fluoro-4-methoxy-phenyl)-pyridin-2-yl]-amine (B14)

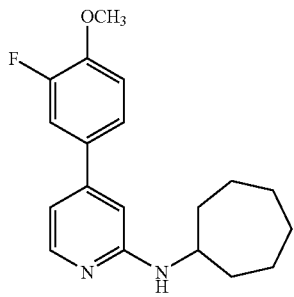

This compound was prepared by a procedure analogous to that disclosed in Example 117. Purification (Biotage Horizon HPFC chromatography system, SiO$_2$, 50:50 hexanes:ethyl acetate) yielded an off-white solid (203.6 mg, 65%); HPLC: Inertsil ODS-3V C18, 30:70[KH$_2$PO$_4$ (0.01M, pH 3.2):CH$_3$CN], 264 nm, R$_t$ 3.2 min, 97.5% purity.

M.P.: 94° C.

$^1$H NMR (600 MHz, CDCl$_3$, 55° C.): δ 1.54-1.72 (m, 10H), 2.03-2.07 (m, 2H), 3.82-3.85 (m, 1H), 3.94 (s, 3H), 6.43 (s, 1H), 6.69 (dd, J=5.4, 1.2 Hz, 1H), 7.03 (t, J=8.4 Hz, 1H), 7.31-7.34 (m, 2H), 8.09 (d, J=5.4 Hz, 1H).

Mass Spec: ES (m/z): 316 (28.2), 315 (M+H, 100).

Example 119

Synthesis of 4-[4-(3-fluoro-4-methoxy-phenyl)-pyridin-2-yl]-morpholine (B15)

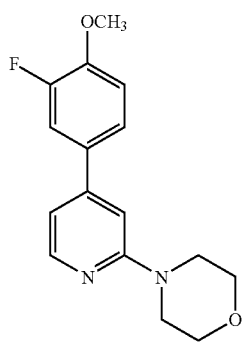

This compound was prepared by a procedure analogous to that disclosed in Example 117. Purification (Biotage Horizon HPFC chromatography system, SiO$_2$, 96:3:1 dichloromethane:methanol:ammonium hydroxide) yielded a mustard yellow solid (206 mg, 71%); HPLC: Inertsil ODS-3V C18, 30:70 [KH$_2$PO$_4$ (0.01M, pH 3.2):CH$_3$CN], 264 nm, R$_t$ 5.0 min, 98.9% purity.

M.P.: 92° C.

$^1$H NMR (600 MHz, CDCl$_3$): δ 3.54-3.56 (m, 4H), 3.83-3.85 (m, 4H), 3.92 s, 3H), 6.72 (s, 1H), 6.82 (dd, J=4.8, 1.2 Hz, 1H), 7.02 (t, J=7.8 Hz, 1H), 7.31-7.35 (m, 2H), 8.21 (d, J=5.4 Hz, 1H).

Mass Spec: ES (m/z): 290 (20.9), 289 (M+H, 100).

Example 120

Synthesis of cyclohexylmethyl-[4-(3-fluoro-4-methoxy-phenyl)-pyridin-2-yl]-amine (B16)

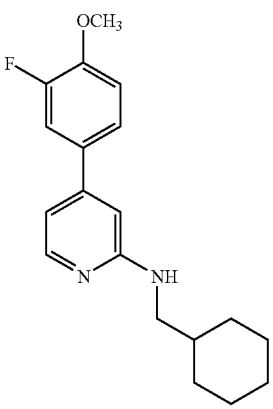

This compound was prepared by a procedure analogous to that disclosed in Example 117. The Celite™ was washed with dichloromethane, and the sample was concentrated and dried overnight under vacuum. Flash column chromatography (SiO$_2$, 50:50 hexanes:ethyl acetate) yielded an off-white solid (94 mg, 30%); HPLC: Inertsil ODS-3V C18, 30:70[KH$_2$PO$_4$ (0.01M, pH 3.2):CH$_3$CN], 264 nm, R$_t$ 3.5 min, 98.8% purity.

M.P.: 62° C.

$^1$H NMR (600 MHz, CDCl$_3$): δ 0.96-1.03 (m, 1H), 1.13-1.28 (m, 2H), 1.55-1.83 (m, 7H), 3.14 (t, J=6.6 Hz, 2H), 3.92 (s, 3H), 4.65 (br s, 1H), 6.46 (s, 1H), 6.70 (d, J=5.4 Hz, 1H), 7.01 (t, J=7.8 Hz, 1H), 7.31-7.34 (m, 2H), 8.07 (d, J=4.8H, 1H).

Mass Spec: ES (m/z): 316 (44.3), 315 (M+H, 100).

Example 121

Synthesis of [4-(3-fluoro-4-methoxy-phenyl)-pyridin-2-yl]-(4-fluoro-phenyl)-amine (B17)

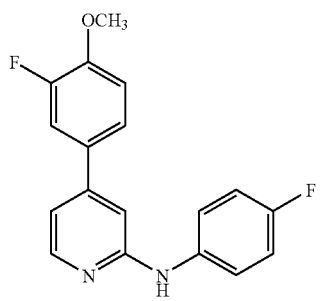

This compound was prepared by a procedure analogous to that disclosed in Example 117. Purification (Biotage Horizon HPFC chromatography system, SiO$_2$, 50:50 hexanes:ethyl acetate) yielded a yellow solid (89 mg, 57%); HPLC: Inertsil ODS-3V C18, 30:70 [KH$_2$PO$_4$ (0.01M, pH 3.2):CH$_3$CN], 264 nm, R$_t$ 8.1 min, 99.5% purity;

M.P.: 122° C.

$^1$H NMR (600 MHz, CDCl$_3$, TMS): δ 3.91 (s, 3H), 6.55 (s, 1H), 6.83 (s, 1H), 6.88 (d, J=5.4 Hz, 1H), 6.99-7.06 (m, 3H), 8.19 (d, J=5.4 Hz, 1H).

Mass Spec: ES (m/z): 314 (27.7), 313 (M+H, 100).

Example 122

Synthesis of (4-fluoro-phenyl)-[4-(4-trifluoromethoxy-phenyl)-pyridin-2-yl]-amine (B20)

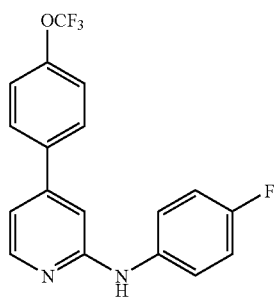

This compound was prepared by a procedure analogous to that disclosed in Example 117. Biotage Horizon HPFC system chromatography (SiO$_2$, 80:20 hexanes:ethyl acetate) yielded a light brown colored solid (410 mg, 78%).

M.P.: 105° C.

HPLC: Inertsil ODS-3V C18, 30:70 [KH$_2$PO$_4$ (0.01M, pH 3.2):CH$_3$CN], 264 nm, R$_t$ 17.2 min, 99.7% purity.

$^1$H NMR (600 MHz, CDCl$_3$, TMS, 55° C.): δ 6.7 (s, 1H), 6.85(s, 1H), 6.9 (dd, J=5.4, 1.8 Hz, 1H), 7.03-7.07 (m, 2H), 7.27 (d, J=7.8 Hz, 2H), 7.31-7.34 (m, 2H), 7.55-7.57 (m, 2H), 8.22 (d, J=5.4 Hz, 1H).

Mass Spec: (TOF MS ES+): m/z 349 (M+H, 100).

In another aspect of the present invention, this invention encompasses salts of the compounds disclosed herein, including pharmaceutically acceptable and non-pharmaceutically acceptable salts. It is envisioned that the compounds, compositions, and all the salts disclosed therein, including the non-pharmaceutically acceptable salts, can have uses and applications beyond pharmaceutical applications. For example, the pyrimidine compounds and compositions comprising pryimidine compounds of this invention can be used in a variety of agricultural uses or applications such as herbicides and pesticides, hardness stabilizers in rubber processing, ultraviolet light absorbers, and other uses.

The foregoing description has been presented for purposes of illustration and description. It is not intended to be exhaustive or to limit the invention to the precise examples or embodiments disclosed. Obvious modifications or variations are possible in light of the above teachings. The embodiment or embodiments discussed were chosen and described to provide the best illustration of the principles of the invention and its practical application to enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly and legally entitled.

We claim:

1. A compound having the formula:

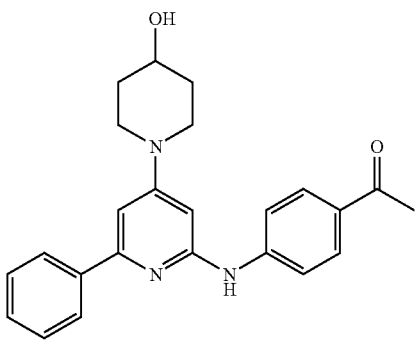

or a salt, a prodrug, a diastereomeric mixture, an enantiomer, a tautomer, or a racemic mixture thereof;

wherein:

$Y^2$ is selected independently from —NR$^5$;

$R^5$ is hydrogen or methyl;

$R^1$ and $R^2$ are selected independently from a substituted or an unsubstituted alkyl, cycloalkyl, aryl, or heterocyclyl or heteroaryl comprising at least one heteroatom or heterogroup selected from —O—, —N—, —S—, —CO or —SO$_2$, any of which having up to 10 carbon atoms; or $Y^2R^2$ is independently selected from a substituted or an unsubstituted morpholinyl, piperazinyl, piperidinyl, or pyrrolidinyl;

$R^4$ is selected from a substituted or an unsubstituted aryl, or a substituted or an unsubstituted heterocyclyl or heteroaryl comprising at least one heteroatom or heterogroup selected from —O—, —N—, —S—, or —CO, any of which having up 10 carbon atoms;

$R^1$ and $R^2$ are optionally substituted with at least one group independently selected from: 1) an alkyl, an alkoxy, a haloalkyl, a haloalkoxy, —COR$^9$, —CO$_2$R$^8$, —CONR$^8{}_2$, —SO$_2$R$^9$, —NHSO$_2$R$^9$, or —SO$_2$NR$^8{}_2$, any of which having up to 10 carbon atoms; or 2) halogen, —OCH$_2$O—, cyano, or hydroxyl;

$R^8$ in each occurrence, is selected independently from: 1) an alkyl, a haloalkyl, or an aryl, any of which having up to 10 carbon atoms; or 2) hydrogen;

$R^9$, in each occurrence, is selected independently from an alkyl, a haloalkyl, an aryl, or a heterocyclyl or heteroaryl comprising at least one heteroatom selected from —O— or —N—, any of which having up to 10 carbon atoms; and $R^4$ is optionally substituted with at least one group independently selected from: 1) an alkyl, a haloalkoxy, an alkoxy, —COR$^9$, —CONR$^8{}_2$, —SO$_2$R$^9$, —SO$_2$NR$^{10}{}_2$, or —NR$^{10}{}_2$, any of which having up to 10 carbon atoms; or 2) halogen, cyano, or hydroxyl; and $R^{10}$ in each occurrence, is selected independently from: 1) an alkyl, an aryl, or a heterocyclyl comprising at least one heteroatom selected from —O— or —N—, any of which having up to 10 carbon atoms; or 2) hydrogen.

2. A compound according to claim 1, having the formula:

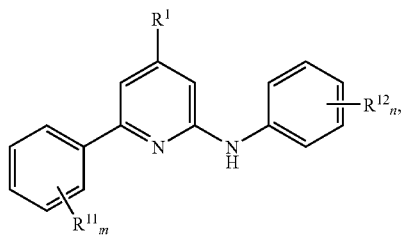

or a salt, a prodrug, a diastereomeric mixture, an enantiomer, a tautomer, or a racemic mixture thereof;
wherein:
R¹ is selected from a substituted or an unsubstituted heterocyclyl comprising at least one heteroatom or heterogroup selected from —O—, —N—, —S—, —SO₂, or —CO, any of which having up to 10 carbon atoms;
n and m are independently an integer from 0 to 3, inclusive;
R¹¹ and R¹² in each occurrence, are selected independently from: 1) an alkyl, an alkoxy, a haloalkyl, a haloalkoxy, —COR⁹, —CO₂R⁸, —CONR⁸₂, —SO₂R⁹, —NHSO₂R⁹, or —SO₂NR⁸₂, any of which having up to 10 carbon atoms; or 2) halogen, cyano, —OCH₂O—, or hydroxyl;
R⁹, in each occurrence, is selected independently from an alkyl, a haloalkyl, an aryl, or a heterocyclyl or heteroaryl comprising at least one heteroatom selected from —O— or —N—, any of which having up to 10 carbon atoms; and
R¹ is optionally substituted with at least one group independently selected from: 1) an alkyl, a cycloalkyl, a haloalkyl, or —OCOCH₂CH₂CO₂R⁸, any of which having up to 10 carbon atoms; or 2) hydroxyl.

3. A compound according to claim 2, wherein:
R¹ is selected from

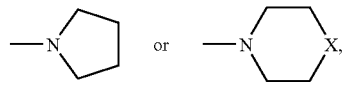

wherein X is selected from CH₂, O, NH, NMe, NEt, S, SO₂, CH(OCOCH₂CH₂CO₂H), or CH(OH);
n and m are independently an integer from 0 to 2, inclusive; and
R¹¹ and R¹², in each occurrence, are selected independently from OCF₃, OMe, Cl, F, SO₂Me, CF₃, Me, COMe, CONHMe, NHSO₂Me, SO₂NH₂, SO₂NHMe, SO₂NMe₂, CONH₂, CONMe₂, CO₂Me, —OCH₂O—, or OH.

4. A compound having the formula:

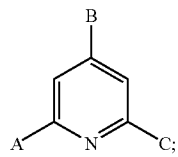

or a salt, a prodrug, a diastereomeric mixture, an enantiomer, a tautomer, or a racemic mixture thereof; wherein:

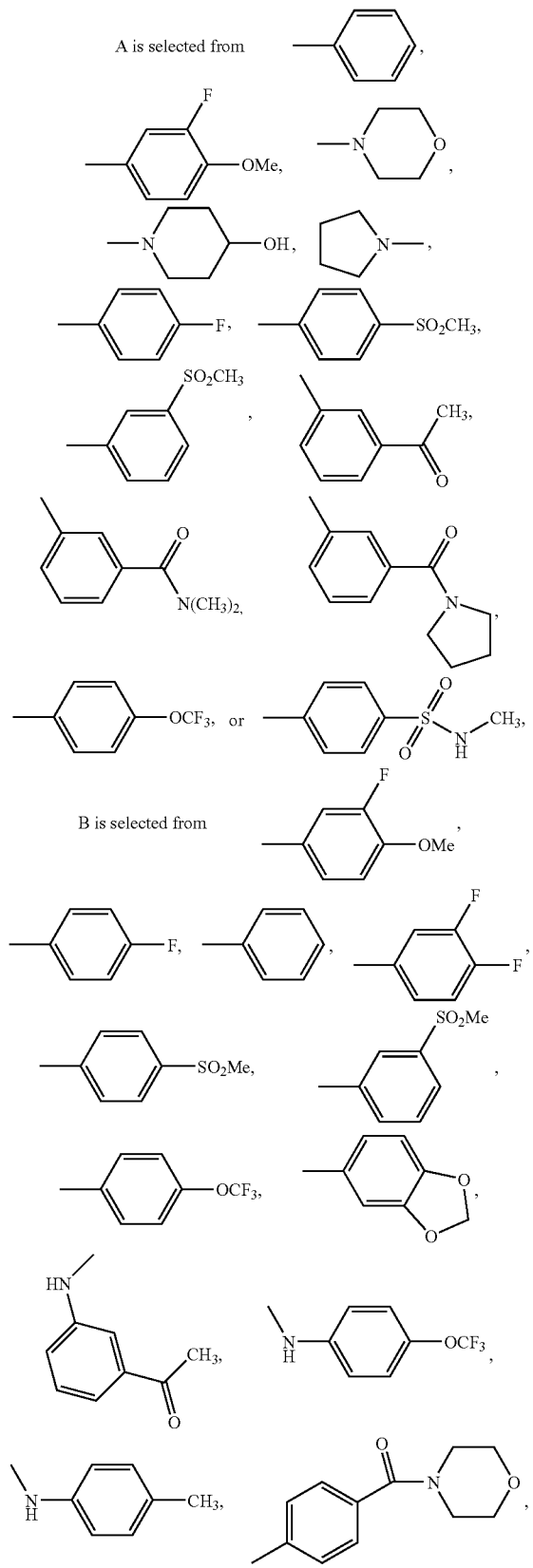

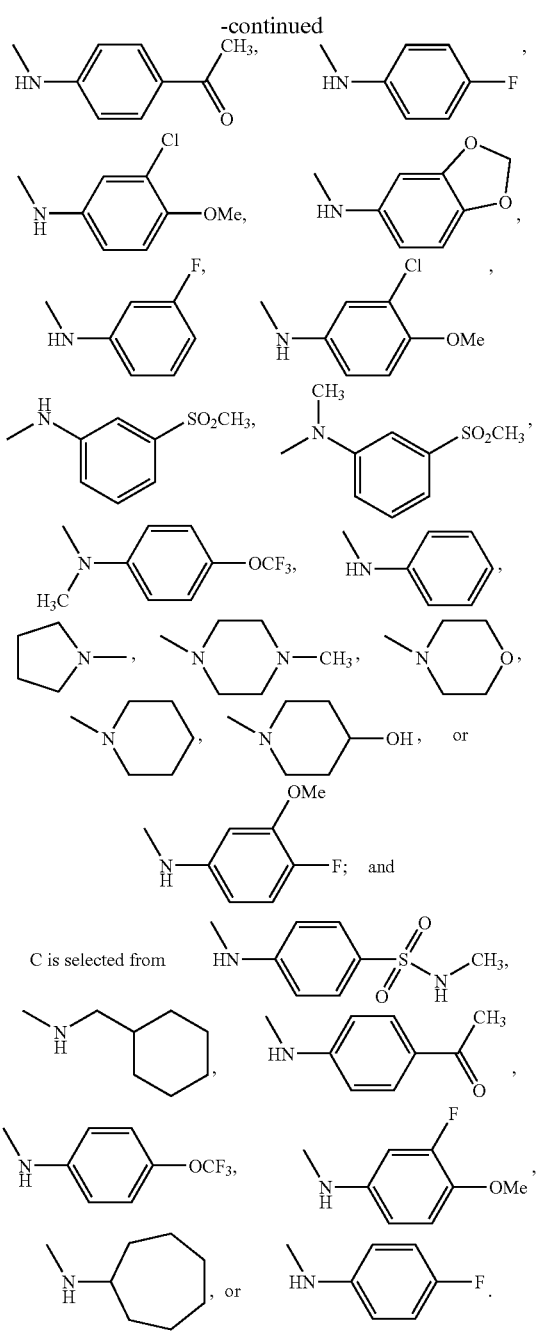

5. A compound selected from:
[6'-(4-Fluoro-phenyl)-3,4,5,6-tetrahydro-2H-[1,4']bipyridinyl-2'-yl]-(4-trifluoromethoxy-phenyl)-amine;
(4-Trifluoromethoxy-phenyl  )-[6'-(4-trifluoromethoxyphenyl )-3,4,5,6-tetrahydro-2H-[1,4']bipyridinyl-2'-yl]-amine;
(6'-Phenyl-3,4,5,6-tetrahydro-2H-[1,4']bipyridinyl-2'-yl)-(4-trifluoro-methoxy-phenyl)-amine;
[6'-(3-Methanesulfonyl-phenyl)-3,4,5,6-tetrahydro-2H-[1,4']bipyridinyl-2'-yl]-(4-trifluoromethoxy-phenyl)-amine;
4-[6'-(4-Fluoro-phenyl)-3,4,5,6-tetrahydro-2H-[1,4']bipyridinyl-2'-ylamino]-N-methyl-benzenesulfonamide;
1-[4-(4-Hydroxy-6'-phenyl-3,4,5,6-tetrahydro-2H-[1,4']bipyridinyl-2'-ylamino)-phenyl]-ethanone;
(6-Phenyl-4-pyrrolidin-1-yl-pyridin-2-yl)-(4-trifluoromethoxy-phenyl)-amine;
[6-(4-Fluoro-phenyl)-4-pyrrolidin-1-yl-pyridin-2-yl]-(4-trifluoromethoxy-phenyl)-amine;
N-Methyl-4-[4-pyrrolidin-1-yl-6-(4-trifluoromethoxyphenyl)-pyridin-2-ylamino]-benzenesulfonamide;
N-Methyl-4-[4-(4-methyl-piperazin-1-yl)-6-(4-trifluoromethoxy-phenylamino)-pyridin-2-yl]-benzenesulfonamide;
[6-(3-Methanesulfonyl-phenyl)-4-morpholin-4-yl-pyridin-2-yl]-(4-trifluoromethoxy-phenyl)-amine;
N-Methyl-4-[4-morpholin-4-yl-6-(4-trifluoromethoxyphenylamino)-pyridin-2-yl]-benzenesulfonamide;
or any combination thereof;
or a salt, a prodrug, a diastereomeric mixture, an enantiomer, a tautomer, or a racemic mixture thereof.

6. A compound according to claim 4, wherein:

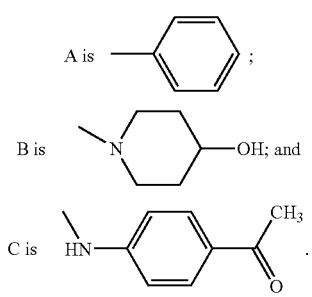

7. A compound according to claim 5 wherein the compound is 1-[4-(4-hydroxy-6'-phenyl-3,4,5,6-tetrahydro-2H-[1,4']bipyridinyl-2'-ylamino)-phenyl]-ethanone.

8. A compound according to claim 1 having the formula:

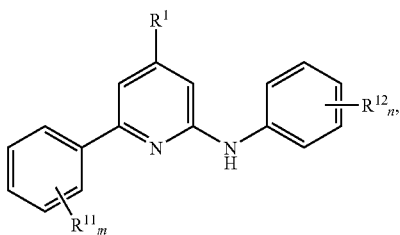

or a salt, a prodrug, a diastereomeric mixture, an enantiomer, a tautomer, or a racemic mixture thereof;
wherein:
$R^1$ is a substituted heterocyclyl with a single heteroatom wherein the heteroatom is —N—;
m is 0;
n is 1;
$R^{12}$ is —$COR^9$;
$R^9$ is an alkyl having one carbon atom; and
$R^1$ is substituted with hydroxyl.

9. A compound according to claim 8, wherein:
R$^1$ is

—N◯X;

X is CH(OH);
m is 0;
n is 1; and
R$^{12}$ is COMe.

10. A compound according to claim 8, having the formula:

[structure: pyridine with R$^2$ at 4-position, R$^4$ at 6-position, and NHR$^1$ at 2-position]

or a pharmaceutically acceptable salt, a prodrug, a diastereomeric mixture, an enantiomer, a tautomer, or a racemic mixture thereof.

11. A pharmaceutical composition comprising a pharmaceutically acceptable carrier and a compound having the formula:

[structure: pyridine with Y$^2$R$^2$ at 4-position, R$^4$ at 6-position, and Y$^1$R$^1$ at 2-position]

wherein:
Y$^2$ is selected independently from —NR$^5$;
R$^5$ is hydrogen or methyl;
R$^1$ and R$^2$ are selected independently from a substituted or an unsubstituted alkyl, cycloalkyl, aryl, or heterocyclyl or heteroaryl comprising at least one heteroatom or heterogroup selected from —O—, —N—, —S—, —CO or —SO$_2$, any of which having up to 10 carbon atoms; or
Y$^2$R$^2$ is independently selected from a substituted or an unsubstituted morpholinyl, piperazinyl, piperidinyl, or pyrrolidinyl
R$^4$ is selected independently from: 1) a substituted or an unsubstituted aryl, or a substituted or an unsubstituted heteroaryl or heterocyclyl comprising at least one heteroatom or heterogroup selected from —O—, —N—, —S—, or —CO, any of which having up to 10 carbon atoms;
wherein any of R$^1$ or R$^2$, is also optionally substituted with at least one group independently selected from: 1) an alkyl, an alkoxy, a haloalkyl, a haloalkoxy, —COR$^9$, —CO$_2$R$^8$, —CONR$^8{}_2$, —SO$_2$R$^9$, —NHSO$_2$R$^9$, or —SO$_2$NR$^8{}_2$, any of which having up to 10 carbon atoms; or 2) hydroxyl, halogen, —OCH$_2$O—, or cyano;
R$^8$, in each occurrence, is selected independently from: 1) an alkyl, a haloalkyl, or an aryl, any of which having up to 10 carbon atoms; or 2) hydrogen;
R$^9$, in each occurrence, is selected independently from an alkyl, a haloalkyl, an aryl, or a heterocyclyl or heteroaryl comprising at least one heteroatom selected from —O—, or —N—, any of which having up to 10 carbon atoms,
R$^4$ is optionally substituted with at least one group selected independently from: 1) an alkyl, an alkoxy, a haloalkoxy, —COR$^9$, —CONR$^8{}_2$, —SO$_2$R$^9$, —SO$_2$NR$^{10}{}_2$, —NR$^{10}{}_2$, any of which having up to 10 carbon atoms; or 2) halogen, cyano, or hydroxyl; and
R$^{10}$, in each occurrence, is selected independently from: 1) an alkyl, an aryl, or a heterocyclyl comprising at least one heteroatom selected from —O— or —N—, any of which having up to 10 carbon atoms; or 2) hydrogen;
or a pharmaceutically acceptable salt, a prodrug, a diastereomeric mixture, an enatiomer, a tautomer, or a racemic mixture thereof.

12. The composition as claimed in claim 11, further comprising:
optionally, a pharmaceutically acceptable auxiliary;
optionally, a pharmaceutically acceptable preservative;
optionally, a pharmaceutically acceptable excipient;
optionally, a pharmaceutically acceptable diluent; and
optionally, a pharmaceutically acceptable solvate.

13. The composition as claimed in claim 11, further comprising an agent selected from an immunosuppressive agent, a cytotoxic agent, an anti-inflammatory agent, an antirheumatic agent, a cardiovascular agent, or any combination thereof.

14. The composition as claimed in claim 11, wherein the composition is in the form of a tablet, a capsule, a cachet, a powder, a granule, a solution, a suspension, an emulsion, a bolus, a lozenge, a suppository, a pessary, a tampon, a cream, a gel, a paste, a foam, a spray, an aerosol, a microcapsule, a liposome, a transdermal patch, a pastille, a paste, or a mouthwash.

15. A pharmaceutical composition comprising a pharmaceutically acceptable carrier and a compound selected from:

[structure: pyridine with B at 4-position, A at 6-position, and C at 2-position]

wherein:

A is selected from [phenyl], [3-fluoro-4-methoxyphenyl], [morpholinyl-N], [4-hydroxypiperidin-1-yl], [pyrrolidin-1-yl], [4-fluorophenyl], [4-(methylsulfonyl)phenyl], -continued

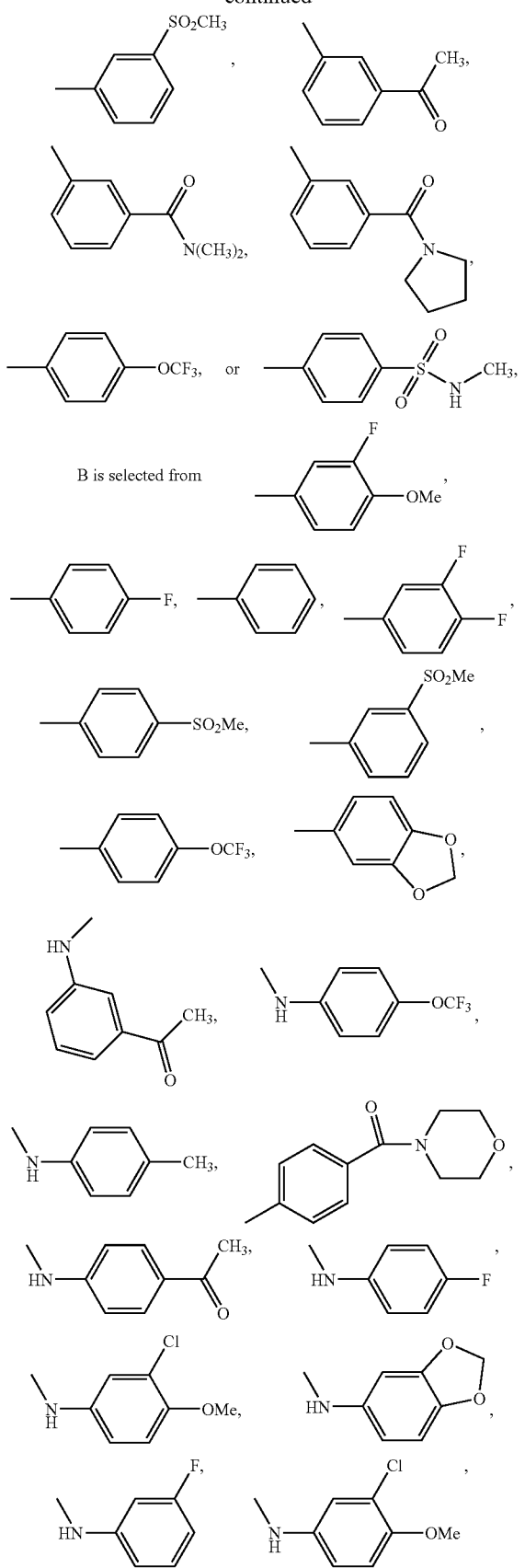

B is selected from

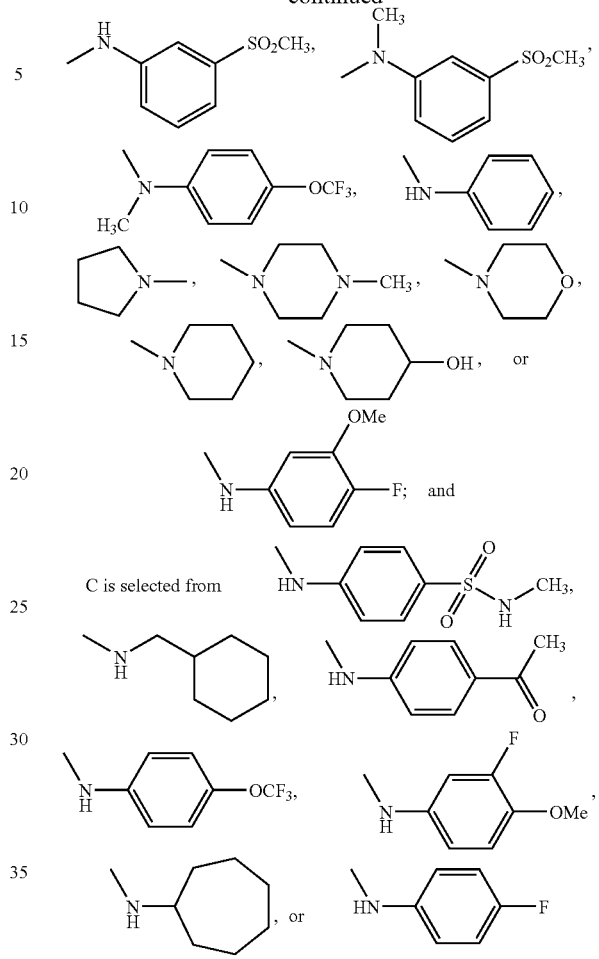

C is selected from or a pharmaceutically acceptable salt, a prodrug, a diastereomeric mixture, an enantiomer, a tautomer, or a racemic mixture thereof.

16. The composition as claimed in claim 15, further comprising:
   optionally, a pharmaceutically acceptable auxiliary;
   optionally, a pharmaceutically acceptable preservative;
   optionally, a pharmaceutically acceptable excipient;
   optionally, a pharmaceutically acceptable diluent; and
   optionally, a pharmaceutically acceptable solvate.

17. The composition as claimed in claim 15, further comprising an agent selected from an immunosuppressive agent, a cytotoxic agent, an anti-inflammatory agent, an antirheumatic agent, a cardiovascular agent, or any combination thereof.

18. The composition as claimed in claim 15, wherein the composition is in the form of a tablet, a capsule, a cachet, a powder, a granule, a solution, a suspension, an emulsion, a bolus, a lozenge, a suppository, a pessary, a tampon, a cream, a gel, a paste, a foam, a spray, an aerosol, a microcapsule, a liposome, a transdermal patch, a pastille, a paste, or a mouthwash.

19. A pharmaceutical composition comprising a pharmaceutically acceptable carrier and a compound selected from:
   [6'-(4-Fluoro-phenyl )-3,4,5,6-tetrahydro-2H-[1,4']bipyridinyl-2'-yl]-(4-trifluoromethoxy-phenyl)-amine;

(4-Trifluoromethoxy-phenyl)-[6'-(4-trifluoromethoxy-phenyl)-3,4,5,6-tetrahydro-2H-[1,4']bipyridinyl-2'-yl]-amine;
(6'-Phenyl-3,4,5,6-tetrahydro-2H-[1,4']bipyridinyl-2'-yl)-(4-trifluoro-methoxy-phenyl)-amine;
[6'-(3-Methanesulfonyl-phenyl)-3,4,5,6-tetrahydro-2H-[1,4']bipyridinyl-2'-yl]-(4-trifluoromethoxy-phenyl)-amine;
4-[6'-(4-Fluoro-phenyl)-3,4,5,6-tetrahydro-2H-[1,4']bipyridinyl-2'-ylamino]-N-methyl-benzenesulfonamide;
1-[4-(4-Hydroxy-6'-phenyl-3,4,5,6-tetrahydro-2H-[1,4']bipyridinyl-2'-ylamino)-phenyl]-ethanone;
(6-Phenyl-4-pyrrolidin-1-yl-pyridin-2-yl)-(4-trifluoromethoxy-phenyl)-amine;
[6-(4-Fluoro-phenyl)-4-pyrrolidin-1-yl-pyridin-2-yl]-(4-trifluoromethoxy-phenyl)-amine;
N-Methyl-4-[4-pyrrolidin-1-yl-6-(4-trifluoromethoxy-phenyl)-pyridin-2-ylamino]-benzenesulfonamide;
N-Methyl-4-[4-(4-methyl-piperazin-1-yl)-6-(4-trifluoromethoxy-phenylamino)-pyridin-2-yl]-benzenesulfonamide;
[6-(3-Methanesulfonyl-phenyl)-4-morpholin-4-yl-pyridin-2-yl]-(4-trifluoromethoxy-phenyl)-amine;
N-Methyl-4-[4-morpholin-4-yl-6-(4-trifluoromethoxy-phenylamino)-pyridin-2-yl]-benzenesulfonamide;
(4-Fluoro-phenyl)-[6-(4-trifluoromethoxy-phenyl)-pyridin-2-yl]-amine;
or any combination thereof;
or a pharmaceutically acceptable salt, a prodrug, a diastereomeric mixture, an enantiomer, a tautomer, or a racemic mixture thereof.

20. A composition according to claim 19, further comprising:
optionally, a pharmaceutically acceptable auxiliary;
optionally, a pharmaceutically acceptable preservative;
optionally, a pharmaceutically acceptable excipient;
optionally, a pharmaceutically acceptable diluent; and
optionally, a pharmaceutically acceptable solvate.

21. The composition as claimed in claim 19, further comprising an agent selected from an immunosuppressive agent, a cytotoxic agent, an anti-inflammatory agent, an antirheumatic agent, a cardiovascular agent, or any combination thereof.

22. The composition as claimed in claim 19, wherein the composition is in the form of a tablet, a capsule, a cachet, a powder, a granule, a solution, a suspension, an emulsion, a bolus, a lozenge, a suppository, a pessary, a tampon, a cream, a gel, a paste, a foam, a spray, an aerosol, a microcapsule, a liposome, a transdermal patch, a pastille, a paste, or a mouthwash.

23. A pharmaceutical composition comprising a pharmaceutically acceptable carrier and a compound according to claim 15 wherein:

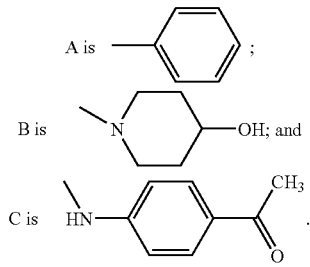

24. A pharmaceutical composition comprising a pharmaceutically acceptable carrier and a compound according to claim 19 wherein the compound is 1-[4-(4-Hydroxy-6'-phenyl-3,4,5,6-tetrahydro-2H-[1,4']bipyridinyl-2'-ylamino)-phenyl]-ethanone.

* * * * *

UNITED STATES PATENT AND TRADEMARK OFFICE
CERTIFICATE OF CORRECTION

PATENT NO.       : 7,622,486 B2                               Page 1 of 3
APPLICATION NO.  : 11/234257
DATED            : November 24, 2009
INVENTOR(S)      : Manojit Pal et al.

It is certified that error appears in the above-identified patent and that said Letters Patent is hereby corrected as shown below:

Column 4, Line 46, replace the term "heterocycly" with the term -- heterocyclyl --.

Column 20, Line 31, replace the term "-SO$_{10}$NR$^2$," with the term -- -SO$_2$NR$^{10}{}_2$, --.

Column 37, Line 43, replace the term "goup" with the term -- group --.

Column 39, Line 67, replace the term "C(O)(NC$_4$H8)," with the term
-- C(O)(NC$_4$H$_8$), --.

Column 41, Line 23, replace the term "CH3," with the term -- CH$_3$ --.

Column 75, Cmpd. No. B45, Name column, replace the term
"[4-(2-morpholin-4-yl-6-phenyl-pyridin-4-ylamino)-phenyl]-ethanone;" with the term
-- 1-[4-(2-morpholin-4-yl-6-phenyl-pyridin-4-ylamino)-phenyl]-ethanone; --.

Column 94, Cmpd. No. B86, Name column, replace the term
"(2-chloro-6-pyrrolidin-1-yl-pyridin-4-yl)-(4-tnfluoromethoxy-phenyl)-amine" with the term
-- (2-chloro-6-pyrrolidin-1-yl-pyridin-4-yl)-(4-trifluoromethoxy-phenyl)-amine --.

Column 103, Table 2, Cmpd. No. B106, Structure column, replace the term "OCF$_3$" with the term
-- OCH$_3$ --.

Column 104, Table 2, Cmpd. No. B103, Name column, replace the term
"2,6-dichloro-4-phenyl-pyridune" with the term -- 2,6-dichloro-4-phenyl-pyridine --.

Column 130, Table 3, Entry 8, Compound Name column, replace the term "N-ethyl-3-[6-(3-methanesuifonyl-phenyl)-4-(4-trifluoromethoxy-phenylamino)-pyridin-2-yl]-benzamide" with the term
-- N-ethyl-3-[6-(3-methanesulfonyl-phenyl)-4-(4-trifluoromethoxy-phenylamino)-pyridin-2-yl]-benzamide --.

Column 138, Table 3, Entry 26, Compound Name column, replace the term "[3[6'-(3-Methanesulfonyl-phenyl)-3,4,5,6-tetrahydro-2H-[1,4']bipyridinyl-2'-yl]-(4-trifluoromethoxy-phenyl)-amine" with the term -- [6'-(3-Methanesulfonyl-phenyl)-3,4,5,6-tetrahydro-2H-[1,4']bipyridinyl-2'-yl]-(4-trifluoromethoxy-phenyl)-amine --.

Column 141, Table 3, Entry 33, Structure column at the top of the structure, replace the term "CH$_3$ with
$|$
N" with the term -- O --.

Column 147, Line 49, replace the terms "patent application" with the terms -- Patent Application --.

CERTIFICATE OF CORRECTION (continued)

Column 165, Line 34, replace the terms "patent application" with the terms -- Patent Application --.

Column 173, line 50, replace the term "anastomosis" with the term -- anastornosis --.

Column 187, Table 9, Patent No. 6573278, Title column, replace the term "arysulfonamides" with the term -- arylsulfonamides --.

Column 213, Line 66, replace the term "(MW$^+$+1, 100%)" with the term -- (M$^+$+1, 100%) --.

Column 214, Line 36, replace the term "1 50° C" with the term -- 150°C --.

Column 216, Line 40, replace the term "KPFC" with the term -- HPFC --.

Column 230, Line 51, replace the term
"19-{3-[6-morpholin-4-yl-4-(4-trifluoromethoxy-phenylamino)-pyridin-2-yl]-phenyl}-ethanone"
with the term
-- 1-{3-[6-morpholin-4-yl-4-(4-trifluoromethoxy-phenylamino)-pyridin-2-yl]-phenyl}-ethanone --.

Column 247, Line 4, replace the term
"2',6'-bis-(4-trifluoromethoxy-phenylamino)-3,4,5,6-tetrahdro-2H[1,4']bipyridinyl-4-ol"
with the term
-- 2',6'-bis-(4-trifluoromethoxy-phenylamino)-3,4,5,6-tetrahydro-2H[1,4']bipyridinyl-4-ol --.

Column 252, Line 55, insert the term -- F    at the top of the structure.
                                              |--

Column 253, Line 42, replace the term "$C_{22}H_{22}F_2N_3$," with the term -- $C_{22}H_{21}F_2N_3$, --.

Column 276, Line 7, replace the term "264 um" with the term -- 264 nm --.

Column 280, Claim 1, Lines 5-19, replace the formula " 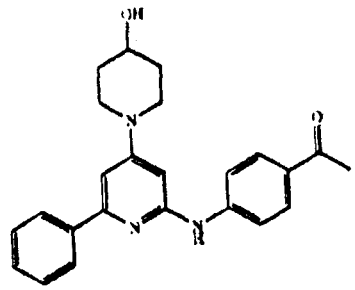 " with the formula 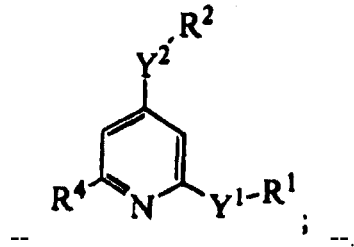 .

CERTIFICATE OF CORRECTION (continued)
U.S. Pat. No. 7,622,486 B2

Column 285, Claim 10, Lines 16-23, replace the formula " 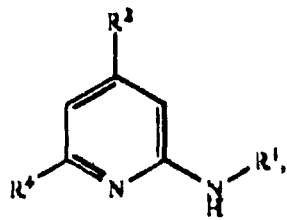 " with the formula

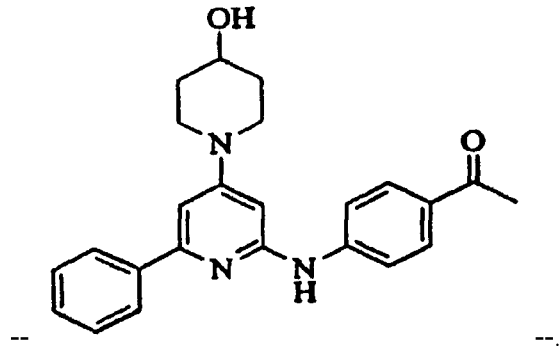

-- --.

Column 285, Claim 11, Lines 31-40, replace the formula " 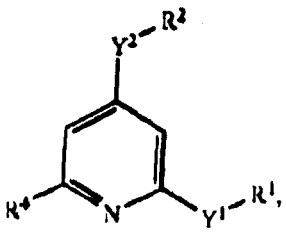 " with the formula

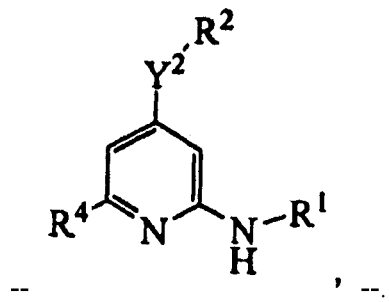

-- , --.

Signed and Sealed this

Sixth Day of April, 2010

David J. Kappos
*Director of the United States Patent and Trademark Office*

UNITED STATES PATENT AND TRADEMARK OFFICE
CERTIFICATE OF CORRECTION

PATENT NO. : 7,622,486 B2 Page 1 of 1
APPLICATION NO. : 11/234257
DATED : November 24, 2009
INVENTOR(S) : Pal et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 900 days.

Signed and Sealed this

Fourteenth Day of December, 2010

David J. Kappos
*Director of the United States Patent and Trademark Office*